United States Patent [19]
Fevig et al.

[11] Patent Number: 6,057,342
[45] Date of Patent: May 2, 2000

[54] AMIDINOPHENYL-PYRROLIDINES, -PYRROLINES, AND -ISOXAZOLIDINES AND DERIVATIVES THEREOF

[75] Inventors: John Matthew Fevig, Lincoln University, Pa.; Donald Joseph Phillip Pinto; Mimi Lifen Quan, both of Newark, Del.; Petrus Fredericus Wilhelmus Stouten, Wilmington, Del.

[73] Assignee: Dupont Pharmaceutical Co., Wilmington, Del.

[21] Appl. No.: 08/888,718

[22] Filed: Jul. 7, 1997

Related U.S. Application Data

[60] Provisional application No. 60/023,417, Aug. 16, 1996, and provisional application No. 60/033,436, Dec. 23, 1996.

[51] Int. Cl.⁷ .................. A61K 31/4025; A61K 31/4427; C07D 401/06; C07D 403/06
[52] U.S. Cl. .................. 514/340; 514/343; 514/344; 514/345; 514/347; 514/348; 514/349; 514/350; 514/351; 514/352; 514/354; 514/356; 514/378; 514/380; 514/422; 514/423; 514/424; 514/426; 514/427; 514/428; 514/444; 514/445; 514/447; 514/448; 514/451; 514/459; 514/460; 514/461; 514/471; 514/472; 514/473; 546/272.1; 546/276.4; 546/278.4; 546/278.7; 546/279.1; 548/240; 548/243; 548/244; 548/517; 548/518; 548/519; 548/521; 548/530; 548/531; 548/532; 548/541; 548/546; 548/547; 548/548; 548/550; 548/556; 548/557; 548/560; 548/561; 548/562; 548/565; 548/566; 548/568; 548/570; 548/571; 548/572; 548/577; 549/59; 549/61; 549/62; 549/64; 549/65; 549/66; 549/70; 549/71; 549/72; 549/74; 549/75; 549/76; 549/78; 549/79; 549/414; 549/416; 549/419; 549/420; 549/424; 549/425; 549/426; 549/427; 549/472; 549/473; 549/474; 549/475; 549/479; 549/480; 549/483; 549/484; 549/491; 549/496; 549/498; 549/499; 549/502; 549/505; 564/244; 564/163; 564/166; 564/171

[58] Field of Search .................. 514/340, 343, 514/345, 351, 352; 546/272.1, 276.4, 278.4, 278.7, 279.1; 548/240, 243, 517; 549/59, 414, 472

[56] References Cited

U.S. PATENT DOCUMENTS

| | | | |
|---|---|---|---|
| 5,418,233 | 5/1995 | Linz et al. | 514/247 |
| 5,463,071 | 10/1995 | Himmelsbach et al. | 548/251 |

FOREIGN PATENT DOCUMENTS

| | | |
|---|---|---|
| 2054850 | 5/1992 | Canada . |
| 9640679 | 12/1996 | WIPO . |

*Primary Examiner*—Johann Richter
*Assistant Examiner*—Jane C. Osvecki

[57] ABSTRACT

The present application describes amidinophenyl-pyrrolidines, -pyrrolines, and -isoxazolidines and derivatives thereof of formula I:

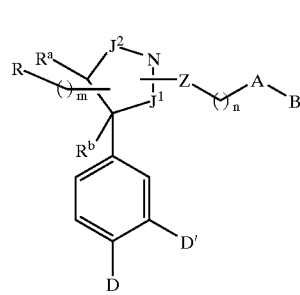

or pharmaceutically acceptable salt forms thereof, wherein one of D and D' may be $C(=NH)NH_2$ and the other H, and $J^1$ and $J^2$ may be O or $CH_2$, which are useful as inhibitors of factor Xa.

19 Claims, No Drawings

AMIDINOPHENYL-PYRROLIDINES, -PYRROLINES, AND -ISOXAZOLIDINES AND DERIVATIVES THEREOF

This application claims the benefit of U.S. Provisional Application No. 60/023,417, filed Aug. 16, 1996, and U.S. Provisional Application No. 60/033,436, filed Dec. 23, 1996.

FIELD OF THE INVENTION

This invention relates generally to amidinophenyl pyrrolidines, -pyrrolines, and -isoxazolidines and derivatives which are inhibitors of trypsin-like serine protease enzymes, especially factor Xa, pharmaceutical compositions containing the same, and methods of using the same as anticoagulant agents for treatment and prevention of thromboembolic disorders.

BACKGROUND OF THE INVENTION

Himmelsbach et al in CA 2,054,850 discuss aggregation inhibiting compounds of the formula:

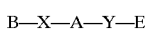

wherein A may be a cyclic imino such as pyrrolidine and amidst the various definitions of B and X one can find amidino and arylene listed. The combination of Y—E, however, is not considered to be useful for the present invention. Thus, the compounds of Himmelsbach et al differ from those of the present invention. Moreover, inhibition of factor Xa is not discussed in Himmelsbach et al as a use for the compounds of the above formula.

In U.S. Pat. No. 5,463,071, Himmelsbach et al depict cell aggregation inhibitors which are 5-membered heterocycles of the formula:

wherein the heterocycle is other than pyrroline and pyrrolidine and groups A—B—C— and F—E—D— are attached to the ring system. A—B—C— can be a wide variety of substituents including a basic group attached to an aromatic ring. The F—E—D— group, however, would appear to be an acidic functionality which differs from the present invention. Furthermore, use of these compounds as inhibitors of factor Xa is not discussed.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. *Thromb. Res.* 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors.

SUMMARY OF THE INVENTION

Accordingly, one object of the present invention is to provide novel amidino-phenylpyrrolidines and analogs thereof which are useful as factor Xa inhibitors or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating thromboembolic disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of formula (I):

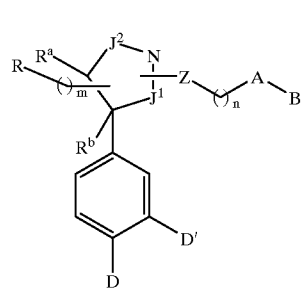

or pharmaceutically acceptable salt or prodrug forms thereof, wherein A, B, D, $D^a$, J, m, n, R, $R^a$, $R^b$ and Z are defined below, are effective factor Xa inhibitors.

DETAILED DESCRIPTION OF PREFERRED EMBODIMENTS

[1] Thus, in a first embodiment, the present invention provides novel compounds of formula I:

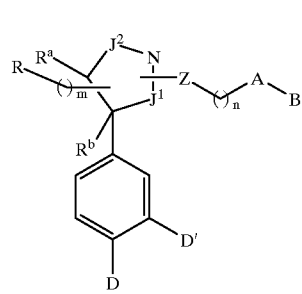

or a stereoisomer or pharmaceutically acceptable salt form thereof, wherein;

one of D and D' is selected from CN, $C(=NR^7)NR^8R^9$, $NHC(=NR^7)NR^8R^9$, $NR^8CH(=NR^7)$, $C(O)NR^8R^9$, and $(CH_2)_rNR^8R^9$ and the other is H;

Z is selected from $CH_2$, $C=O$, $CH_2C(O)$, $C(O)O$, $CONH$, $CH_2NH_2$, $CH_2O$, $SO_2$, and $SO_2NH$;

$J^1$ and $J^2$ are independently selected from O and $CH_2$, provided that if $J^1$ is O, then $J^2$ is $CH_2$ and if $J^2$ is O, then $J^1$ is $CH_2$;

R is selected from $CO_2R^1$, $COR^1$, $OR^1$, $NR^2R^{2a}$, $CONR^2R^{2a}$, $S(O)_pR^{1a}$, and $S(O)_pNR^2R^{2a}$;

$R^a$ is selected from H and $C_{1-4}$ alkyl;

$R^b$ is H;

when $J^1$ and $J^2$ are $CH_2$, then $R^a$ and $R^b$ can combine to form a bond;

$R^1$ is selected from:
H,
$C_{1-4}$ alkyl substituted with 0–1 $R^3$,
$C_{3-6}$ carbocyclic residue substituted with 0–2 $R^4$, and
5–6 membered heterocyclic system containing from 1–4 heteroatoms selected from the group consisting of N, O, and S substituted with 0–2 $R^4$;

$R^{1a}$ is selected from:
$C_{1-4}$ alkyl substituted with 0–1 $R^3$,
$C_{3-6}$ carbocyclic residue substituted with 0–2 $R^4$, and
5–6 membered heterocyclic system containing from 1–4 heteroatoms selected from the group consisting of N, O, and S substituted with 0–2 $R^4$;

$R^2$ and $R^{2a}$ are independently selected from H, $C_{1-4}$ alkyl, and phenyl;

$R^2$ and $R^{2a}$ may be taken together to form a 5 or 6 membered ring substituted with 0–2 $R^4$ which may contain from 0–1 heteroatoms selected from the group consisting of N, O, and S;

$R^{2a}$ may also be $C_{1-4}$ alkoxy;

$R^3$ is selected from:
phenyl substituted with 0–2 $R^4$, and
5–6 membered heterocyclic system containing from 1–4 heteroatoms selected from the group consisting of N, O, and S substituted with 0–2 $R^4$;

A is selected from:
$C_{3-13}$ carbocyclic residue substituted with 0–2 $R^4$, and
5–10 membered heterocyclic system containing from 1–4 heteroatoms selected from the group consisting of N, O, and S substituted with 0–2 $R^4$;

B is selected from:
X-Y, $NR^2R^{2a}$, $C(=NR^2)NR^2R^{2a}$, $NR^2C(=NR^2)NR^2R^{2a}$, benzyl substituted with 0–2 $R^{4a}$,
$C_{3-10}$ carbocyclic residue substituted with 0–2 $R^{4a}$, and
5–10 membered heterocyclic system containing from 1–4 heteroatoms selected from the group consisting of N, O, and S substituted with 0–2 $R^4$, provided that B is other than tetrazol-5-yl;

X is selected from $C_{1-4}$ alkylene, —C(O)—, —C(O)$CR^2R^{2a}$—, —$CR^2R^{2a}$C(O), —S(O)$_p$—, —S(O)$_p$$CR^2R^{2a}$—, —$CR^2R^{2a}$S(O)$_p$—, —S(O)$_2$$NR^2$—, —$NR^2$S(O)$_2$—, —$NR^2$S(O)$_2$$CR^2R^{2a}$—, —$CR^2R^{2a}$S(O)$_2$$NR^2$—, —$NR^2$S(O)$_2$$NR^2$—, —C(O)$NR^2$—, —$NR^2$C(O)—, —C(O)$NR^2$$CR^2R^{2a}$—, —$NR^2$C(O)$CR^2R^{2a}$—, —$CR^2R^{2a}$C(O)$NR^2$—, —$CR^2R^{2a}$$NR^2$C(O)—, —$NR^2$C(O)O—, —OC(O)$NR^2$—, —$NR^2$C(O)$NR^2$—, —$NR^2$—, —$NR^2CR^2R^{2a}$—, —$CR^2R^{2a}NR^2$—, O, —$CR^2R^{2a}$O—, —$OCR^2R^{2a}$—, and S;

Y is selected from:
$C_{3-10}$ carbocyclic residue substituted with 0–2 $R^4$, and
5–10 membered heterocyclic system containing from 1–4 heteroatoms selected from the group consisting of N, O, and S substituted with 0–2 $R^4$, provided that Y is other than tetrazol-5-yl;

$R^4$ is selected from OH, $(CH_2)_rOR^2$, halo, $C_{1-4}$ alkyl, CN, $NO_2$, $(CH_2)_rNR^2R^{2a}$, $(CH_2)_rC(O)R^2$, $NR^2C(O)R^{2a}$, $NR^2C(O)NR^2R^{2a}$, $CH(=NH)NH_2$, $NHC(=NH)NH_2$, $SO_2NR^2R^{2a}$, $NR^2SO_2NR^2R^{2a}$, $NR^2SO_2$—$C_{1-4}$ alkyl, $NR^2SO_2R^5$, $S(O)_pR^{1a}$, and $CF_3$;

$R^{4a}$ is selected from OH, halo, $C_{1-4}$ alkyl, $NO_2$, $(CH_2)_rNR^2R^{2a}$, $(CH_2)_rC(O)R^2$, $NR^2C(O)R^{2a}$, $NR^2C(O)NR^2R^{2a}$, $CH(=NH)NH_2$, $NHC(=NH)NH_2$, $SO_2NR^2R^{2a}$, $NR^2SO_2NR^2R^{2a}$, $NR^2SO_2$—$C_{1-4}$ alkyl $NR^2SO_2R^5$, $S(O)_pR^{1a}$, and $CF_3$;

$R^5$ is selected from:
$C_{3-10}$ carbocyclic residue substituted with 0–2 $R^6$, and
5–10 membered heterocyclic system containing from 1–4 heteroatoms selected from the group consisting of N, O, and S substituted with 0–2 $R^6$;

$R^6$ is selected from H, OH, $(CH_2)_rOR^2$, halo, $C_{1-4}$ alkyl, CN, $NO_2$, $(CH_2)_rNR^2R^{2a}$, $(CH_2)_rC(O)R^2$, $NR^2C(O)R^{2a}$, $NR^2C(O)NR^2R^{2a}$, $CH(=NH)NH_2$, $NHC(=NH)NH_2$, $SO_2NR^2R^{2a}$, $NR^2SO_2NR^2R^{2a}$, and $NR^2SO_2C_{1-4}$ alkyl;

$R^7$ is selected from H, OH, $C_{1-6}$ alkyl, $C_{1-6}$ alkylcarbonyl, $C_{1-6}$ alkoxy, $C_{1-4}$ alkoxycarbonyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$ is selected from H, $C_{1-6}$ alkyl and $(CH_2)_n$-phenyl;

$R^9$ is selected from H, $C_{1-6}$ alkyl and $(CH_2)_n$-phenyl;

n is selected from 0, 1, 2, and 3;

m is selected from 0, 1, and 2;

p is selected from 0, 1, and 2; and, r is selected from 0, 1, and 2;

provided that if B is tetrazolyl, $R^4$ is present.

[2] In a preferred embodiment, the present invention provides novel compounds of formula Ia:

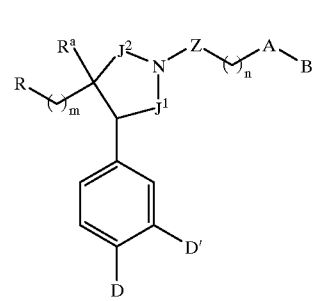

Ia or a stereoisomer or pharmaceutically acceptable salt form thereof, wherein;

Z is selected from $CH_2$, C=O, C(O)O, and $SO_2$.

[3] In a more preferred embodiment, the present invention provides compounds of formula Ia wherein;

one of D and D' is $C(=NR^7)NH_2$ and the other is H;

B is selected from:
X-Y, $NR^2R^{2a}$,
benzyl substituted with 0–2 $R^{4a}$,
$C_{3-10}$ carbocyclic residue substituted with 0–2 $R^{4a}$, and
5–10 membered heterocyclic system containing from 1–4 heteroatoms selected from the group consisting of N, O, and S substituted with 0–2 $R^4$, provided that B is other than tetrazol-5-yl;

X is selected from $C_{1-4}$ alkylene, —C(O)—, —C(O)$CR^2R^{2a}$—, —$CR^2R^{2a}$C(O), —S(O)$_p$—, —S(O)$_p$ $CR^2R^{2a}$—, —$CR^2R^{2a}$S(O)$_p$—, —S(O)$_2$NR$^2$—, —NR$^2$S(O)$_2$—, —C(O)NR$^2$—, —NR$^2$C(O)—, —NR$^2$—, —NR$^2$CR$^2$R$^{2a}$—, —CR$^2$R$^{2a}$NR$^2$—, O, —CR$^2$R$^{2a}$O—, and —OCR$^2$R$^{2a}$—;

$R^4$ is selected from OH, $(CH_2)_rOR^2$, halo, $C_{1-4}$ alkyl, CN, $NO_2$, $(CH_2)_rNR^2R^{2a}$, $(CH_2)_rC(O)R^2$, $NR^2C(O)R^{2a}$, $NR^2C(O)NR^2R^{2a}$, $CH(=NH)NH_2$, $NHC(=NH)NH_2$, $SO_2NR^2R^{2a}$, $NR^2SO_2NR^2R^{2a}$, $NR^2SO_2$—$C_{1-4}$ alkyl, $S(O)_pR^{1a}$, and $CF_3$;

$R^{4a}$ is selected from OH, halo, $C_{1-4}$ alkyl, $NO_2$, $(CH_2)_r$ $NR^2R^{2a}$, $(CH_2)_rC(O)R^2$, $NR^2C(O)R^{2a}$, $NR^2C(O)$ $NR^2R^{2a}$, $CH(=NH)NH_2$, $NHC(=NH)NH_2$, $SO_2NR^2R^{2a}$, $NR^2SO_2NR^2R^{2a}$, $NR^2SO_2$—$C_{1-4}$ alkyl, $S(O)_pR^{1a}$, and $CF_3$; and, n is selected from 0 and 1.

[4] In an even more preferred embodiment, the present invention provides compounds of formula II:

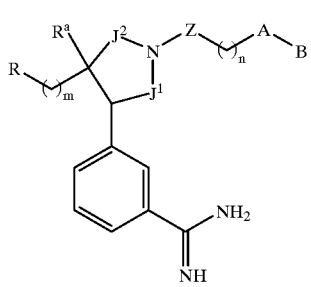

II or a stereoisomer or pharmaceutically acceptable salt form thereof, wherein;

R is selected from $CO_2R^1$, $COR^1$, $OR^1$, $CONR^2R^{2a}$, $S(O)_pR^{1a}$, and $S(O)_pNR^2R^{2a}$;

$R^1$ and $R^{1a}$ are independently selected from:
$C_{1-4}$ alkyl substituted with 0–1 $R^3$,
$C_{3-6}$ carbocyclic residue substituted with 0–2 $R^4$, and
5–6 membered heterocyclic system containing from 1–4 heteroatoms selected from the group consisting of N, O, and S substituted with 0–2 $R^4$;

X is selected from $C_{1-4}$ alkylene, —C(O)—, —S(O)$_p$—, —NR$^2$—, and O; and, m is selected from 0 and 1.

[5] In a further preferred embodiment, the present invention provides compounds of formula II wherein;

R is selected from $CO_2R^1$, $COR^1$, $OR^1$, and $CONR^2R^{2a}$;

$R^1$ and $R^{1a}$ are independently selected from:
$C_{1-4}$ alkyl substituted with 0–1 $R^3$, and
$C_{3-6}$ carbocyclic residue substituted with 0–2 $R^4$; and, $R^2$ and $R^{2a}$ may be taken together to form a 5 or 6 membered ring substituted with 0–2 $R^4$.

[6] In a still further preferred embodiment, the present invention provides compounds of formula II wherein;

$R^a$ is selected from H and $C_{1-4}$ alkyl;

$R^1$ and $R^{1a}$ are independently selected from $C_{1-4}$ alkyl substituted with 0–1 $R^3$;

$R^3$ is phenyl substituted with 0–2 $R^4$; and,

Y is a $C_{3-10}$ carbocyclic residue substituted with 0–2 $R^4$.

[7] Specifically preferred compounds of this invention are compounds, or pharmaceutically acceptable salt forms thereof, selected from the group consisting of:

trans-1-(4-amidinophenyl)methyl-3-carbomethoxy-4-(3-amidinophenyl)pyrrolidine;

trans-1-[(2'-aminosulfonyl-[1,1']-biphenyl-4-yl)methyl]-3-carbomethoxy-4-(3-amidinophenyl)pyrrolidine;

(3S,4R)-1-[(2'-aminosulfonyl-[1,1']-biphenyl-4-yl) methyl]-3-carbomethoxy-4-(3-amidinophenyl) pyrrolidine;

(3R,4S)-1-[(2'-aminosulfonyl-[1,1']-biphenyl-4-yl) methyl]-3-carbomethoxy-4-(3-amidinophenyl) pyrrolidine;

trans-1-[(2'-aminosulfonyl-[1,1']-biphenyl-4-yl)methyl]-4-(3-amidinophenyl)pyrrolidin-3-ylcarboxylic acid trans-1-[(2'-aminosulfonyl-[1,1']-biphenyl-4-yl)methyl]-4-(3-amidinophenyl)pyrrolidin-3-ylcarboxylic amide trans-1-[(2'-aminosulfonyl-[1,1']-biphenyl-4-yl)methyl]-4-(3-amidinophenyl)pyrrolidin-3-ylcarboxylic N,N-dimethylamide cis-1-[(2'-aminosulfonyl-[1,1']-biphenyl-4-yl)methyl]-3-carbomethoxy-4-(3-amidinophenyl)pyrrolidine;

cis-1-[(2'-aminosulfonyl-[1,1']-biphenyl-4-yl)methyl]-4-(3-amidinophenyl)pyrrolidin-3-ylcarboxylic acid trans-1-[(2'-aminosulfonyl-[1,1']-biphenyl-4-yl)methyl]-3-carboisopropoxy-4-(3-amidinophenyl)pyrrolidine;

trans-1-[(2'-aminosulfonyl-[1,1']-biphenyl-4-yl)methyl]-3-carbobutoxy-4-(3-amidinophenyl)pyrrolidine;

trans-1-[(2'-aminosulfonyl-[1,1']-biphenyl-4-yl)methyl]-3-acetyl-4-(3-amidinophenyl)pyrrolidine;

trans-1-[(2'-aminosulfonyl-[1,1']-biphenyl-4-yl)methyl]-3-carboethoxy-3-methyl-4-(3-amidinophenyl) pyrrolidine;

trans-1-[[2-(2-cyanophenylthio)phenyl]carbonyl]-3-carbomethoxy-4-(3-amidinophenyl)pyrrolidine;

trans-1-[[2-(2-cyanophenylthio)phenyl]methyl]-3-carbomethoxy-4-(3-amidinophenyl)pyrrolidine;

trans-1-[(2'-aminosulfonyl-[1,1']-biphenyl-4-yl) sulfonyl]-3-carbomethoxy-4-(3-amidinophenyl) pyrrolidine;

trans-1-[(2'-aminosulfonyl-[1,1']-biphenyl-4-yl) sulfonyl]-3-carboisopropoxy-4-(3-amidinophenyl) pyrrolidine;

trans-1-[9-fluorenylmethoxycarbonyl]-3-carbomethoxy-4-(3-amidinophenyl)pyrrolidine;

trans-2-benzyl-4-carbomethoxy-5-(3-amidinophenyl) isoxazolidine;

trans-2-[(2'-aminosulfonyl-[1,1']-biphenyl-4-yl)methyl]-4-carbomethoxy-5-(3-amidinophenyl)isoxazolidine;

trans-2-[(2'-aminosulfonyl-[1,1']-biphenyl-4-yl)methyl]-4-carboisopropoxy-5-(3-amidinophenyl)isoxazolidine; and, trans-2-[(2'-aminosulfonyl-[1,1']-biphenyl-4-yl)methyl]-4-methoxymethyl-5-(3-amidinophenyl)isoxazolidine.

[8] In another preferred embodiment, the present invention provides novel compounds of formula Ib:

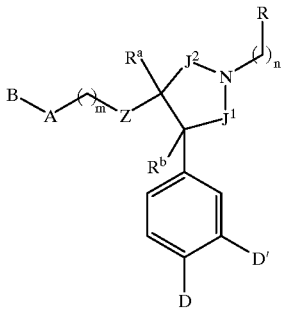

Ib or a stereoisomer or pharmaceutically acceptable salt form thereof, wherein;

[9] In another more preferred embodiment, the present invention provides compounds of formula Ib wherein;

one of D and D' is $C(=NR^7)NH_2$ and the other is H;

B is selected from:
X-Y, $NR^2R^{2a}$,
benzyl substituted with 0–2 $R^{4a}$,
$C_{3-10}$ carbocyclic residue substituted with 0–2 $R^{4a}$, and
5–10 membered heterocyclic system containing from 1–4 heteroatoms selected from the group consisting of N, O, and S substituted with 0–2 $R^4$, provided that B is other than tetrazol-5-yl;

X is selected from $C_{1-4}$ alkylene, —C(O)—, —C(O)$CR^2R^{2a}$—, —$CR^2R^{2a}C(O)$, —$S(O)_p$—, —$S(O)_p$$CR^2R^{2a}$—, —$CR^2R^{2a}S(O)_p$—, —$S(O)_2NR^2$—, —$NR^2S(O)_2$—, —$C(O)NR^2$—, —$NR^2C(O)$—, —$NR^2$—, —$NR^2CR^2R^{2a}$—, —$CR^2R^{2a}NR^2$—, O, —$CR^2R^{2a}O$—, and —$OCR^2R^{2a}$—;

$R^4$ is selected from OH, $(CH_2)_rOR^2$, halo, $C_{1-4}$ alkyl, CN, $NO_2$, $(CH_2)_rNR^2R^{2a}$, $(CH_2)_rC(O)R^2$, $NR^2C(O)R^{2a}$, $NR^2C(O)NR^2R^{2a}$, $CH(=NH)NH_2$, $NHC(=NH)NH_2$, $SO_2NR^2R^{2a}$, $NR^2SO_2NR^2R^{2a}$, $NR^2SO_2$—$C_{1-4}$ alkyl, $S(O)_pR^{1a}$, and $CF_3$;

$R^{4a}$ is selected from OH, halo, $C_{1-4}$ alkyl, $NO_2$, $(CH_2)_rNR^2R^{2a}$, $(CH_2)_rC(O)R^2$, $NR^2C(O)R^{2a}$, $NR^2C(O)NR^2R^{2a}$, $CH(=NH)NH_2$, $NHC(=NH)NH_2$, $SO_2NR^2R^{2a}$, $NR^2SO_2NR^2R^{2a}$, $NR^2SO_2$—$C_{1-4}$ alkyl, $S(O)_pR^{1a}$, and $CF_3$; and, n is selected from 0 and 1.

[10] In another even more preferred embodiment, the present invention provides compounds of formula IIa:

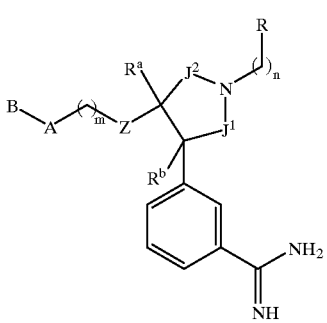

IIa or a stereoisomer or pharmaceutically acceptable salt form thereof, wherein;

R is selected from $CO_2R^1$, $COR^1$, $OR^1$, $CONR^2R^{2a}$, $S(O)_pR^{1a}$, and $S(O)_pNR^2R^{2a}$;

$R^1$ and $R^{1a}$ are independently selected from:
$C_{1-4}$ alkyl substituted with 0–1 $R^3$,
$C_{3-6}$ carbocyclic residue substituted with 0–2 $R^4$, and
5–6 membered heterocyclic system containing from 1–4 heteroatoms selected from the group consisting of N, O, and S substituted with 0–2 $R^4$;

X is selected from $C_{1-4}$ alkylene, —C(O)—, —$S(O)_p$—, —$NR^2$—, and O; and, m is selected from 0 and 1.

[11] In another further preferred embodiment, the present invention provides compounds of formula IIa wherein;

R is selected from $CO_2R^1$, $COR^1$, $OR^1$, and $CONR^2R^{2a}$;

$R^1$ and $R^{1a}$ are independently selected from:
$C_{1-4}$ alkyl substituted with 0–1 $R^3$, and
$C_{3-6}$ carbocyclic residue substituted with 0–2 $R^4$; and, $R^2$ and $R^{2a}$ may be taken together to form a 5 or 6 membered ring substituted with 0–2 $R^4$.

[12] In another still further preferred embodiment, the present invention provides compounds of formula IIa wherein;

$R^1$ and $R^{1a}$ are independently selected from $C_{1-4}$ alkyl substituted with 0–1 $R^3$;

$R^3$ is phenyl substituted with 0–2 $R^4$; and,

Y is a $C_{3-10}$ carbocyclic residue substituted with 0–2 $R^4$.

[13] Additional specifically preferred compounds of the present invention are compounds, or pharmaceutically acceptable salt forms thereof, selected from the group consisting of:

trans-1-(methylsulfonyl)-3-([2'-aminosulfonyl-[1,1']-biphenyl-4-yl)aminocarbonyl)-4-(3-amidinophenyl) pyrrolidine;

trans-1-(methylsulfonyl)-3-([2'-tert-butylaminosulfonyl-[1,1']-biphenyl-4-yl)aminocarbonyl)-4-(3-amidinophenyl)pyrrolidine;

cis-1-(methylsulfonyl)-3-([2'-aminosulfonyl-[1,1']-biphenyl-4-yl)aminocarbonyl)-4-(3-amidinophenyl) pyrrolidine;

trans-1-(methylsulfonyl)-3-[[5-(2'-aminosulfonylphenyl-1-yl)pyridin-2-yl]aminocarbonyl]-4-(3-amidinophenyl)pyrrolidine;

trans-1-(methylsulfonyl)-3-[[5-(2'-tert-butylaminosulfonylphenyl-1-yl)pyridin-2-yl]aminocarbonyl]-4-(3-amidinophenyl)pyrrolidine;

1-(methylsulfonyl)-3-([2'-aminosulfonyl-[1,1']-biphenyl-4-yl)aminocarbonyl)-4-(3-amidinophenyl)-$\Delta^3$-pyrroline;

1-(benzyl)-3-([2'-aminosulfonyl-[1,1']-biphenyl-4-yl) aminocarbonyl)-4-(3-amidinophenyl)-$\Delta^3$-pyrroline;

trans-1-(methylsulfonyl)-3-([2'-aminosulfonyl-[1,1']-biphenyl-4-yl)methylcarbonyl)-4-(3-amidinophenyl) pyrrolidine.

In a second embodiment, the present invention provides novel pharmaceutical compositions, comprising: a pharmaceutically acceptable carrier and a therapeutically effective amount of a compound of formula (I) or a pharmaceutically acceptable salt or prodrug form thereof.

In a third embodiment, the present invention provides a novel method for treating or preventing a thromboembolic disorder, comprising: administering to a patient in need thereof a therapeutically effective amount of a compound of formula (I) or a pharmaceutically acceptable salt or prodrug form thereof.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-6}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl; "Alkenyl" is intended to include hydrocarbon chains of either a straight or branched configuration and one or more unsaturated carbon—carbon bonds which may occur in any stable point along the chain, such as ethenyl, propenyl, and the like.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of N, O and S. It is preferred that the total number of S and O atoms in the aromatic heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thenoimidazolyl, thiophenyl, triazinyl, 1,2, 3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like. Preferred prodrugs are amidine prodrugs wherein D is $C(=NR^7)NH_2$, and $R^7$ is selected from OH, $C_{1-4}$ alkoxy, $C_{6-10}$ aryloxy, $C_{1-4}$ alkoxycarbonyl, $C_{6-10}$ aryloxycarbonyl, $C_{6-10}$ arylmethylcarbonyl, $C_{1-4}$ alkylcarbonyloxy $C_{1-4}$ alkoxycarbonyl, and $C_{6-10}$ arylcarbonyloxy $C_{1-4}$ alkoxycarbonyl. More preferred prodrugs are where $R^7$ is OH, methoxy, ethoxy, benzyloxycarbonyl, methoxycarbonyl, and methylcarbonyloxymethoxycarbonyl.

"Stable compound" and "stable structure" are meant to indicate a compound that is sufficiently robust to survive isolation to a useful degree of purity from a reaction mixture, and formulation into an efficacious therapeutic agent.

SYNTHESIS

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley and Sons, 1991). All references cited herein are hereby incorporated in their entirety herein by reference.

The compounds of the present invention represented by Formula I are 1,3,4-trisubstituted and 1,3,3,4-tetrasubstituted pyrrolidines, 1,3,4-trisubstituted $\Delta^3$-pyrrolines, and 2,4,5-trisubstituted, 2,4,4,5-tetrasubstituted and 2,4,5,5-tetrasubstituted isoxazolidines. A convenient method for the preparation of these heterocycles utilizes a 1,3-dipolar cycloaddition of an appropriate 1,3-dipole with an appropriate dipolarophile. To prepare the pyrrolidine nucleus, the appropriate 1,3-dipole is an azomethine ylide. To prepare the isoxazolidine nucleus the appropriate 1,3-dipole is a nitrone (for reviews of 1,3-dipolar cycloaddition chemistry of azomethine ylides and nitrones, see 1,3-*Dipolar Cycloaddition Chemistry* (A. Padwa, Ed.), Wiley-Interscience, New York, 1984; Tsuge and Kanemasa, in *Advances in Heterocyclic Chemistry* (A. Katritzky, Ed.), 1989, 45, p. 232; Torssell, in *Nitrile Oxides, Nitrones and Nitronates in Organic Synthesis*, VCh Publishers, Inc., New York, 1988; Breuer, Aurich and Nielsen, in *Nitrones, Nitronates, and Nitroxides*, Wiley, New York, 1989).

Although there are several methods known in the literature for generating stabilized azomethine ylides, fewer methods are available for generating the non-stabilized azomethine ylides required for the preparation of the pyrrolidine-containing compounds of the present invention. However, the decomposition of an appropriately substituted tertiary amine was found to be a suitable method for the purposes of the present invention. A general scheme for the generation and reaction of non-stabilized azomethine ylides using this method is shown in Scheme 1. The azomethine ylide precursors 1a and 1b are either commercially available or are readily prepared by methods known to those skilled in the art. Shown at the bottom of Scheme 1 are some preferred methods beginning with the readily available secondary amines 4 (Hosomi et al *Chem. Letters* 1984, 1117; Padwa et al. *J. Org. Chem.* 1985, 50, 4006). Treatment of 4 with aqueous formaldehyde in the presence of either methanol or potassium cyanide at near neutral pH generates the tertiary amines 1a and 1b, respectively. Alternatively, the anion of 4 can be generated with a suitable base, such as n-butyllithium or sodium hydride, and alkylated with chloromethyl methyl ether to generate 1a. The substituent R' can be benzyl, substituted benzyl, aikyl, cycloalkyl, etc., but preferably is benzyl.

Scheme 1

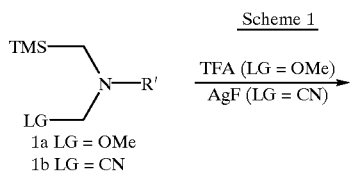
1a LG = OMe
1b LG = CN

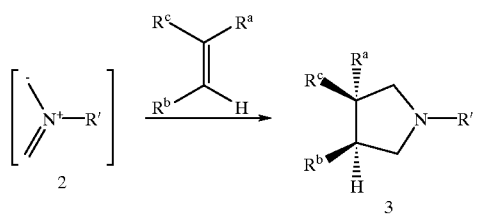

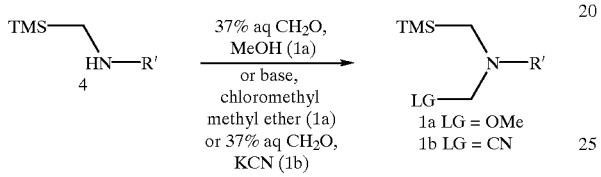
1a LG = OMe
1b LG = CN

The generation of the azomethine ylide 2 from 1a and 1b is straightforward. Treatment of 1a with a number of acidic catalysts, such as trifluoroacetic acid, acetic acid, titanium tetrachloride or trifluoromethanesulfonic acid, causes its rapid decomposition to the azomethine ylide 2 (Terao et al *Chem. Pharm. Bull.* 1985, 33, 2762). The preferred catalyst is 5–25% trifluoroacetic acid in dichloromethane solvent. Treatment of 1b with silver fluoride in the dark also generates 2 (Padwa et al. *J. Org. Chem.* 1985, 50, 4006). This method relies on the silylophilic nature of fluoride ion and is generally carried out in acetonitrile solvent. Once generated, the non-stabilized azomethine ylide 2 reacts with olefins to produce pyrrolidines 3 by 1,3-dipolar cycloaddition. Generally the olefin needs to be activated by a suitable electron withdrawing group, such as carboxylic ester, carboxylic amide, ketone, nitrile, sulfone, nitro, etc. Styrenes which are substituted with electron withdrawing groups, such as carboxylic ester, carboxylic amide, ketone, nitrile, sulfone, nitro, etc., also are able to undergo reaction with 2 to produce aryl-substituted pyrrolidines. The 1,3-dipolar cycloaddition is stereospecific in that the stereochemistry of the olefin is retained and translated into the relative stereochemistry of the pyrrolidine product. Thus, trans-disubstituted olefins undergo cyclization to produce pyrrolidines 3 with a trans configuration of the 3,4-substituents on the pyrrolidine ring.

In Scheme 2 is shown how the just described 1,3-dipolar cycloaddition can be applied to the synthesis of the 1,3,4-trisubstituted and 1,3,3,4-tetrasubstituted pyrrolidine nucleus contained in the compounds of the present invention. The required di- or trisubstituted olefins 6 are readily available from cyanobenzaldehydes 5 by reaction with stabilized Wittig reagents or with the sodium or potassium anions of phosponate reagents. The stabilized Wittig reagents react with 5 to give E-disubstituted olefins 6 ($R^c$=hydrogen, $R^a$=carbomethoxy, acetyl). The phosphonate anions also give E-di- or trisubstituted olefins 6 when $R^c$ of the phosphonate is hydrogen or methyl, $R^a$ is carbomethoxy or carboethoxy and $R^d$ is methyl or ethyl. Modification of the phosphonate also allows for the preparation of the Z-disubstituted olefins 6. Thus, treatment of bis(2,2,2-trifluoroethyl)(methoxycarbonylmethyl)phosphonate ($R^d$=—$CH_2CF_3$) with potassium bis(trimethylsilyl)amide and 18-crown-6 generates a potassium anion of the phosphonate that reacts with 5 to give selectively the Z-disubstituted 6 where $R^c$ is carbomethoxy and $R^a$ is hydrogen.

Scheme 2

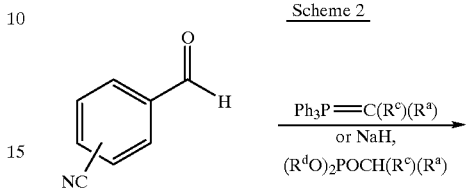

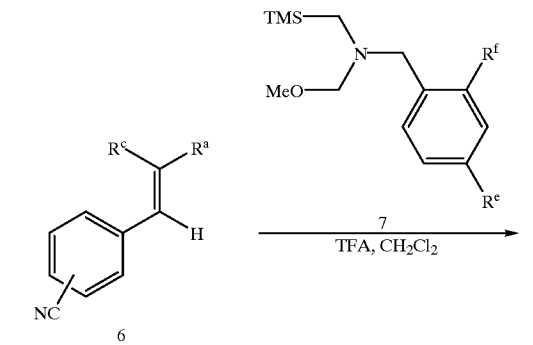

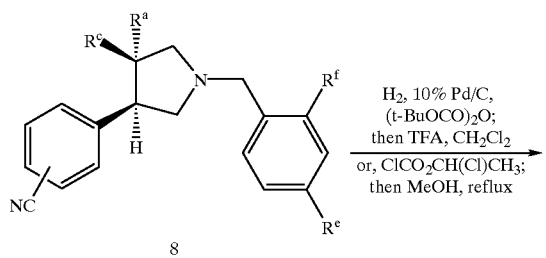

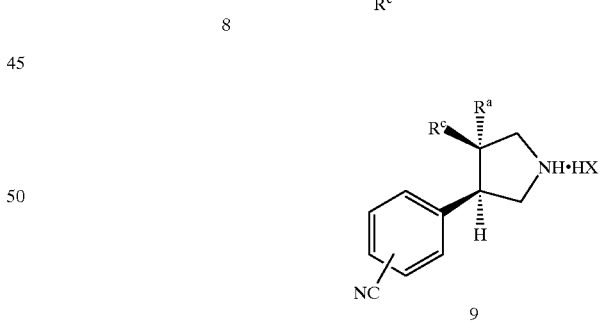

The 1,3-dipolar cycloaddition of olefins 6 with N-benzyl derivatives of 7 under TFA catalysis smoothly affords the pyrrolidines 8. The relative stereochemistry about the pyrrolidine ring is determined by the geometry of the olefin 6 as described in connection with Scheme 1. Deprotection of the N-benzyl group ($R^e$, $R^f$=hydrogen) can be accomplished in several ways. Two preferred methods are catalytic hydrogenation in the presence of di-tert-butyl dicarbonate followed by trifluoroacetic acid deprotection of the N-tert-butyl carbamate intermediate. This procedure affords 9 as the trifluoroacetic acid salt. Another method involves refluxing 8 in the presence of αchloroethyl chloroformate in a solvent such as 1,2-dichloroethane followed by refluxing in methanol to deprotect the αchloroethyl carbamate intermediate (Olofson et al *J. Org. Chem.* 1984, 49, 2081). This methods affords 9 as the hydrochloride salt.

In Scheme 3 is shown how to prepare compounds of Formula I in which J is CO, $SO_2$ or $CO_2$ attached to the pyrrolidine nucleus. Where J in Formula I is CO, the compounds can be prepared by two preferred methods. The first is the reaction of the pyrrolidine 9 with an acid chloride in the presence of a suitable base such as triethylamine. In cases where the required acid chloride is not commercially available, it can be prepared from the corresponding carboxylic acid by treatment with thionyl chloride or other methods known to those skilled in the art. Alternatively, the pyrrolidine 9 can be coupled to a carboxylic acid using any of a number of peptide coupling methods (mixed anhydride, HBTU, DCC, etc.) well known to those skilled in the art of organic synthesis. The product of these methods is the amide 10. To prepare the carbamate compounds 11, where J in Formula I is $CO_2$, the pyrrolidine 9 can be coupled to the appropriate chloroformate or succinimidyl carbonate in the presence of an appropriate base such as triethylamine. The compounds of Formula I where J is $SO_2$ can be prepared from pyrrolidine 9 by treatment with the appropriate sulfonyl chloride to afford the sulfonamides 12. In cases where the sulfonyl chloride is not commercially available, it can be prepared from the corresponding sulfonic acid 13 using phosphorous pentachloride or thionyl chloride. Where the sulfonic acid 13 is not commercially available, it can be prepared from the corresponding bromide 14 by displacement with sodium sulfite.

To prepare compounds where J in Formula I is $CH_2$, a simple alkylation of the pyrrolidine 9 with the appropriate primary alkyl bromide or chloride in the presence of a base such as triethylamine can provide the required compounds.

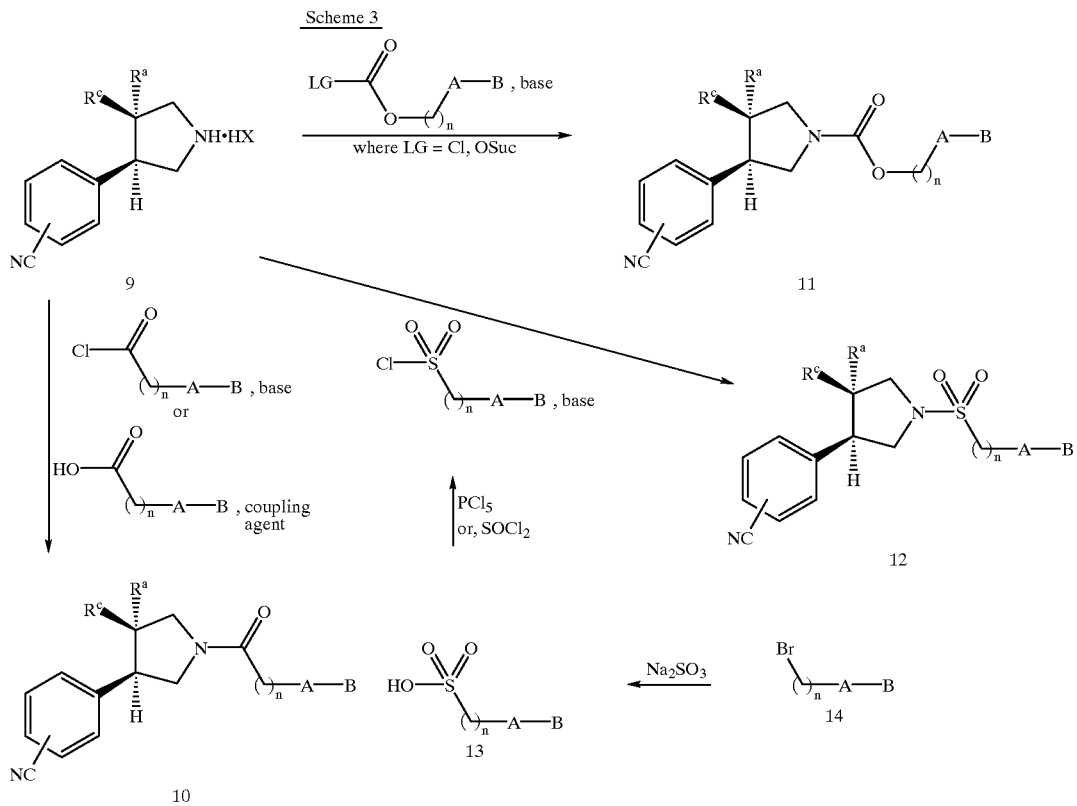

To prepare pyrrolidine-containing compounds of Formula I where A-B is a biphenyl residue, the chemistry described in Scheme 4 can be used. For compounds where —$J(CH_2)_n$— is $CH_2$ the preferred method involves preparing the bromo-containing reagent 15 through alkylation of trimethylsilylmethylamine followed by reaction of the resulting secondary amine with aqueous formaldehyde in methanol as described previously. Other methods known to those skilled in the art can be envisioned to prepare this compound. The 1,3-dipolar cycloaddition described earlier with olefin 6 affords the pyrrolidine 16. The biphenyl residue can be constructed using the palladium-catalyzed Suzuki coupling of 16 with an appropriate arylboronic acid (Miyaura et al *Syn. Comm.* 1981, 11, 513). The product from the Suzuki coupling is the biphenyl compound 17. The arylboronic acid can be prepared from the corresponding arylbromide by transmetallation to the aryllithium reagent with n-butyllithium or t-butyllithium followed by reaction with trimethylborate and hydrolysis to the boronic acid.

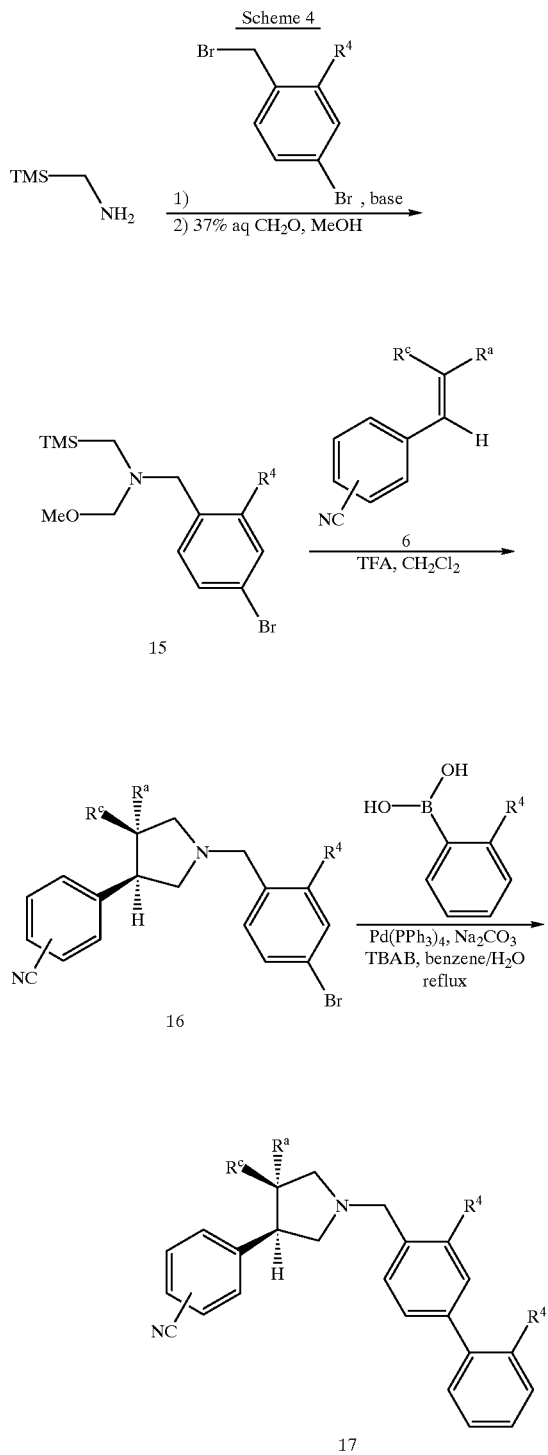

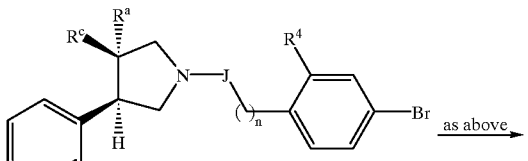

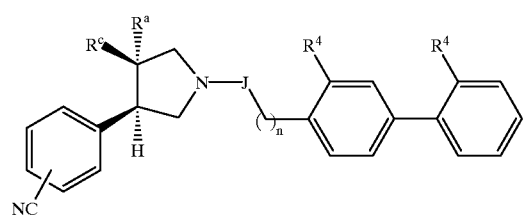

Compounds containing different J—(CH$_2$)$_n$— groups such as 18, which are available following the procedures described in Scheme 3, can be transformed in an analogous fashion into the corresponding biphenyl-containing pyrrolidine compounds 19.

Scheme 5 describes methods used to elaborate the R—(CH$_2$)$_m$— group of Formula I in the pyrrolidine series of compounds. Compound 20 (m=0) is obtainable by the procedures described in earlier schemes. Compound 20 (m=1) is a one carbon homolog which can be prepared from the appropriate 20 (m=0) analog by homologation procedures known to those skilled in the art of organic chemistry. To prepare carboxylic amide analogs, the ester 20 is first hydrolyzed to the carboxylic acid and then is converted to the desired amide 21 by any of a variety of procedures known to those skilled in the art, such as the mixed anhydride method, DCC-mediated coupling, etc. Alcohol derivatives are available by reduction of the carboxylic acid derived from 20 by either borane tetrahydrofuran complex or by a procedure involving sodium borohydride reduction of the mixed anhydride of the carboxylic acid. The ether derivatives 23 are readily available by etherification of the alcohol 22 with an alkyl halide and a suitable base such as sodium hydride. The alcohol 22 can also be transformed into the thioether derivatives by first converting the alcohol into a good leaving group, for example by converting it into its mesylate or tosylate with the appropriate sulfonyl chloride and a base such as pyridine or triethylamine. Displacement of the leaving group with a thiol in the presence of a base will then yield the thioether derivatives 24. Oxidation of 24 by any of a variety of well know oxidizing agents can then afford the corresponding sulfone derivatives 25.

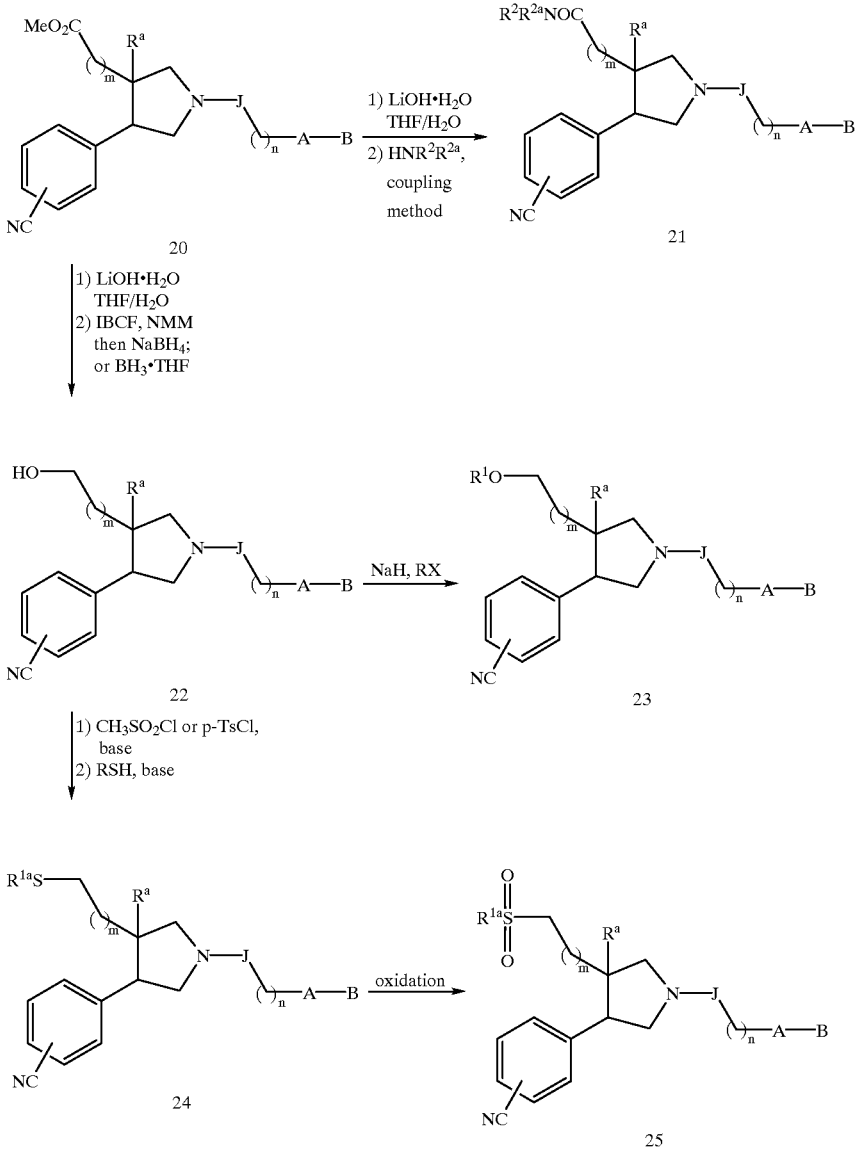

Scheme 5

All of the pyrrolidine derivatives described in Schemes 2–5 contain an aromatic cyano group which must be converted to its amidine derivative to prepare the final compounds described by Formula I. Generally, in the course of preparing the compounds of this present invention, this conversion has been the final step in each synthetic sequence and it is shown in Scheme 6. The preferred method was first described by Pinner and Klein (*Ber.*, 1877, 10, 1889; for a more recent review see: Decroix, *J. Chem. Res.*, 1978, 134). By this method the nitrile 26 is dissolved in an anhydrous alcohol or a mixture of at least one equivalent of an alcohol and an anhydrous aprotic cosolvent, such as chloroform or an acetate ester of the selected alcohol (i.e., methyl acetate for methyl alcohol). Typically, this mixture is cooled to below ambient temperature and dry hydrogen chloride gas is added via a gas dispersion tube until the solvent is saturated with HCl. The mixture is then sealed and stirred at ambient temperature or below to form an intermediate imidate. The imidate is isolated and dissolved in an anhydrous alcohol solvent and treated with ammonia, ammonium carbonate, ammonium acetate or alcoholic ammonia solution to afford the desired amidine 27. These compounds are conveniently purified by preparative reverse phase HPLC or by recrystallization to give the pyrrolidine compounds defined by Formula I.

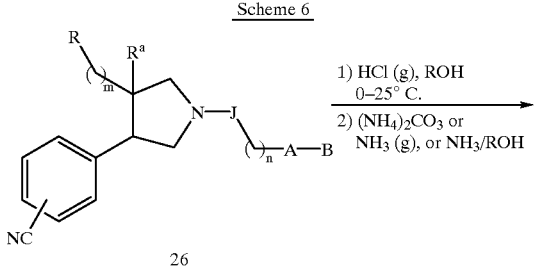

Scheme 6

-continued

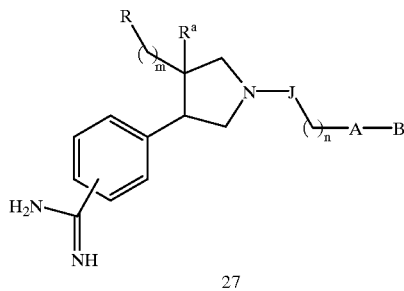

27

In cases where A or B in compound 26 is substituted with a tert-butylsulfonamide group, the tert-butyl protecting group can be removed by refluxing in trifluoroacetic acid prior to subjecting these compounds to the Pinner sequence.

Although the Pinner sequence to produce the amidines 27 is generally the final step in the preparation of the pyrrolidine compounds of Formula I, some transformations can be carried out on the amidine derivatives themselves, as shown in Scheme 7. To prepare the carboxylic acid derivatives of the present invention, the methyl ester 28 can be treated with an excess of lithium hydroxide in aqueous tetrahydrofuran to afford the acid 29. To prepare esters other than methyl esters, the methyl ester 28 can be treated at reflux with an excess of another alcohol, such as isopropanol or n-butanol, in the presence of a catalytic amount of a titanium (IV) tetraalkoxide, such as titanium (IV) tetraisopropoxide. This reaction produces the alternate ester 30. Due to the large excess of alcohol used, the titanium reagent does not have to match the alcohol, thus reaction of 28 with excess n-butanol in the presence of catalytic titanium (IV) tetraisopropoxide produces the n-butyl ester derivative of 30.

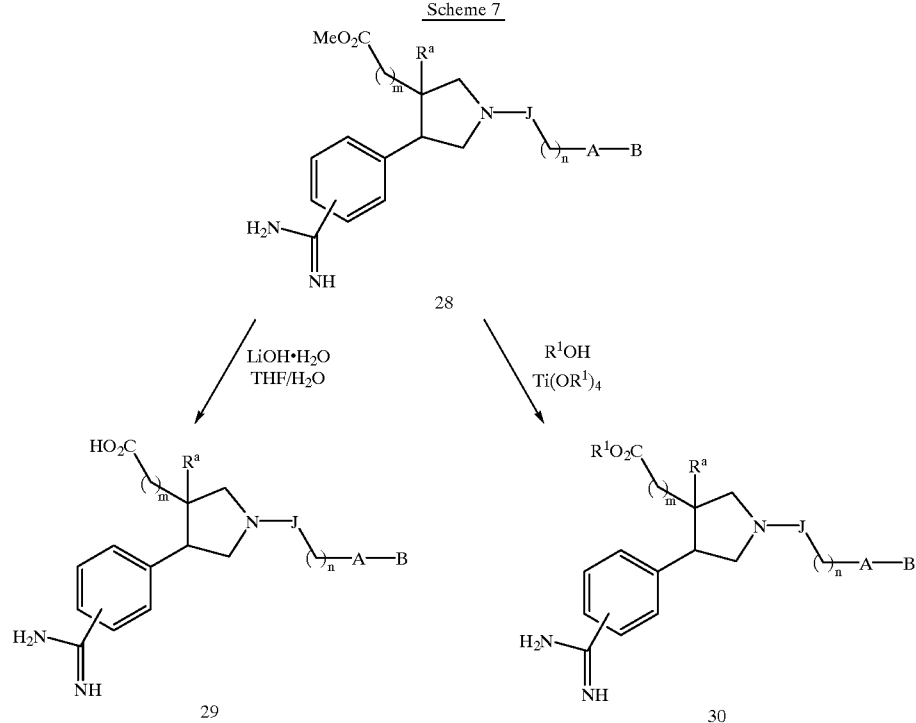

The syntheses of the pyrrolidine compounds described in the preceeding schemes were all described for racemic compounds, despite the presence of one or more chiral centers in all of the compounds presented. It is also possible to prepare many of the pyrrolidine compounds contained in this invention as single enantiomers in a well-defined manner by asymmetric synthesis. Presumably many of the compounds would also be amenable to resolution methods to prepare single enantiomers. In Scheme 8 is described a method for the asymmetric synthesis of the pyrrolidine compounds of this invention. The preferred, but not the only, method for preparing single enantiomers of these compounds is by employing a 1,3-dipolar cycloaddition of an azomethine ylide with an olefin derivative which contains a chiral auxiliary to induce asymmetry. Although there are many chiral auxiliaries which would presumably be capable of inducing an enantioselective 1,3-dipolar cycloaddition, preferred auxiliaries are (1S)-(−)-2,10-camphorsultam and (1R)-(+)-2,10-camphorsultam, both of which are commercially available. A preferred, but not the only, method of introducing the camphorsultam auxiliary is by reaction of the aluminum reagent derived from the auxiliary 32 with an ester 31 to give the amide 33. The reaction of 33 with the azomethine ylide precursor described earlier in the presence of trifluoroacetic acid results in a 1,3-dipolar cycloaddition to give a mixture of diastereomeric pyrrolidines 34 and 35 (Fevig, *Bioorg. Med. Chem. Lett.* 1996, 6, 295). The diastereomers can be separated by flash chromatography and separately elaborated to enantiomerically pure pyrrolidine compounds of Formula I. The removal of the camphorsultam chiral auxiliary can be accomplished by two preferred methods. The first involves treating the cycloaddition product with lithium hydroxide in aqueous tetrahydrofuran which furnishes the carboxylic acid 36, which can be transformed into the corresponding methyl ester 37 by a variety of methods known to those skilled in the art. Additionally, the cycloaddition product can be treated with methanolic magnesium methoxide to afford the corresponding methyl ester 37 directly. The enantiomerically pure methyl esters 37 can be elaborated to enantiomerically pure pyrrolidine-containing compounds of Formula I by the procedures described in Schemes 2–7.

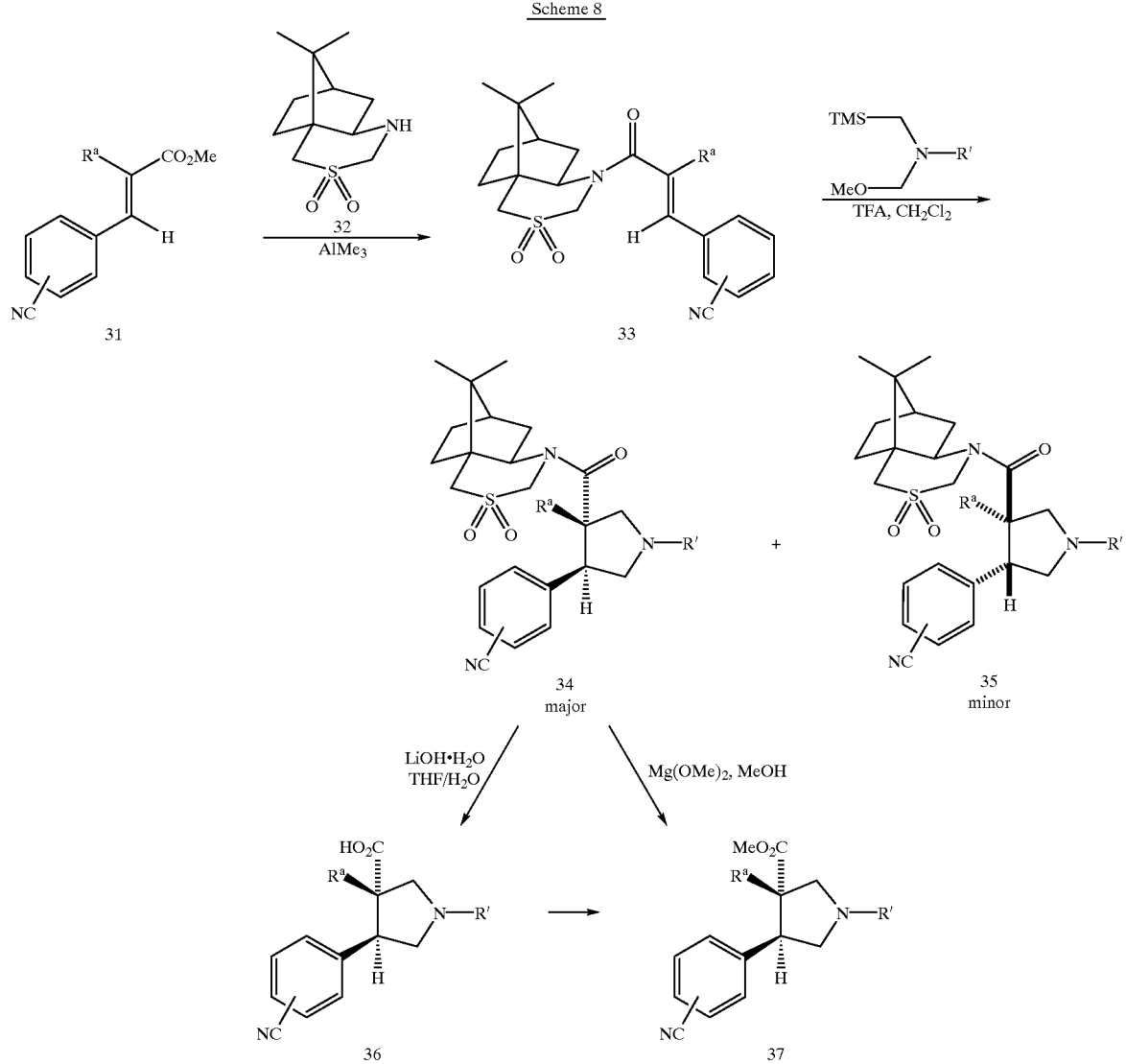

Scheme 8

The isoxazolidine-containing compounds of the present invention are preferably prepared by the 1,3-dipolar cycloaddition of an appropriate nitrone with an appropriate dipolarophile, as described earlier. Although there are several methods known in the literature for the generation of nitrone intermediates, a preferred method for generating the compounds of the present invention is shown in Scheme 9. In this method the nitrone is generated from the hydroxyl amine 38 by treatment with paraformaldehyde with concur rent removal of water (Wityak et al *J. Org. Chem.* 1987, 52, 2179). This is conveniently accomplished by refluxing the reaction mixture (to crack the paraformaldehyde polymer) in a solvent such as benzene in the presence of a drying agent such as crushed activated molecular sieves to remove water produced in the reaction. The nitrone 39 thus generated reacts with a variety of olefins to produce the regioisomeric isoxazolidines 40 and 41.

Scheme 9

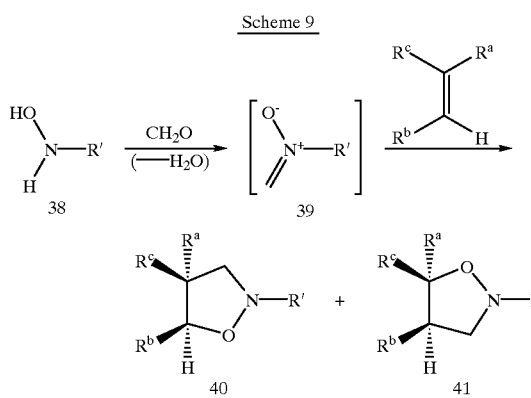

The R' group on 38 can be hydrogen, alkyl, alkylaryl, aryl, etc. The reaction is stereospecific in that the geometry of the olefin is translated into the relative stereochemistry of the cycloaddition product, as is the case for the azomethine ylide 1,3-dipolar cycloadditions discussed earlier. Thus, an E-disubstituted olefin ($R^c$=H, $R^b,R^a$=substituents) gives rise to isoxazolidines 40 and 41 having a trans relationship between $R^a$ and $R^b$. The regioselectivity of the cycloaddition is dependent on the nature and substitution pattern of the olefin. In some cases mixtures of 40 and 41 are produced while in other cases a certain olefin will result in a regioselective reaction and give rise to only 40 or 41.

Much of the chemistry described for the pyrrolidine compounds in Schemes 2–8 can also be applied to the isoxazolidine compounds. In Scheme 10 is shown how the just described nitrone 1,3-dipolar cycloaddition can be applied to the synthesis of the 2,4,5-trisubstituted, 2,4,4,5-tetrasubstituted and 2,4,5,5-tetrasubstituted isoxazolidines contained in the compounds of the present invention in which A-B of Formula I is a biphenyl residue and $J(CH_2)_n$ is $CH_2$. The preferred, but not the only, method for preparing compounds of this type is to prepare the appropriate 4-bromobenzylhydroxylamine 43 from the corresponding 4-bromobenzaldehyde 42. This is readily accomplished by standard formation of the oxime by standard methods, followed by reduction of the oxime to give 43. This reduction can be accomplished with borane-pyridine complex under acidic conditions or with sodium cyanoborohydride under acidic conditions.

Scheme 10

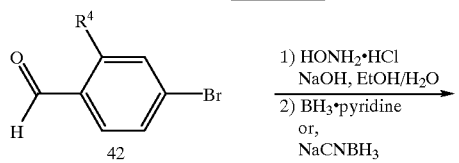

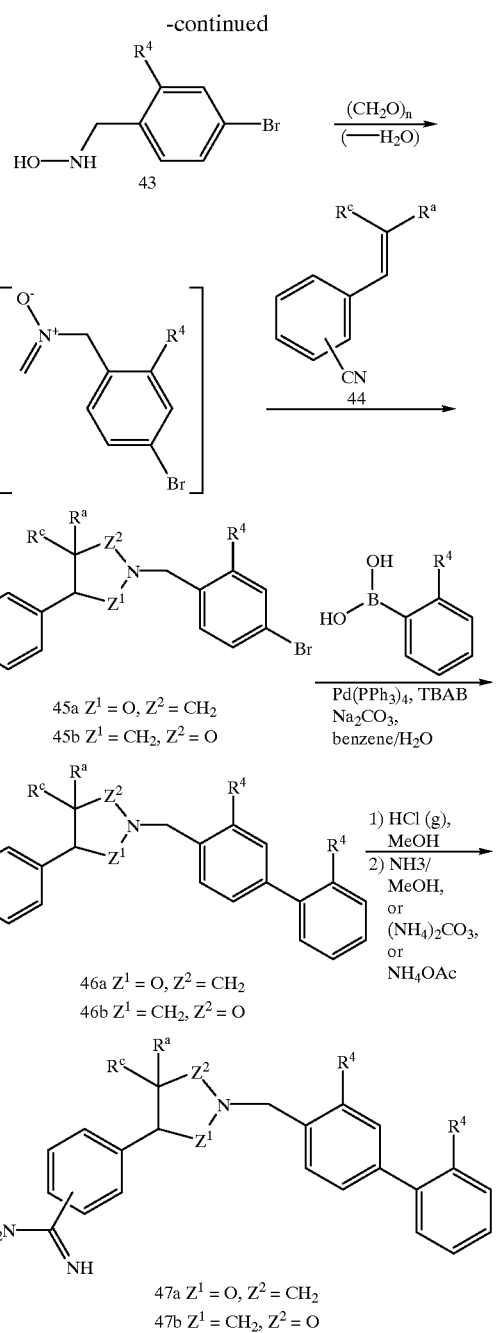

Generation of the nitrone with paraformaldehyde as described in Scheme 9 and reaction with the appropriate olefinic benzonitrile 44 leads to a regioisomeric mixture of isoxazolidines 45a and 45b. Suzuki coupling of 45a and 45b with the appropriate boronic acid, as described in Scheme 4, gives the isoxazolidines 46a and 46b. The amidine compounds 47a and 47b, corresponding to compounds described by Formula I, can be prepared by the Pinner protocol as described in Scheme 6.

To prepare isoxazolidine compounds of Formula I where $J(CH_2)_n$ is other than $CH_2$ ($J(CH_2)_n$=$(CH_2)_n$, $SO_2$ $(CH_2)_n$, $CO(CH_2)_n$, $CO_2(CH_2)_n$, etc.) the methods described in Scheme 11 can be used. Generation of the nitrone 49 can be accomplished by treatment of hydroxylamine hydrochloride 48 with paraformaldehyde as described in Scheme 9. Reaction of 49 with an olefin 6 can afford the N-unsubstituted regioisomeric isoxazolidines 50a and 50b. Treatment of 50a and 50b with compounds of type 51 can be used to prepare a variety of N-substituted isoxazolidines 52a and 52b. Compounds 51 can include alkyl halides (LG=Br, Cl; J=CH$_2$), sulfonyl chlorides (LG=Cl; J=SO$_2$), carboxylic acids (LG=OH; J=CO), carboxylic acid chlorides (LG=Cl; J=CO) and chloroformates (LG=Cl; J=CO$_2$). The reaction conditions to afford N-substituted isoxazolidines 52a and 52b can be those described in Scheme 3 for the pyrrolidine compounds or other procedures known to those skilled in the art of organic chemistry. The products 52 can be carried onto the final products described by Formula I following procedures described for the pyrrolidines in Schemes 4–8.

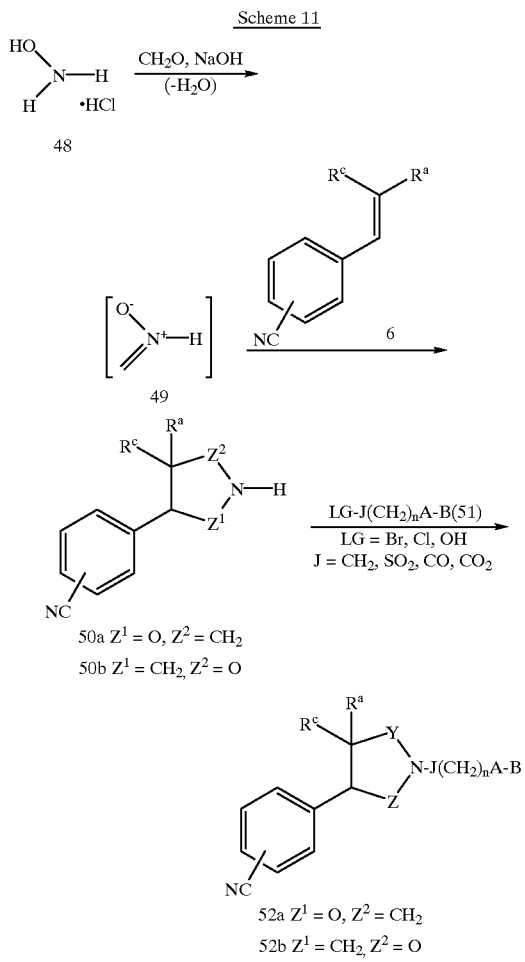

In Scheme 12 is shown how the previously described 1,3-dipolar cycloaddition can be applied to the synthesis of the 1,3,4-trisubstituted Δ$^3$-pyrroline nucleus contained in compounds of the present invention. The required dipolarophile for Δ$^3$-pyrroline synthesis is an alkyne such as 54. These compounds can best be prepared by a variety of palladium-catalyzed aryl-alkyne coupling reactions. Two such examples are shown in Scheme 12. In one case an alkynylzinc species of an appropriate substituted alkyne is generated with n-BuLi and zinc chloride. This species is then coupled to the appropriate aryl halide or aryl triflate 53 in the presence of a palladium (II) catalyst to give alkyne 54. Alternatively, the aryl halide or aryl triflate 53 can be coupled to an appropriate substituted alkyne in the presence of a palladium (0) catalyst, copper iodide and an organic amine base to give 54. Other procedures to produce 54 are available and known to those skilled in the art. Reaction of 7 with alkyne 54, in which R$^a$ is an electron-withdrawing group such as a carboxylic ester, carboxylic amide, ketone, nitrile, sulfone, nitro, etc., should produce the desired Δ$^3$-pyrroline 55. The N-benzyl group can readily be removed by the 1-chloroethyl chloroformate procedure described in Scheme 1 to afford the Δ$^3$-pyrroline nucleus 56.

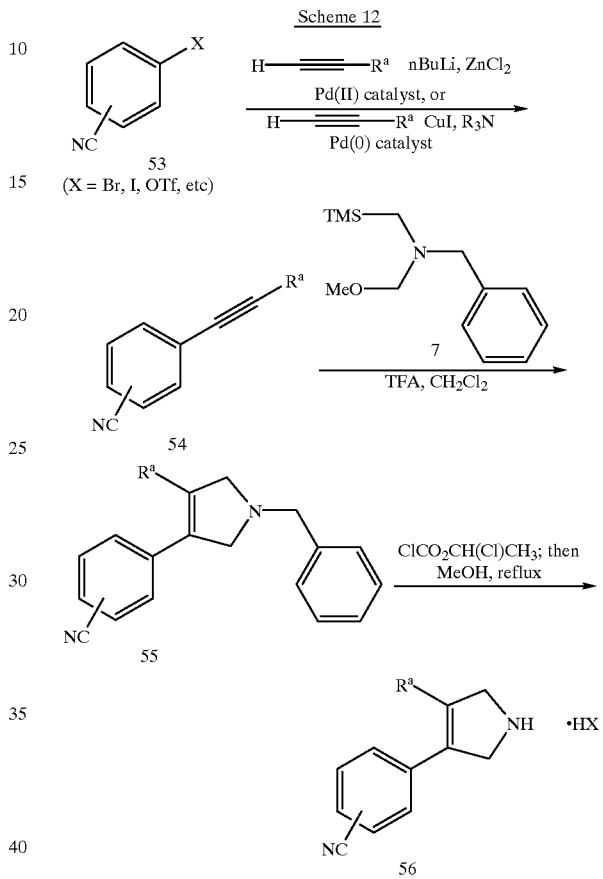

In Scheme 13 is shown how to prepare compounds of Formula I in which R is COR$^d$, CO$_2$R$^d$, SO$_2$R$^d$ or R$^d$ attached to the pyrrolidine or Δ$^3$-pyrroline nitrogen, where R$^d$ is alkyl, aryl or alkylaryl. Where R in Formula I is COR$^d$, the compounds can be prepared by two preferred methods. The first is the reaction of the pyrrolidine or Δ$^3$-pyrroline 57 with an acid chloride in the presence of a suitable base such as triethylamine. In cases where the required acid chloride is not commercially available, it can be prepared from the corresponding carboxylic acid by treatment with thionyl chloride or other methods known to those skilled in the art. Alternatively, the pyrrolidine or Δ$^3$-pyrroline 57 can be coupled to a carboxylic acid using any of a number of peptide coupling methods (mixed anhydride, HBTU, DCC, etc.) well known to those skilled in the art of organic synthesis. The product of these methods is amide 58. To prepare carbamate compounds 59, where R in Formula I is CO$_2$R$^d$, the pyrrolidine or Δ$^3$-pyrroline 57 can be coupled to the appropriate chloroformate or succinimidyl carbonate in the presence of an appropriate base such as triethylamine. The compounds of Formula I where R is SO$_2$R$^d$ can be prepared from pyrrolidine or Δ$^3$-pyrroline 57 by treatment with the appropriate sulfonyl chloride to afford the sulfonamides 60. In cases where the sulfonyl chloride is not commercially available, it can be prepared from the corresponding sulfonic acid 62 using phosphorous pentachloride or thionyl chloride. Where the sulfonic acid 62 is not commercially available, it can be prepared from the corresponding bromide 61 by displacement with sodium sulfite. To prepare compounds where R in Formula I is $R^d$, a simple alkylation of the pyrrolidine or $\Delta^3$-pyrroline 57 with the appropriate primary alkyl bromide, chloride or tosylate in the presence of a base such as triethylamine can provide the required compounds (Formula I, $R=R^d$).

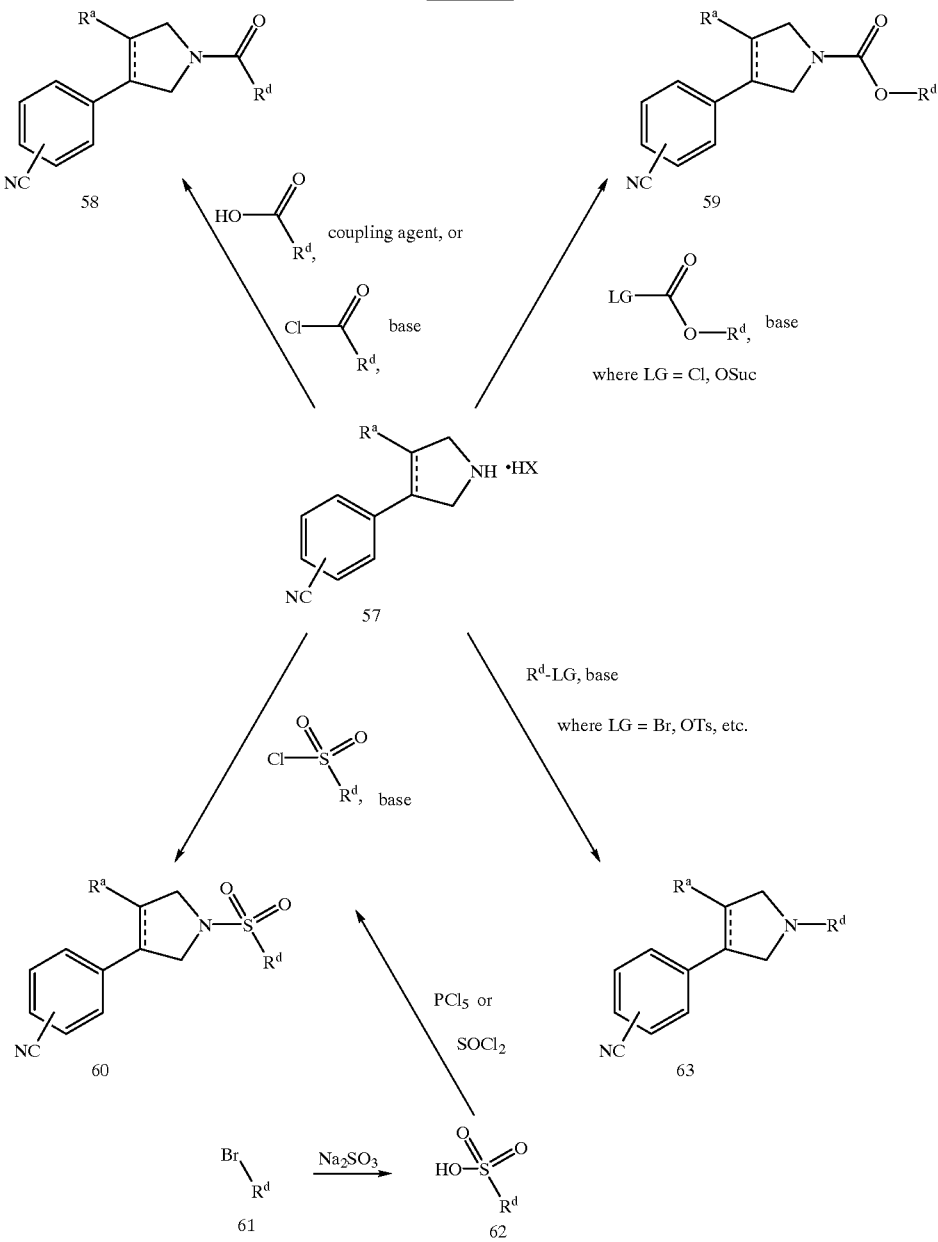

Scheme 13

The compounds of Formula I contain a linking group Z connecting the pyrrolidine and $\Delta^3$-pyrroline rings to the A-B moiety. In Schemes 14–17 is shown how the various linking groups can be synthesized and incorporated into the structures of Formula Ib. It will be appreciated by those skilled in the art of organic synthesis that depending on the groups R and A-B of Formula Ib, some modification of reaction order or use of suitable protecting groups may be required to prepare the desired compounds. Many of the various linking groups can be derived from a carboxylic ester group when the azomethine ylide cyclizations of Scheme 2 are carried out on dipolarophiles 6 in which $R^a$ or $R^c$ is a carboxylic ester or when those of Scheme 3 are carried out on dipolarophiles 54 in which $R^a$ is a carboxylic ester. For compounds of Formula Ib in which Z is an amide (—CONH—) there is a variety of methods for preparing the desired compounds (Scheme 14). One preferred method is to treat the ester 64 directly with an aluminum reagent derived from a suitable amine 65. This is accomplished by first treating the amine 65 with trimethylaluminum in a solvent such as methylene chloride or toluene and then adding the ester 64 and stirring at temperatures ranging from room temperature to 100° C. This procedure affords the amide 66 directly. Another preferred method is to hydrolyze the ester 64 to the carboxylic acid 67 under basic conditions. The acid 67 can then be coupled to a suitable amine by many methods well known to those skilled in the art. One preferred method for this transformation is to treat 67 with oxalyl chloride or thionyl chloride to form the corresponding acid chloride. This intermediate can then be treated with amine 65 to afford the amide 66. Another method is to allow the acid 67 and the amine 65 to react in the presence of a suitable peptide coupling reagent, such as BOP-Cl, HBTU, DCC or any of a variety of such agents that are well known to those skilled in the art.

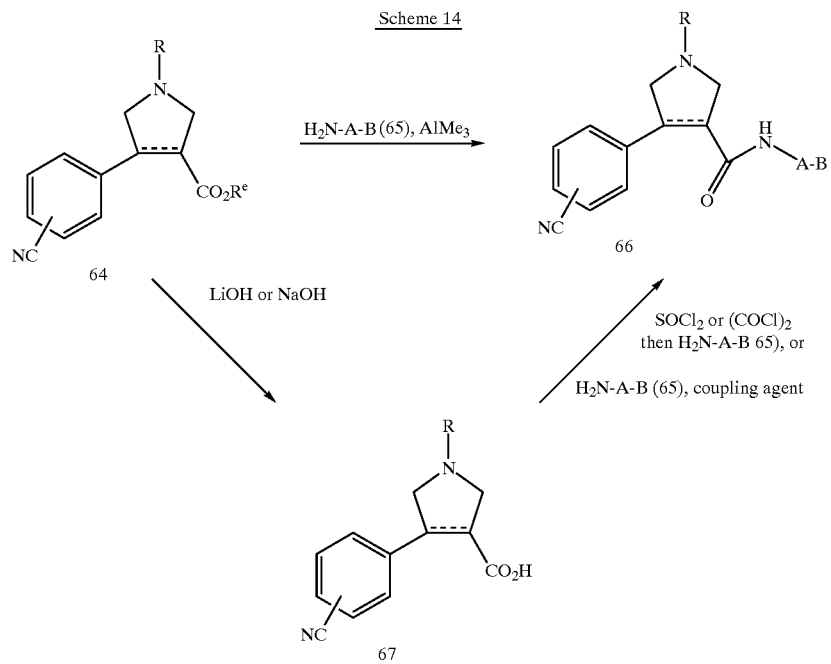

Scheme 14

In Scheme 15 is shown how the ether, amine and ketone linking groups Z of Formula Ib compounds can be prepared from the carboxylic ester 64. To prepare the ether-linked compounds (Z=—CH$_2$O—), reduction of ester 64 to the corresponding primary alcohol is required. This transformation is possible by a variety of techniques. The preferred procedures involve the intermede carboxylic acid 67. The acid 67 can be reduced to the alcohol 68 directly with borane tetrahydrofuran complex or by a procedure involving sodium borohydride reduction of a mixed anhydride derived from carboxylic acid 67. Completion of the ether linked compounds of Formula Ib is readily accomplished from 68 by the Mitsonobu protocol with an appropriate phenol or hydroxyheterocycle 69 to give 70 (Formula Ib, A=aryl or heteroaryl). To prepare the amine-linked compounds of Formula Ib (Z=—CH$_2$NH—) alcohol 68 can be oxidized to aldehyde 71 by a number of procedures, two preferred methods of which are the Swern oxidation and oxidation with pyridinium chlorochromate (PCC). Reductive amination of aldehyde 71 with an appropriate amine 65 and sodium cyanoborohydride then affords the amine linked compounds 72. The aldehyde 71 also can be used to prepare the ketone-linked compounds of Formula Ib (Z=—COCH$_2$—). Treatment of 71 with an organometallic species of structure 73 affords the alcohol 74. Compound 73 (where M=magnesium or zinc) is best prepared from the corresponding halide by treatment with metallic magnesium or zinc. These reagents readily react with aldehydes to afford alcohols. Oxidation of alcohol 74 by any of a number of procedures, such as the Swern oxidation or PCC oxidation, affords the ketones 75. Alternatively, the ketones 75 can be prepared from the appropriate cinnamic or propionic acid derivatives 76. Treatment of 76 with the appropriate organomagnesium or organozinc reagent 76 affords either the unsaturated ketone 77 directly (when X in 76 is Cl, N(Me) OMe) or an intermediate alcohol (when X in 76 is H) which can subsequently be oxidized to 77 by procedures described above. Following the procedures described in Schemes 12 and 13, the unsaturated ketone 77 can be cyclized to the pyrrolidine or Δ³-pyrroline and subsequently converted to 32.

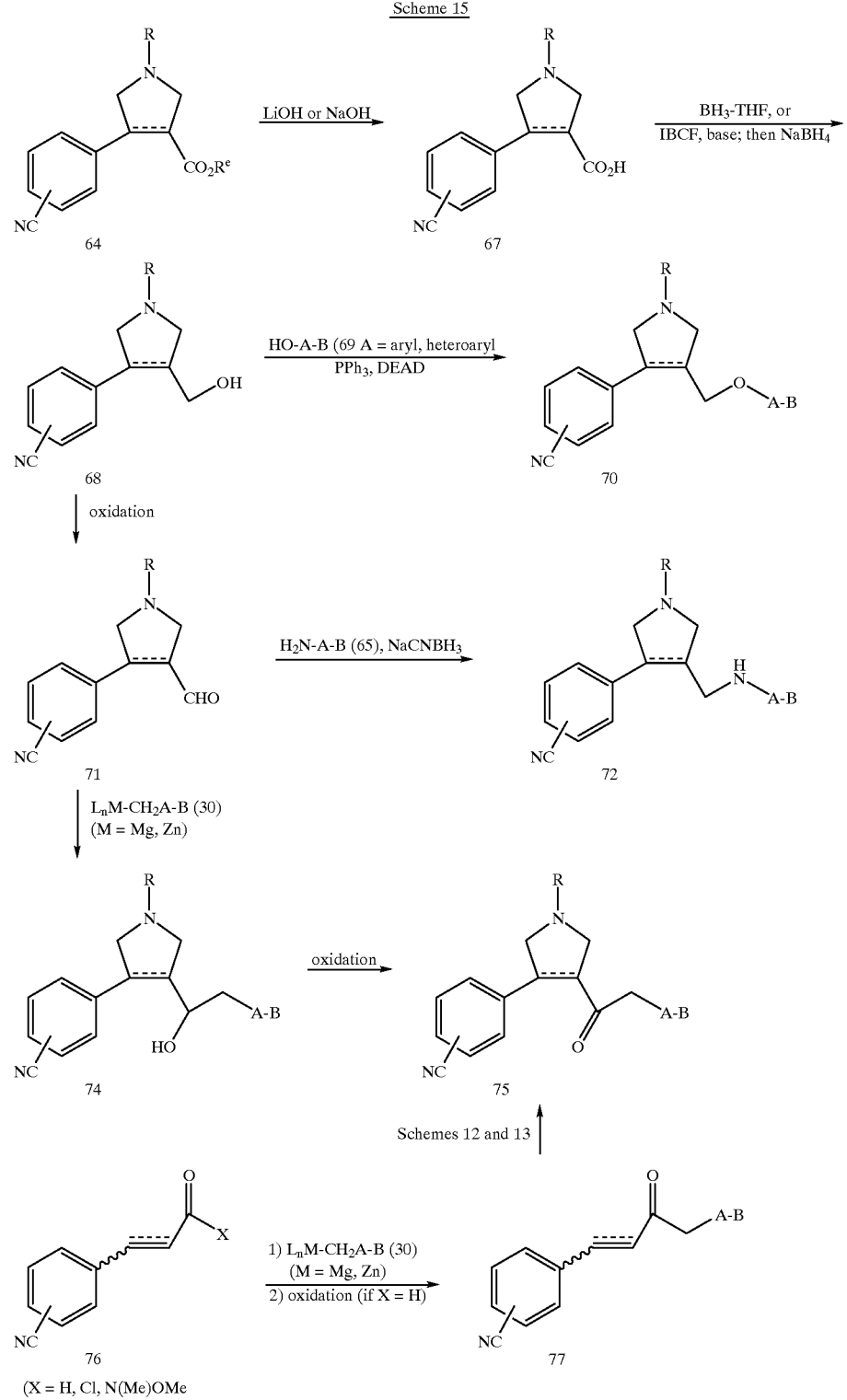

Scheme 15

In Scheme 16 is shown how compounds of Formula I containing the sulfonamide linking group (Z=—SO$_2$NH—) can be prepared. The styrene 78 can be treated with a variety of reagents, such as sulfuryl chloride or sulfur trioxide and phosphorous pentachloride, to afford the unsaturated sulfonyl chloride 79. Treatment with an appropriate amine 65 affords the sulfonamide 80 which can subsequently be converted into the sulfonamide-linked compounds 81 following the procedures described in Schemes 12 and 13.

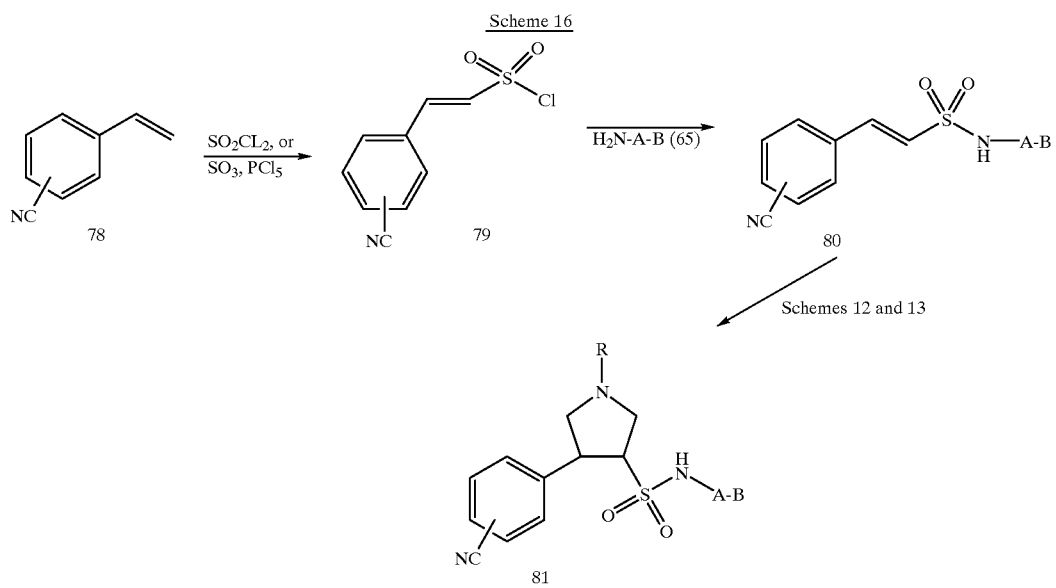

In Scheme 17 is shown how compounds of Formula Ib containing the sulfone linking group (Z=—SO$_2$CH$_2$—) can be prepared. Treatment of readily available 82 with trimethylphosphite affords a phosphonate which, after treatment with a suitable base such as sodium hydride, reacts with the aldehyde 5 to afford the unsaturated sulfide 83. Oxidation to the corresponding sulfone 84 can be accomplished by a variety of reagents, such as KMnO$_4$. Alternatively, the oxidation can be carried out prior to the condensation with aldehyde 5, in which case reaction of the anion of the sulfone phosphonate with 5 would give 84 directly. Following the procedures described in Schemes 12 and 13, the sulfone 84 can be converted to the sulfone-linked compounds 85.

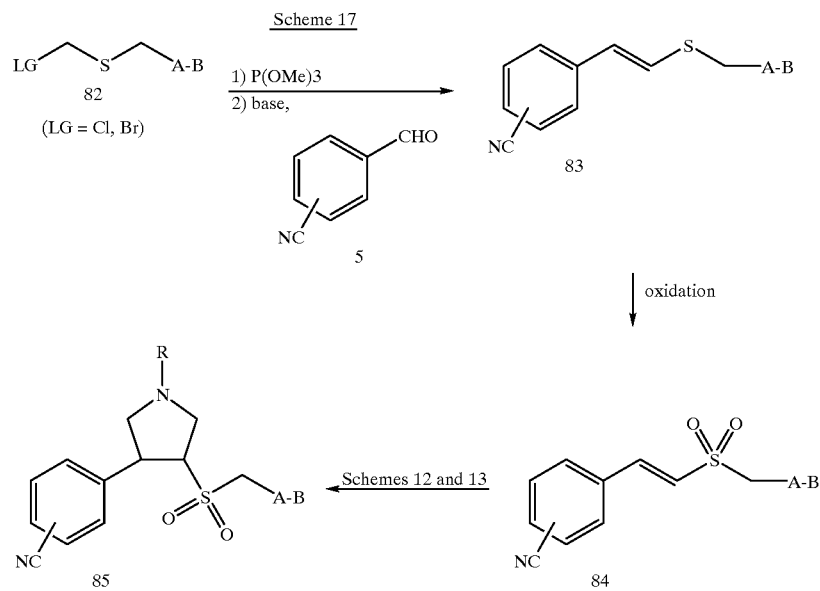

All of the pyrrolidine and Δ³-pyrroline derivatives described in Schemes 14–17 contain an aromatic cyano group which must be converted to its amidine derivative to prepare the final compounds described by Formula Ib. This can be accomplished using the reduction procedures described above in Scheme 6.

Where the group A-B in compounds of Formula Ib is a biphenyl residue, the chemistry described in Scheme 18 can be used. The biphenyl residue can be constructed using the palladium-catalyzed Suzuki coupling of an appropriate aryl halide 86 with an appropriate arylboronic acid 87 to give the biphenyl 88 (Miyaura et. al. *Syn. Comm.* 1981, 11, 513).

This reaction in general is tolerant of a wide variety of substituents on both of the reacting partners. Thus, the reaction can be performed on a variety of compounds 86 where R' is a suitable precursor to the Z linking group found in compounds of Formula Ib. Alternatively, the coupling can be performed on a more fully elaborated aryl halide such as 89, where the pyrrolidine, Δ³-pyrroline or isoxazolidine heterocycle is intact. Reaction with a suitable boronic acid 90 then would afford 91. The biphenyl compounds 88 and 91 can be carried on to the final products described by Formula Ib according to the procedures described in Schemes 14–17.

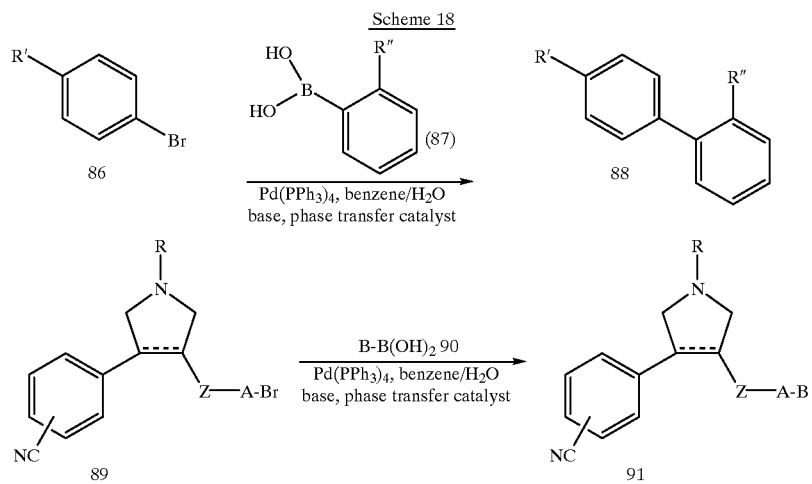

Scheme 18

Groups A and B are available either through commercial sources, known in the literature or readily synthesized by the adaptation of standard procedures known to practioners skilled in the art of organic synthesis. The required reactive functional groups appended to analogs of A and B are also available either through commercial sources, known in the literature or readily synthesized by the adaptation of standard procedures known to practioners skilled in the art of organic synthesis. In the tables that follow the chemistry required to effect the coupling of A to B is outlined.

TABLE A

Preparation of Amide, Ester, Urea, Sulfonamide and Sulfamide linkages between A and B

| Rxn. No. | if A contains : | reactive substituent of Y is : | to give the following product A-X-Y : |
|---|---|---|---|
| 1 | A—$NHR^2$ as a substituent | ClC(O)—Y | A—$NR^2$-C(O)—Y |
| 2 | a secondary NH as part of a ring or chain | ClC(O)—Y | A—C(O)—Y |
| 3 | A—OH as a substituent | ClC(O)—Y | A—O—C(O)—Y |
| 4 | A—$NHR^2$ as a substituent | ClC(O)—$CR^2R^{2'}$-Y | A—$NR^2$-C(O)—$CR^2R^{2'}$-Y |
| 5 | a secondary NH as part of a ring or chain | ClC(O)—$CR^2R^{2'}$-Y | A—C(O)—$CR^2R^{2'}$-Y |
| 6 | A—OH as a substituent | ClC(O)—$CR^2R^{2'}$-Y | A—O—C(O)—$CR^2R^{2'}$-Y |

TABLE A-continued

Preparation of Amide, Ester, Urea, Sulfonamide and Sulfamide linkages between A and B

| Rxn. No. | if A contains: | reactive substituent of Y is: | to give the following product A-X-Y: |
|---|---|---|---|
| 7 | A—$NHR^3$ as a substituent | $ClC(O)NR^2$-Y | A—$NR^2$-$C(O)NR^2$-Y |
| 8 | a secondary NH as part of a ring or chain | $ClC(O)NR^2$-Y | A—$C(O)NR^2$-Y |
| 9 | A—OH as a substituent | $ClC(O)NR^2$-Y | A—O—$C(O)NR^2$-Y |
| 10 | A—$NHR^2$ as a substituent | $ClSO_2$-Y | A—$NR^2$-$SO_2$-Y |
| 11 | a secondary NH as part of a ring or chain | $ClSO_2$-Y | A—$SO_2$-Y |
| 12 | A—$NHR^2$ as a substituent | $ClSO_2$-$CR^2R^{2'}$-Y | A—$NR^2$-$SO_2$-$CR_2R_{2'}$-Y |
| 13 | a secondary NH as part of a ring or chain | $ClSO_2$-$CR^2R^{2'}$-Y | A—$SO_2$-$CR^2R^{2'}$-Y |
| 14 | A—$NHR^2$ as a substituent | $ClSO_2$-$NR^2$-Y | A—$NR^2$-$SO_2$-$NR^2$-Y |
| 15 | a secondary NH as part of a ring or chain | $ClSO_2$-$NR^2$-Y | A—$SO_2$-$NR^2$-Y |
| 16 | A—C(O)Cl | HO—Y as a substituent | A—C(O)—O—Y |
| 17 | A—C(O)Cl | $NHR^2$-Y as a substituent | A—C(O)—$NR^2$-Y |
| 18 | A—C(O)Cl | a secondary NH as part of a ring or chain | A—C(O)—Y |
| 19 | A—$CR^2R^{2'}$C(O)Cl | HO—Y as a substituent | A—$CR^2R^{2'}$C(O)—O—Y |
| 20 | A—$CR^2R^{2'}$C(O)Cl | $NHR^2$-Y as a substituent | A—$CR^2R^{2'}$C(O)—$NR^2$-Y |
| 21 | A—$CR^2R^{2'}$C(O)Cl | a secondary NH as part of a ring or chain | A—$CR^2R^{2'}$C(O)—Y |
| 22 | A—$SO_2$Cl | $NHR^2$-Y as a substituent | A—$SO_2$-$NR^2$-Y |
| 23 | A—$SO_2$Cl | a secondary NH as part of a ring or chain | A—$SO_2$-Y |
| 24 | A—$CR^2R^{2'}SO_2$Cl | $NHR^2$-Y as a substituent | A—$CR^2R^{2'}SO_2$-$NR^2$-Y |
| 25 | A—$CR^2R^{2'}SO_2$Cl | a secondary NH as part of a ring or chain | A—$CR^2R^{2'}SO_2$-Y |

The chemistry of Table A can be carried out in aprotic solvents such as a chlorocarbon, pyridine, benzene or toluene, at temperatures ranging from −20° C. to the reflux point of the solvent and with or without a trialkylamine base.

TABLE B

Preparation of ketone linkages between A and B

| Rxn. No. | if A contains: | then the reactive substituent of Y is: | to give the following product A-X-Y: |
|---|---|---|---|
| 1 | A—C(O)Cl | BrMg—Y | A—C(O)—Y |
| 2 | A—$CR^2R^{2'}$C(O)Cl | BrMg—Y | A—$CR^2R^{2'}_2$C(O)—Y |
| 3 | A—C(O)Cl | $BrMgCR^2R^{2'}$-Y | A—C(O)$CR^2R^{2'}$-Y |
| 4 | A—$CR^2R^{2'}$C(O)Cl | $BrMgCR^2R^{2'}$-Y | A—$CR^2R^{2'}$C(O)$CR^2R^{2'}$-Y |

The coupling chemistry of Table B can be carried out by a variety of methods. The Grignard reagent required for Y is prepared from a halogen analog of Y in dry ether, dimethoxyethane or tetrahydrofuran at 0° C. to the reflux point of the solvent. This Grignard reagent can be reacted directly under very controlled conditions, that is low temperature (−20° C. or lower) and with a large excess of acid chloride or with catalytic or stoichiometric copper bromide dimethyl sulfide complex in dimethyl sulfide as a solvent or with a variant thereof. Other methods available include transforming the Grignard reagent to the cadmium reagent and coupling according to the procedure of Carson and Prout (Org. Syn. Col. Vol. 3 (1955) 601) or a coupling mediated by Fe(acac)$_3$ according to Fiandanese et al.(Tetrahedron Lett., (1984) 4805), or a coupling mediated by manganese (II) catalysis (Cahiez and Laboue, Tetrahedron Lett., 33(31), (1992) 4437).

TABLE C

Preparation of ether and thioether linkages between A and B

| Rxn. No. | if A contains : | then the reactive substituent of Y is : | to give the following product A-X-Y : |
|---|---|---|---|
| 1 | A—OH | Br—Y | A—O—Y |
| 2 | A—CR$^2$R$^{2'}$-OH | Br—Y | A—CR$^2$R$^{2'}$O—Y |
| 3 | A—OH | Br—CR$^2$R$^{2'}$-Y | A—OCR$^2$R$^{2'}$-Y |
| 4 | A—SH | Br—Y | A—S—Y |
| 5 | A—CR$^2$R$^{2'}$-SH | Br—Y | A—CR$^2$R$^{2'}$S—Y |
| 6 | A—SH | Br—CR$^2$R$^{2'}$-Y | A—SCR$^2$R$^{2'}$-Y |

The ether and thioether linkages of Table C can be prepared by reacting the two components in a polar aprotic solvent such as acetone, dimethylformamide or dimethylsulfoxide in the presence of a base such as potassium carbonate, sodium hydride or potassium t-butoxide at temperature ranging from ambient temperature to the reflux point of the solvent used.

TABLE D

Preparation of —SO— and —SO2- linkages from thioethers of TABLE 3

| Rxn. No. | if the starting material is : | and it is oxidized with Alumina (wet)/ Oxone (Greenhalgh, Synlett, (1992) 235) the product is : | and it is oxidized with m-chloroperbenzoic acid (Satoh et al., Chem. Lett. (1992) 381), the product is : |
|---|---|---|---|
| 1 | A—S—Y | A—S(O)—Y | A—SO$_2$-Y |
| 2 | A—CR$^2$R$^{2'}$S—Y | A—CR$^2$R$^{2'}$S(O)—Y | A—CR$^2$R$^{2'}$SO$_2$-Y |
| 3 | A—SCR$^2$R$^{2'}$-Y | A—S(O)CR$^2$R$^{2'}$-Y | A—SO$_2$CR$^2$R$^{2'}$-Y |

The thioethers of Table C serve as a convenient starting material for the preparation of the sulfoxide and sulfone analogs of Table D. A combination of wet alumina and oxone provides a reliable reagent for the oxidation of the thioether to the sulfoxide while m-chloroperbenzoic acid oxidation will give the sulfone.

Other features of the invention will become apparent in the course of the following descriptions of exemplary embodiments which are given for illustration fo the invention and are not intended to be limiting thereof.

EXAMPLES

Example 1 trans-1-benzyl-3-carbomethoxy-4-(3-amidinophenyl) pyrrolidine, bistrifluoroacetic acid salt.

Part A. Preparation of methyl trans-3-cyanocinnamate.

To a solution of 3-cyanobenzaldehyde (10.0 g, 76 mmol) in 500 mL of methylene chloride was added methyl (triphenylphosphoranylidene)acetate (25.4 g, 76 mmol). The mixture was allowed to stir at room temperature for 16 h. The solvent was removed in vacuo and the residue was taken up in hexane/ethyl acetate and filtered through a large pad of silica gel. The solution was concentrated to afford 12.75 g (89%) of the cinnamate as a white solid which was sufficiently pure for further reactions. MS (H$_2$O-GC/MS): 188 (M+H)+.

Part B. Preparation of N-benzyl-N-(trimethylsilylmethyl) aminomethyl methyl ether.

To a stirred mixture of methanol (1.25 mL, 31 mmol) and 37% aqueous formaldehyde (2.56 mL, 31 mmol) at 0° C. was added N-benzyl-N-(trimethylsilylmethyl)amine (5.0 g, 26 mmol) dropwise over 5 minutes. The resulting mixture was stirred for 2 h. Anhydrous potassium carbonate (1.02 g, 7.4 mmol) was added and the mixture was stirred at 0° C. for 30 min. The reaction mixture was diluted with water and extracted twice with ether. The combined organic extracts were washed with brine, dried over sodium sulfate and concentrated in vacuo to afford 5.6 g (92%) of the title compound. $^1$H NMR (CDCl$_3$): δ 7.30–7.15 (m, 5H), 3.95 (s, 2H), 3.71 (s, 2H), 3.19 (s, 3H), 2.14 (s, 2H).

Part C. Preparation of trans-1-benzyl-3-carbomethoxy-4-(3-cyanophenyl)pyrrolidine.

To a solution of N-benzyl-N-(trimethylsilylmethyl) aminomethyl methyl ether (1.64 g, 6.9 mmol) in 20 mL of methylene chloride at 0° C. was added methyl trans-3-cyanocinnamate (0.99 g, 5.3 mmol) followed by trifluoroacetic acid (0.041 mL, 0.53 mmol). The mixture was allowed to warm to room temperature and was stirred for 2 h. The reaction mixture was diluted with methylene chloride, washed with saturated aqueous NaHCO$_3$ and brine, dried over K$_2$CO$_3$ and concentrated in vacuo to afford 1.67 g (98%) of the title compound which was sufficiently pure for further reactions. MS (ESI) 321.1 (M+H)+.

Part D. Preparation of trans-1-benzyl-3-carbomethoxy-4-(3-amidinophenyl)pyrrolidine, bistrifluoroacetic acid salt.

A solution of trans-1-benzyl-3-carbomethoxy-4-(3-cyanophenyl)pyrrolidine (150 mg, 0.47 mmol) in 10 mL of anhydrous methanol and 30 mL of anhydrous chloroform was cooled to −10° C. Anhydrous HCl gas was bubbled through the solution for about 30 min (until solution saturated). The flask was then sealed and allowed to stand for 16 h at 0° C. The reaction mixture was concentrated in vacuo. The resulting solid was dissolved in 20 mL of anhydrous methanol and ammonium carbonate (0.26 g, 2.8 mmol) was added and the mixture was allowed to stir at room temperature for 24 h. The reaction mixture was concentrated in vacuo and purified by prep HPLC (C18 reverse phase column, elution with a H$_2$O/CH$_3$CN gradient with 0.5% TFA) to afford 23 mg (13%) of the title compound as a white powder. MS (ESI) 169.8 (M+2H)2+.

Example 2 trans-1-(4-amidinophenyl)methyl-3-carbomethoxy-4-(3-amidinophenyl)pyrrolidine, bistrifluoroacetic acid salt.

Part A. Preparation of trans-1-tert-butyloxycarbonyl-3-carbomethoxy-4-(3-cyanophenyl)pyrrolidine.

To a solution of trans-1-benzyl-3-carbomethoxy-4-(3-cyanophenyl)pyrrolidine from Example 1, Part C (2.56 g, 8.00 mmol) in 250 mL of absolute ethanol was added 10% palladium on carbon (0.5 g) and di-tert-butyldicarbonate (1.92 g, 8.80 mmol). This mixture was allowed to stir under 1 atm of hydrogen (maintained by a balloon) for 24 h. The reaction mixture was filtered through a pad of celite and concentrated in vacuo to afford 2.6 g (98%) of the title compound which was sufficiently pure for further reactions. MS (ESI) 331.3 (M+H)+.

Part B. Preparation of trans-3-carbomethoxy-4-(3-cyanophenyl)pyrrolidine, trifluoroacetic acid salt.

To a solution of trans-1-tert-butyloxycarbonyl-3-carbomethoxy-4-(3-cyanophenyl)pyrrolidine in 50 mL of methylene chloride was added 50 mL of trifluoroacetic acid. The resulting solution was allowed to stir at room temperature for 4 h and then was concentrated in vacuo to afford 2.75 g (99%) of the title compound which was sufficiently pure for further reactions. MS (ESI) 231.2 (M+H)+.

Part C. Preparation of trans-1-(4-cyanophenyl)methyl-3-carbomethoxy-4-(3-cyanophenyl)pyrrolidine.

To a solution of trans-3-carbomethoxy-4-(3-cyanophenyl) pyrrolidine, trifluoroacetic acid salt (0.52 g, 1.5 mmol) in 50 mL of acetonitrile was added 4-cyanobenzyl bromide (0.29 g, 1.5 mmol) and sodium bicarbonate (0.32 g, 3.8 mmol). The resulting mixture was stirred at 80° C. for 16 h. The mixture was allowed to cool to room temperature and the acetonitrile was removed in vacuo. The residue was diluted with ethyl acetate, washed with $H_2O$ and brine, dried over $MgSO_4$ and concentrated in vacuo. The residue was purified by flash chromatography (elution gradient with 5:1 to 2:1 hexanes/ethyl acetate) to afford 0.113 g (22%) of the title compound. MS (ESI) 346.2 (M+H)+.

Part D. Preparation of trans-1-(4-amidinophenyl)methyl-3-carbomethoxy-4-(3-amidinophenyl)pyrrolidine, bistrifluoroacetic acid salt.

By the procedure described in Example 1, Part D, trans-1-(4-cyanophenyl)methyl-3-carbomethoxy-4-(3-cyanophenyl)pyrrolidine (0.114 g, 0.33 mmol) was treated with HCl/methanol and then with ammonium carbonate (0.32 g, 3.3 mmol) to afford after HPLC purification (C18 reverse phase column, elution with a $H_2O/CH_3CN$ gradient with 0.5% TFA) 0.032 g (21%) of the title compound as a white powder. MS (ESI) 190.8 (M+2H)2+.

Example 3 trans-1-[(2'-aminosulfonyl-[1,1']-biphenyl-4-yl)methyl]-3-carbomethoxy-4-(3-amidinophenyl)pyrrolidine, bistrifluoroacetic acid salt.

Part A. Preparation of N-(4-bromobenzyl)-N-(trimethylsilylmethyl)amine.

To a solution of (trimethylsilyl)methylamine (10.7 mL, 80 mmol) in 500 mL of tetrahydrofuran was added 4-bromobenzyl bromide (5.0 g, 20 mmol) and sodium bicarbonate (3.4 g, 40 mmol). The resulting mixture was stirred at 65° C. for 16 h. The reaction mixture was allowed to cool to room temperature and concentrated in vacuo. The residue was dissolved in ethyl acetate, washed with $H_2O$ and brine, dried over $MgSO_4$ and concentrated in vacuo to afford 5.4 g (98%) of the title compound which was sufficiently pure for further reactions. $^1H$ NMR ($CDCl_3$): δ 7.40 (d, 2H), 7.15 (d, 2H), 3.70 (s, 2H), 1.98 (s, 2H), 1.08 (broad s, 1H), 0.0 (s, 9H).

Part B. Preparation of N-(4-bromobenzyl)-N-(trimethylsilylmethyl)aminomethyl methyl ether.

To a stirred mixture of methanol (1.32 mL, 32.4 mmol) and 37% aqueous formaldehyde (2.63 mL, 32.4 mmol) at 0° C. was added N-(4-bromobenzyl)-N-(trimethylsilylmethyl) amine (7.35 g, 27.0 mmol) dropwise over 15 minutes. The resulting mixture was stirred for 3 h. Anhydrous potassium carbonate (1.04 g, 7.56 mmol) was added and the mixture was stirred at 0° C. for 1 h. The reaction mixture was diluted with water and extracted twice with ether. The combined organic extracts were washed with brine, dried over sodium sulfate and concentrated in vacuo to afford 8.52 g (99%) of the title compound. $^1H$ NMR ($CDCl_3$): δ 7.48 (d, 2H), 7.15 (d, 2H), 3.95 (s, 2H), 3.66 (s, 2H), 3.19 (s, 3H), 2.11 (s, 2H), 0.0 (s, 9H).

Part C. Preparation of trans-1-(4-bromobenzyl)-3-carbomethoxy-4-(3-cyanophenyl)pyrrolidine.

To a solution of N-(4-bromobenzyl)-N-(trimethylsilylmethyl)aminomethyl methyl ether (13.85 g, 43.8 mmol) in 300 mL of methylene chloride at 0° C. was added methyl trans-3-cyanocinnamate from Example 1, Part A (7.13 g, 38.1 mmol) followed by trifluoroacetic acid (0.30 mL, 3.8 mmol). The reaction was allowed to warm to room temperature and was stirred for 2 h. The reaction mixture was diluted with methylene chloride, washed with saturated aqueous $NaHCO_3$ and brine, dried over $K_2CO_3$, filtered through a large pad of silica gel and concentrated in vacuo to afford 13.2 g (86%) of the title compound which was sufficiently pure for further reactions. MS (ESI) 399.2/401.2 (M+H)+.

Part D. Preparation of trans-1-[(2'-tert-butylaminosulfonyl-[1,1']-biphenyl-4-yl)methyl]-3-carbomethoxy-4-(3-cyanophenyl)pyrrolidine.

To a solution of trans-1-(4-bromobenzyl)-3-carbomethoxy-4-(3-cyanophenyl)pyrrolidine (1.0 g, 2.5 mmol) in 50 mL of benzene was added 2-(tert-butylaminosulfonyl)phenylboronic acid (0.90 g, 3.5 mmol), tetrabutylammonium bromide (0.04 g, 0.12 mmol), sodium carbonate (0.79 g, 7.5 mmol) and 8.2 mL of $H_2O$. This mixture was degassed with a stream of nitrogen and then tetrakis(triphenylphosphine)palladium (0.14 g, 0.12 mmol) was added and the reaction mixture was stirred at 80° C. for 6 h. The mixture was allowed to cool to room temperature and then was diluted with ethyl acetate, washed with $H_2O$ and brine, dried over $MgSO_4$ and was concentrated in vacuo. The residue was purified by flash chromatography (elution with 3:1 hexanes/ethyl acetate) to afford 0.65 g (49%) of the title compound. MS (ESI) 532.2 (M+H)+.

Part E. Preparation of trans-1-[(2'-aminosulfonyl-[1,1']-biphenyl-4-yl)methyl]-3-carbomethoxy-4-(3-amidinophenyl)pyrrolidine, bistrifluoroacetic acid salt.

A solution of trans-1-[(2'-tert-butylaminosulfonyl-[1,1']-biphenyl-4-yl)methyl]-3-carbomethoxy-4-(3-cyanophenyl)pyrrolidine (0.195 g, 0.37 mmol) in 20 mL of trifluoroacetic acid was stirred at 70° C. for 1 h and then was allowed to cool to room temperature and was concentrated in vacuo. $^1H$ NMR ($CDCl_3$) indicated complete removal of the tert-butyl group. The crude residue was dissolved in 8 mL of anhydrous methanol and 25 mL of chloroform and was cooled to 0° C. Anhydrous HCl gas was bubbled through the solution for about 30 min (until solution saturated). The flask was then sealed and allowed to stand for 16 h at 0° C. The reaction mixture was concentrated in vacuo. The resulting solid was dissolved in 35 mL of anhydrous methanol and ammonium carbonate (0.16 g, 1.65 mmol) was added and the mixture was allowed to stir at room temperature for 24 h. The reaction mixture was concentrated in vacuo and purified by prep HPLC (C18 reverse phase column, elution with a $H_2O/CH_3CN$ gradient with 0.5% TFA) to afford 112 mg (47%) of the title compound as a white powder. MS (ESI) 247.2 (M+2H)2+.

Example 4

(3S,4R)-1-[(2'-aminosulfonyl-[1,1']-biphenyl-4-yl)methyl]-3-carbomethoxy-4-(3-amidinophenyl)pyrrolidine, bistrifluoroacetic acid salt.

Part A. Preparation of (3aS-[1(E),3aα6α,7aβ]]-hexahydro-8,8-dimethyl-1-[1-oxo-3-(3-cyanophenyl)-2-propenyl]-3H-3a,6-methano-2,1-benzisothiazole-2,2-dioxide.

To a solution of (1S)-(−)-2,10-camphorsultam (3.0 g, 13.9 mmol) in 50 mL of toluene was added trimethylaluminum (6.97 mL of a 2M solution in toluene, 13.9 mmol) dropwise. The resulting solution was stirred at room temperature for about 2 h or until gas evolution had ceased. There was then added methyl trans-3-cyanocinnamate from Example 1, Part A (2.6 g, 13.9 mmol) and the mixture was stirred at 60° C. for 16 h. The reaction mixture was allowed to cool to room temperature and was quenched by the addition of saturated aqueous $NH_4Cl$. The reaction was diluted with ethyl acetate and the organic layer was washed with brine, dried over $MgSO_4$ and concentrated in vacuo. The residue was recrystallized from hexanes/ethyl acetate to afford 3.65 g (70%) of the title compound as a white solid. MS (ESI) 371.3 (M+H)+.

Part B. Preparation of [3aS-[1(3S*,4R*),3aα6α,7aβ]]-1-[[1-(4-bromobenzyl)-4-(3-cyanophenyl)- 3-pyrrolidinyl] carbonyl]hexahydro-8,8-dimethyl-3H-3a,6-methano-2,1-benzisothiazole-2,2-dioxide.

To a solution of [3aS-[1(E),3aα6α,7aβ]]-hexahydro-8,8-dimethyl-1-[1-oxo-3-(3-cyanophenyl)-2-propenyl]-3H-3a, 6-methano-2,1-benzisothiazole-2,2-dioxide (2.0 g, 5.4 mmol) in 40 mL of methylene chloride was added N-(4-bromobenzyl)-N-(trimethylsilylmethyl)aminomethyl methyl ether from Example 3, Part B (2.1 g, 6.7 mmol) and trifluoroacetic acid (0.042 mL, 0.54 mmol). The resulting solution was stirred at room temperature for 2 h and then was concentrated in vacuo. The residue was taken up in ethyl acetate, washed with saturated aqueous NaHCO$_3$ and brine, dried over MgSO$_4$ and concentrated in vacuo. The residue was purified by flash chromatography (elution with 7:1 to 2:1 hexanes/ethyl acetate gradient) to afford 1.8 g (57%) of the title compound as the major diastereomer. MS (ESI) 582.2/584.2 (M+H)+. Also isolated was 0.8 g (25%) of a minor diastereomer which is presumed to be (3aS-[1(3R*, 4S*),3aα6α,7aβ]]-1-[[1-(4-bromobenzyl)-4-(3-cyanophenyl)-3-pyrrolidinyl]carbonyl]hexahydro-8,8-dimethyl-3H-3a,6-methano-2,1-benzisothiazole-2,2-dioxide. MS (ESI) 582.2/584.2 (M+H)+.

Part C. Preparation of [3aS-[1(3S*,4R*),3aα6α,7aβ]]-1-([1-[(2'-tert-butylaminosulfonyl-[1,1']-biphenyl-4-yl)methyl]-4-(3-cyanophenyl)-3-pyrrolidinyl]carbonyl]hexahydro-8,8-dimethyl-3H-3a,6-methano-2,1-benzisothiazole-2,2-dioxide.

(3aS-[1(3S*,4R*),3aα6α,7aβ]]-1-[[1-(4-bromobenzyl)-4-(3-cyanophenyl)-3-pyrrolidinyl]carbonyl]hexahydro-8,8-dimethyl-3H-3a,6-methano-2,1-benzisothiazole-2,2-dioxide (0.58 g, 1.0 mmol) was converted into the title compound (0.40 g, 56%) following the procedure described in Example 3, Part D. MS (ESI) 715.4 (M+H)+.

Part D. Preparation of (3S,4R)-1-[(2'-tert-butylaminosulfonyl-[(1,1']-biphenyl-4-yl)methyl]-4-(3-cyanophenyl)pyrrolidin-3-ylcarboxylic acid.

To a solution of [3aS-[1(3S*,4R*),3aα6α,7aβ]]-1-[[1-[(2'-tert-butylaminosulfonyl-[1,1']-biphenyl-4-yl)methyl]-4-(3-cyanophenyl)-3-pyrrolidinyl]carbonyl]hexahydro-8,8-dimethyl-3H-3a,6-methano-2,1-benzisothiazole-2,2-dioxide (0.35 g, 0.49 mmol) in 10 mL of tetrahydrofuran and 5 mL of H$_2$O was added lithium hydroxide monohydrate (62 mg, 1.47 mmol). The resulting mixture was stirred at room temperature for 16 h. The mixture was concentrated in vacuo, diluted with H$_2$O and saturated aqueous HaHCO$_3$ and extracted with hexane. The organic layer was discarded and the aqueous layer was acidified to about pH 6 and extracted twice with ethyl acetate. The combined ethyl acetate extracts were washed with brine, dried over MgSO$_4$ and concentrated in vacuo to afford 80 mg (32%) of the title compound. MS (ESI) 518.3 (M+H)+.

Part E. Preparation of (3S,4R)-1-[(2'-aminosulfonyl-[1,1']-biphenyl-4-yl)methyl]-3-carbomethoxy-4-(3-amidinophenyl)pyrrolidine, bistrifluoroacetic acid salt.

(3S,4R)-1-[(2'-tert-butylaminosulfonyl-[1,1']-biphenyl-4-yl)methyl]-4-(3-cyanophenyl)pyrrolidin-3-ylcarboxylic acid (50 mg, 0.1 mmol) was converted to the title compound following the procedure in Example 3, Part E to afford after HPLC purification 25 mg (35%). The enantiomeric excess was determined to be >99% by chiral HPLC analysis.

Example 5
(3R,4S)-1-[(2'-aminosulfonyl-[1,1']-biphenyl-4-yl)methyl]-3-carbomethoxy-4-(3-amidinophenyl)pyrrolidine, bistrifluoroacetic acid salt.

The title compound was prepared by the identical sequence of reactions described in Example 4 except that in Part A (1R)-(+)-2,10-camphorsultam was used as the chiral auxiliary. Chiral HPLC analysis of the title compound showed the enantiomeric excess to be >99%. MS (ESI) 247.3 (M+2H)2+.

Example 6
trans-1-[(2'-aminosulfonyl-[1,1']-biphenyl-4-yl)methyl]-4-(3-amidinophenyl)pyrrolidin-3-ylcarboxylic acid, bistrifluoroacetic acid salt.

To a solution of trans-1-[(2'-aminosulfonyl-[1,1']-biphenyl-4-yl)methyl]-3-carbomethoxy-4-(3-amidinophenyl)pyrrolidine, bistrifluoroacetic acid salt from Example 3, Part E (100 mg, 0.14 mmol) in 20 mL of tetrahydrofuran and 10 mL of H$_2$O was added lithium hydroxide monohydrate (40 mg, 0.96 mmol). The resulting mixture was allowed to stir at room temperature overnight. The reaction mixture was concentrated in vacuo and the residue was purified by prep HPLC (C18 reverse phase column, elution with a H$_2$O/CH$_3$CN gradient with 0.5% TFA) to afford 25 mg (25%) of the title compound as a white powder. MS (ESI) 240.2 (M+2H)2+.

Example 7
trans-1-[(2'-aminosulfonyl-[1,1']-biphenyl-4-yl)methyl]-4-(3-amidinophenyl)pyrrolidin-3-ylcarboxylic amide, bistrifluoroacetic acid salt.
Part A. Preparation of trans-1-[(2'-aminosulfonyl-[1,1']-biphenyl-4-yl)methyl]-3-carbomethoxy-4-(3-cyanophenyl) pyrrolidine, trifluoroacetic acid salt.

A solution of trans-1-[(2'-tert-butylaminosulfonyl-[1,1']-biphenyl-4-yl)methyl]-3-carbomethoxy-4-( 3-cyanophenyl) pyrrolidine from Example 3, Part D (1.28 g, 2.4 mmol) in 20 mL of trifluoroacetic acid was stirred at 70° C. for 1 h and then was allowed to cool to room temperature and was concentrated to afford 1.0 g (88%) of the title compound. MS (ESI) 476.2 (M+H)+.

Part B. Preparation of trans-1-[(2'-aminosulfonyl-[1,1']-biphenyl-4-yl)methyl]-4-(3-cyanophenyl)pyrrolidin-3-ylcarboxylic acid.

To a solution of trans-1-[(2'-aminosulfonyl-[1,1']-biphenyl-4-yl)methyl]-3-carbomethoxy-4-(3-cyanophenyl) pyrrolidine, trifluoroacetic acid salt (0.504 g, 1.06 mmol) in 40 mL of tetrahydrofuran and 20 mL of H$_2$O was added lithium hydroxide monohydrate (0.13 g, 3.18 mmol). The resulting mixture was allowed to stir at room temperature for 16 h. The tetrahydrofuran was removed in vacuo and the residue was taken up in H$_2$O and saturated aqueous NaHCO$_3$ and washed once with hexane. The organic layer was discarded. The aqueous layer was acidified with aqueous HCl to about pH 6 and extracted twice with ethyl acetate. The ethyl acetate extracts were washed with brine, dried over MgSO$_4$ and concentrated in vacuo to afford 0.29 g (59%) of the title compound which was sufficiently pure for further reactions. MS (ESI) 462.2 (M+H)+.

Part C. Preparation of trans-1-[(2'-aminosulfonyl-[1,1']-biphenyl-4-yl)methyl]-4-(3-cyanophenyl)pyrrolidin-3-ylcarboxylic amide.

To a solution of trans-1-[(2'-aminosulfonyl-[1,1']-biphenyl-4-yl)methyl]-4-(3-cyanophenyl)pyrrolidin-3-ylcarboxylic acid (0.166 g, 0.36 mmol) in 10 mL of tetrahydrofuran at −78° C. was added N-methylmorpholine (0.08 mL, 0.72 mmol) and isobutyl chloroformate (0.05 mL, 0.36 mmol). The resulting solution was allowed to stir for 30 min and then there was added 2M ammonia in methanol (0.70 mL, 1.08 mmol). The reaction mixture was allowed to slowly warm to room temperature and then was stirred for 6 h. The solvent was removed in vacuo. The residue was taken up in ethyl acetate, washed with saturated aqueous NaHCO$_3$ and brine, dried over MgSO$_4$ and concentrated in vacuo to afford 0.144 g (87%) of the title compound which was sufficiently pure for further reactions. MS (ESI) 461.3 (M+H)+.

Part D. Preparation of trans-1-[(2'-aminosulfonyl-[1,1']-biphenyl-4-yl)methyl]-4-(3-amidinophenyl)pyrrolidin-3-ylcarboxylic amide, bistrifluoroacetic acid salt.

A solution of trans-1-[(2'-aminosulfonyl-(1,1']-biphenyl-4-yl)methyl]-4-(3-cyanophenyl)pyrrolidin-3-ylcarboxylic amide (0.143 g, 0.31 mmol) in 50 mL of anhydrous methanol was cooled to 0° C. Anhydrous HCl gas was bubbled through the solution for about 30 min (until solution saturated). The flask was then sealed and allowed to stand for 16 h at 0° C. The reaction mixture was concentrated in vacuo. The resulting solid was dissolved in 20 mL of anhydrous methanol and ammonium carbonate (0.15 g, 1.55 mmol) was added and the mixture was allowed to stir at room temperature for 24 h. The reaction mixture was concentrated in vacuo and purified by prep HPLC (C18 reverse phase column, elution with a H$_2$O/CH$_3$CN gradient with 0.5% TFA) to afford 27 mg (18%) of the title compound as a white powder. MS (ESI) 239.8 (M+2H)2+.

Example 8 trans-1-[(2'-aminosulfonyl-[1,1']-biphenyl-4-yl)methyl]-4-(3-amidinophenyl)pyrrolidin-3-ylcarboxylic N,N-dimethylamide, bistrifluoroacetic acid salt.

Part A. Preparation of trans-1-[(2'-aminosulfonyl-[1,1']-biphenyl-4-yl)methyl]-4-(3-cyanophenyl)pyrrolidin-3-ylcarboxylic N,N-dimethylamide.

To a solution of trans-1-[(2'-aminosulfonyl-[1,1']-biphenyl-4-yl)methyl]-4-(3-cyanophenyl)pyrrolidin-3-ylcarboxylic acid from Example 7, Part B (0.11 g, 0.24 mmol) in 20 mL of tetrahydrofuran at −78° C. was added N-methylmorpholine (0.08 mL, 0.72 mmol) and isobutyl chloroformate (0.03 mL, 0.24 mmol). The resulting mixture was allowed to stir for 30 min and then dimethylamine hydrochloride (0.02 g, 0.24 mmol) was added and the mixture was allowed to slowly warm to room temperature and then was stirred for 16 h. The solvent was removed in vacuo. The residue was taken up in ethyl acetate, washed with saturated aqueous NaHCO$_3$ and brine, dried over MgSO$_4$ and concentrated in vacuo to afford 0.097 g (83%) of the title compound which was sufficiently pure for further reactions. MS (ESI) 489.3 (M+H)+.

Part B. Preparation of trans-1-[(2'-aminosulfonyl-[1,1']-biphenyl-4-yl)methyl]-4-(3-amidinophenyl)pyrrolidin-3-ylcarboxylic N,N-dimethylamide, bistrifluoroacetic acid salt.

Following the procedure of Example 7, Part D, trans-1-[(2'-aminosulfonyl-[1,1']-biphenyl-4-yl)methyl]-4-(3-cyanophenyl)pyrrolidin-3-ylcarboxylic N,N-dimethylamide (0.098 g, 0.20 mmol) was converted with HCl gas/methanol and ammonium carbonate (0.10 g, 1.0 mmol) into the title compound (22 mg, 22%) following HPLC purification. MS (ESI) 253.8 (M+2H)2+.

Example 9 cis-1-[(2'-aminosulfonyl-[1,1']-biphenyl-4-yl)methyl]-3-carbomethoxy-4-(3-amidinophenyl)pyrrolidine, bistrifluoroacetic acid salt.

Part A. Preparation of methyl cis-3-cyanocinnamate.

To a solution of bis(2,2,2-trifluoroethyl) (methoxycarbonylmethyl)phosphonate (5.0 g, 15.7 mmol) and 18-crown-6 (20.7 g, 78.5 mmol) in 300 mL of tetrahydrofuran at −78° C. was added potassium bis(trimethylsilyl) amide (31.4 mL of a 0.5 M solution in toluene, 15.7 mmol) dropwise. After the addition was complete 3-cyanobenzaldehyde (2.06 g, 15.7 mmol) was added and the resulting mixture was stirred for 30 minutes at −78° C. The reaction was quenched by the addition of saturated aqueous NH$_4$Cl and then extracted three times with ether. The combined ether extracts were washed with brine, dried over Na$_2$SO$_4$ and concentrated in vacuo to afford 2.86 g (97%) of the product which was sufficiently pure for further reactions. $^1$H NMR (CDCl$_3$) δ 7.85 (s, 1H), 7.76 (d, 1H), 7.60 (d, 1H), 7.45 (t, 1H), 6.93 (d, 1H), 6.05 (d, 1H), 3.70 (s, 3H).

Part B. Preparation of cis-1-[(2'-aminosulfonyl-[1,1']-biphenyl-4-yl)methyl]-3-carbomethoxy-4-(3-amidinophenyl)pyrrolidine, bistrifluoroacetic acid salt.

Following the procedures described in Example 3, Parts C–E, methyl cis-3-cyanocinnamate was converted into the title compound, a white powder following HPLC purification. MS (ESI) 247.2 (M+2H)2+.

Example 10 cis-1-[(2'-aminosulfonyl-[1,1']-biphenyl-4-yl)methyl]-4-(3-amidinophenyl)pyrrolidin-3-ylcarboxylic acid, bistrifluoroacetic acid salt.

Following the procedure described in Example 6, Part A, cis-1-[(2'-aminosulfonyl-[1,1']-biphenyl-4-yl)methyl]-3-carbomethoxy-4-(3-amidinophenyl)pyrrolidine, bistrifluoroacetic acid salt (0.10 g, 0.14 mmol) was treated with lithium hydroxide monohydrate (0.04 g, 0.96 mmol) to afford, after HPLC purification, 46 mg (46%) of the title compound as a white powder. MS (ESI) 240.2 (M+2H)2+.

Example 11 trans-1-[(2'-aminosulfonyl-[1,1']-biphenyl-4-yl)methyl]-3-carboisopropoxy-4-(3-amidinophenyl)pyrrolidine, bistrifluoroacetic acid salt.

To a solution of trans-1-[(2'-aminosulfonyl-[1,1']-biphenyl-4-yl)methyl]-3-carbomethoxy-4-(3-amidinophenyl)pyrrolidine, bistrifluoroacetic acid salt (0.50 g, 0.69 mmol) in 50 mL of isopropanol was added several drops of titanium (IV) isopropoxide. The resulting mixture was stirred at 80° C. for 16 h. The reaction was allowed to cool to room temperature and the solvent was removed in vacuo. The residue was triturated with ether and then was purified by HPLC under the conditions described in Example 1 to afford 0.30 g (58%) of the title compound as a white powder. MS (ESI) 261.3 (M+2H)2+.

Example 12 trans-1-[(2'-aminosulfonyl-[1,1']-biphenyl-4-yl)methyl]-3-carbobutoxy-4-(3-amidinophenyl)pyrrolidine, bistrifluoroacetic acid salt.

To a solution of trans-1-[(2'-aminosulfonyl-[1,1']-biphenyl-4-yl)methyl]-3-carbomethoxy-4-(3-amidinophenyl)pyrrolidine, bistrifluoroacetic acid salt (0.50 g, 0.69 mmol) in 50 mL of n-butanol was added several drops of titanium (IV) isopropoxide. The resulting mixture was stirred at 115° C. for 16 h. The reaction was allowed to cool to room temperature and the solvent was removed in vacuo. The residue was triturated with ether and then was purified by HPLC under the conditions described in Example 1 to afford 0.32 g (60%) of the title compound as a white powder. MS (ESI) 268.4 (M+2H)2+.

Example 13 trans-1-[(2'-aminosulfonyl-[1,1']-biphenyl-4-yl)methyl]-3-acetyl-4-(3-amidinophenyl)pyrrolidine, bistrifluoroacetic acid salt.

Part A. Preparation of (E)-4-(3-cyanophenyl)-3-buten-2-one.

To a solution of 3-cyanobenzaldehyde (4.98 g, 38 mmol) in 250 mL of methylene chloride was added acetylmethylene triphenylphosphorane (12.1 g, 38 mmol) and the resulting mixture was allowed to stir at room temperature for 16 h. The solution was concentrated in vacua and the residue was taken up in hexane/ethyl acetate and filtered through a large pad of silica gel. The solvents were removed in vacuo to afford 5.63 g (87%) of the title compound which was sufficiently pure for further reactions. $^1$H NMR (CDCl$_3$) δ 7.8 (s, 1H), 7.76 (d, 1H), 7.65 (d, 1H), 7.53 (d, 1H), 7.45 (d, 1H), 6.75 (d, 1H), 2.40 (s, 3H).

Part B. Preparation of trans-1-[(2'-aminosulfonyl-[1,1']-biphenyl-4-yl)methyl]-3-acetyl-4-(3-amidinophenyl) pyrrolidine, bistrifluoroacetic acid salt.

Following the procedures described in Example 3, Parts C–E, (E)-4-(3-cyanophenyl)-3-buten-2-one was converted to the title compound as a white solid following HPLC purification. MS (ES) 239.3 (M+2H)2+.

Example 14
trans-1-[(2'-aminosulfonyl-[1,1']-biphenyl-4-yl)methyl]-3-carboethoxy-3-methyl-4-(3-amidinophenyl)pyrrolidine, bis-trifluoroacetic acid salt.
Part A. Preparation of ethyl (E)-αmethyl-3-cyanocinnamate.

To a suspension of sodium hydride (0.5 g, 21 mmol) in 50 mL of THF was added triethyl 2-phosphonopropionate (5.0 g, 21 mmol). The resulting mixture was stirred at room temperature until gas evolution ceased and the sodium hydride was consumed (about 1 h). To the resulting clear solution was added 3-cyanobenzaldehyde (2.75 g, 21 mmol) and the mixture was stirred at 60° C. for 3 h. The reaction mixture was allowed to cool to room temperature and was diluted with ethyl acetate, washed with 10% aqueous HCl, saturated aqueous NaHCO$_3$ and brine, dried over MgSO$_4$ and concentrated in vacuo. The residue was purified by flash chromatography (elution with 6:1 hexanes/ethyl acetate) to afford 2.8 g (62%) of the title compound. $^1$H NMR (CDCl$_3$): d 7.65–7.48 (m, 5H), 4.29 (q, J=7.2 Hz, 2H), 2.09 (d, J=1.5 Hz, 3H), 1.35 (t, J=7.2 Hz, 3H). MS (H$_2$O-GC/MS) 216 (M+H)+.
Part B. Preparation of trans-1-[(2'-aminosulfonyl-[1,1']-biphenyl-4-yl)methyl]-3-carboethoxy-3-methyl-4-(3-amidinophenyl)pyrrolidine, bistrifluoroacetic acid salt.

Following the procedures of Example 3, Parts C–E, ethyl (E)-α-methyl-3-cyanocinnamate was converted into the title compound, a white powder following HPLC purification. MS (ESI) 261.3 (M+2H)2+.

Example 15
trans-1-[[2-(2-cyanophenylthio)phenyl]carbonyl]-3-carbomethoxy-4-(3-amidinophenyl)pyrrolidine, trifluoroacetic acid salt.
Part A. Preparation of trans-1-[[2-(2-cyanophenylthio) phenyl]carbonyl]-3-carbomethoxy-4-(3-cyanophenyl) pyrrolidine.

To a solution of trans-3-carbomethoxy-4-(3-cyanophenyl) pyrrolidine, trifluoroacetic acid salt from Example 2, Part B (0.50 g, 1.45 mmol) in 25 mL of dimethylformamide was added 2-(2-cyanophenylthio)benzoic acid (0.37 g, 1.45 mmol), HBTU (0.55 g, 1.45 mmol) and diisopropylethylamine (0.56 mL, 3.19 mmol). The resulting mixture was stirred at room temperature for 24 h. The reaction mixture was then diluted with ethyl acetate and washed twice with H$_2$O, then once with 10% aqueous HCl, saturated aqueous NaHCO$_3$ and brine. The organics were dried over MgSO4 and concentrated in vacuo. The residue was purified by flash chromatography (elution gradient 3:1 hexanes/ethyl acetate to 1:1 hexanes/ethyl acetate) to afford 0.41 g (60%) of the title compound. MS (ESI) 468.2 (M+H)+.

Part B. Preparation of trans-1-[[2-(2-cyanophenylthio) phenyl]carbonyl]-3-carbomethoxy-4-(3-amidinophenyl) pyrrolidine, trifluoroacetic acid salt.

Following the procedure of Example 7, Part D, trans-1-[[2-(2-cyanophenylthio)phenyl]carbonyl])-3-carbomethoxy-4-(3-cyanophenyl)pyrrolidine (0.107 g, 0.23 mmol) was converted with HCl gas/methanol and ammonium carbonate (0.22 g, 2.3 mmol) into the title compound (33 mg, 29%) following HPLC purification. MS (ESI) 485.3 (M+H)+.

Example 16
trans-1-[[2-(2-cyanophenylthio)phenyl]methyl]-3-carbomethoxy-4-(3-amidinophenyl)pyrrolidine, bistrifluoroacetic acid salt.
Part A. Preparation of 2-(2-cyanophenylthio)benzyl alcohol.

To a solution of 2-(2-cyanophenylthio)benzoic acid (9.96 g, 39 mmol) in 300 mL of tetrahydrofuran at –15° C. was added triethylamine (5.4 mL, 39 mmol) followed by isobutylchloroformate (5.1 mL, 39 mmol). The resulting mixture was stirred for 15 minutes and then was filtered into another flask and cooled to –15° C. Then there was added sodium borohydride (2.95 g, 78 mmol) in 5 mL of H$_2$O. The resulting mixture was allowed to stir at –15° C. for 20 minutes and then at room temperature for 1 h. The reaction was quenched with 10% aqueous HCl and the solvent was removed in vacuo. The residue was taken up in ethyl acetate, washed with brine, dried over MgSO$_4$, filtered through a pad of silica gel and concentrated in vacuo to afford 7.03 g (75%) of the title compound which was sufficiently pure for further reactions. MS (NH$_3$-DCI) 259 (M+NH$_4$)+.
Part B. Preparation of 2-(2-cyanophenylthio)benzyl bromide.

To a solution of 2-(2-cyanophenylthio)benzyl alcohol (2.03 g, 8.3 mmol) in 100 mL of methylene chloride at 0° C. was added carbon tetrabromide (3.02 g, 9.1 mmol) and triphenylphosphine (2.39 g, 9.1 mmol). The resulting mixture was allowed warm to room temperature and was stirred for 16 h. The reaction mixture was concentrated in vacuo, taken up in hexanes/ethyl acetate, washed with brine, dried over MgSO$_4$, filtered through a pad of silica gel and concentrated. The residue was taken up in hexanes/ether and filtered through a pad of silica gel to remove residual triphenylphosphine oxide. Concentration in vacuo afforded 2.49 g (98%) of the title compound which was sufficiently pure for further reactions. MS (NH$_3$-DCI) 321/323 (M+NH$_4$)+.
Part C. Preparation of trans-1-[[2-(2-cyanophenylthio) phenyl]methyl]-3-carbomethoxy-4-(3-cyanophenyl) pyrrolidine.

To a solution of trans-3-carbomethoxy-4-(3-cyanophenyl) pyrrolidine, trifluoroacetic acid salt from Example 2, Part B (0.59 g, 1.7 mmol) in 50 mL of acetonitrile was added 2-(2-cyanophenylthio)benzyl bromide (0.52 g, 1.7 mmol) and sodium bicarbonate (0.43 g, 5.1 mmol). The resulting mixture was stirred at 80° C. for 16 h. The reaction was allowed to cool to room temperature and was concentrated in vacuo. The residue was taken up in ethyl acetate, washed with H$_2$O and brine, dried over MgSO$_4$ and concentrated in vacuo. The residue was purified by flash chromatography (elution gradient 5:1 hexanes/ethyl acetate to 2:1 hexanes/ ethyl acetate) to afford 0.10 g (13%) of the title compound. MS (ESI) 454.2 (M+H)+.
Part D. Preparation of trans-1-[[2-(2-cyanophenylthio) phenyl]methyl]-3-carbomethoxy-4-(3-amidinophenyl) pyrrolidine, bistrifluoroacetic acid salt.

Following the procedure of Example 7, Part D, trans-1-[[2-(2-cyanophenylthio)phenyl]methyl]-3-carbomethoxy-4-

(3-cyanophenyl)pyrrolidine (0.104 g, 0.23 mmol) was converted with HCl gas/methanol and ammonium carbonate (0.10 g, 1.05 immol) into the title compound (12 mg, 10%) following HPLC purification. MS (ESI) 236.3 (M+2H)2+.

Example 17 trans-1-[(2'-aminosulfonyl-[1,1']-biphenyl-4-yl)sulfonyl]-3-carbomethoxy-4-(3-amidinophenyl)pyrrolidine, trifluoroacetic acid salt.
Part A. Preparation of trans-1-[(4-bromophenyl)sulfonyl]-3-carbomethoxy-4-(3-cyanophenyl)pyrrolidine.

To a solution of trans-3-carbomethoxy-4-(3-cyanophenyl)pyrrolidine, trifluoroacetic acid salt from Example 2, Part B (0.52 g, 1.5 mmol) in 100 mL of tetrahydrofuran at room temperature was added 4-bromobenzenesulfonyl chloride (0.38 g, 1.5 mmol) and triethylamine (0.4 mL, 3.0 mmol). The resulting mixture was allowed to stir for 16 h. The solvent was removed in vacuo and the residue was taken up in ethyl acetate, washed with saturated aqueous $NaHCO_3$ and brine, dried over $MgSO_4$ and concentrated in vacuo to afford 0.56 g (84%) of the title compound which was sufficiently pure for further reactions. MS (ESI) 449/451 (M+H)+.
Part B. Preparation of trans-1-[(2'-tert-butylaminosulfonyl-[1,1']-biphenyl-4-yl)sulfonyl]-3-carbomethoxy-4-(3-cyanophenyl)pyrrolidine.

Following the procedure described in Example 3, Part D, trans-1-[(4-bromophenyl)sulfonyl]-3-carbomethoxy-4-(3-cyanophenyl)pyrrolidine (0.40 g, 0.9 mmol) was converted into 0.20 g (38%) of the title compound following purification by flash chromatography (elution with 3:1 hexanes/ethyl acetate). MS (ESI) 582.3 (M+H)+.
Part C. Preparation of trans-1-[(2'-aminosulfonyl-[1,1']-biphenyl-4-yl)sulfonyl]-3-carbomethoxy-4-(3-amidinophenyl)pyrrolidine, trifluoroacetic acid salt.

Following the procedure of Example 3, Part E, trans-1-[(2'-tert-butylaminosulfonyl-[1,1']-biphenyl-4-yl)sulfonyl]-3-carbomethoxy-4-(3-cyanophenyl)pyrrolidine (0.20 g, 0.35 mmol) was converted sequentially with trifluoroacetic acid, HCl gas/methanol and ammonium carbonate (0.168 g, 1.75 mmol) into the title compound (15 mg, 7%) following HPLC purification. MS (ESI) 543.3 (M+H)+.

Example 18 trans-1-[(2'-aminosulfonyl-[1,1']-biphenyl-4-yl)sulfonyl]-3-carboisopropoxy-4-(3-amidinophenyl)pyrrolidine, trifluoroacetic acid salt.
Part A. Preparation of trans-1-[(2'-aminosulfonyl-[1,1']-biphenyl-4-yl)sulfonyl]-3-carboisopropoxy-4-(3-amidinophenyl)pyrrolidine, trifluoroacetic acid salt.

Following the procedure described in Example 11, Part A, trans-1-[(2'-aminosulfonyl-[1,1']-biphenyl- 4-yl)sulfonyl]-3-carbomethoxy-4-(3-amidinophenyl)pyrrolidine, trifluoroacetic acid salt (0.023 g, 0.035 mmol) was converted into 0.016 g (67%) of the title compound as a white powder following HPLC purification. MS (ESI) 571.3 (M+H)+.

Example 19 trans-1-[9-fluorenylmethoxycarbonyl]-3-carbomethoxy-4-(3-amidinophenyl)pyrrolidine, trifluoroacetic acid salt.
Part A. Preparation of trans-1-[9-fluorenylmethoxycarbonyl]-3-carbomethoxy-4-(3-cyanophenyl)pyrrolidine.

To a solution of trans-3-carbomethoxy-4-(3-cyanophenyl)pyrrolidine, trifluoroacetic acid salt (0.53 g, 1.54 mmol) from Example 2, Part B in 15 mL of acetonitrile was added 9-fluorenylmethyl succinimidyl carbonate (0.52 g, 1.54 mmol) and triethylamine (0.21 mL, 1.54 mmol). The resulting mixture was allowed to stir at room temperature for 16 h. The reaction mixture was diluted with ethyl acetate, washed with 10% aqueous HCl, saturated aqueous NaHCO3 and brine, dried over MgSO4 and concentrated in vacuo. The residue was purified by flash chromatography (elution with 3:1 hexanes/ethyl acetate) to afford 0.55 g (79%) of the title compound. MS (ESI) 453.4 (M+H)+.
Part B. Preparation of trans-1-[9-fluorenylmethoxycarbonyl]-3-carbomethoxy-4-(3-amidinophenyl)pyrrolidine, trifluoroacetic acid salt.

Following the procedure described in Example 1, Part D, trans-1-[9-fluorenylmethoxycarbonyl]-3-carbomethoxy-4-(3-cyanophenyl)pyrrolidine (0.11 g, 0.24 mmol) was treated with HCl/methanol and then with ammonium carbonate (0.14 g, 1.5 mmol) to afford after HPLC purification (C18 reverse phase column, elution with a $H_2O/CH_3CN$ gradient with 0.5% TFA) 0.050 g (36%) of the title compound as a white powder. MS (ESI) 470.3 (M+H)+.

Example 20 trans-2-benzyl-4-carbomethoxy-5-(3-amidinophenyl)isoxazolidine, trifluoroacetic acid salt.
Part A. Preparation of trans-2-benzyl-4-carbomethoxy-5-(3-cyanophenyl)isoxazolidine.

To a solution of methyl trans-3-cyanocinnamate (1.2 g, 6.5 mmol) in 20 mL of benzene was added benzylhydroxylamine (0.89 g, 7.2 mmol), paraformaldehyde (0.98 g, 32.5 mmol) and crushed 4 Å molecular sieves. The resulting mixture was stirred at 80° C. for 16 h. The reaction mixture was allowed to cool to room temperature, was filtered through celite and diluted with ethyl acetate. The solution was washed with $H_2O$ and brine, dried over $MgSO_4$, filtered through a pad of silica gel and concentrated in vacuo to afford 1.4 g (67%) of the title compound which was sufficiently pure for further reactions. MS ($CH_4$-CI) 323.1 (M+H)+.
Part B. Preparation of trans-2-benzyl-4-carbomethoxy-5-(3-amidinophenyl)isoxazolidine, trifluoroacetic acid salt.

A solution of trans-2-benzyl-4-carbomethoxy-5-(3-cyanophenyl)isoxazolidine (150 mg, 0.47 mmol) in 10 mL of anhydrous methanol and 30 mL of anhydrous chloroform was cooled to 0° C. Anhydrous HCl gas was bubbled through the solution for about 30 min (until solution saturated). The flask was then sealed and allowed to stand for 16 h at 0° C. The reaction mixture was concentrated in vacuo. The resulting solid was dissolved in 10 mL of anhydrous methanol and ammonium carbonate (0.27 g, 2.8 mmol) was added and the mixture was allowed to stir at room temperature for 24 h. The reaction mixture was concentrated in vacuo and purified by prep HPLC (C18 reverse phase column, elution with a $H_2O/CH_3CN$ gradient with 0.5% TFA) to afford 100 mg (47%) of the title compound as a white powder. MS (ESI) 340.2 (M+H)+.

Example 21 trans-2-[(2'-aminosulfonyl-[1,1']-biphenyl-4-yl)methyl]-4-carbomethoxy-5-(3-amidinophenyl)isoxazolidine, trifluoroacetic acid salt.
Part A. Preparation of 4-bromobenzaldehyde oxime.

To a solution of 4-bromobenzaldehyde (10.0 g, 54 mmol) in 200 mL of absolute ethanol and 50 mL of water was added hydroxylamine hydrochloride (4.5 g, 64.8 mmol) and sodium hydroxide (3.25 g, 81 mmol) as a solution in water. The resulting mixture was allowed to stir at room temperature for 16 h. A white solid had fallen out of solution. The mixture was concentrated in vacuo to about half its volume and the solid was collected by filtration, azeotroped with benzene and dried in vacuo to afford 9.8 g (90%) of the title compound as a white powder. $^1$H NMR (DMSO-$d_6$) d 8.1 (s, 1H), 7.52 (app q, 4H). MS ($H_2O$-GC/MS) 200/202 (M+H)+.

Part B. Preparation of 4-bromobenzylhydroxylamine.

To a solution of 4-bromobenzaldehyde oxime (2.0 g, 10 mmol) in 20 mL of methanol at 0° C. was added borane-pyridine complex (3.75 mL of an 8M in pyridine, 30 mmol) dropwise. To this solution was added 10% aqueous HCl dropwise over about 10 minutes. The resulting mixture was allowed to stir at 0° C. an additional 20 minutes and then it was made basic with solid $Na_2CO_3$. The mixture was diluted with ethyl acetate and washed with $H_2O$ and 10% aqueous HCl. The organics were discarded and the aqueous layer was made basic with $Na_2CO_3$ and extracted with ethyl acetate. This ethyl acetate layer was washed with brine, dried over $MgSO_4$ and concentrated in vacuo to afford 1.3 g (65%) of the title compound as a white solid. $^1H$ NMR ($CDCl_3$) d 7.45 (d, 2H), 7.19 (d, 2H), 5.35 (broad s, 2H), 3.93 (s, 2H).

Part C. Preparation of trans-2-(4-bromobenzyl)-4-carbomethoxy-5-(3-cyanophenyl)isoxazolidine.

To a solution of methyl trans-3-cyanocinnamate from Example 1, Part A (0.57 g, 3.04 mmol) in 10 mL of benzene was added 4-bromobenzylhydroxylamine (0.74 g, 3.65 mmol), paraformaldehyde (0.46 g, 15.2 mmol) and about 1 g of crushed 4 Å molecular sieves. The resulting mixture was stirred at 80° C. for 16 h. The reaction mixture was allowed to cool to room temperature, and was filtered through celite and diluted with ethyl acetate. The solution was washed with $H_2O$ and brine, dried over $MgSO_4$ and concentrated in vacuo. The residue was purified by flash chromatography (elution with 3:1 hexanes/ethyl acetate) to afford 0.75 g (63%) of the title compound as an oil. MS ($NH_3$-CI) 401/403 (M+H)+.

Part D. Preparation of trans-2-[(2'-tert-butylaminosulfonyl-[1,1']-biphenyl-4-yl)methyl]-4-carbomethoxy-5-(3-cyanophenyl)isoxazolidine.

To a solution of trans-2-(4-bromobenzyl)-4-carbomethoxy-5-(3-cyanophenyl)isoxazolidine (0.46 g, 1.15 mmol) in 20 mL of benzene was added 2-(tert-butylaminosulfonyl)phenylboronic acid (0.45 g, 1.72 mmol), tetrabutylammonium bromide (0.04 g, 0.12 mmol), sodium carbonate (0.36 g, 3.4 mmol) and 2 mL of $H_2O$. This mixture was degassed with a stream of nitrogen and then tetrakis(triphenylphosphine)palladium (0.14 g, 0.12 mmol) was added and the reaction mixture was stirred at 80° C. for 6 h. The mixture was allowed to cool to room temperature and then was diluted with ethyl acetate, washed with $H_2O$ and brine, dried over $MgSO_4$ and was concentrated in vacuo. The residue was purified by flash chromatography (elution with 2:1 hexanes/ethyl acetate) to afford 0.52 g (85%) of the title compound. MS (ESI) 534.4 (M+H)+.

Part E. Preparation of trans-2-[(2'-aminosulfonyl-[1,1']-biphenyl-4-yl)methyl]-4-carbomethoxy-5-(3-amidinophenyl)isoxazolidine, trifluoroacetic acid salt.

A solution of trans-1-[(2'-tert-butylaminosulfonyl-[1,1']-biphenyl-4-yl)methyl]-3-carbomethoxy-4-(3-cyanophenyl)isoxazolidine (0.52 g, 0.97 mmol) in 20 mL of trifluoroacetic acid was stirred at 70° C. for 1 h and then was allowed to cool to room temperature and was concentrated in vacuo. $^1H$ NMR ($CDCl_3$) indicated complete removal of the tert-butyl group. The crude residue was dissolved in 40 mL of anhydrous HCl and was cooled to 0° C. Anhydrous HCl gas was bubbled through the solution for about 30 min (until solution saturated). The flask was then sealed and allowed to stand for 16 h at 0° C. The reaction mixture was concentrated in vacuo. The resulting solid was dissolved in 35 mL of anhydrous methanol and ammonium carbonate (0.56 g, 5.8 mmol) was added and the mixture was allowed to stir at room temperature for 24 h. The reaction mixture was concentrated in vacuo and purified by prep HPLC (C18 reverse phase column, elution with a $H_2O/CH_3CN$ gradient with 0.5% TFA) to afford 350 mg (59%) of the title compound as a white powder. MS (ESI) 495.4 (M+H)+.

Example 22 trans-2-[(2'-aminosulfonyl-[1,1']-biphenyl-4-yl)methyl]-4-carboisopropoxy-5-(3-amidinophenyl)isoxazolidine, trifluoroacetic acid salt.

Part A. Preparation of trans-2-[(2'-aminosulfonyl-[1,1']-biphenyl-4-yl)methyl]-4-carboisopropoxy-5-(3-amidinophenyl)isoxazolidine, trifluoroacetic acid salt.

To a solution of trans-2-[(2'-aminosulfonyl-[1,1']-biphenyl-4-yl)methyl]-4-carbomethoxy-5-(3-amidinophenyl)isoxazolidine, trifluoroacetic acid salt (300 mg, 0.49 mmol) in 30 mL of isopropanol was added several drops of titanium (IV) isopropoxide. The resulting mixture was stirred at 80° C. for 16 h. The reaction was allowed to cool to room temperature and the solvent was removed in vacuo. The residue was triturated with ether and then was purified by HPLC under the conditions described in Example 1, Part D to afford 0.25 g (80%) of the title compound as a white powder. MS (ESI) 523.5 (M+H)+.

Example 23 trans-2-[(2'-aminosulfonyl-[1,1']-biphenyl-4-yl)methyl]-4-methoxymethyl-5-(3-amidinophenyl)isoxazolidine, trifluoroacetic acid salt.

Part A. Preparation of trans-3-cyanocinnamic acid.

To a solution of methyl trans-3-cyanocinnamate (4.74 g, 25.3 mmol) in 100 mL of tetrahydrofuran and 50 mL of $H_2O$ at room temperature was added lithium hydroxide monohydrate (2.65 g, 63.2 mmol). The resulting mixture was allowed to stir for 16 h. The tetrahydrofuran was removed in vacuo and the residue was diluted with saturated aqueous $NaHCO_3$ and washed with hexane. The organic layer was discarded. The aqueous layer was acidified and extracted with ethyl acetate. The organics were washed with brine, dried over $MgSO_4$ and concentrated in vacuo to afford 4.35 g (99%) of the title compound. $^1H$ NMR ($CDCl_3$): δ 8.21 (s, 1H), 8.02 (d, 1H), 7.85 (d, 1H), 7.62 (t, 1H), 7.61 (d, 1H), 6.73 (d, 1H).

Part B. Preparation of trans-3-cyanocinnamyl alcohol.

To a solution of trans-3-cyanocinnamic acid (1.66 g, 9.6 mmol) in 100 mL of tetrahydrofuran at −15° C. was added triethylamine (1.3 mL, 9.6 mmol) and isobutylchloroformate (1.3 mL, 9.6 mmol). The mixture was stirred for 15 minutes and then was filtered into another flask and cooled to −15° C. Sodium borohydride (0.73 g, 19.2 mmol) was added in 2 mL of $H_2O$ and the mixture was allowed to stir at −15° C. for 20 minutes and then at room temperature for 1 h. The reaction was quenched with 10% aqueous HCl and the solvent was removed in vacuo. The residue was diluted with ethyl acetate, washed with brine, dried over $MgSO_4$ and concentrated in vacuo to afford 1.43 g (93%) of the title compound. $^1H$ NMR ($CDCl_3$): δ 7.59 (s, 1H), 7.57 (d, 1H), 7.49 (d, 1H), 7.40 (t, 1H), 6.60 (d, 1H), 6.40 (dt, 1H), 4.35 (m, 2H), 2.23 (broad s, 1H).

Part C. Preparation of trans-3-cyanocinnamyl alcohol methyl ether.

To a suspension of 60% sodium hydride in mineral oil (0.36 g, washed with petroleum ether before use, 9.0 mmol) in 100 mL of tetrahydrofuran was added trans-3-cyanocinnamyl alcohol (1.43 g, 9.0 mmol). The resulting mixture was stirred at 60° C. for 1 h and then was allowed to cool to room temperature. To the resulting homogeneous solution was added methyl iodide (0.56 mL, 9.0 mmol) and the mixture was then stirred at 60° C. for 16 h. The reaction was quenched with ethanol and the solvent was removed in vacuo. The residue was dissolved in ethyl acetate, washed with brine, dried over MgSO$_4$ and concentrated in vacuo. The residue was purified by flash chromatography (elution with 6:1 hexanes/ethyl acetate to afford 1.21 g (78%) of the title compound. $^1$H NMR (CDCl$_3$): δ 7.59 (m, 2H), 7.45 (d, 1H), 7.39 (t, 1H), 6.57 (d, 1H), 6.30 (dt, 1H), 4.08 (dd, 2H), 3.38 (s, 3H).

Part D. Preparation of trans-2-[(2'-aminosulfonyl-[1,1']-biphenyl-4-yl)methyl]-4-methoxymethyl-5-(3-amidinophenyl)isoxazolidine, trifluoroacetic acid salt.

Following the procedures described in Example 21, Parts C–E, trans-3-cyanocinnamyl alcohol methyl ether was converted into the title compound which was a white powder following HPLC purification. MS (ESI) 481.3 (M+H)+.

Example 24 and Example 25 trans-1-(methylsulfonyl)-3-([2'-aminosulfonyl-[1,1']-biphenyl-4-yl)aminocarbonyl)-4-(3-amidinophenyl)pyrrolidine, trifluoroacetic acid salt (Example 24) and trans-1-(methylsulfonyl)-3-([2'-tert-butylaminosulfonyl-[1,1']-biphenyl-4-yl)aminocarbonyl)-4-(3-amidinophenyl) pyrrolidine, trifluoroacetic acid salt. (Example 25).

Part A. Preparation of methyl trans-3-cyanocinnamate.

To a solution of 3-cyanobenzaldehyde (10.0 g, 76 mmol) in 500 mL of methylene chloride was added methyl (triphenylphosphoranylidene)acetate (25.4 g, 76 mmol). The mixture was allowed to stir at room temperature for 16 h. The solvent was removed in vacuo and the residue was taken up in hexane/ethyl acetate and filtered through a large pad of silica gel. The solution was concentrated to afford 12.75 g (89%) of the cinnamate as a white solid which was sufficiently pure for further reactions. MS (H$_2$O-GC/MS): 188 (M+H)+.

Part B. Preparation of N-benzyl-N-(trimethylsilylmethyl)aminomethyl methyl ether.

To a stirred mixture of methanol (1.25 mL, 31 mmol) and 37% aqueous formaldehyde (2.56 mL, 31 mmol) at 0° C. was added N-benzyl-N-(trimethylsilylmethyl)amine (5.0 g, 26 mmol) dropwise over 5 minutes. The resulting mixture was stirred for 2 h. Anhydrous potassium carbonate (1.02 g, 7.4 mmol) was added and the mixture was stirred at 0° C. for 30 min. The reaction mixture was diluted with water and extracted twice with ether. The combined organic extracts were washed with brine, dried over sodium sulfate and concentrated in vacuo to afford 5.6 g (92%) of the title compound. $^1$H NMR (CDCl3): δ 7.30–7.15 (m, 5H), 3.95 (s, 2H), 3.71 (s, 2H), 3.19 (s, 3H), 2.14 (s, 2H).

Part C. Preparation of trans-1-benzyl-3-carbomethoxy-4-(3-cyanophenyl)pyrrolidine.

To a solution of N-benzyl-N-(trimethylsilylmethyl)aminomethyl methyl ether (1.64 g, 6.9 mmol) in 20 mL of methylene chloride at 0° C. was added methyl trans-3-cyanocinnamate (0.99 g, 5.3 mmol) followed by trifluoroacetic acid (0.041 mL, 0.53 mmol). The mixture was allowed to warm to room temperature and was stirred for 2 h. The reaction mixture was diluted with methylene chloride, washed with saturated aqueous NaHCO$_3$ and brine, dried over K$_2$CO$_3$ and concentrated in vacuo to afford 1.67 g (98%) of the title compound which was sufficiently pure for further reactions. MS (ESI) 321.1 (M+H)+.

Part D. Preparation of trans-3-carbomethoxy-4-(3-cyanophenyl)pyrrolidine, hydrochloride salt.

To a solution of trans-1-benzyl-3-carbomethoxy-4-(3-cyanophenyl)pyrrolidine (40.8 g, 127 mmol) in 600 mL of methylene chloride at 0° C. was added 1-chloroethyl chloroformate (12.8 mL, 127 mmol) dropwise. After stirring for 15 min the ice bath was removed and the mixture was stirred at 40° C. for 1 h. The reaction mixture was cooled and concentrated in vacuo. The residue was dissolved in absolute methanol and stirred at 60° C. for 1 h. The reaction mixture was cooled and concentrated in vacuo. The residue was dissolved in methylene chloride and then crashed out of solution by the addition of ether. The solid was filtered and dried in vacuo to give 23.3 g (69%) of the title compound as a white solid. MS (NH$_3$-CI) 231.3 (M+H)+.

Part E. Preparation of trans-1-(methylsuifonyl)-3-carbomethoxy-4-(3-cyanophenyl)pyrrolidine.

To a solution of trans-3-carbomethoxy-4-(3-cyanophenyl) pyrrolidine, hydrochloride salt (0.50 g, 1.87 mmol) in 10 mL of methylene chloride was added methanesulfonyl chloride (0.15 mL, 1.87 mmol) and triethylamine (0.52 mL, 3.74 mmol). The resulting mixture was allowed to stir at 25° C. for 16 h. The reaction was diluted with ethyl acetate, washed with 10% aq HCl, saturated aq NaHCO$_3$ and brine, dried (MgSO$_4$), filtered through a pad of silica gel and concentrated in vacuo to afford 0.54 g (93%) of the title compound which was sufficiently pure to be used directly in subsequent reactions. MS (ESI) 309.1 (M+H)+.

Part F. Preparation of trans-1-(methylsulfonyl)-3-carboxy-4-(3-cyanophenyl)pyrrolidine.

To a solution of trans-1-(methylsulfonyl)-3-carbomethoxy-4-(3-cyanophenyl)pyrrolidine (0.54 g, 1.75 mmol) in 10 mL of tetrahydrofuran and 5 mL of water was added lithium hydroxide monohydrate (0.15 g, 3.5 mmol). The mixture was allowed to stir at 25° C. for 3 h. Added saturated aq NaHCO3, extracted with 1:1 hexanes/ethyl acetate and discarded the organic layer. The aqueous layer was acidified with aq HCl and extracted with ethyl acetate. The organic layer was washed with brine, dried (MgSO$_4$) and concentrated in vacuo to afford 0.44 g (86%) of the title compound which was sufficiently pure to be used directly in subsequent reactions. MS (ESI) 295.3 (M+H)+.

Part G. Preparation of trans-1-(methylsulfonyl)-3-([2'-tert-butylaminosulfonyl-[1,1']-biphenyl-4-yl)aminocarbonyl)-4-(3-cyanophenyl)pyrrolidine.

To a solution of trans-1-(methylsulfonyl)-3-carboxy-4-(3-cyanophenyl)pyrrolidine (0.44 g, 1.5 mmol) in 15 mL of acetonitrile was added thionyl chloride (1.1 mL, 15 mmol). This mixture was stirred at 80° C. for 30 min and then cooled and concentrated in vacuo. The residue was dissolved in 10 mL of methylene chloride whereupon ([2'-tert-butylaminosulfonyl-[1,1']-biphenyl-4-yl)amine (0.59 g, 1.95 mmol) and triethylamine (2.1 mL, 15 mmol) were added. The reaction mixture was allowed to stir at 25° C. for 16 h. The reaction was diluted with ethyl acetate, washed with 10% aq HCl, saturated aq NaHCO$_3$ and brine, dried (MgSO$_4$), filtered through a pad of silica gel and concentrated in vacuo to afford 0.65 g (75%) of the title compound which was sufficiently pure to be used directly in subsequent reactions. MS (ESI) 581.5 (M+H)+.

Part H. Preparation of trans-1-(methylsulfonyl)-3-([2'-aminosulfonyl-[1,1']-biphenyl-4-yl)aminocarbonyl)-4-(3-amidinophenyl)pyrrolidine, trifluoroacetic acid salt and trans-1-(methylsulfonyl)-3-([2'-tert-butylaminosulfonyl-[1,1']-biphenyl-4-yl)aminocarbonyl)-4-(3-amidinophenyl) pyrrolidine, trifluoroacetic acid salt.

A solution of trans-1-(methylsulfonyl)-3-([2'-tert-butylaminosulfonyl-[1,1']-biphenyl-4-yl)aminocarbonyl)-4-(3-cyanophenyl)pyrrolidine (0.63 g, 1.08 mmol) in 50 mL of anhydrous methanol was cooled to 0° C. Anhydrous HCl gas was bubbled through the solution for about 30 min (until solution saturated). The flask was then sealed and allowed to stand for 16 h at 0° C. The reaction mixture was concentrated in vacuo. The resulting solid was dissolved in 20 mL of anhydrous methanol and ammonium carbonate (0.62 g, 6.48 mmol) was added and the mixture was allowed to stir at room temperature for 24 h. The reaction mixture was concentrated in vacuo and 120 mg of the residue was purified by prep HPLC (C18 reverse phase column, elution with a $H_2O/CH_3CN$ gradient with 0.5% TFA) to afford 65 mg (54%) of trans-1-(methylsulfonyl)-3-([2'-aminosulfonyl-[1,1']-biphenyl-4-yl)aminocarbonyl)-4-(3-amidinophenyl)pyrrolidine, trifluoroacetic acid salt as a white powder following lyophilization. MS (ESI) 542.3 (M+H)+. There was also obtained 20 mg (17%) of trans-1-(methylsulfonyl)-3-([2'-tert-butylaminosulfonyl-[1,1']-biphenyl-4-yl) aminocarbonyl)-4-(3-amidinophenyl)pyrrolidine, trifluoroacetic acid salt as a white powder following lyophilization. MS (ESI) 598.4 (M+H)+.

Example 26 cis-1-(methylsulfonyl)-3-([2'-aminosulfonyl-[1,1']-biphenyl-4-yl)aminocarbonyl)-4-(3-amidinophenyl) pyrrolidine, trifluoroacetic acid salt.

Part A. Preparation of methyl cis-3-cyanocinnamate.

To a solution of bis(2,2,2-trifluoroethyl) (methoxycarbonylmethyl)phosphonate (5.0 g, 15.7 mmol) and 18-crown-6 (20.7 g, 78.5 mmol) in 300 mL of tetrahydrofuran at −78° C. was added potassium bis(trimethylsilyl) amide (31.4 mL of a 0.5 M solution in toluene, 15.7 mmol) dropwise. After the addition was complete 3-cyanobenzaldehyde (2.06 g, 15.7 mmol) was added and the resulting mixture was stirred for 30 minutes at −78° C. The reaction was quenched by the addition of saturated aqueous $NH_4Cl$ and then extracted three times with ether. The combined ether extracts were washed with brine, dried over $Na_2SO_4$ and concentrated in vacuo to afford 2.86 g (97%) of the product which was sufficiently pure for further reactions. $^1H$ NMR ($CDCl_3$) δ 7.85 (s, 1H), 7.76 (d, 1H), 7.60 (d, 1H), 7.45 (t, 1H), 6.93 (d, 1H), 6.05 (d, 1H), 3.70 (s, 3H).

Part B. Preparation of cis-1-(methylsulfonyl)-3-([2'-aminosulfonyl-[1,1']-biphenyl-4-yl)aminocarbonyl)-4-(3-amidinophenyl)pyrrolidine, trifluoroacetic acid salt.

Following the procedures described in Example 1, Parts C–H, methyl cis-3-cyanocinnamate was converted into the title compound, a white powder following HPLC purification. MS (ESI) 542.4 (M+H)+.

Example 27 and Example 28 trans-1-(methylsulfonyl)-3-[[5-(2'-aminosulfonylphenyl-1-yl)pyridin-2-yl]aminocarbonyl]-4-(3-amidinophenyl) pyrrolidine, trifluoroacetic acid salt (Example 27) and trans-1-(methylsulfonyl)-3-[[5-(2'-tert-butylaminosulfonyl-phenyl-1-yl)pyridin-2-yl]aminocarbonyl]-4-(3-amidinophenyl)pyrrolidine, trifluoroacetic acid salt (Example 28).

Part A. Preparation of trans-1-(methylsulfonyl)-3-[[5-(2'-tert-butylaminosulfonylphenyl-1-yl)pyridin-2-yl] aminocarbonyl]-4-(3-cyanophenyl)pyrrolidine.

To a solution of trans-1-(methylsulfonyl)-3-carboxy-4-(3-cyanophenyl)pyrrolidine from Example 1, Part F (0.31 g, 1.06 mmol) in 15 mL of acetonitrile was added thionyl chloride (1.26 mL, 10.6 mmol). This mixture was stirred at 80° C. for 30 min and then cooled and concentrated in vacuo. The residue was dissolved in 10 mL of methylene chloride whereupon [[5-(2'-tert-butylaminosulfonylphenyl-1-yl)pyridin-2-yl]amine (0.41 g, 1.35 mmol) and triethylamine (1.5 mL, 10.6 mmol) were added. The reaction mixture was allowed to stir at 25° C. for 16 h. The reaction was diluted with ethyl acetate, washed with 10% aq HCl, saturated aq $NaHCO_3$ and brine, dried ($MgSO_4$), filtered through a pad of silica gel and concentrated in vacuo. The residue was purified by flash chromatography (elution with 2:1 hexanes/ethyl acetate) to afford 0.47 g (75%) of the title compound. MS (ESI) 582.5 (M+H)+.

Part B. Preparation of trans-1-(methylsulfonyl)-3-[[5-(2'-aminosulfonylphenyl-1-yl)pyridin-2-yl]aminocarbonyl]-4-(3-amidinophenyl)pyrrolidine, trifluoroacetic acid salt and trans-1-(methylsulfonyl)-3-[[5-(2'-tert-butylaminosulfonyl-phenyl-1-yl)pyridin-2-yl]aminocarbonyl]-4-(3-amidinophenyl)pyrrolidine, trifluoroacetic acid salt.

Following the procedures described in Example 1 and Example 2, Part H, trans-1-(methylsulfonyl)-3-[[5-(2'-tert-butylaminosulfonylphenyl-1-yl)pyridin-2-yl] aminocarbonyl]-4-(3-cyanophenyl)pyrrolidine was converted into the title compounds which were isolated as white powders following HPLC purification and lyophilization. trans-1-(methylsulfonyl)-3-[[5-(2'-aminosulfonylphenyl-1-yl)pyridin-2-yl]aminocarbonyl]-4-(3-amidinophenyl) pyrrolidine, trifluoroacetic acid salt (Example 27), MS (ESI) 272.3 (M+2H)2+. trans-1-(methylsulfonyl)-3-[[5-(2'-tert-butylaminosulfonylphenyl-1-yl)pyridin-2-yl] aminocarbonyl]-4-(3-amidinophenyl)pyrrolidine, trifluoroacetic acid salt (Example 28), MS (ESI) 300.3 (M+2H)2+.

Example 29

1-(methylsulfonyl)-3-([2'-aminosulfonyl-[1,1']-biphenyl-4-yl)aminocarbonyl)-4-(3-amidinophenyl)-$\Delta^3$-pyrroline, trifluoroacetic acid salt.

Part A. Preparation of ethyl 3-(3-cyanophenyl)propiolate.

To a solution of ethyl propiolate (5.0 g, 51 mmol) in 150 mL of tetrahydrofuran at −78° C. was added n-butyllithium (20.4 mL of a 2.5 M solution in hexane, 51 mmol) dropwise. The mixture was allowed to stir for 1 h at −78° C. and then zinc chloride (20.9 g, 153 mmol) was added in 150 mL of tetrahydrofuran and the resulting mixture was allowed to stir with warming to room temperature for 30 min. The mixture was cooled to 0° C. whereupon 3-iodobenzonitrile (5.84 g, 25.5 mmol) and bistriphenylphosphine palladium (II) chloride (0.91 g, 1.3 mmol) were added. The resulting mixture was allowed to stir at 50° C. for 16 h. After cooling to room temperature, the reaction was diluted with 150 mL of water and 150 mL of ether and then filtered through a pad of celite. The filtrate was extracted twice with ether and the combined organics were dried ($MgSO_4$) and concentrated in vacuo. The residue was purified by flash chromatography (elution with 10:1 hexanes/ethyl acetate) to afford 2.23 g (44%) of the title compound as a solid. $^1H$ NMR ($CDCl_3$) δ 7.85 (s, 1H), 7.80 (d, 1H), 7.74 (d, 1H), 7.53 (t, 1H), 4.31 (q, 2H), 1.37 (t, 3H).

Part B. Preparation of 1-benzyl-3-carbethoxy-4-(3-cyanophenyl)-$\Delta^3$-pyrroline.

To a solution of N-benzyl-N-(trimethylsilylmethyl) aminomethyl methyl ether from Example 1, Part B (3.09 g, 12.9 mmol) in 40 mL of methylene chloride at 0° C. was added ethyl 3-(3-cyanophenyl)propiolate (2.0 g, 10 mmol) followed by trifluoroacetic acid (0.06 mL, 0.75 mmol). The mixture was allowed to warm to room temperature and was stirred for 2 h. The reaction mixture was diluted with methylene chloride, washed with saturated aqueous $NaHCO_3$ and brine, dried over $K_2CO_3$ and concentrated in vacuo. The residue was purified by flash chromatography (elution with 3:1 hexanes/ethyl acetate) to afford 1.7 g (51%) of the title compound. MS (ESI) 333.4 (M+H)+.

Part C. Preparation of 3-carbethoxy-4-(3-cyanophenyl)-$\Delta^3$-pyrroline, hydrochloride salt.

Following the procedure of Example 1, Part D, 1-benzyl-3-carbethoxy-4-(3-cyanophenyl)-$\Delta^3$-pyrroline (1.3 g, 3.3 mmol) was converted into 0.8 g (73%) of the title compound. MS (ESI) 243.3 (M+H)+.

Part D. Preparation of 1-(methylsulfonyl)-3-carbethoxy-4-(3-cyanophenyl)-Δ³-pyrroline.

Following the procedure of Example 1, Part E, 3-carbethoxy-4-(3-cyanophenyl)-Δ³-pyrroline, hydrochloride salt (0.35 g, 1.26 mmol) was converted into 0.35 g (87%) of the title compound. MS (ESI) 323.4 (M+H)+. $^1$H NMR (CDCl$_3$) δ 7.62 (s, 1H), 7.58 (d, 1H), 7.50 (d, 1H), 7.42 (t, 1H), 4.50 (broad s, 4H), 4.05 (q, 2H), 2.85 (s, 3H), 1.10 (t, 3H).

Part E. Preparation of 1-(methylsulfonyl)-3-carboxy-4-(3-cyanophenyl)-Δ³-pyrroline.

To a solution of 1-(methylsulfonyl)-3-carbethoxy-4-(3-cyanophenyl)-Δ³-pyrroline (0.35 g, 1.1 mmol) in 5 mL of methanol and 5 mL of water was added potassium hydroxide (0.12 g, 2.2 mmol). This mixture was stirred at 60° C. for 2 h and then cooled to room temperature, diluted with water and extracted with 1:1 hexanes/ethyl acetate. The organics were discarded and the aqueous layer was acidified with aq HCl and extracted with ethyl acetate. The organic layer was washed with brine, dried (MgSO$_4$) and concentrated in vacuo to afford 0.20 g (63%) of the title compound which was sufficiently pure to be used directly in subsequent reactions. MS (ESI) 293.3 (M+H)+.

Part F. Preparation of 1-(methylsulfonyl)-3-([2'-tert-butylaminosulfonyl-[1,1']-biphenyl-4-yl)aminocarbonyl)-4-(3-cyanophenyl)-Δ³-pyrroline.

Following the procedures described in Example 1, Part G, 1-(methylsulfonyl)-3-carboxy-4-(3-cyanophenyl)-Δ³-pyrroline (0.2 g, 0.68 mmol) was converted into 0.1 g (26%) of the title compound. MS (ESI)

Part G. Preparation of 1-(methylsulfonyl)-3-([2'-aminosulfonyl-[1,1']-biphenyl-4-yl)aminocarbonyl)-4-(3-amidinophenyl)-Δ³-pyrroline, trifluoroacetic acid salt.

A solution of 1-(methylsulfonyl)-3-([2'-tert-butylaminosulfonyl-[1,1']-biphenyl-4-yl)aminocarbonyl)-4-(3-cyanophenyl)-Δ³-pyrroline (93 mg, 0.16 mmol) in 30 mL of anhydrous methanol was cooled to 0° C. Anhydrous HCl gas was bubbled through the solution for about 30 min (until solution saturated). The flask was then sealed and allowed to stand for 16 h at 0° C. The reaction mixture was concentrated in vacuo. The resulting solid was dissolved in 10 mL of anhydrous methanol and ammonium carbonate (80 mg, 0.8 mmol) was added and the mixture was allowed to stir at room temperature for 24 h. The reaction mixture was concentrated in vacuo and the residue was purified by prep HPLC (C18 reverse phase column, elution with a H$_2$O/CH$_3$CN gradient with 0.5% TFA) to afford 25 mg (25%) of the title compound as a white powder following lyophilization. MS (ESI) 540.3 (M+H)+.

Example 30

1-(benzyl)-3-([2'-aminosulfonyl-[1,1']-biphenyl-4-yl) aminocarbonyl)-4-(3-amidinoohenyl)-Δ³-pyrroline, bistrifluoroacetic acid salt.

Part A. Preparation of 1-(benzyl)-3-([2'-tert-butylaminosulfonyl-[1,1']-biphenyl-4-yl)aminocarbonyl)-4-(3-cyanophenyl)-Δ³-pyrroline.

To a solution of ([2'-tert-butylaminosulfonyl-[1,1']-biphenyl-4-yl)amine (1.10 g, 3.6 mmol) in methylene chloride was added trimethylaluminum dropwise (6.6 mL of a 2.0M solution in toluene, 13.2 mmol). The resulting solution was stirred at 25° C. for 30 min at which time gas evolution had ceased. To this solution was then added 1-benzyl-3-carbethoxy-4-(3-cyanophenyl)-Δ³-pyrroline from Example 6, Part B (1.0 g, 3.0 mmol) as a solution in methylene chloride. The resulting solution was stirred at 40° C. for 4 h, at which time the reaction mixture was cooled to 0° C. and quenched with saturated aq NH$_4$Cl. The mixture was diluted with ethyl acetate, washed with brine, dried (MgSO$_4$) and concentrated in vacuo. The residue was purified by flash chromatography (elution with 1:1 hexanes/ethyl acetate) to afford 0.8 g (45%) of the title compound. MS (ESI)

Part B. Preparation of 1-(benzyl)-3-([2'-aminosulfonyl-[1,1']-biphenyl-4-yl)aminocarbonyl)-4-(3-amidinophenyl)-Δ³-pyrroline, bistrifluoroacetic acid salt.

A solution of 1-(benzyl)-3-([2'-tert-butylaminosulfonyl-[1,1']-biphenyl-4-yl)aminocarbonyl)-4-(3-cyanophenyl)-Δ³-pyrroline (0.13 g, 0.2 mmol) in 10 mL of trifluoroacetic acid was stirred at 70° C. for 30 min and then was allowed to cool to room temperature and was concentrated in vacuo. $^1$H NMR (CDCl$_3$) indicated complete removal of the tert-butyl group. The crude residue was dissolved in 40 mL of anhydrous methanol and was cooled to 0° C. Anhydrous HCl gas was bubbled through the solution for about 30 min (until solution saturated). The flask was then sealed and allowed to stand for 16 h at 0° C. The reaction mixture was concentrated in vacuo. The resulting solid was dissolved in 10 mL of anhydrous methanol and ammonium carbonate (0.10 g, 1.0 mmol) was added and the mixture was allowed to stir at room temperature for 24 h. The reaction mixture was concentrated in vacuo and purified by prep HPLC (C18 reverse phase column, elution with a H$_2$O/CH$_3$CN gradient with 0.5% TFA) to afford 60 mg (45%) of the title compound as a white powder. MS (ESI) 276.8 (M+2H)2+.

Example 31 trans-1-(methylsulfonyl)-3-([2'-aminosulfonyl-[1,1']-biphenyl-4-yl)methylcarbonyl)-4-(3-amidinophenyl) pyrrolidine, trifluoroacetic acid salt.

Part A. Preparation of trans-3-cyanocinnamic acid.

To a solution of methyl trans-3-cyanocinnamate from Example 1, Part A, (4.74 g, 25.3 mmol) in 100 mL of tetrahydrofuran and 50 mL of H$_2$O at room temperature was added lithium hydroxide monohydrate (2.65 g, 63.2 mmol). The resulting mixture was allowed to stir for 16 h. The tetrahydrofuran was removed in vacuo and the residue was diluted with saturated aqueous NaHCO$_3$ and washed with hexane. The organic layer was discarded. The aqueous layer was acidified and extracted with ethyl acetate. The organics were washed with brine, dried over MgSO$_4$ and concentrated in vacuo to afford 4.35 g (99%) of the title compound. $^1$H NMR (CDCl$_3$): δ 8.21 (s, 1H), 8.02 (d, 1H), 7.85 (d, 1H), 7.62 (t, 1H), 7.61 (d, 1H), 6.73 (d, 1H).

Part B. Preparation of trans-3-cyanocinnamoyl chloride.

To a solution of trans-3-cyanocinnamic acid (1.25 g, 7.2 mmol) in 20 mL of benzene was added thionyl chloride (5 mL, 68 mmol). The reaction was stirred at 80° C. for 2 h at which time gas evolution had ceased. The mixture was cooled and concentrated in vacuo and was used directly in Part C without purification or characterization.

Part C. Preparation of (E)-1-(3-cyanophenyl)-4-(4-bromophenyl)-1-buten-3-one.

To a suspension of activated zinc dust (0.71 g, 10.8 mmol) in 20 mL of tetrahydrofuran was added a few drops of 1,2-dibromoethane and the resulting mixture was heated to 60° C. and stirred for 10 min. The reaction was cooled to 0° C. and then there was added 4-bromobenzyl bromide (2.2 g, 8.64 mmol) in 10 mL of tetrahydrofuran. This mixture was stirred at 0° C. for 2 h. This mixture was then added via cannula to a separate flask which contained lithium chloride (0.73 g, 17.3 mmol) and copper cyanide (0.77 g, 8.64 mmol) in 10 mL of tetrahydrofuran at −78° C. This solution was warmed to −10° C., stirred for 5 min and then cooled back to −78° C. To this mixture was then added the crude trans-3-cyanocinnamoyl chloride from Part B in 10 mL of tetrahydrofuran. The reaction was stirred with warming to room temperature for 4 h and then was quenched with saturated aq NH₄Cl. The mixture was diluted with ethyl acetate, washed with saturated aq NaHCO₃ and brine, dried (MgSO₄) and concentrated in vacuo. The residue was purified by flash chromatography (elution with 6:1 hexanes/ethyl acetate) to afford 0.8 g (35%) of the title compound. MS (NH₃-CI) 343/345 (M+NH₄)+.

Part D. Preparation of trans-1-benzyl-3-[(4-bromophenyl)methylcarbonyl]-4-(3-cyanophenyl)pyrrolidine.

To a solution of (E)-1-(3-cyanophenyl)-4-(4-bromophenyl)-1-buten-3-one (0.5 g, 1.53 mmol) in 10 mL of methylene chloride was added N-benzyl-N-(trimethylsilylmethyl)aminomethyl methyl ether from Example 1, Part B, (0.47 g, 2.0 mmol) and trifluoroacetic acid (0.012 mL, 0.15 mmol). The resulting solution was stirred at 25° C. for 2 h. The reaction was diluted with ethyl acetate, washed with saturated aq NaHCO₃ and brine, dried (MgSO₄), filtered through a pad of silica gel and concentrated in vacuo to afford 0.7 g (100%) of the title compound which was sufficiently pure to be used without purification. MS (ESI) 459.3/461.2 (M+H)+.

Part E. Preparation of trans-3-[(4-bromophenyl)methylcarbonyl]-4-(3-cyanophenyl)pyrrolidine, hydrochloride salt.

Following the procedures described in Example 1, Part D, trans-1-benzyl-3-[(4-bromophenyl)methylcarbonyl]-4-(3-cyanophenyl)pyrrolidine (0.7 g, 1.52 mmol) was converted into 0.5 g (82%) of the title compound which was sufficiently pure to be used without purification. MS (ESI) 369/371 (M+H)+.

Part F. Preparation of trans-1-(methylsulfonyl)-3-[(4-bromophenyl)methylcarbonyl]-4-(3-cyanophenyl)pyrrolidine.

Following the procedures described in Example 1, Part E, trans-3-[(4-bromophenyl)methylcarbonyl]-4-(3-cyanophenyl)pyrrolidine, hydrochloride salt (0.5 g, 1.23 mmol) was converted into 0.25 g (45%) of the title compound following flash chromatography purification (elution with 3:1 hexanes/ethyl acetate). ¹H NMR (CDCl₃) δ 7.48 (m, 1H), 7.35–7.25 (m, 5H), 6.8 (d, 2H), 3.7–3.6 (m, 3H), 3.50 (s, 2H), 3.42–3.30 (m, 3H), 2.81 (s, 3H).

Part G. Preparation of trans-1-(methylsulfonyl)-3-([2'-tert-butylaminosulfonyl-[1,1']-biphenyl-4-yl)methylcarbonyl)-4-(3-cyanophenyl)pyrrolidine.

To a solution of trans-1-(methylsulfonyl)-3-[(4-bromophenyl)methylcarbonyl]-4-(3-cyanophenyl)pyrrolidine (0.25 g, 0.56 mmol) in 10 mL of benzene was added 2-(tert-butylaminosulfonyl)phenylboronic acid (0.29 g, 1.12 mmol), tetrabutylammonium bromide (0.04 g, 0.11 mmol) and aqueous sodium carbonate (1.12 mL of a 2.0M aq solution, 2.24 mmol). This mixture was degassed with a stream of nitrogen and then tetrakis(triphenylphosphine)palladium (0.07 g, 0.06 mmol) was added and the reaction mixture was stirred at 80° C. for 6 h. The mixture was allowed to cool to room temperature and then was diluted with ethyl acetate, washed with H₂O and brine, dried over MgSO₄ and was concentrated in vacuo. The residue was purified by flash chromatography (elution with 1:1 hexanes/ethyl acetate) to afford 0.22 g (69%) of the title compound. MS (ESI) 580.4 (M+H)+.

Part H. Preparation of trans-1-(methylsulfonyl)-3-([2'-aminosulfonyl-[1,1']-biphenyl-4-yl)methylcarbonyl)-4-(3-amidinophenyl)pyrrolidine, trifluoroacetic acid salt.

Following the procedures of Example 29, Part G, trans-1-(methylsulfonyl)-3-([2'-tert-butylaminosulfonyl-[1,1']-biphenyl-4-yl)methylcarbonyl)-4-(3-cyanophenyl)pyrrolidine (0.15 g, 0.26 mmol) converted into 35 mg (21%) of the title compound as a white powder. MS (ESI) 541.4 (M+H)+.

Following the procedures described above, the compounds listed in Tables 1a and 1b were prepared.

TABLE 1a

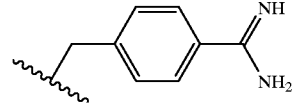

| Ex # | Ra | R⟨⟩m | Z | * * stereochemistry | J⟨⟩nA—B | MS (M + 2H)2+ |
|---|---|---|---|---|---|---|
| 1 | H | —CO₂Me | CH₂ | (±)-trans | —CH₂Ph | 169.8 |
| 2 | H | —CO₂Me | CH₂ | (±)-trans | 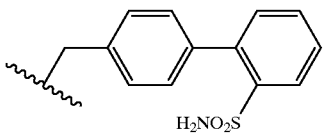 | 190.8 |
| 3 | H | —CO₂Me | CH₂ | (±)-trans | | 247.2 |

TABLE 1a-continued
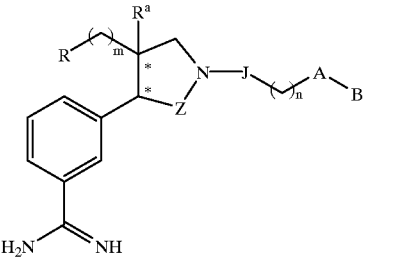
| Ex # | Ra | R$\left(\phantom{x}\right)_m$ | Z | **stereochemistry | J$\left(\phantom{x}\right)_n$A—B | MS (M + 2H)2+ |
|---|---|---|---|---|---|---|
| 4 | H | —CO$_2$Me | CH$_2$ | (3S, 4R) | 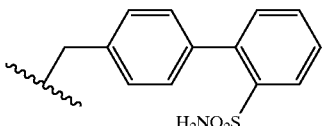 | 247.3 |
| 5 | H | —CO$_2$Me | CH$_2$ | (3R, 4S) |  | 247.3 |
| 6 | H | —CO$_2$H | CH$_2$ | (±)-trans | 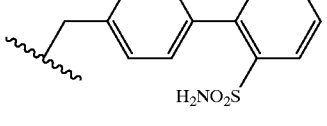 | 240.2 |
| 7 | H | —CONH$_2$ | CH$_2$ | (±)-trans |  | 239.8 |
| 8 | H | —CONMe$_2$ | CH$_2$ | (±)-trans | 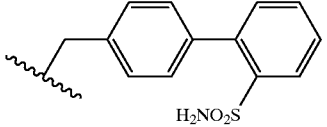 | 253.8 |
| 9 | H | —CO$_2$Me | CH$_2$ | (±)-cis |  | 247.2 |
| 10 | H | —CO$_2$H | CH$_2$ | (±)-cis | 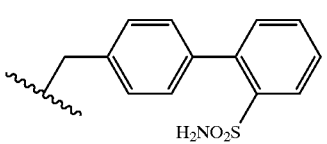 | 240.2 |
| 11 | H | —CO$_2$i-Pr | CH$_2$ | (±)-trans |  | 261.3 |

TABLE 1a-continued
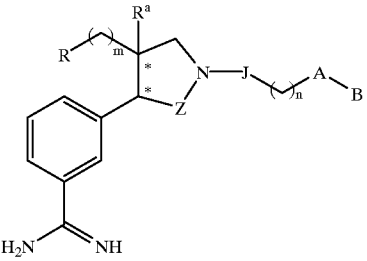
| Ex # | Ra | R⌒ₘ | Z | ** stereochemistry | J(⌒)ₙA~B | MS (M + 2H)2+ |
|---|---|---|---|---|---|---|
| 12 | H | —CO₂n-Bu | CH₂ | (±)-trans | 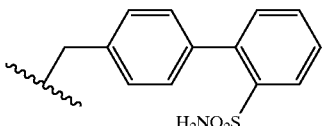 | 268.4 |
| 13 | H | —COMe | CH₂ | (±)-trans | 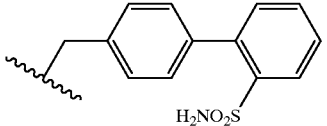 | 239.3 |
| 14 | CH₃ | —CO₂Et | CH₂ | (±)-trans | 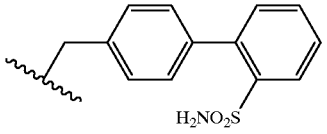 | 261.3 |
| 15 | H | —CO₂Me | CH₂ | (±)-trans | 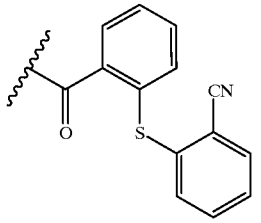 | 485.3 (M + H)+ |
| 16 | H | —CO₂Me | CH₂ | (±)-trans | 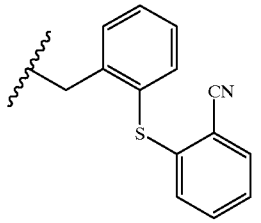 | 236.3 |
| 17 | H | —CO₂Me | CH₂ | (±)-trans | 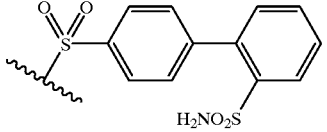 | 543.4 (M + H)+ |
| 18 | H | —CO₂i-Pr | CH₂ | (±)-trans | 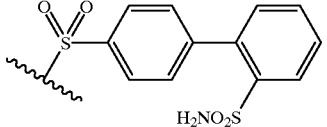 | 571.3 (M + H)+ |

TABLE 1a-continued

| Ex # | Ra | R~m~ | Z | ** stereochemistry | J(~n~)A-B | MS (M + 2H)2+ |
|---|---|---|---|---|---|---|
| 19 | H | —CO$_2$Me | CH$_2$ | (±)-trans | (fluorenylmethyl ester) | 470.3 (M + H)+ |
| 20 | H | —CO$_2$Me | O | (±)-trans | —CH$_2$Ph | 340.2 (M + H)+ |
| 21 | H | —CO$_2$Me | O | (±)-trans | (4'-(2-H$_2$NO$_2$S-phenyl)benzyl) | 495.4 (M + H)+ |
| 22 | H | —CO$_2$i-Pr | O | (±)-trans | (4'-(2-H$_2$NO$_2$S-phenyl)benzyl) | 523.5 (M + H)+ |
| 23 | H | —CH$_2$OMe | O | (±)-trans | (4'-(2-H$_2$NO$_2$S-phenyl)benzyl) | 481.3 (M + H)+ |

TABLE 1b

| Ex # | R | bond a | J' | A' | R$^4$ | MS (ESI) (M + H)+ |
|---|---|---|---|---|---|---|
| 24 | SO$_2$Me | (±)-trans | NH | CH | SO$_2$NH$_2$ | 542.3 |
| 25 | SO$_2$Me | (±)-trans | NH | CH | SO$_2$NHt-Bu | 598.4 |
| 26 | SO$_2$Me | (±)-cis | NH | CH | SO$_2$NH$_2$ | 542.4 |

TABLE 1b-continued

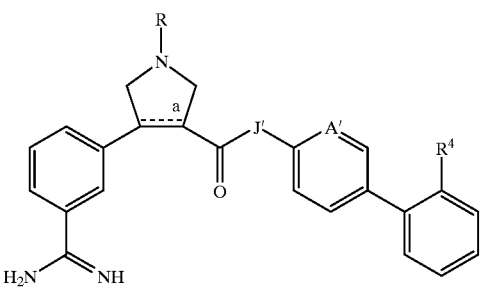

| Ex # | R | bond a | J' | A' | R[4] | MS (ESI) | (M + H)+ |
|---|---|---|---|---|---|---|---|
| 27 | SO$_2$Me | (±)-trans | NH | N | SO$_2$NH$_2$ | 272.3 | (M + 2H)2+ |
| 28 | SO$_2$Me | (±)-trans | NH | N | SO$_2$NHt-Bu | 300.3 | (M + 2H)2+ |
| 29 | SO$_2$Me | double | NH | CH | SO$_2$NH$_2$ | 540.3 | |
| 30 | CH$_2$Ph | double | NH | CH | SO$_2$NH$_2$ | 276.8 | (M + 2H)2+ |
| 31 | SO$_2$Me | (±)-trans | CH$_2$ | CH | SO$_2$NH$_2$ | 541.4 | |

Tables 2 through 18 identify additional representative conpounds of this invention which can be prepared by the methods described in Schemes 1–18 and in Examples 1–31 above.

TABLE 2

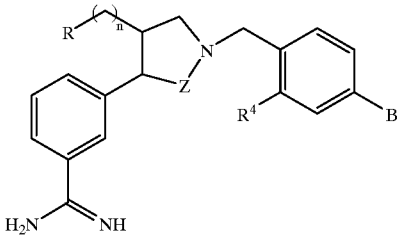

| Ex # | R | n | Z | R[4] | B |
|---|---|---|---|---|---|
| 1 | —CO$_2$Me | 0 | CH$_2$ | F | 2-sulfonamidophenyl |
| 2 | —CO$_2$Me | 0 | CH$_2$ | CH$_3$ | 2-sulfonamidophenyl |
| 3 | —CO$_2$Me | 0 | CH$_2$ | F | 2-CF$_3$-phenyl |
| 4 | —CO$_2$Me | 0 | CH$_2$ | CH$_3$ | 2-CF$_3$-phenyl |
| 5 | —CO$_2$Me | 0 | CH$_2$ | H | 2-CF$_3$-phenyl |
| 6 | —CO$_2$Me | 0 | CH$_2$ | F | phenyl |
| 7 | —CO$_2$Me | 0 | CH$_2$ | CH$_3$ | phenyl |
| 8 | —CO$_2$Me | 0 | CH$_2$ | H | phenyl |
| 9 | —CO$_2$Me | 0 | CH$_2$ | F | amidino |
| 10 | —CO$_2$Me | 0 | CH$_2$ | CH$_3$ | amidino |
| 11 | —CH$_2$OMe | 0 | CH$_2$ | H | 2-methylaminosulfonylphenyl |
| 12 | —CH$_2$OMe | 0 | CH$_2$ | F | 2-sulfonamidophenyl |
| 13 | —CH$_2$OMe | 0 | CH$_2$ | CH$_3$ | 2-sulfonamidophenyl |
| 14 | —CH$_2$OMe | 0 | CH$_2$ | F | 2-CF$_3$-phenyl |
| 15 | —CH$_2$OMe | 0 | CH$_2$ | CH$_3$ | 2-CF$_3$-phenyl |
| 16 | —CH$_2$OMe | 0 | CH$_2$ | H | 2-CF$_3$-phenyl |
| 17 | —CH$_2$OMe | 0 | CH$_2$ | F | phenyl |
| 18 | —CH$_2$OMe | 0 | CH$_2$ | CH$_3$ | phenyl |
| 19 | —CH$_2$OMe | 0 | CH$_2$ | H | phenyl |
| 20 | —CH$_2$OMe | 0 | CH$_2$ | F | amidino |
| 21 | —CH$_2$OMe | 0 | CH$_2$ | CH$_3$ | amidino |
| 22 | —CH$_2$OMe | 0 | CH$_2$ | H | amidino |
| 23 | —SO$_2$CH$_3$ | 0 | CH$_2$ | H | 2-sulfonamidophenyl |
| 24 | —SO$_2$CH$_3$ | 0 | CH$_2$ | F | 2-sulfonamidophenyl |
| 25 | —SO$_2$CH$_3$ | 0 | CH$_2$ | CH$_3$ | 2-sulfonamidophenyl |
| 26 | —SO$_2$CH$_3$ | 0 | CH$_2$ | F | 2-CF$_3$-phenyl |
| 27 | —SO$_2$CH$_3$ | 0 | CH$_2$ | CH$_3$ | 2-CF$_3$-phenyl |
| 28 | —SO$_2$CH$_3$ | 0 | CH$_2$ | H | 2-CF$_3$-phenyl |
| 29 | —SO$_2$CH$_3$ | 0 | CH$_2$ | F | phenyl |
| 30 | —SO$_2$CH$_3$ | 0 | CH$_2$ | CH$_3$ | phenyl |
| 31 | —SO$_2$CH$_3$ | 0 | CH$_2$ | H | phenyl |

TABLE 2-continued

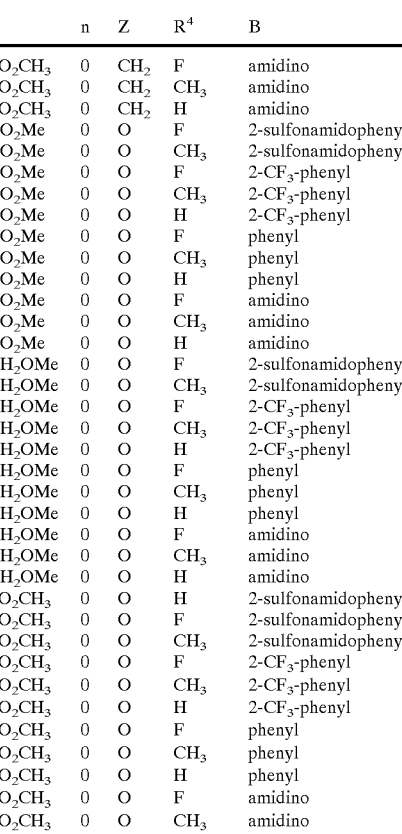

| Ex # | R | n | Z | R[4] | B |
|---|---|---|---|---|---|
| 32 | —SO$_2$CH$_3$ | 0 | CH$_2$ | F | amidino |
| 33 | —SO$_2$CH$_3$ | 0 | CH$_2$ | CH$_3$ | amidino |
| 34 | —SO$_2$CH$_3$ | 0 | CH$_2$ | H | amidino |
| 35 | —CO$_2$Me | 0 | O | F | 2-sulfonamidophenyl |
| 36 | —CO$_2$Me | 0 | O | CH$_3$ | 2-sulfonamidophenyl |
| 37 | —CO$_2$Me | 0 | O | F | 2-CF$_3$-phenyl |
| 38 | —CO$_2$Me | 0 | O | CH$_3$ | 2-CF$_3$-phenyl |
| 39 | —CO$_2$Me | 0 | O | H | 2-CF$_3$-phenyl |
| 40 | —CO$_2$Me | 0 | O | F | phenyl |
| 41 | —CO$_2$Me | 0 | O | CH$_3$ | phenyl |
| 42 | —CO$_2$Me | 0 | O | H | phenyl |
| 43 | —CO$_2$Me | 0 | O | F | amidino |
| 44 | —CO$_2$Me | 0 | O | CH$_3$ | amidino |
| 45 | —CO$_2$Me | 0 | O | H | amidino |
| 46 | —CH$_2$OMe | 0 | O | F | 2-sulfonamidophenyl |
| 47 | —CH$_2$OMe | 0 | O | CH$_3$ | 2-sulfonamidophenyl |
| 48 | —CH$_2$OMe | 0 | O | F | 2-CF$_3$-phenyl |
| 49 | —CH$_2$OMe | 0 | O | CH$_3$ | 2-CF$_3$-phenyl |
| 50 | —CH$_2$OMe | 0 | O | H | 2-CF$_3$-phenyl |
| 51 | —CH$_2$OMe | 0 | O | F | phenyl |
| 52 | —CH$_2$OMe | 0 | O | CH$_3$ | phenyl |
| 53 | —CH$_2$OMe | 0 | O | H | phenyl |
| 54 | —CH$_2$OMe | 0 | O | F | amidino |
| 55 | —CH$_2$OMe | 0 | O | CH$_3$ | amidino |
| 56 | —CH$_2$OMe | 0 | O | H | amidino |
| 57 | —SO$_2$CH$_3$ | 0 | O | H | 2-sulfonamidophenyl |
| 58 | —SO$_2$CH$_3$ | 0 | O | F | 2-sulfonamidophenyl |
| 59 | —SO$_2$CH$_3$ | 0 | O | CH$_3$ | 2-sulfonamidophenyl |
| 60 | —SO$_2$CH$_3$ | 0 | O | F | 2-CF$_3$-phenyl |
| 61 | —SO$_2$CH$_3$ | 0 | O | CH$_3$ | 2-CF$_3$-phenyl |
| 62 | —SO$_2$CH$_3$ | 0 | O | H | 2-CF$_3$-phenyl |
| 63 | —SO$_2$CH$_3$ | 0 | O | F | phenyl |
| 64 | —SO$_2$CH$_3$ | 0 | O | CH$_3$ | phenyl |
| 65 | —SO$_2$CH$_3$ | 0 | O | H | phenyl |
| 66 | —SO$_2$CH$_3$ | 0 | O | F | amidino |
| 67 | —SO$_2$CH$_3$ | 0 | O | CH$_3$ | amidino |

TABLE 2-continued

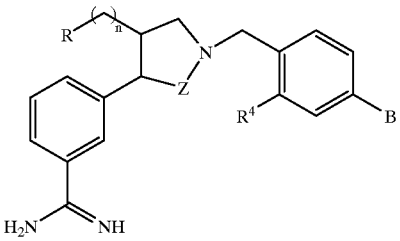

| Ex # | R | n | Z | R4 | B |
|---|---|---|---|---|---|
| 68 | —SO$_2$CH$_3$ | 0 | O | H | amidino |
| 69 | —CO$_2$Me | 1 | CH$_2$ | H | 2-ethylaminosulfonylphenyl |
| 70 | —CO$_2$Me | 1 | CH$_2$ | F | 2-sulfonamidophenyl |
| 71 | —CO$_2$Me | 1 | CH$_2$ | CH$_3$ | 2-sulfonamidophenyl |
| 72 | —CO$_2$Me | 1 | CH$_2$ | F | 2-CF$_3$-phenyl |
| 73 | —CO$_2$Me | 1 | CH$_2$ | CH$_3$ | 2-CF$_3$-phenyl |
| 74 | —CO$_2$Me | 1 | CH$_2$ | H | 2-CF$_3$-phenyl |
| 75 | —CO$_2$Me | 1 | CH$_2$ | F | phenyl |
| 76 | —CO$_2$Me | 1 | CH$_2$ | CH$_3$ | phenyl |
| 77 | —CO$_2$Me | 1 | CH$_2$ | H | phenyl |
| 78 | —CO$_2$Me | 1 | CH$_2$ | F | amidino |
| 79 | —CO$_2$Me | 1 | CH$_2$ | CH$_3$ | amidino |
| 80 | —CO$_2$Me | 1 | CH$_2$ | H | amidino |
| 81 | —CH$_2$OMe | 1 | CH$_2$ | H | 2-sulfonamidophenyl |
| 82 | —CH$_2$OMe | 1 | CH$_2$ | F | 2-methylaminosulfonylphenyl |
| 83 | —CH$_2$OMe | 1 | CH$_2$ | CH$_3$ | 2-sulfonamidophenyl |
| 84 | —CH$_2$OMe | 1 | CH$_2$ | F | 2-CF$_3$-phenyl |
| 85 | —CH$_2$OMe | 1 | CH$_2$ | CH$_3$ | 2-CF$_3$-phenyl |
| 86 | —CH$_2$OMe | 1 | CH$_2$ | H | 2-CF$_3$-phenyl |
| 87 | —CH$_2$OMe | 1 | CH$_2$ | F | phenyl |
| 88 | —CH$_2$OMe | 1 | CH$_2$ | CH$_3$ | phenyl |
| 89 | —CH$_2$OMe | 1 | CH$_2$ | H | phenyl |
| 90 | —CH$_2$OMe | 1 | CH$_2$ | F | amidino |
| 91 | —CH$_2$OMe | 1 | CH$_2$ | CH$_3$ | amidino |
| 92 | —CH$_2$OMe | 1 | CH$_2$ | H | amidino |
| 93 | —SO$_2$CH$_3$ | 1 | CH$_2$ | H | 2-sulfonamidophenyl |
| 94 | —SO$_2$CH$_3$ | 1 | CH$_2$ | F | 2-sulfonamidophenyl |
| 95 | —SO$_2$CH$_3$ | 1 | CH$_2$ | CH$_3$ | 2-sulfonamidophenyl |
| 96 | —SO$_2$CH$_3$ | 1 | CH$_2$ | F | 2-CF$_3$-phenyl |
| 97 | —SO$_2$CH$_3$ | 1 | CH$_2$ | CH$_3$ | 2-CF$_3$-phenyl |
| 98 | —SO$_2$CH$_3$ | 1 | CH$_2$ | H | 2-CF$_3$-phenyl |
| 99 | —SO$_2$CH$_3$ | 1 | CH$_2$ | F | phenyl |
| 101 | —SO$_2$CH$_3$ | 1 | CH$_2$ | CH$_3$ | phenyl |
| 102 | —SO$_2$CH$_3$ | 1 | CH$_2$ | H | phenyl |
| 103 | —SO$_2$CH$_3$ | 1 | CH$_2$ | F | amidino |
| 104 | —SO$_2$CH$_3$ | 1 | CH$_2$ | CH$_3$ | amidino |
| 105 | —SO$_2$CH$_3$ | 1 | CH$_2$ | H | amidino |
| 106 | —CO$_2$Me | 1 | O | H | 2-sulfonamidophenyl |
| 107 | —CO$_2$Me | 1 | O | F | 2-sulfonamidophenyl |
| 108 | —CO$_2$Me | 1 | O | CH$_3$ | 2-ethylaminosulfonylphenyl |
| 109 | —CO$_2$Me | 1 | O | F | 2-CF$_3$-phenyl |
| 110 | —CO$_2$Me | 1 | O | CH$_3$ | 2-CF$_3$-phenyl |
| 111 | —CO$_2$Me | 1 | O | H | 2-CF$_3$-phenyl |
| 112 | —CO$_2$Me | 1 | O | F | phenyl |
| 113 | —CO$_2$Me | 1 | O | CH$_3$ | phenyl |
| 114 | —CO$_2$Me | 1 | O | H | phenyl |
| 115 | —CO$_2$Me | 1 | O | F | amidino |
| 116 | —CO$_2$Me | 1 | O | CH$_3$ | amidino |
| 117 | —CO$_2$Me | 1 | O | H | amidino |
| 118 | —CH$_2$OMe | 1 | O | H | 2-sulfonamidophenyl |
| 119 | —CH$_2$OMe | 1 | O | F | 2-sulfonamidophenyl |
| 120 | —CH$_2$OMe | 1 | O | CH$_3$ | 2-sulfonamidophenyl |
| 121 | —CH$_2$OMe | 1 | O | F | 2-CF$_3$-phenyl |
| 122 | —CH$_2$OMe | 1 | O | CH$_3$ | 2-CF$_3$-phenyl |
| 123 | —CH$_2$OMe | 1 | O | H | 2-CF$_3$-phenyl |
| 124 | —CH$_2$OMe | 1 | O | F | phenyl |
| 125 | —CH$_2$OMe | 1 | O | CH$_3$ | phenyl |
| 126 | —CH$_2$OMe | 1 | O | H | phenyl |
| 127 | —CH$_2$OMe | 1 | O | F | amidino |
| 128 | —CH$_2$OMe | 1 | O | CH$_3$ | amidino |
| 129 | —CH$_2$OMe | 1 | O | H | amidino |
| 130 | —SO$_2$CH$_3$ | 1 | O | H | 2-sulfonamidophenyl |
| 131 | —SO$_2$CH$_3$ | 1 | O | F | 2-sulfonamidophenyl |
| 132 | —SO$_2$CH$_3$ | 1 | O | CH$_3$ | 2-sulfonamidophenyl |

TABLE 2-continued

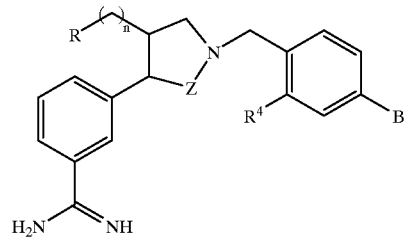

| Ex # | R | n | Z | R4 | B |
|---|---|---|---|---|---|
| 133 | —SO$_2$CH$_3$ | 1 | O | F | 2-CF$_3$-phenyl |
| 134 | —SO$_2$CH$_3$ | 1 | O | CH$_3$ | 2-CF$_3$-phenyl |
| 135 | —SO$_2$CH$_3$ | 1 | O | H | 2-CF$_3$-phenyl |
| 136 | —SO$_2$CH$_3$ | 1 | O | F | phenyl |
| 137 | —SO$_2$CH$_3$ | 1 | O | CH$_3$ | phenyl |
| 138 | —SO$_2$CH$_3$ | 1 | O | H | phenyl |
| 139 | —SO$_2$CH$_3$ | 1 | O | F | amidino |
| 140 | —SO$_2$CH$_3$ | 1 | O | CH$_3$ | amidino |
| 141 | —SO$_2$CH$_3$ | 1 | O | H | amidino |

TABLE 3

| Ex # | R | n | Z | R4 | B |
|---|---|---|---|---|---|
| 1 | —CO$_2$Me | 0 | CH$_2$ | H | 2-sulfonamidophenyl |
| 2 | —CO$_2$Me | 0 | CH$_2$ | F | 2-sulfonamidophenyl |
| 3 | —CO$_2$Me | 0 | CH$_2$ | CH$_3$ | 2-methylaminosulfonylphenyl |
| 4 | —CO$_2$Me | 0 | CH$_2$ | F | 2-CF$_3$-phenyl |
| 5 | —CO$_2$Me | 0 | CH$_2$ | CH$_3$ | 2-CF$_3$-phenyl |
| 6 | —CO$_2$Me | 0 | CH$_2$ | H | 2-CF$_3$-phenyl |
| 7 | —CO$_2$Me | 0 | CH$_2$ | F | phenyl |
| 8 | —CO$_2$Me | 0 | CH$_2$ | CH$_3$ | phenyl |
| 9 | —CO$_2$Me | 0 | CH$_2$ | H | phenyl |
| 10 | —CO$_2$Me | 0 | CH$_2$ | F | amidino |
| 11 | —CO$_2$Me | 0 | CH$_2$ | CH$_3$ | amidino |
| 12 | —CH$_2$OMe | 0 | CH$_2$ | H | 2-sulfonamidophenyl |
| 13 | —CH$_2$OMe | 0 | CH$_2$ | F | 2-ethylaminosulfonylphenyl |
| 14 | —CH$_2$OMe | 0 | CH$_2$ | CH$_3$ | 2-sulfonamidophenyl |
| 15 | —CH$_2$OMe | 0 | CH$_2$ | F | 2-CF$_3$-phenyl |
| 16 | —CH$_2$OMe | 0 | CH$_2$ | CH$_3$ | 2-CF$_3$-phenyl |
| 17 | —CH$_2$OMe | 0 | CH$_2$ | H | 2-CF$_3$-phenyl |
| 18 | —CH$_2$OMe | 0 | CH$_2$ | F | phenyl |
| 19 | —CH$_2$OMe | 0 | CH$_2$ | CH$_3$ | phenyl |
| 20 | —CH$_2$OMe | 0 | CH$_2$ | H | phenyl |
| 21 | —CH$_2$OMe | 0 | CH$_2$ | F | amidino |
| 22 | —CH$_2$OMe | 0 | CH$_2$ | CH$_3$ | amidino |
| 23 | —CH$_2$OMe | 0 | CH$_2$ | H | amidino |
| 24 | —SO$_2$CH$_3$ | 0 | CH$_2$ | H | 2-sulfonamidophenyl |
| 25 | —SO$_2$CH$_3$ | 0 | CH$_2$ | F | 2-sulfonamidophenyl |
| 26 | —SO$_2$CH$_3$ | 0 | CH$_2$ | CH$_3$ | 2-sulfonamidophenyl |
| 27 | —SO$_2$CH$_3$ | 0 | CH$_2$ | F | 2-CF$_3$-phenyl |
| 28 | —SO$_2$CH$_3$ | 0 | CH$_2$ | CH$_3$ | 2-CF$_3$-phenyl |
| 29 | —SO$_2$CH$_3$ | 0 | CH$_2$ | H | 2-CF$_3$-phenyl |
| 30 | —SO$_2$CH$_3$ | 0 | CH$_2$ | F | phenyl |
| 31 | —SO$_2$CH$_3$ | 0 | CH$_2$ | CH$_3$ | phenyl |
| 32 | —SO$_2$CH$_3$ | 0 | CH$_2$ | H | phenyl |
| 33 | —SO$_2$CH$_3$ | 0 | CH$_2$ | F | amidino |
| 34 | —SO$_2$CH$_3$ | 0 | CH$_2$ | CH$_3$ | amidino |
| 35 | —SO$_2$CH$_3$ | 0 | CH$_2$ | H | amidino |
| 36 | —CO$_2$Me | 0 | O | H | 2-sulfonamidophenyl |

TABLE 3-continued

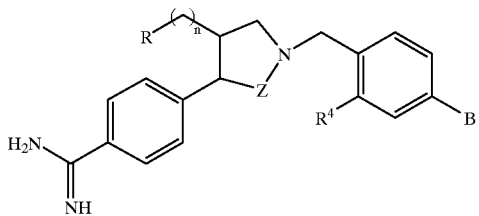

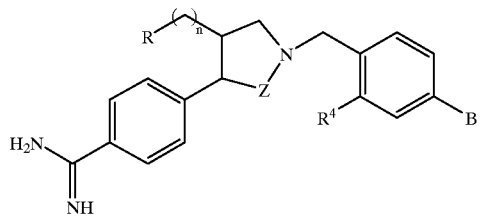

| Ex # | R | n | Z | R⁴ | B |
|---|---|---|---|---|---|
| 37 | —CO₂Me | 0 | O | F | 2-ethylaminosulfonylphenyl |
| 38 | —CO₂Me | 0 | O | CH₃ | 2-sulfonamidophenyl |
| 39 | —CO₂Me | 0 | O | F | 2-CF₃-phenyl |
| 40 | —CO₂Me | 0 | O | CH₃ | 2-CF₃-phenyl |
| 41 | —CO₂Me | 0 | O | H | 2-CF₃-phenyl |
| 42 | —CO₂Me | 0 | O | F | phenyl |
| 43 | —CO₂Me | 0 | O | CH₃ | phenyl |
| 44 | —CO₂Me | 0 | O | H | phenyl |
| 45 | —CO₂Me | 0 | O | F | amidino |
| 46 | —CO₂Me | 0 | O | CH₃ | amidino |
| 47 | —CO₂Me | 0 | O | H | amidino |
| 48 | —CH₂OMe | 0 | O | H | 2-sulfonamidophenyl |
| 49 | —CH₂OMe | 0 | O | F | 2-sulfonamidophenyl |
| 50 | —CH₂OMe | 0 | O | CH₃ | 2-methylaminosulfonylphenyl |
| 51 | —CH₂OMe | 0 | O | F | 2-CF₃-phenyl |
| 52 | —CH₂OMe | 0 | O | CH₃ | 2-CF₃-phenyl |
| 53 | —CH₂OMe | 0 | O | H | 2-CF₃-phenyl |
| 54 | —CH₂OMe | 0 | O | F | phenyl |
| 55 | —CH₂OMe | 0 | O | CH₃ | phenyl |
| 56 | —CH₂OMe | 0 | O | H | phenyl |
| 57 | —CH₂OMe | 0 | O | F | amidino |
| 58 | —CH₂OMe | 0 | O | CH₃ | amidino |
| 59 | —CH₂OMe | 0 | O | H | amidino |
| 60 | —SO₂CH₃ | 0 | O | H | 2-sulfonamidophenyl |
| 61 | —SO₂CH₃ | 0 | O | F | 2-sulfonamidophenyl |
| 62 | —SO₂CH₃ | 0 | O | CH₃ | 2-sulfonamidophenyl |
| 63 | —SO₂CH₃ | 0 | O | F | 2-CF₃-phenyl |
| 64 | —SO₂CH₃ | 0 | O | CH₃ | 2-CF₃-phenyl |
| 65 | —SO₂CH₃ | 0 | O | H | 2-CF₃-phenyl |
| 66 | —SO₂CH₃ | 0 | O | F | phenyl |
| 67 | —SO₂CH₃ | 0 | O | CH₃ | phenyl |
| 68 | —SO₂CH₃ | 0 | O | H | phenyl |
| 69 | —SO₂CH₃ | 0 | O | F | amidino |
| 70 | —SO₂CH₃ | 0 | O | CH₃ | amidino |
| 71 | —SO₂CH₃ | 0 | O | H | amidino |
| 72 | —CO₂Me | 1 | CH₂ | H | 2-sulfonamidophenyl |
| 73 | —CO₂Me | 1 | CH₂ | F | 2-methylaminosulfonylphenyl |
| 74 | —CO₂Me | 1 | CH₂ | CH₃ | 2-sulfonamidophenyl |
| 75 | —CO₂Me | 1 | CH₂ | F | 2-CF₃-phenyl |
| 76 | —CO₂Me | 1 | CH₂ | CH₃ | 2-CF₃-phenyl |
| 77 | —CO₂Me | 1 | CH₂ | H | 2-CF₃-phenyl |
| 78 | —CO₂Me | 1 | CH₂ | F | phenyl |
| 79 | —CO₂Me | 1 | CH₂ | CH₃ | phenyl |
| 80 | —CO₂Me | 1 | CH₂ | H | phenyl |
| 81 | —CO₂Me | 1 | CH₂ | F | amidino |
| 82 | —CO₂Me | 1 | CH₂ | CH₃ | amidino |
| 83 | —CO₂Me | 1 | CH₂ | H | amidino |
| 84 | —CH₂OMe | 1 | CH₂ | H | 2-sulfonamidophenyl |
| 85 | —CH₂OMe | 1 | CH₂ | F | 2-sulfonamidophenyl |
| 86 | —CH₂OMe | 1 | CH₂ | CH₃ | 2-methylaminosulfonylphenyl |
| 87 | —CH₂OMe | 1 | CH₂ | F | 2-CF₃-phenyl |
| 88 | —CH₂OMe | 1 | CH₂ | CH₃ | 2-CF₃-phenyl |
| 89 | —CH₂OMe | 1 | CH₂ | H | 2-CF₃-phenyl |
| 90 | —CH₂OMe | 1 | CH₂ | F | phenyl |
| 91 | —CH₂OMe | 1 | CH₂ | CH₃ | phenyl |
| 92 | —CH₂OMe | 1 | CH₂ | H | phenyl |
| 93 | —CH₂OMe | 1 | CH₂ | F | amidino |
| 94 | —CH₂OMe | 1 | CH₂ | CH₃ | amidino |
| 95 | —CH₂OMe | 1 | CH₂ | H | amidino |
| 96 | —SO₂CH₃ | 1 | CH₂ | H | 2-sulfonamidophenyl |
| 97 | —SO₂CH₃ | 1 | CH₂ | F | 2-sulfonamidophenyl |
| 98 | —SO₂CH₃ | 1 | CH₂ | CH₃ | 2-sulfonamidophenyl |
| 99 | —SO₂CH₃ | 1 | CH₂ | F | 2-CF₃-phenyl |
| 100 | —SO₂CH₃ | 1 | CH₂ | CH₃ | 2-CF₃-phenyl |
| 101 | —SO₂CH₃ | 1 | CH₂ | H | 2-CF₃-phenyl |
| 102 | —SO₂CH₃ | 1 | CH₂ | F | phenyl |
| 103 | —SO₂CH₃ | 1 | CH₂ | CH₃ | phenyl |
| 104 | —SO₂CH₃ | 1 | CH₂ | H | phenyl |
| 105 | —SO₂CH₃ | 1 | CH₂ | F | amidino |
| 106 | —SO₂CH₃ | 1 | CH₂ | CH₃ | amidino |
| 107 | —SO₂CH₃ | 1 | CH₂ | H | amidino |
| 108 | —CO₂Me | 1 | O | H | 2-sulfonamidophenyl |
| 109 | —CO₂Me | 1 | O | F | 2-ethylaminosulfonylphenyl |
| 110 | —CO₂Me | 1 | O | CH₃ | 2-sulfonamidophenyl |
| 111 | —CO₂Me | 1 | O | F | 2-CF₃-phenyl |
| 112 | —CO₂Me | 1 | O | CH₃ | 2-CF₃-phenyl |
| 113 | —CO₂Me | 1 | O | H | 2-CF₃-phenyl |
| — | —CO₂Me | 1 | O | F | phenyl |
| 114 | —CO₂Me | 1 | O | CH₃ | phenyl |
| 115 | —CO₂Me | 1 | O | H | phenyl |
| 116 | —CO₂Me | 1 | O | F | amidino |
| 117 | —CO₂Me | 1 | O | CH₃ | amidino |
| 118 | —CO₂Me | 1 | O | H | amidino |
| 119 | —CH₂OMe | 1 | O | H | 2-sulfonamidophenyl |
| 120 | —CH₂OMe | 1 | O | F | 2-sulfonamidophenyl |
| 121 | —CH₂OMe | 1 | O | CH₃ | 2-methylaminosulfonylphenyl |
| 122 | —CH₂OMe | 1 | O | F | 2-CF₃-phenyl |
| 123 | —CH₂OMe | 1 | O | CH₃ | 2-CF₃-phenyl |
| 124 | —CH₂OMe | 1 | O | H | 2-CF₃-phenyl |
| 225 | —CH₂OMe | 1 | O | F | phenyl |
| 226 | —CH₂OMe | 1 | O | CH₃ | phenyl |
| 127 | —CH₂OMe | 1 | O | H | phenyl |
| 128 | —CH₂OMe | 1 | O | F | amidino |
| 129 | —CH₂OMe | 1 | O | CH₃ | amidino |
| 130 | —CH₂OMe | 1 | O | H | amidino |
| 131 | —SO₂CH₃ | 1 | O | H | 2-sulfonamidophenyl |
| 132 | —SO₂CH₃ | 1 | O | F | 2-sulfonamidophenyl |
| 133 | —SO₂CH₃ | 1 | O | CH₃ | 2-sulfonamidophenyl |
| 134 | —SO₂CH₃ | 1 | O | F | 2-CF₃-phenyl |
| 135 | —SO₂CH₃ | 1 | O | CH₃ | 2-CF₃-phenyl |
| 136 | —SO₂CH₃ | 1 | O | H | 2-CF₃-phenyl |
| 137 | —SO₂CH₃ | 1 | O | F | phenyl |
| 138 | —SO₂CH₃ | 1 | O | CH₃ | phenyl |
| 139 | —SO₂CH₃ | 1 | O | H | phenyl |
| 140 | —SO₂CH₃ | 1 | O | F | amidino |
| 141 | —SO₂CH₃ | 1 | O | CH₃ | amidino |
| 142 | —SO₂CH₃ | 1 | O | H | amidino |

TABLE 4

| Ex# | R | n | Z | R⁴ | B |
|---|---|---|---|---|---|
| 1 | —CO₂Me | 0 | CH₂ | H | 2-methylaminosulfonyl-phenyl |

TABLE 4-continued

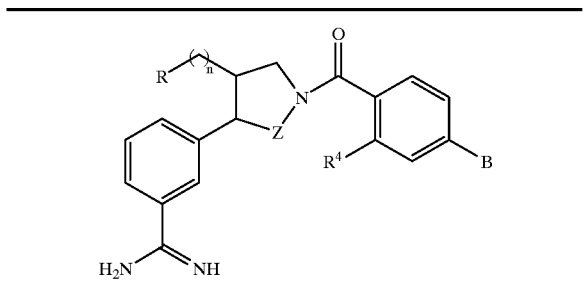

| Ex# | R | n | Z | R⁴ | B |
|---|---|---|---|---|---|
| 2 | —CO₂Me | 0 | CH₂ | F | 2-sulfonamidophenyl |
| 3 | —CO₂Me | 0 | CH₂ | CH₃ | 2-sulfonamidophenyl |
| 4 | —CO₂Me | 0 | CH₂ | F | 2-CF₃-phenyl |
| 5 | —CO₂Me | 0 | CH₂ | CH₃ | 2-CF₃-phenyl |
| 6 | —CO₂Me | 0 | CH₂ | H | 2-CF₃-phenyl |
| 7 | —CO₂Me | 0 | CH₂ | F | phenyl |
| 8 | —CO₂Me | 0 | CH₂ | CH₃ | phenyl |
| 9 | —CO₂Me | 0 | CH₂ | H | phenyl |
| 10 | —CO₂Me | 0 | CH₂ | F | amidino |
| 11 | —CO₂Me | 0 | CH₂ | CH₃ | amidino |
| 12 | —CH₂OMe | 0 | CH₂ | H | 2-sulfonamidophenyl |
| 13 | —CH₂OMe | 0 | CH₂ | F | 2-methylaminosulfonyl-phenyl |
| 14 | —CH₂OMe | 0 | CH₂ | CH₃ | 2-sulfonamidophenyl |
| 15 | —CH₂OMe | 0 | CH₂ | F | 2-CF₃-phenyl |
| 16 | —CH₂OMe | 0 | CH₂ | CH₃ | 2-CF₃-phenyl |
| 17 | —CH₂OMe | 0 | CH₂ | H | 2-CF₃-phenyl |
| 18 | —CH₂OMe | 0 | CH₂ | F | phenyl |
| 19 | —CH₂OMe | 0 | CH₂ | CH₃ | phenyl |
| 20 | —CH₂OMe | 0 | CH₂ | H | phenyl |
| 21 | —CH₂OMe | 0 | CH₂ | F | amidino |
| 22 | —CH₂OMe | 0 | CH₂ | CH₃ | amidino |
| 23 | —CH₂OMe | 0 | CH₂ | H | amidino |
| 24 | —SO₂CH₃ | 0 | CH₂ | H | 2-sulfonamidophenyl |
| 25 | —SO₂CH₃ | 0 | CH₂ | F | 2-sulfonamidophenyl |
| 26 | —SO₂CH₃ | 0 | CH₂ | CH₃ | 2-sulfonamidophenyl |
| 27 | —SO₂CH₃ | 0 | CH₂ | F | 2-CF₃-phenyl |
| 28 | —SO₂CH₃ | 0 | CH₂ | CH₃ | 2-CF₃-phenyl |
| 29 | —SO₂CH₃ | 0 | CH₂ | H | 2-CF₃-phenyl |
| 30 | —SO₂CH₃ | 0 | CH₂ | F | phenyl |
| 31 | —SO₂CH₃ | 0 | CH₂ | CH₃ | phenyl |
| 32 | —SO₂CH₃ | 0 | CH₂ | H | phenyl |
| 33 | —SO₂CH₃ | 0 | CH₂ | F | amidino |
| 34 | —SO₂CH₃ | 0 | CH₂ | CH₃ | amidino |
| 35 | —SO₂CH₃ | 0 | CH₂ | H | amidino |
| 36 | —CO₂Me | 0 | O | H | 2-methylaminosulfonyl-phenyl |
| 37 | —CO₂Me | 0 | O | F | 2-sulfonamidophenyl |
| 38 | —CO₂Me | 0 | O | CH₃ | 2-sulfonamidophenyl |
| 39 | —CO₂Me | 0 | O | F | 2-CF₃-phenyl |
| 40 | —CO₂Me | 0 | O | CH₃ | 2-CF₃-phenyl |
| 41 | —CO₂Me | 0 | O | H | 2-CF₃-phenyl |
| 42 | —CO₂Me | 0 | O | F | phenyl |
| 43 | —CO₂Me | 0 | O | CH₃ | phenyl |
| 44 | —CO₂Me | 0 | O | H | phenyl |
| 45 | —CO₂Me | 0 | O | F | amidino |
| 46 | —CO₂Me | 0 | O | CH₃ | amidino |
| 47 | —CO₂Me | 0 | O | H | amidino |
| 48 | —CH₂OMe | 0 | O | H | 2-sulfonamidophenyl |
| 49 | —CH₂OMe | 0 | O | F | 2-methylaminosulfonyl-phenyl |
| 50 | —CH₂OMe | 0 | O | CH₃ | 2-sulfonamidophenyl |
| 51 | —CH₂OMe | 0 | O | F | 2-CF₃-phenyl |
| 52 | —CH₂OMe | 0 | O | CH₃ | 2-CF₃-phenyl |
| 53 | —CH₂OMe | 0 | O | H | 2-CF₃-phenyl |
| 54 | —CH₂OMe | 0 | O | F | phenyl |
| 55 | —CH₂OMe | 0 | O | CH₃ | phenyl |
| 56 | —CH₂OMe | 0 | O | H | phenyl |
| 57 | —CH₂OMe | 0 | O | F | amidino |
| 58 | —CH₂OMe | 0 | O | CH₃ | amidino |
| 59 | —CH₂OMe | 0 | O | H | amidino |
| 60 | —SO₂CH₃ | 0 | O | H | 2-sulfonamidophenyl |
| 61 | —SO₂CH₃ | 0 | O | F | 2-sulfonamidophenyl |
| 62 | —SO₂CH₃ | 0 | O | CH₃ | 2-sulfonamidophenyl |
| 63 | —SO₂CH₃ | 0 | O | F | 2-CF₃-phenyl |
| 64 | —SO₂CH₃ | 0 | O | CH₃ | 2-CF₃-phenyl |
| 65 | —SO₂CH₃ | 0 | O | H | 2-CF₃-phenyl |
| 66 | —SO₂CH₃ | 0 | O | F | phenyl |
| 67 | —SO₂CH₃ | 0 | O | CH₃ | phenyl |
| 68 | —SO₂CH₃ | 0 | O | H | phenyl |
| 69 | —SO₂CH₃ | 0 | O | F | amidino |
| 70 | —SO₂CH₃ | 0 | O | CH₃ | amidino |
| 71 | —SO₂CH₃ | 0 | O | H | amidino |
| 72 | —CO₂Me | 1 | CH₂ | H | 2-methylaminosulfonyl-phenyl |
| 73 | —CO₂Me | 1 | CH₂ | F | 2-sulfonamidophenyl |
| 74 | —CO₂Me | 1 | CH₂ | CH₃ | 2-sulfonamidophenyl |
| 75 | —CO₂Me | 1 | CH₂ | F | 2-CF₃-phenyl |
| 76 | —CO₂Me | 1 | CH₂ | CH₃ | 2-CF₃-phenyl |
| 77 | —CO₂Me | 1 | CH₂ | H | 2-CF₃-phenyl |
| 78 | —CO₂Me | 1 | CH₂ | F | phenyl |
| 79 | —CO₂Me | 1 | CH₂ | CH₃ | phenyl |
| 80 | —CO₂Me | 1 | CH₂ | H | phenyl |
| 81 | —CO₂Me | 1 | CH₂ | F | amidino |
| 82 | —CO₂Me | 1 | CH₂ | CH₃ | amidino |
| 83 | —CO₂Me | 1 | CH₂ | H | amidino |
| 84 | —CH₂OMe | 1 | CH₂ | H | 2-sulfonamidophenyl |
| 85 | —CH₂OMe | 1 | CH₂ | F | 2-methylaminosulfonyl-phenyl |
| 86 | —CH₂OMe | 1 | CH₂ | CH₃ | 2-sulfonamidophenyl |
| 87 | —CH₂OMe | 1 | CH₂ | F | 2-CF₃-phenyl |
| 88 | —CH₂OMe | 1 | CH₂ | CH₃ | 2-CF₃-phenyl |
| 89 | —CH₂OMe | 1 | CH₂ | H | 2-CF₃-phenyl |
| 90 | —CH₂OMe | 1 | CH₂ | F | phenyl |
| 91 | —CH₂OMe | 1 | CH₂ | CH₃ | phenyl |
| 92 | —CH₂OMe | 1 | CH₂ | H | phenyl |
| 93 | —CH₂OMe | 1 | CH₂ | F | amidino |
| 94 | —CH₂OMe | i | CH₂ | CH₃ | amidino |
| 95 | —CH₂OMe | 1 | CH₂ | H | amidino |
| 96 | —SO₂CH₃ | 1 | CH₂ | H | 2-sulfonamidophenyl |
| 97 | —SO₂CH₃ | 1 | CH₂ | F | 2-sulfonamidophenyl |
| 98 | —SO₂CH₃ | 1 | CH₂ | CH₃ | 2-sulfonamidophenyl |
| 99 | —SO₂CH₃ | 1 | CH₂ | F | 2-CF₃-phenyl |
| 100 | —SO₂CH₃ | 1 | CH₂ | CH₃ | 2-CF₃-phenyl |
| 101 | —SO₂CH₃ | 1 | CH₂ | H | 2-CF₃-phenyl |
| 102 | —SO₂CH₃ | 1 | CH₂ | F | phenyl |
| 103 | —SO₂CH₃ | 1 | CH₂ | CH₃ | phenyl |
| 104 | —SO₂CH₃ | 1 | CH₂ | H | phenyl |
| 105 | —SO₂CH₃ | 1 | CH₂ | F | amidino |
| 106 | —SO₂CH₃ | 1 | CH₂ | CH₃ | amidino |
| 107 | —SO₂CH₃ | 1 | CH₂ | H | amidino |
| 108 | —CO₂Me | 1 | O | H | 2-sulfonamidophenyl |
| 109 | —CO₂Me | 1 | O | F | 2-sulfonamidophenyl |
| 110 | —CO₂Me | 1 | O | CH₃ | 2-methylaminosulfonyl-phenyl |
| 111 | —CO₂Me | 1 | O | F | 2-CF₃-phenyl |
| 112 | —CO₂Me | 1 | O | CH₃ | 2-CF₃-phenyl |
| 113 | —CO₂Me | 1 | O | H | 2-CF₃-phenyl |
| 114 | —CO₂Me | 1 | O | F | phenyl |
| 115 | —CO₂Me | 1 | O | CH₃ | phenyl |
| 116 | —CO₂Me | 1 | O | H | phenyl |
| 117 | —CO₂Me | 1 | O | F | amidino |
| 118 | —CO₂Me | 1 | O | CH₃ | amidino |
| 119 | —CO₂Me | 1 | O | H | amidino |
| 120 | —CH₂OMe | 1 | O | H | 2-methylaminosulfonyl-phenyl |

TABLE 4-continued

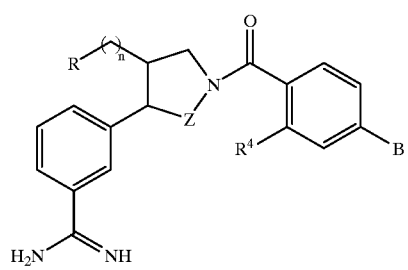

| Ex# | R | n | Z | R⁴ | B |
|---|---|---|---|---|---|
| 121 | —CH₂OMe | 1 | O | F | 2-sulfonamidophenyl |
| 122 | —CH₂OMe | 1 | O | CH₃ | 2-sulfonamidophenyl |
| 123 | —CH₂OMe | 1 | O | F | 2-CF₃-phenyl |
| 124 | —CH₂OMe | 1 | O | CH₃ | 2-CF₃-phenyl |
| 125 | —CH₂OMe | 1 | O | H | 2-CF₃-phenyl |
| 126 | —CH₂OMe | 1 | O | F | phenyl |
| 127 | —CH₂OMe | 1 | O | CH₃ | phenyl |
| 128 | —CH₂OMe | 1 | O | H | phenyl |
| 129 | —CH₂OMe | 1 | O | F | amidino |
| 130 | —CH₂OMe | 1 | O | CH₃ | amidino |
| 131 | —CH₂OMe | 1 | O | H | amidino |
| 132 | —SO₂CH₃ | 1 | O | H | 2-sulfonamidophenyl |
| 133 | —SO₂CH₃ | 1 | O | F | 2-sulfonamidophenyl |
| 134 | —SO₂CH₃ | 1 | O | CH₃ | 2-sulfonamidophenyl |
| 135 | —SO₂CH₃ | 1 | O | F | 2-CF₃-phenyl |
| 136 | —SO₂CH₃ | 1 | O | CH₃ | 2-CF₃-phenyl |
| 137 | —SO₂CH₃ | 1 | O | H | 2-CF₃-phenyl |
| 138 | —SO₂CH₃ | 1 | O | F | phenyl |
| 139 | —SO₂CH₃ | 1 | O | CH₃ | phenyl |
| 140 | —SO₂CH₃ | 1 | O | H | phenyl |
| 141 | —SO₂CH₃ | 1 | O | F | amidino |
| 142 | —SO₂CH₃ | 1 | O | CH₃ | amidino |
| 143 | —SO₂CH₃ | 1 | O | H | amidino |

TABLE 5

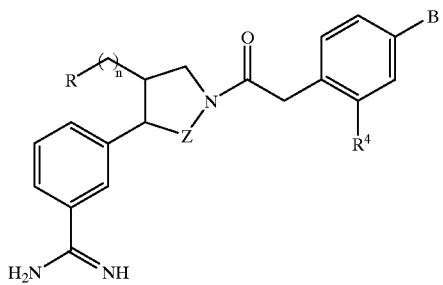

| Ex# | R | n | Z | R⁴ | B |
|---|---|---|---|---|---|
| 1 | —CO₂Me | 0 | CH₂ | H | 2-sulfonamidophenyl |
| 2 | —CO₂Me | 0 | CH₂ | F | 2-sulfonamidophenyl |
| 3 | —CO₂Me | 0 | CH₂ | CH₃ | 2-sulfonamidophenyl |
| 4 | —CO₂Me | 0 | CH₂ | F | 2-CF₃-phenyl |
| 5 | —CO₂Me | 0 | CH₂ | CH₃ | 2-CF₃-phenyl |
| 6 | —CO₂Me | 0 | CH₂ | H | 2-CF₃-phenyl |
| 7 | —CO₂Me | 0 | CH₂ | F | phenyl |
| 8 | —CO₂Me | 0 | CH₂ | CH₃ | phenyl |
| 9 | —CO₂Me | 0 | CH₂ | H | phenyl |
| 10 | —CO₂Me | 0 | CH₂ | F | amidino |
| 11 | —CO₂Me | 0 | CH₂ | CH₃ | amidino |
| 12 | —CH₂OMe | 0 | CH₂ | H | 2-methylaminosulfonyl-phenyl |
| 13 | —CH₂OMe | 0 | CH₂ | F | 2-sulfonamidophenyl |
| 14 | —CH₂OMe | 0 | CH₂ | CH₃ | 2-sulfonamidophenyl |
| 15 | —CH₂OMe | 0 | CH₂ | F | 2-CF₃-phenyl |
| 16 | —CH₂OMe | 0 | CH₂ | CH₃ | 2-CF₃-phenyl |
| 17 | —CH₂OMe | 0 | CH₂ | H | 2-CF₃-phenyl |

TABLE 5-continued

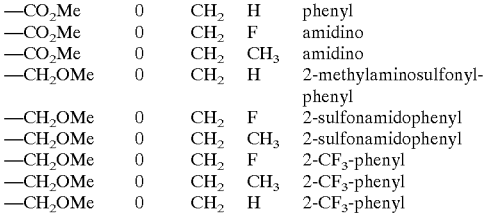

| Ex# | R | n | Z | R⁴ | B |
|---|---|---|---|---|---|
| 18 | —CH₂OMe | 0 | CH₂ | F | phenyl |
| 19 | —CH₂OMe | 0 | CH₂ | CH₃ | phenyl |
| 20 | —CH₂OMe | 0 | CH₂ | H | phenyl |
| 21 | —CH₂OMe | 0 | CH₂ | F | amidino |
| 22 | —CH₂OMe | 0 | CH₂ | CH₃ | amidino |
| 23 | —CH₂OMe | 0 | CH₂ | H | amidino |
| 24 | —SO₂CH₃ | 0 | CH₂ | H | 2-sulfonamidophenyl |
| 25 | —SO₂CH₃ | 0 | CH₂ | F | 2-sulfonamidophenyl |
| 26 | —SO₂CH₃ | 0 | CH₂ | CH₃ | 2-sulfonamidophenyl |
| 27 | —SO₂CH₃ | 0 | CH₂ | F | 2-CF₃-phenyl |
| 28 | —SO₂CH₃ | 0 | CH₂ | CH₃ | 2-CF₃-phenyl |
| 29 | —SO₂CH₃ | 0 | CH₂ | H | 2-CF₃-phenyl |
| 30 | —SO₂CH₃ | 0 | CH₂ | F | phenyl |
| 31 | —SO₂CH₃ | 0 | CH₂ | CH₃ | phenyl |
| 32 | —SO₂CH₃ | 0 | CH₂ | H | phenyl |
| 33 | —SO₂CH₃ | 0 | CH₂ | F | amidino |
| 34 | —SO₂CH₃ | 0 | CH₂ | CH₃ | amidino |
| 35 | —SO₂CH₃ | 0 | CH₂ | H | amidino |
| 36 | —CO₂Me | 0 | O | H | 2-sulfonamidophenyl |
| 37 | —CO₂Me | 0 | O | F | 2-sulfonamidophenyl |
| 38 | —CO₂Me | 0 | O | CH₃ | 2-methylaminosulfonyl-phenyl |
| 39 | —CO₂Me | 0 | O | F | 2-CF₃-phenyl |
| 40 | —CO₂Me | 0 | O | CH₃ | 2-CF₃-phenyl |
| 41 | —CO₂Me | 0 | O | H | 2-CF₃-phenyl |
| 42 | —CO₂Me | 0 | O | F | phenyl |
| 43 | —CO₂Me | 0 | O | CH₃ | phenyl |
| 44 | —CO₂Me | 0 | O | H | phenyl |
| 45 | —CO₂Me | 0 | O | F | amidino |
| 46 | —CO₂Me | 0 | O | CH₃ | amidino |
| 47 | —CO₂Me | 0 | O | H | amidino |
| 48 | —CH₂OMe | 0 | O | H | 2-methylaminosulfonyl-phenyl |
| 49 | —CH₂OMe | 0 | O | F | 2-sulfonamidophenyl |
| 50 | —CH₂OMe | 0 | O | CH₃ | 2-sulfonamidophenyl |
| 51 | —CH₂OMe | 0 | O | F | 2-CF₃-phenyl |
| 52 | —CH₂OMe | 0 | O | CH₃ | 2-CF₃-phenyl |
| 53 | —CH₂OMe | 0 | O | H | 2-CF₃-phenyl |
| 54 | —CH₂OMe | 0 | O | F | phenyl |
| 55 | —CH₂OMe | 0 | O | CH₃ | phenyl |
| 56 | —CH₂OMe | 0 | O | H | phenyl |
| 57 | —CH₂OMe | 0 | O | F | amidino |
| 58 | —CH₂OMe | 0 | O | CH₃ | amidino |
| 59 | —CH₂OMe | 0 | O | H | amidino |
| 60 | —SO₂CH₃ | 0 | O | H | 2-sulfonamidophenyl |
| 61 | —SO₂CH₃ | 0 | O | F | 2-sulfonamidophenyl |
| 62 | —SO₂CH₃ | 0 | O | CH₃ | 2-sulfonamidophenyl |
| 63 | —SO₂CH₃ | 0 | O | F | 2-CF₃-phenyl |
| 64 | —SO₂CH₃ | 0 | O | CH₃ | 2-CF₃-phenyl |
| 65 | —SO₂CH₃ | 0 | O | H | 2-CF₃-phenyl |
| 66 | —SO₂CH₃ | 0 | O | F | phenyl |
| 67 | —SO₂CH₃ | 0 | O | CH₃ | phenyl |
| 68 | —SO₂CH₃ | 0 | O | H | phenyl |
| 69 | —SO₂CH₃ | 0 | O | F | amidino |
| 70 | —SO₂CH₃ | 0 | O | CH₃ | amidino |
| 71 | —SO₂CH₃ | 0 | O | H | amidino |
| 72 | —CO₂Me | 1 | CH₂ | H | 2-sulfonamidophenyl |
| 73 | —CO₂Me | 1 | CH₂ | F | 2-sulfonamidophenyl |
| 74 | —CO₂Me | 1 | CH₂ | CH₃ | 2-methylaminosulfonyl-phenyl |
| 75 | —CO₂Me | 1 | CH₂ | F | 2-CF₃-phenyl |
| 76 | —CO₂Me | 1 | CH₂ | CH₃ | 2-CF₃-phenyl |

TABLE 5-continued

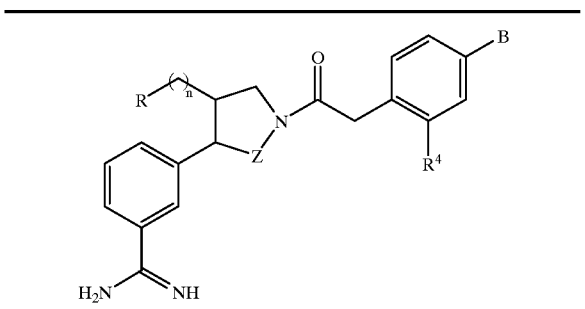

| Ex# | R | n | Z | R⁴ | B |
|---|---|---|---|---|---|
| 77 | —CO₂Me | 1 | CH₂ | H | 2-CF₃-phenyl |
| 78 | —CO₂Me | 1 | CH₂ | F | phenyl |
| 79 | —CO₂Me | 1 | CH₂ | CH₃ | phenyl |
| 80 | —CO₂Me | 1 | CH₂ | H | phenyl |
| 81 | —CO₂Me | 1 | CH₂ | F | amidino |
| 82 | —CO₂Me | 1 | CH₂ | CH₃ | amidino |
| 83 | —CO₂Me | 1 | CH₂ | H | amidino |
| 84 | —CH₂OMe | 1 | CH₂ | H | 2-methylaminosulfonyl-phenyl |
| 85 | —CH₂OMe | 1 | CH₂ | F | 2-sulfonamidophenyl |
| 86 | —CH₂OMe | 1 | CH₂ | CH₃ | 2-sulfonamidophenyl |
| 87 | —CH₂OMe | 1 | CH₂ | F | 2-CF₃-phenyl |
| 88 | —CH₂OMe | 1 | CH₂ | CH₃ | 2-CF₃-phenyl |
| 89 | —CH₂OMe | 1 | CH₂ | H | 2-CF₃-phenyl |
| 90 | —CH₂OMe | 1 | CH₂ | F | phenyl |
| 91 | —CH₂OMe | 1 | CH₂ | CH₃ | phenyl |
| 92 | —CH₂OMe | 1 | CH₂ | H | phenyl |
| 93 | —CH₂OMe | 1 | CH₂ | F | amidino |
| 94 | —CH₂OMe | 1 | CH₂ | CH₃ | amidino |
| 95 | —CH₂OMe | 1 | CH₂ | H | amidino |
| 96 | —SO₂CH₃ | 1 | CH₂ | H | 2-sulfonamidophenyl |
| 97 | —SO₂CH₃ | 1 | CH₂ | F | 2-sulfonamidophenyl |
| 98 | —SO₂CH₃ | 1 | CH₂ | CH₃ | 2-sulfonamidophenyl |
| 99 | —SO₂CH₃ | 1 | CH₂ | F | 2-CF₃-phenyl |
| 100 | —SO₂CH₃ | 1 | CH₂ | CH₃ | 2-CF₃-phenyl |
| 101 | —SO₂CH₃ | 1 | CH₂ | H | 2-CF₃-phenyl |
| 102 | —SO₂CH₃ | 1 | CH₂ | F | phenyl |
| 103 | —SO₂CH₃ | 1 | CH₂ | CH₃ | phenyl |
| 104 | —SO₂CH₃ | 1 | CH₂ | H | phenyl |
| 105 | —SO₂CH₃ | 1 | CH₂ | F | amidino |
| 106 | —SO₂CH₃ | 1 | CH₂ | CH₃ | amidino |
| 107 | —SO₂CH₃ | 1 | CH₂ | H | amidino |
| 108 | —CO₂Me | 1 | O | H | 2-sulfonamidophenyl |
| 109 | —CO₂Me | 1 | O | F | 2-sulfonamidophenyl |
| 110 | —CO₂Me | 1 | O | CH₃ | 2-methylaminosulfonyl-phenyl |
| 111 | —CO₂Me | 1 | O | F | 2-CF₃-phenyl |
| 112 | —CO₂Me | 1 | O | CH₃ | 2-CF₃-phenyl |
| 113 | —CO₂Me | 1 | O | H | 2-CF₃-phenyl |
| 114 | —CO₂Me | 1 | O | F | phenyl |
| 115 | —CO₂Me | 1 | O | CH₃ | phenyl |
| 116 | —CO₂Me | 1 | O | H | phenyl |
| 117 | —CO₂Me | 1 | O | F | amidino |
| 118 | —CO₂Me | 1 | O | CH₃ | amidino |
| 119 | —CO₂Me | 1 | O | H | amidino |
| 120 | —CH₂OMe | 1 | O | H | 2-methylaminosulfonyl-phenyl |
| 121 | —CH₂OMe | 1 | O | F | 2-sulfonamidophenyl |
| 122 | —CH₂OMe | 1 | O | CH₃ | 2-sulfonamidophenyl |
| 123 | —CH₂OMe | 1 | O | F | 2-CF₃-phenyl |
| 124 | —CH₂OMe | 1 | O | CH₃ | 2-CF₃-phenyl |
| 125 | —CH₂OMe | 1 | O | H | 2-CF₃-phenyl |
| 126 | —CH₂OMe | 1 | O | F | phenyl |
| 127 | —CH₂OMe | 1 | O | CH₃ | phenyl |
| 128 | —CH₂OMe | 1 | O | H | phenyl |
| 129 | —CH₂OMe | 1 | O | F | amidino |
| 130 | —CH₂OMe | 1 | O | CH₃ | amidino |
| 131 | —CH₂OMe | 1 | O | H | amidino |
| 132 | —SO₂CH₃ | 1 | O | H | 2-sulfonamidophenyl |
| 133 | —SO₂CH₃ | 1 | O | F | 2-sulfonamidophenyl |
| 134 | —SO₂CH₃ | 1 | O | CH₃ | 2-sulfonamidophenyl |
| 135 | —SO₂CH₃ | 1 | O | F | 2-CF₃-phenyl |
| 136 | —SO₂CH₃ | 1 | O | CH₃ | 2-CF₃-phenyl |
| 137 | —SO₂CH₃ | 1 | O | H | 2-CF₃-phenyl |
| 138 | —SO₂CH₃ | 1 | O | F | phenyl |
| 139 | —SO₂CH₃ | 1 | O | CH₃ | phenyl |
| 140 | —SO₂CH₃ | 1 | O | H | phenyl |
| 141 | —SO₂CH₃ | 1 | O | F | amidino |
| 142 | —SO₂CH₃ | 1 | O | CH₃ | amidino |
| 143 | —SO₂CH₃ | 1 | O | H | amidino |

TABLE 6

| Ex# | R | n | Z | R⁴ | B |
|---|---|---|---|---|---|
| 1 | —CO₂Me | 0 | CH₂ | H | 2-sulfonamidophenyl |
| 2 | —CO₂Me | 0 | CH₂ | F | 2-sulfonamidophenyl |
| 3 | —CO₂Me | 0 | CH₂ | CH₃ | 2-sulfonamidophenyl |
| 4 | —CO₂Me | 0 | CH₂ | F | 2-CF₃-phenyl |
| 5 | —CO₂Me | 0 | CH₂ | CH₃ | 2-CF₃-phenyl |
| 6 | —CO₂Me | 0 | CH₂ | H | 2-CF₃-phenyl |
| 7 | —CO₂Me | 0 | CH₂ | F | phenyl |
| 8 | —CO₂Me | 0 | CH₂ | CH₃ | phenyl |
| 9 | —CO₂Me | 0 | CH₂ | H | phenyl |
| 10 | —CO₂Me | 0 | CH₂ | F | amidino |
| 11 | —CO₂Me | 0 | CH₂ | CH₃ | amidino |
| 12 | —CH₂OMe | 0 | CH₂ | H | 2-methylaminosulfonyl-phenyl |
| 13 | —CH₂OMe | 0 | CH₂ | F | 2-sulfonamidophenyl |
| 14 | —CH₂OMe | 0 | CH₂ | CH₃ | 2-sulfonamidophenyl |
| 15 | —CH₂OMe | 0 | CH₂ | F | 2-CF₃-phenyl |
| 16 | —CH₂OMe | 0 | CH₂ | CH₃ | 2-CF₃-phenyl |
| 17 | —CH₂OMe | 0 | CH₂ | H | 2-CF₃-phenyl |
| 18 | —CH₂OMe | 0 | CH₂ | F | phenyl |
| 19 | —CH₂OMe | 0 | CH₂ | CH₃ | phenyl |
| 20 | —CH₂OMe | 0 | CH₂ | H | phenyl |
| 21 | —CH₂OMe | 0 | CH₂ | F | amidino |
| 22 | —CH₂OMe | 0 | CH₂ | CH₃ | amidino |
| 23 | —CH₂OMe | 0 | CH₂ | H | amidino |
| 24 | —SO₂CH₃ | 0 | CH₂ | H | 2-sulfonamidophenyl |
| 25 | —SO₂CH₃ | 0 | CH₂ | F | 2-sulfonamidophenyl |
| 26 | —SO₂CH₃ | 0 | CH₂ | CH₃ | 2-sulfonamidophenyl |
| 27 | —SO₂CH₃ | 0 | CH₂ | F | 2-CF₃-phenyl |
| 28 | —SO₂CH₃ | 0 | CH₂ | CH₃ | 2-CF₃-phenyl |
| 29 | —SO₂CH₃ | 0 | CH₂ | H | 2-CF₃-phenyl |
| 30 | —SO₂CH₃ | 0 | CH₂ | F | phenyl |

TABLE 6-continued

| Ex# | R | n | Z | R⁴ | B |
|---|---|---|---|---|---|
| 31 | —SO₂CH₃ | 0 | CH₂ | CH₃ | phenyl |
| 32 | —SO₂CH₃ | 0 | CH₂ | H | phenyl |
| 33 | —SO₂CH₃ | 0 | CH₂ | F | amidino |
| 34 | —SO₂CH₃ | 0 | CH₂ | CH₃ | amidino |
| 35 | —SO₂CH₃ | 0 | CH₂ | H | amidino |
| 36 | —CO₂Me | 0 | O | H | 2-sulfonamidophenyl |
| 37 | —CO₂Me | 0 | O | F | 2-methylaminosulfonyl-phenyl |
| 38 | —CO₂Me | 0 | O | CH₃ | 2-sulfonamidophenyl |
| 39 | —CO₂Me | 0 | O | F | 2-CF₃-phenyl |
| 40 | —CO₂Me | 0 | O | CH₃ | 2-CF₃-phenyl |
| 41 | —CO₂Me | 0 | O | H | 2-CF₃-phenyl |
| 42 | —CO₂Me | 0 | O | F | phenyl |
| 43 | —CO₂Me | 0 | O | CH₃ | phenyl |
| 44 | —CO₂Me | 0 | O | H | phenyl |
| 45 | —CO₂Me | 0 | O | F | amidino |
| 46 | —CO₂Me | 0 | O | CH₃ | amidino |
| 47 | —CO₂Me | 0 | O | H | amidino |
| 48 | —CH₂OMe | 0 | O | H | 2-sulfonamidophenyl |
| 49 | —CH₂OMe | 0 | O | F | 2-sulfonamidophenyl |
| 50 | —CH₂OMe | 0 | O | CH₃ | 2-sulfonamidophenyl |
| 51 | —CH₂OMe | 0 | O | F | 2-CF₃-phenyl |
| 52 | —CH₂OMe | 0 | O | CH₃ | 2-CF₃-phenyl |
| 53 | —CH₂OMe | 0 | O | H | 2-CF₃-phenyl |
| 54 | —CH₂OMe | 0 | O | F | phenyl |
| 55 | —CH₂OMe | 0 | O | CH₃ | phenyl |
| 56 | —CH₂OMe | 0 | O | H | phenyl |
| 57 | —CH₂OMe | 0 | O | F | amidino |
| 58 | —CH₂OMe | 0 | O | CH₃ | amidino |
| 59 | —CH₂OMe | 0 | O | H | amidino |
| 60 | —SO₂CH₃ | 0 | O | H | 2-sulfonamidophenyl |
| 61 | —SO₂CH₃ | 0 | O | F | 2-sulfonamidophenyl |
| 62 | —SO₂CH₃ | 0 | O | CH₃ | 2-sulfonamidophenyl |
| 63 | —SO₂CH₃ | 0 | O | F | 2-CF₃-phenyl |
| 64 | —SO₂CH₃ | 0 | O | CH₃ | 2-CF₃-phenyl |
| 65 | —SO₂CH₃ | 0 | O | H | 2-CF₃-phenyl |
| 66 | —SO₂CH₃ | 0 | O | F | phenyl |
| 67 | —SO₂CH₃ | 0 | O | CH₃ | phenyl |
| 68 | —SO₂CH₃ | 0 | O | H | phenyl |
| 69 | —SO₂CH₃ | 0 | O | F | amidino |
| 70 | —SO₂CH₃ | 0 | O | CH₃ | amidino |
| 71 | —SO₂CH₃ | 0 | O | H | amidino |
| 72 | —CO₂Me | 1 | CH₂ | H | 2-sulfonamidophenyl |
| 73 | —CO₂Me | 1 | CH₂ | F | 2-methylaminosulfonyl-phenyl |
| 74 | —CO₂Me | 1 | CH₂ | CH₃ | 2-sulfonamidophenyl |
| 75 | —CO₂Me | 1 | CH₂ | F | 2-CF₃-phenyl |
| 76 | —CO₂Me | 1 | CH₂ | CH₃ | 2-CF₃-phenyl |
| 77 | —CO₂Me | 1 | CH₂ | H | 2-CF₃-phenyl |
| 78 | —CO₂Me | 1 | CH₂ | F | phenyl |
| 79 | —CO₂Me | 1 | CH₂ | CH₃ | phenyl |
| 80 | —CO₂Me | 1 | CH₂ | H | phenyl |
| 81 | —CO₂Me | 1 | CH₂ | F | amidino |
| 82 | —CO₂Me | 1 | CH₂ | CH₃ | amidino |
| 83 | —CO₂Me | 1 | CH₂ | H | amidino |
| 84 | —CH₂OMe | 1 | CH₂ | H | 2-sulfonamidophenyl |
| 85 | —CH₂OMe | 1 | CH₂ | F | 2-sulfonamidophenyl |
| 86 | —CH₂OMe | 1 | CH₂ | CH₃ | 2-methylaminosulfonyl-phenyl |
| 87 | —CH₂OMe | 1 | CH₂ | F | 2-CF₃-phenyl |
| 88 | —CH₂OMe | 1 | CH₂ | CH₃ | 2-CF₃-phenyl |
| 89 | —CH₂OMe | 1 | CH₂ | H | 2-CF₃-phenyl |
| 90 | —CH₂OMe | 1 | CH₂ | F | phenyl |
| 91 | —CH₂OMe | 1 | CH₂ | CH₃ | phenyl |
| 92 | —CH₂OMe | 1 | CH₂ | H | phenyl |
| 93 | —CH₂OMe | 1 | CH₂ | F | amidino |
| 94 | —CH₂OMe | 1 | CH₂ | CH₃ | amidino |
| 95 | —CH₂OMe | 1 | CH₂ | H | amidino |
| 96 | —SO₂CH₃ | 1 | CH₂ | H | 2-sulfonamidophenyl |
| 97 | —SO₂CH₃ | 1 | CH₂ | F | 2-sulfonamidophenyl |
| 98 | —SO₂CH₃ | 1 | CH₂ | CH₃ | 2-sulfonamidophenyl |
| 99 | —SO₂CH₃ | 1 | CH₂ | F | 2-CF₃-phenyl |
| 100 | —SO₂CH₃ | 1 | CH₂ | CH₃ | 2-CF₃-phenyl |
| 101 | —SO₂CH₃ | 1 | CH₂ | H | 2-CF₃-phenyl |
| 102 | —SO₂CH₃ | 1 | CH₂ | F | phenyl |
| 103 | —SO₂CH₃ | 1 | CH₂ | CH₃ | phenyl |
| 104 | —SO₂CH₃ | 1 | CH₂ | H | phenyl |
| 105 | —SO₂CH₃ | 1 | CH₂ | F | amidino |
| 106 | —SO₂CH₃ | 1 | CH₂ | CH₃ | amidino |
| 107 | —SO₂CH₃ | 1 | CH₂ | H | amidino |
| 108 | —CO₂Me | 1 | O | H | 2-methylaminosulfonyl-phenyl |
| 109 | —CO₂Me | 1 | O | F | 2-sulfonamidophenyl |
| 110 | —CO₂Me | 1 | O | CH₃ | 2-sulfonamidophenyl |
| 111 | —CO₂Me | 1 | O | F | 2-CF₃-phenyl |
| 112 | —CO₂Me | 1 | O | CH₃ | 2-CF₃-phenyl |
| 113 | —CO₂Me | 1 | O | H | 2-CF₃-phenyl |
| 114 | —CO₂Me | 1 | O | F | phenyl |
| 115 | —CO₂Me | 1 | O | CH₃ | phenyl |
| 116 | —CO₂Me | 1 | O | H | phenyl |
| 117 | —CO₂Me | 1 | O | F | amidino |
| 118 | —CO₂Me | 1 | O | CH₃ | amidino |
| 119 | —CO₂Me | 1 | O | H | amidino |
| 120 | —CH₂OMe | 1 | O | H | 2-sulfonamidophenyl |
| 121 | —CH₂OMe | 1 | O | F | 2-methylaminosulfonyl-phenyl |
| 122 | —CH₂OMe | 1 | O | CH₃ | 2-sulfonamidophenyl |
| 123 | —CH₂OMe | 1 | O | F | 2-CF₃-phenyl |
| 124 | —CH₂OMe | 1 | O | CH₃ | 2-CF₃-phenyl |
| 125 | —CH₂OMe | 1 | O | H | 2-CF₃-phenyl |
| 126 | —CH₂OMe | 1 | O | F | phenyl |
| 127 | —CH₂OMe | 1 | O | CH₃ | phenyl |
| 128 | —CH₂OMe | 1 | O | H | phenyl |
| 129 | —CH₂OMe | 1 | O | F | amidino |
| 130 | —CH₂OMe | 1 | O | CH₃ | amidino |
| 131 | —CH₂OMe | 1 | O | H | amidino |
| 132 | —SO₂CH₃ | 1 | O | H | 2-sulfonamidophenyl |
| 133 | —SO₂CH₃ | 1 | O | F | 2-sulfonamidophenyl |
| 134 | —SO₂CH₃ | 1 | O | CH₃ | 2-sulfonamidophenyl |
| 135 | —SO₂CH₃ | 1 | O | F | 2-CF₃-phenyl |
| 136 | —SO₂CH₃ | 1 | O | CH₃ | 2-CF₃-phenyl |
| 137 | —SO₂CH₃ | 1 | O | H | 2-CF₃-phenyl |
| 138 | —SO₂CH₃ | 1 | O | F | phenyl |
| 139 | —SO₂CH₃ | 1 | O | CH₃ | phenyl |
| 140 | —SO₂CH₃ | 1 | O | H | phenyl |
| 141 | —SO₂CH₃ | 1 | O | F | amidino |
| 142 | —SO₂CH₃ | 1 | O | CH₃ | amidino |
| 143 | —SO₂CH₃ | 1 | O | H | amidino |

TABLE 7

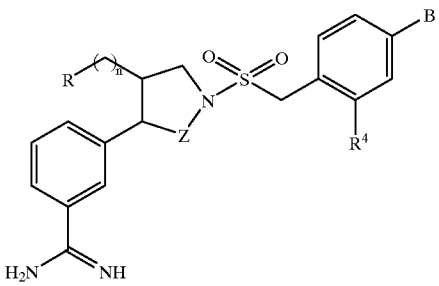

| Ex # | R | n | Z | R4 | B |
|---|---|---|---|---|---|
| 1 | —CO2Me | 0 | CH2 | H | 2-sulfonamidophenyl |
| 2 | —CO2Me | 0 | CH2 | F | 2-sulfonamidophenyl |
| 3 | —CO2Me | 0 | CH2 | CH3 | 2-methylaminosulfonylphenyl |
| 4 | —CO2Me | 0 | CH2 | F | 2-CF3-phenyl |
| 5 | —CO2Me | 0 | CH2 | CH3 | 2-CF3-phenyl |
| 6 | —CO2Me | 0 | CH2 | H | 2-CF3-phenyl |
| 7 | —CO2Me | 0 | CH2 | F | phenyl |
| 8 | —CO2Me | 0 | CH2 | CH3 | phenyl |
| 9 | —CO2Me | 0 | CH2 | H | phenyl |
| 10 | —CO2Me | 0 | CH2 | F | amidino |
| 11 | —CO2Me | 0 | CH2 | CH3 | amidino |
| 12 | —CH2OMe | 0 | CH2 | H | 2-sulfonamidophenyl |
| 13 | —CH2OMe | 0 | CH2 | F | 2-sulfonamidophenyl |
| 14 | —CH2OMe | 0 | CH2 | CH3 | 2-sulfonamidophenyl |
| 15 | —CH2OMe | 0 | CH2 | F | 2-CF3-phenyl |
| 16 | —CH2OMe | 0 | CH2 | CH3 | 2-CF3-phenyl |
| 17 | —CH2OMe | 0 | CH2 | H | 2-CF3-phenyl |
| 18 | —CH2OMe | 0 | CH2 | F | phenyl |
| 19 | —CH2OMe | 0 | CH2 | CH3 | phenyl |
| 20 | —CH2OMe | 0 | CH2 | H | phenyl |
| 21 | —CH2OMe | 0 | CH2 | F | amidino |
| 22 | —CH2OMe | 0 | CH2 | CH3 | amidino |
| 23 | —CH2OMe | 0 | CH2 | H | amidino |
| 24 | —SO2CH3 | 0 | CH2 | H | 2-sulfonamidophenyl |
| 25 | —SO2CH3 | 0 | CH2 | F | 2-sulfonamidophenyl |
| 26 | —SO2CH3 | 0 | CH2 | CH3 | 2-sulfonamidophenyl |
| 27 | —SO2CH3 | 0 | CH2 | F | 2-CF3-phenyl |
| 28 | —SO2CH3 | 0 | CH2 | CH3 | 2-CF3-phenyl |
| 29 | —SO2CH3 | 0 | CH2 | H | 2-CF3-phenyl |
| 30 | —SO2CH3 | 0 | CH2 | F | phenyl |
| 31 | —SO2CH3 | 0 | CH2 | CH3 | phenyl |
| 32 | —SO2CH3 | 0 | CH2 | H | phenyl |
| 33 | —SO2CH3 | 0 | CH2 | F | amidino |
| 34 | —SO2CH3 | 0 | CH2 | CH3 | amidino |
| 35 | —SO2CH3 | 0 | CH2 | H | amidino |
| 36 | —CO2Me | 0 | O | H | 2-methylaminosulfonylphenyl |
| 37 | —CO2Me | 0 | O | F | 2-sulfonamidophenyl |
| 38 | —CO2Me | 0 | O | CH3 | 2-sulfonamidophenyl |
| 39 | —CO2Me | 0 | O | F | 2-CF3-phenyl |
| 40 | —CO2Me | 0 | O | CH3 | 2-CF3-phenyl |
| 41 | —CO2Me | 0 | O | H | 2-CF3-phenyl |
| 42 | —CO2Me | 0 | O | F | phenyl |
| 43 | —CO2Me | 0 | O | CH3 | phenyl |
| 44 | —CO2Me | 0 | O | H | phenyl |
| 45 | —CO2Me | 0 | O | F | amidino |
| 46 | —CO2Me | 0 | O | CH3 | amidino |
| 47 | —CO2Me | 0 | O | H | amidino |
| 48 | —CH2OMe | 0 | O | H | 2-sulfonamidophenyl |
| 49 | —CH2OMe | 0 | O | F | 2-sulfonamidophenyl |
| 50 | —CH2OMe | 0 | O | CH3 | 2-sulfonamidophenyl |
| 51 | —CH2OMe | 0 | O | F | 2-CF3-phenyl |
| 52 | —CH2OMe | 0 | O | CH3 | 2-CF3-phenyl |
| 53 | —CH2OMe | 0 | O | H | 2-CF3-phenyl |
| 54 | —CH2OMe | 0 | O | F | phenyl |
| 55 | —CH2OMe | 0 | O | CH3 | phenyl |
| 56 | —CH2OMe | 0 | O | H | phenyl |
| 57 | —CH2OMe | 0 | O | F | amidino |
| 58 | —CH2OMe | 0 | O | CH3 | amidino |
| 59 | —CH2OMe | 0 | O | H | amidino |
| 60 | —SO2CH3 | 0 | O | H | 2-sulfonamidophenyl |
| 61 | —SO2CH3 | 0 | O | F | 2-sulfonamidophenyl |
| 62 | —SO2CH3 | 0 | O | CH3 | 2-sulfonamidophenyl |
| 63 | —SO2CH3 | 0 | O | F | 2-CF3-phenyl |
| 64 | —SO2CH3 | 0 | O | CH3 | 2-CF3-phenyl |
| 65 | —SO2CH3 | 0 | O | H | 2-CF3-phenyl |
| 66 | —SO2CH3 | 0 | O | F | phenyl |
| 67 | —SO2CH3 | 0 | O | CH3 | phenyl |
| 68 | —SO2CH3 | 0 | O | H | phenyl |
| 69 | —SO2CH3 | 0 | O | F | amidino |
| 70 | —SO2CH3 | 0 | O | CH3 | amidino |
| 71 | —SO2CH3 | 0 | O | H | amidino |
| 72 | —CO2Me | 1 | CH2 | H | 2-sulfonamidophenyl |
| 73 | —CO2Me | 1 | CH2 | F | 2-methylaminosulfonylphenyl |
| 74 | —CO2Me | 1 | CH2 | CH3 | 2-sulfonamidophenyl |
| 75 | —CO2Me | 1 | CH2 | F | 2-CF3-phenyl |
| 76 | —CO2Me | 1 | CH2 | CH3 | 2-CF3-phenyl |
| 77 | —CO2Me | 1 | CH2 | H | 2-CF3-phenyl |
| 78 | —CO2Me | 1 | CH2 | F | phenyl |
| 79 | —CO2Me | 1 | CH2 | CH3 | phenyl |
| 80 | —CO2Me | 1 | CH2 | H | phenyl |
| 81 | —CO2Me | 1 | CH2 | F | amidino |
| 82 | —CO2Me | 1 | CH2 | CH3 | amidino |
| 83 | —CO2Me | 1 | CH2 | H | amidino |
| 84 | —CH2OMe | 1 | CH2 | H | 2-sulfonamidophenyl |
| 85 | —CH2OMe | 1 | CH2 | F | 2-sulfonamidophenyl |
| 86 | —CH2OMe | 1 | CH2 | CH3 | 2-methylaminosulfonylphenyl |
| 87 | —CH2OMe | 1 | CH2 | F | 2-CF3-phenyl |
| 88 | —CH2OMe | 1 | CH2 | CH3 | 2-CF3-phenyl |
| 89 | —CH2OMe | 1 | CH2 | H | 2-CF3-phenyl |
| 90 | —CH2OMe | 1 | CH2 | F | phenyl |
| 91 | —CH2OMe | 1 | CH2 | CH3 | phenyl |
| 92 | —CH2OMe | 1 | CH2 | H | phenyl |
| 93 | —CH2OMe | 1 | CH2 | F | amidino |
| 94 | —CH2OMe | 1 | CH2 | CH3 | amidino |
| 95 | —CH2OMe | 1 | CH2 | H | amidino |
| 96 | —SO2CH3 | 1 | CH2 | H | 2-sulfonamidophenyl |
| 97 | —SO2CH3 | 1 | CH2 | F | 2-sulfonamidophenyl |
| 98 | —SO2CH3 | 1 | CH2 | CH3 | 2-sulfonamidophenyl |
| 99 | —SO2CH3 | 1 | CH2 | F | 2-CF3-phenyl |
| 100 | —SO2CH3 | 1 | CH2 | CH3 | 2-CF3-phenyl |
| 101 | —SO2CH3 | 1 | CH2 | H | 2-CF3-phenyl |
| 102 | —SO2CH3 | 1 | CH2 | F | phenyl |
| 103 | —SO2CH3 | 1 | CH2 | CH3 | phenyl |
| 104 | —SO2CH3 | 1 | CH2 | H | phenyl |
| 105 | —SO2CH3 | 1 | CH2 | F | amidino |
| 106 | —SO2CH3 | 1 | CH2 | CH3 | amidino |
| 107 | —SO2CH3 | 1 | CH2 | H | amidino |
| 108 | —CO2Me | 1 | O | H | 2-sulfonamidophenyl |
| 109 | —CO2Me | 1 | O | F | 2-sulfonamidophenyl |
| 110 | —CO2Me | 1 | O | CH3 | 2-sulfonamidophenyl |
| 111 | —CO2Me | 1 | O | F | 2-CF3-phenyl |
| 112 | —CO2Me | 1 | O | CH3 | 2-CF3-phenyl |
| 113 | —CO2Me | 1 | O | H | 2-CF3-phenyl |
| 114 | —CO2Me | 1 | O | F | phenyl |
| 115 | —CO2Me | 1 | O | CH3 | phenyl |
| 116 | —CO2Me | 1 | O | H | phenyl |
| 117 | —CO2Me | 1 | O | F | amidino |
| 118 | —CO2Me | 1 | O | CH3 | amidino |
| 119 | —CO2Me | 1 | O | H | amidino |
| 120 | —CH2OMe | 1 | O | H | 2-sulfonamidophenyl |
| 121 | —CH2OMe | 1 | O | F | 2-sulfonamidophenyl |
| 122 | —CH2OMe | 1 | O | CH3 | 2-sulfonamidophenyl |
| 123 | —CH2OMe | 1 | O | F | 2-CF3-phenyl |
| 124 | —CH2OMe | 1 | O | CH3 | 2-CF3-phenyl |

TABLE 7-continued

| Ex # | R | n | Z | R⁴ | B |
|---|---|---|---|---|---|
| 125 | —CH₂OMe | 1 | O | H | 2-CF₃-phenyl |
| 126 | —CH₂OMe | 1 | O | F | phenyl |
| 127 | —CH₂OMe | 1 | O | CH₃ | phenyl |
| 128 | —CH₂OMe | 1 | O | H | phenyl |
| 129 | —CH₂OMe | 1 | O | F | amidino |
| 130 | —CH₂OMe | 1 | O | CH₃ | amidino |
| 131 | —CH₂OMe | 1 | O | H | amidino |
| 132 | —SO₂CH₃ | 1 | O | F | 2-sulfonamidophenyl |
| 133 | —SO₂CH₃ | 1 | O | CH₃ | 2-sulfonamidophenyl |
| 134 | —SO₂CH₃ | 1 | O | F | 2-CF₃-phenyl |
| 135 | —SO₂CH₃ | 1 | O | CH₃ | 2-CF₃-phenyl |
| 136 | —SO₂CH₃ | 1 | O | H | 2-CF₃-phenyl |
| 137 | —SO₂CH₃ | 1 | O | F | phenyl |
| 138 | —SO₂CH₃ | 1 | O | CH₃ | phenyl |
| 139 | —SO₂CH₃ | 1 | O | H | phenyl |
| 140 | —SO₂CH₃ | 1 | O | F | amidino |
| 141 | —SO₂CH₃ | 1 | O | CH₃ | amidino |
| 142 | —SO₂CH₃ | 1 | O | H | amidino |

TABLE 8

| Ex # | R | n | Z | R⁴ | B |
|---|---|---|---|---|---|
| 1 | —CO₂Me | 0 | CH₂ | H | 2-methylaminosulfonylphenyl |
| 2 | —CO₂Me | 0 | CH₂ | F | 2-sulfonamidophenyl |
| 3 | —CO₂Me | 0 | CH₂ | CH₃ | 2-sulfonamidophenyl |
| 4 | —CO₂Me | 0 | CH₂ | F | 2-CF₃-phenyl |
| 5 | —CO₂Me | 0 | CH₂ | CH₃ | 2-CF₃-phenyl |
| 6 | —CO₂Me | 0 | CH₂ | H | 2-CF₃-phenyl |
| 7 | —CO₂Me | 0 | CH₂ | F | phenyl |
| 8 | —CO₂Me | 0 | CH₂ | CH₃ | phenyl |
| 9 | —CO₂Me | 0 | CH₂ | H | phenyl |
| 10 | —CO₂Me | 0 | CH₂ | F | amidino |
| 11 | —CO₂Me | 0 | CH₂ | CH₃ | amidino |
| 12 | —CH₂OMe | 0 | CH₂ | H | 2-sulfonamidophenyl |
| 13 | —CH₂OMe | 0 | CH₂ | F | 2-methylaminosulfonylphenyl |
| 14 | —CH₂OMe | 0 | CH₂ | CH₃ | 2-sulfonamidophenyl |
| 15 | —CH₂OMe | 0 | CH₂ | F | 2-CF₃-phenyl |
| 16 | —CH₂OMe | 0 | CH₂ | CH₃ | 2-CF₃-phenyl |
| 17 | —CH₂OMe | 0 | CH₂ | H | 2-CF₃-phenyl |
| 18 | —CH₂OMe | 0 | CH₂ | F | phenyl |
| 19 | —CH₂OMe | 0 | CH₂ | CH₃ | phenyl |
| 20 | —CH₂OMe | 0 | CH₂ | H | phenyl |
| 21 | —CH₂OMe | 0 | CH₂ | F | amidino |
| 22 | —CH₂OMe | 0 | CH₂ | CH₃ | amidino |
| 23 | —CH₂OMe | 0 | CH₂ | H | amidino |
| 24 | —SO₂CH₃ | 0 | CH₂ | H | 2-sulfonamidophenyl |
| 25 | —SO₂CH₃ | 0 | CH₂ | F | 2-sulfonamidophenyl |
| 26 | —SO₂CH₃ | 0 | CH₂ | CH₃ | 2-sulfonamidophenyl |
| 27 | —SO₂CH₃ | 0 | CH₂ | F | 2-CF₃-phenyl |
| 28 | —SO₂CH₃ | 0 | CH₂ | CH₃ | 2-CF₃-phenyl |
| 29 | —SO₂CH₃ | 0 | CH₂ | H | 2-CF₃-phenyl |
| 30 | —SO₂CH₃ | 0 | CH₂ | F | phenyl |
| 31 | —SO₂CH₃ | 0 | CH₂ | CH₃ | phenyl |
| 32 | —SO₂CH₃ | 0 | CH₂ | H | phenyl |
| 33 | —SO₂CH₃ | 0 | CH₂ | F | amidino |
| 34 | —SO₂CH₃ | 0 | CH₂ | CH₃ | amidino |
| 35 | —SO₂CH₃ | 0 | CH₂ | H | amidino |
| 36 | —CO₂Me | 0 | O | H | 2-sulfonamidophenyl |
| 37 | —CO₂Me | 0 | O | F | 2-sulfonamidophenyl |
| 38 | —CO₂Me | 0 | O | CH₃ | 2-methylaminosulfonylphenyl |
| 39 | —CO₂Me | 0 | O | F | 2-CF₃-phenyl |
| 40 | —CO₂Me | 0 | O | CH₃ | 2-CF₃-phenyl |
| 41 | —CO₂Me | 0 | O | H | 2-CF₃-phenyl |
| 42 | —CO₂Me | 0 | O | F | phenyl |
| 43 | —CO₂Me | 0 | O | CH₃ | phenyl |
| 44 | —CO₂Me | 0 | O | H | phenyl |
| 45 | —CO₂Me | 0 | O | F | amidino |
| 46 | —CO₂Me | 0 | O | CH₃ | amidino |
| 47 | —CO₂Me | 0 | O | H | amidino |
| 48 | —CH₂OMe | 0 | O | H | 2-sulfonamidophenyl |
| 49 | —CH₂OMe | 0 | O | F | 2-sulfonamidophenyl |
| 50 | —CH₂OMe | 0 | O | CH₃ | 2-sulfonamidophenyl |
| 51 | —CH₂OMe | 0 | O | F | 2-CF₃-phenyl |
| 52 | —CH₂OMe | 0 | O | CH₃ | 2-CF₃-phenyl |
| 53 | —CH₂OMe | 0 | O | H | 2-CF₃-phenyl |
| 54 | —CH₂OMe | 0 | O | F | phenyl |
| 55 | —CH₂OMe | 0 | O | CH₃ | phenyl |
| 56 | —CH₂OMe | 0 | O | H | phenyl |
| 57 | —CH₂OMe | 0 | O | F | amidino |
| 58 | —CH₂OMe | 0 | O | CH₃ | amidino |
| 59 | —CH₂OMe | 0 | O | H | amidino |
| 60 | —SO₂CH₃ | 0 | O | H | 2-sulfonamidophenyl |
| 61 | —SO₂CH₃ | 0 | O | F | 2-sulfonamidophenyl |
| 62 | —SO₂CH₃ | 0 | O | CH₃ | 2-sulfonamidophenyl |
| 63 | —SO₂CH₃ | 0 | O | F | 2-CF₃-phenyl |
| 64 | —SO₂CH₃ | 0 | O | CH₃ | 2-CF₃-phenyl |
| 65 | —SO₂CH₃ | 0 | O | H | 2-CF₃-phenyl |
| 66 | —SO₂CH₃ | 0 | O | F | phenyl |
| 67 | —SO₂CH₃ | 0 | O | CH₃ | phenyl |
| 68 | —SO₂CH₃ | 0 | O | H | phenyl |
| 69 | —SO₂CH₃ | 0 | O | F | amidino |
| 70 | —SO₂CH₃ | 0 | O | CH₃ | amidino |
| 71 | —SO₂CH₃ | 0 | O | H | amidino |
| 72 | —CO₂Me | 1 | CH₂ | H | 2-sulfonamidophenyl |
| 73 | —CO₂Me | 1 | CH₂ | F | 2-sulfonamidophenyl |
| 74 | —CO₂Me | 1 | CH₂ | CH₃ | 2-sulfonamidophenyl |
| 75 | —CO₂Me | 1 | CH₂ | F | 2-CF₃-phenyl |
| 76 | —CO₂Me | 1 | CH₂ | CH₃ | 2-CF₃-phenyl |
| 77 | —CO₂Me | 1 | CH₂ | H | 2-CF₃-phenyl |
| 78 | —CO₂Me | 1 | CH₂ | F | phenyl |
| 79 | —CO₂Me | 1 | CH₂ | CH₃ | phenyl |
| 80 | —CO₂Me | 1 | CH₂ | H | phenyl |
| 81 | —CO₂Me | 1 | CH₂ | F | amidino |
| 82 | —CO₂Me | 1 | CH₂ | CH₃ | amidino |
| 83 | —CO₂Me | 1 | CH₂ | H | amidino |
| 84 | —CH₂OMe | 1 | CH₂ | H | 2-sulfonamidophenyl |

TABLE 8-continued

[Structure: pyrrolidine ring with Z, R(CH2)n substituent, connected to 3-amidinophenyl group and to N-CH2CH2-(phenyl with R4 and B substituents)]

| Ex # | R | n | Z | R⁴ | B |
|---|---|---|---|---|---|
| 85 | —CH₂OMe | 1 | CH₂ | F | 2-sulfonamidophenyl |
| 86 | —CH₂OMe | 1 | CH₂ | CH₃ | 2-sulfonamidophenyl |
| 87 | —CH₂OMe | 1 | CH₂ | F | 2-CF₃-phenyl |
| 88 | —CH₂OMe | 1 | CH₂ | CH₃ | 2-CF₃-phenyl |
| 89 | —CH₂OMe | 1 | CH₂ | H | 2-CF₃-phenyl |
| 90 | —CH₂OMe | 1 | CH₂ | F | phenyl |
| 91 | —CH₂OMe | 1 | CH₂ | CH₃ | phenyl |
| 92 | —CH₂OMe | 1 | CH₂ | H | phenyl |
| 93 | —CH₂OMe | 1 | CH₂ | F | amidino |
| 94 | —CH₂OMe | 1 | CH₂ | CH₃ | amidino |
| 95 | —CH₂OMe | 1 | CH₂ | H | amidino |
| 96 | —SO₂CH₃ | 1. | CH₂ | H | 2-sulfonamidophenyl |
| 97 | —SO₂CH₃ | 1 | CH₂ | F | 2-sulfonamidophenyl |
| 98 | —SO₂CH₃ | 1 | CH₂ | CH₃ | 2-sulfonamidophenyl |
| 99 | —SO₂CH₃ | 1 | CH₂ | F | 2-CF₃-phenyl |
| 100 | —SO₂CH₃ | 1 | CH₂ | CH₃ | 2-CF₃-phenyl |
| 101 | —SO₂CH₃ | 1 | CH₂ | H | 2-CF₃-phenyl |
| 102 | —SO₂CH₃ | 1 | CH₂ | F | phenyl |
| 103 | —SO₂CH₃ | 1 | CH₂ | CH₃ | phenyl |
| 104 | —SO₂CH₃ | 1 | CH₂ | H | phenyl |
| 105 | —SO₂CH₃ | 1 | CH₂ | F | amidino |
| 106 | —SO₂CH₃ | 1 | CH₂ | CH₃ | amidino |
| 107 | —SO₂CH₃ | 1 | CH₂ | H | amidino |
| 108 | —CO₂Me | 1 | O | H | 2-sulfonamidophenyl |
| 109 | —CO₂Me | 1 | O | F | 2-sulfonamidophenyl |
| 110 | —CO₂Me | 1 | O | CH₃ | 2-sulfonamidophenyl |
| 111 | —CO₂Me | 1 | O | F | 2-CF₃-phenyl |
| 112 | —CO₂Me | 1 | O | CH₃ | 2-CF₃-phenyl |
| 113 | —CO₂Me | 1 | O | H | 2-CF₃-phenyl |
| 114 | —CO₂Me | 1 | O | F | phenyl |
| 115 | —CO₂Me | 1 | O | CH₃ | phenyl |
| 116 | —CO₂Me | 1 | O | H | phenyl |
| 117 | —CO₂Me | 1 | O | F | amidino |
| 118 | —CO₂Me | 1 | O | CH₃ | amidino |
| 119 | —CO₂Me | 1 | O | H | amidino |
| 120 | —CH₂OMe | 1 | O | H | 2-sulfonamidophenyl |
| 121 | —CH₂OMe | 1 | O | F | 2-sulfonamidophenyl |
| 122 | —CH₂OMe | 1 | O | CH₃ | 2-sulfonamidophenyl |
| 123 | —CH₂OMe | 1 | O | F | 2-CF₃-phenyl |
| 124 | —CH₂OMe | 1 | O | CH₃ | 2-CF₃-phenyl |
| 125 | —CH₂OMe | 1 | O | H | 2-CF₃-phenyl |
| 126 | —CH₂OMe | 1 | O | F | phenyl |
| 127 | —CH₂OMe | 1 | O | CH₃ | phenyl |
| 128 | —CH₂OMe | 1 | O | H | phenyl |
| 129 | —CH₂OMe | 1 | O | F | amidino |
| 130 | —CH₂OMe | 1 | O | CH₃ | amidino |
| 131 | —CH₂OMe | 1 | O | H | amidino |
| 132 | —SO₂CH₃ | 1 | O | F | 2-sulfonamidophenyl |
| 133 | —SO₂CH₃ | 1 | O | CH₃ | 2-sulfonamidophenyl |
| 134 | —SO₂CH₃ | 1 | O | F | 2-CF₃-phenyl |
| 135 | —SO₂CH₃ | 1 | O | CH₃ | 2-CF₃-phenyl |
| 136 | —SO₂CH₃ | 1 | O | H | 2-CF₃-phenyl |
| 137 | —SO₂CH₃ | 1 | O | F | phenyl |
| 138 | —SO₂CH₃ | 1 | O | CH₃ | phenyl |
| 139 | —SO₂CH₃ | 1 | O | H | phenyl |
| 140 | —SO₂CH₃ | 1 | O | F | amidino |
| 141 | —SO₂CH₃ | 1 | O | CH₃ | amidino |
| 142 | —SO₂CH₃ | 1 | O | H | amidino |

TABLE 9

[Structure: pyrrolidine ring with Z, R(CH2)n substituent, connected to 3-amidinophenyl group and to N-CH2-(phenyl with R4 and B substituents)]

| Ex # | R | n | Z | R⁴ | B |
|---|---|---|---|---|---|
| 1 | —CO₂Me | 0 | O | H | 2-sulfonamidophenyl |
| 2 | —CO₂Me | 0 | O | F | 2-sulfonamidophenyl |
| 3 | —CO₂Me | 0 | O | CH₃ | 2-sulfonamidophenyl |
| 4 | —CO₂Me | 0 | O | F | 2-CF₃-phenyl |
| 5 | —CO₂Me | 0 | O | CH₃ | 2-CF₃-phenyl |
| 6 | —CO₂Me | 0 | O | H | 2-CF₃-phenyl |
| 7 | —CO₂Me | 0 | O | F | phenyl |
| 8 | —CO₂Me | 0 | O | CH₃ | phenyl |
| 9 | —CO₂Me | 0 | O | H | phenyl |
| 10 | —CO₂Me | 0 | O | F | amidino |
| 11 | —CO₂Me | 0 | O | CH₃ | amidino |
| 12 | —CO₂Me | 0 | O | H | amidino |
| 13 | —CH₂OMe | 0 | O | H | 2-sulfonamidophenyl |
| 14 | —CH₂OMe | 0 | O | F | 2-methylaminosulfonylphenyl |
| 15 | —CH₂OMe | 0 | O | CH₃ | 2-sulfonamidophenyl |
| 16 | —CH₂OMe | 0 | O | F | 2-CF₃-phenyl |
| 17 | —CH₂OMe | 0 | O | CH₃ | 2-CF₃-phenyl |
| 18 | —CH₂OMe | 0 | O | H | 2-CF₃-phenyl |
| 19 | —CH₂OMe | 0 | O | F | phenyl |
| 20 | —CH₂OMe | 0 | O | CH₃ | phenyl |
| 21 | —CH₂OMe | 0 | O | H | phenyl |
| 22 | —CH₂OMe | 0 | O | F | amidino |
| 23 | —CH₂OMe | 0 | O | CH₃ | amidino |
| 24 | —CH₂OMe | 0 | O | H | amidino |
| 25 | —SO₂CH₃ | 0 | O | H | 2-sulfonamidophenyl |
| 26 | —SO₂CH₃ | 0 | O | F | 2-sulfonamidophenyl |
| 27 | —SO₂CH₃ | 0 | O | CH₃ | 2-sulfonamidophenyl |
| 28 | —SO₂CH₃ | 0 | O | F | 2-CF₃-pheny1 |
| 29 | —SO₂CH₃ | 0 | O | CH₃ | 2-CF₃-phenyl |
| 30 | —SO₂CH₃ | 0 | O | H | 2-CF₃-phenyl |
| 31 | —SO₂CH₃ | 0 | O | F | phenyl |
| 32 | —SO₂CH₃ | 0 | O | CH₃ | phenyl |
| 33 | —SO₂CH₃ | 0 | O | H | phenyl |
| 34 | —SO₂CH₃ | 0 | O | F | amidino |
| 35 | —SO₂CH₃ | 0 | O | CH₃ | amidino |
| 36 | —SO₂CH₃ | 0 | O | H | amidino |
| 37 | —CO₂Me | 1 | O | H | 2-methylaminosulfonylphenyl |
| 38 | —CO₂Me | 1 | O | F | 2-sulfonamidophenyl |
| 39 | —CO₂Me | 1 | O | CH₃ | 2-sulfonamidophenyl |
| 40 | —CO₂Me | 1 | O | F | 2-CF₃-phenyl |
| 41 | —CO₂Me | 1 | O | CH₃ | 2-CF₃-phenyl |
| 42 | —CO₂Me | 1 | O | H | 2-CF₃-phenyl |
| 43 | —CO₂Me | 1 | O | F | phenyl |
| 44 | —CO₂Me | 1 | O | CH₃ | phenyl |
| 45 | —CO₂Me | 1 | O | H | phenyl |
| 46 | —CO₂Me | 1 | O | F | amidino |
| 47 | —CO₂Me | 1 | O | CH₃ | amidino |
| 48 | —CO₂Me | 1 | O | H | amidino |
| 49 | —CH₂OMe | 1 | O | H | 2-sulfonamidophenyl |
| 50 | —CH₂OMe | 1 | O | F | 2-methylaminosulfonylphenyl |
| 51 | —CH₂OMe | 1 | O | CH₃ | 2-sulfonamidophenyl |
| 52 | —CH₂OMe | 1 | O | F | 2-CF₃-phenyl |
| 53 | —CH₂OMe | 1 | O | CH₃ | 2-CF₃-phenyl |
| 54 | —CH₂OMe | 1 | O | H | 2-CF₃-phenyl |
| 55 | —CH₂OMe | 1 | O | F | phenyl |
| 56 | —CH₂OMe | 1 | O | CH₃ | phenyl |
| 57 | —CH₂OMe | 1 | O | H | phenyl |
| 58 | —CH₂OMe | 1 | O | F | amidino |
| 59 | —CH₂OMe | 1 | O | CH₃ | amidino |
| 60 | —CH₂OMe | 1 | O | H | amidino |
| 61 | —SO₂CH₃ | 1 | O | H | 2-sulfonamidophenyl |
| 62 | —SO₂CH₃ | 1 | O | F | 2-sulfonamidophenyl |
| 63 | —SO₂CH₃ | 1 | O | CH₃ | 2-sulfonamidophenyl |
| 64 | —SO₂CH₃ | 1 | O | F | 2-CF₃-phenyl |

TABLE 9-continued

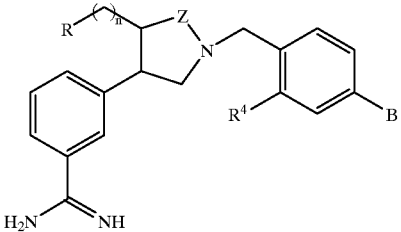

| Ex # | R | n | Z | R⁴ | B |
|---|---|---|---|---|---|
| 65 | —SO₂CH₃ | 1 | O | CH₃ | 2-CF₃-phenyl |
| 66 | —SO₂CH₃ | 1 | O | H | 2-CF₃-phenyl |
| 67 | —SO₂CH₃ | 1 | O | F | phenyl |
| 68 | —SO₂CH₃ | 1 | O | CH₃ | phenyl |
| 69 | —SO₂CH₃ | 1 | O | H | phenyl |
| 70 | —SO₂CH₃ | 1 | O | F | amidino |
| 71 | —SO₂CH₃ | 1 | O | CH₃ | amidino |
| 72 | —SO₂CH₃ | 1 | O | H | amidino |

TABLE 10

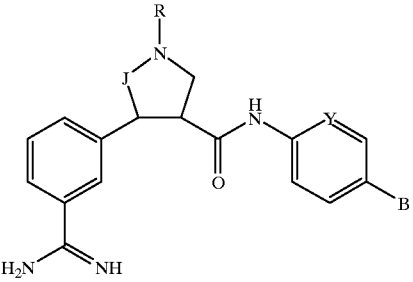

| Ex # | R | J | Y | B |
|---|---|---|---|---|
| 1 | SO₂Me | CH₂ | CH | 2-(aminosulfonyl)phenyl |
| 2 | SO₂Me | CH₂ | CH | 2-(methylsulfonyl)phenyl |
| 3 | SO₂Me | CH₂ | CH | 2-(trifluoromethyl)phenyl |
| 4 | SO₂Me | CH₂ | N | 2-(aminosulfonyl)phenyl |
| 5 | SO₂Me | CH₂ | N | 2-(methylsulfonyl)phenyl |
| 6 | SO₂Me | CH₂ | N | 2-(trifluoromethyl)phenyl |
| 7 | SO₂Me | CH₂ | CF | 2-(aminosulfonyl)phenyl |
| 8 | SO₂Me | CH₂ | CF | 2-(methylsulfonyl)phenyl |
| 9 | SO₂Me | CH₂ | CF | 2-(trifluoromethyl)phenyl |
| 10 | SO₂Me | CH₂ | CCl | 2-(aminosulfonyl)phenyl |
| 11 | SO₂Me | CH₂ | CCl | 2-(methylsulfonyl)phenyl |
| 12 | SO₂Me | CH₂ | CCl | 2-(trifluoromethyl)phenyl |
| 13 | SO₂Me | O | CH | 2-(aminosulfonyl)phenyl |
| 14 | SO₂Me | O | CH | 2-(methylsulfonyl)phenyl |
| 15 | SO₂Me | O | CH | 2-(trifluoromethyl)phenyl |
| 16 | SO₂Me | O | N | 2-(aminosulfonyl)phenyl |
| 17 | SO₂Me | O | N | 2-(methylsulfonyl)phenyl |
| 18 | SO₂Me | O | N | 2-(trifluoromethyl)phenyl |
| 19 | SO₂Me | O | CF | 2-(aminosulfonyl)phenyl |
| 20 | SO₂Me | O | CF | 2-(methylsulfonyl)phenyl |
| 21 | SO₂Me | O | CF | 2-(trifluoromethyl)phenyl |
| 22 | SO₂Me | O | CCl | 2-(aminosulfonyl)phenyl |
| 23 | SO₂Me | O | CCl | 2-(methylsulfonyl)phenyl |
| 24 | SO₂Me | O | CCl | 2-(trifluoromethyl)phenyl |
| 25 | CO₂Me | CH₂ | CH | 2-(aminosulfonyl)phenyl |
| 26 | CO₂Me | CH₂ | CH | 2-(methylsulfonyl)phenyl |
| 27 | CO₂Me | CH₂ | CH | 2-(trifluoromethyl)phenyl |
| 28 | CO₂Me | CH₂ | N | 2-(aminosulfonyl)phenyl |
| 29 | CO₂Me | CH₂ | N | 2-(methylsulfonyl)phenyl |
| 30 | CO₂Me | CH₂ | N | 2-(trifluoromethyl)phenyl |
| 31 | CO₂Me | CH₂ | CF | 2-(aminosulfonyl)phenyl |
| 32 | CO₂Me | CH₂ | CF | 2-(methylsulfonyl)phenyl |
| 33 | CO₂Me | CH₂ | CF | 2-(trifluoromethyl)phenyl |
| 34 | CO₂Me | CH₂ | CCl | 2-(aminosulfonyl)phenyl |
| 35 | CO₂Me | CH₂ | CCl | 2-(methylsulfonyl)phenyl |
| 36 | CO₂Me | CH₂ | CCl | 2-(trifluoromethyl)phenyl |
| 37 | CO₂Me | O | CH | 2-(aminosulfonyl)phenyl |
| 38 | CO₂Me | O | CH | 2-(methylsulfonyl)phenyl |
| 39 | CO₂Me | O | CH | 2-(trifluoromethyl)phenyl |
| 40 | CO₂Me | O | N | 2-(aminosulfonyl)phenyl |
| 41 | CO₂Me | O | N | 2-(methylsulfonyl)phenyl |
| 42 | CO₂Me | O | N | 2-(trifluoromethyl)phenyl |
| 43 | CO₂Me | O | CF | 2-(aminosulfonyl)phenyl |
| 44 | CO₂Me | O | CF | 2-(methylsulfonyl)phenyl |
| 45 | CO₂Me | O | CF | 2-(trifluoromethyl)phenyl |
| 46 | CO₂Me | O | CCl | 2-(aminosulfonyl)phenyl |
| 47 | CO₂Me | O | CCl | 2-(methylsulfonyl)phenyl |
| 48 | CO₂Me | O | CCl | 2-(trifluoromethyl)phenyl |
| 49 | COCH₃ | CH₂ | CH | 2-(aminosulfonyl)phenyl |
| 50 | COCH₃ | CH₂ | CH | 2-(methylsulfonyl)phenyl |
| 51 | COCH₃ | CH₂ | CH | 2-(trifluoromethyl)phenyl |
| 52 | COCH₃ | CH₂ | N | 2-(aminosulfonyl)phenyl |
| 53 | COCH₃ | CH₂ | N | 2-(methylsulfonyl)phenyl |
| 54 | COCH₃ | CH₂ | N | 2-(trifluoromethyl)phenyl |
| 55 | COCH₃ | CH₂ | CF | 2-(aminosulfonyl)phenyl |
| 56 | COCH₃ | CH₂ | CF | 2-(methylsulfonyl)phenyl |
| 57 | COCH₃ | CH₂ | CF | 2-(trifluoromethyl)phenyl |
| 58 | COCH₃ | CH₂ | CCl | 2-(aminosulfonyl)phenyl |
| 59 | COCH₃ | CH₂ | CCl | 2-(methylsulfonyl)phenyl |
| 60 | COCH₃ | CH₂ | CCl | 2-(trifluoromethyl)phenyl |
| 61 | COCH₃ | O | CH | 2-(aminosulfonyl)phenyl |
| 62 | COCH₃ | O | CH | 2-(methylsulfonyl)phenyl |
| 63 | COCH₃ | O | CH | 2-(trifluoromethyl)phenyl |
| 64 | COCH₃ | O | N | 2-(aminosulfonyl)phenyl |
| 65 | COCH₃ | O | N | 2-(methylsulfonyl)phenyl |
| 66 | COCH₃ | O | N | 2-(trifluoromethyl)phenyl |
| 67 | COCH₃ | O | CF | 2-(aminosulfonyl)phenyl |
| 68 | COCH₃ | O | CF | 2-(methylsulfonyl)phenyl |
| 69 | COCH₃ | O | CF | 2-(trifluoromethyl)phenyl |
| 70 | COCH₃ | O | CCl | 2-(aminosulfonyl)phenyl |
| 71 | COCH₃ | O | CCl | 2-(methylsulfonyl)phenyl |
| 72 | COCH₃ | O | CCl | 2-(trifluoromethyl)phenyl |
| 73 | CH₃ | CH₂ | CH | 2-(aminosulfonyl)phenyl |
| 74 | CH₃ | CH₂ | CH | 2-(methylsulfonyl)phenyl |
| 75 | CH₃ | CH₂ | CH | 2-(trifluoromethyl)phenyl |
| 76 | CH₃ | CH₂ | N | 2-(aminosulfonyl)phenyl |
| 77 | CH₃ | CH₂ | N | 2-(methylsulfonyl)phenyl |
| 78 | CH₃ | CH₂ | N | 2-(trifluoromethyl)phenyl |
| 79 | CH₃ | CH₂ | CF | 2-(aminosulfonyl)phenyl |
| 80 | CH₃ | CH₂ | CF | 2-(methylsulfonyl)phenyl |
| 81 | CH₃ | CH₂ | CF | 2-(trifluoromethyl)phenyl |
| 82 | CH₃ | CH₂ | CCl | 2-(aminosulfonyl)phenyl |
| 83 | CH₃ | CH₂ | CCl | 2-(methylsulfonyl)phenyl |
| 84 | CH₃ | CH₂ | CCl | 2-(trifluoromethyl)phenyl |
| 85 | CH₃ | O | CH | 2-(aminosulfonyl)phenyl |
| 86 | CH₃ | O | CH | 2-(methylsulfonyl)phenyl |
| 87 | CH₃ | O | CH | 2-(trifluoromethyl)phenyl |
| 88 | CH₃ | O | N | 2-(aminosulfonyl)phenyl |
| 89 | CH₃ | O | N | 2-(methylsulfonyl)phenyl |
| 90 | CH₃ | O | N | 2-(trifluoromethyl)phenyl |
| 91 | CH₃ | O | CF | 2-(aminosulfonyl)phenyl |
| 92 | CH₃ | O | CF | 2-(methylsulfonyl)phenyl |
| 93 | CH₃ | O | CF | 2-(trifluoromethyl)phenyl |
| 94 | CH₃ | O | CCl | 2-(aminosulfonyl)phenyl |
| 95 | CH₃ | O | CCl | 2-(methylsulfonyl)phenyl |
| 96 | CH₃ | O | CCl | 2-(trifluoromethyl)phenyl |

TABLE 10-continued

[Structure: pyrrolidine with R-N, J linker, 3-aryl group with meta-amidine (C(=NH)NH2), and 4-carboxamide N-H linked to phenyl with Y and B substituents]

| Ex # | R | J | Y | B |
|---|---|---|---|---|
| 97 | CH₂Ph | CH₂ | CH | 2-(aminosulfonyl)phenyl |
| 98 | CH₂Ph | CH₂ | CH | 2-(methylsulfonyl)phenyl |
| 99 | CH₂Ph | CH₂ | CH | 2-(trifluoromethyl)phenyl |
| 100 | CH₂Ph | CH₂ | N | 2-(aminosulfonyl)phenyl |
| 101 | CH₂Ph | CH₂ | N | 2-(methylsulfonyl)phenyl |
| 102 | CH₂Ph | CH₂ | N | 2-(trifluoromethyl)phenyl |
| 103 | CH₂Ph | CH₂ | CF | 2-(aminosulfonyl)phenyl |
| 104 | CH₂Ph | CH₂ | CF | 2-(methylsulfonyl)phenyl |
| 105 | CH₂Ph | CH₂ | CF | 2-(trifluoromethyl)phenyl |
| 106 | CH₂Ph | CH₂ | CCl | 2-(aminosulfonyl)phenyl |
| 107 | CH₂Ph | CH₂ | CCl | 2-(methylsulfonyl)phenyl |
| 108 | CH₂Ph | CH₂ | CCl | 2-(trifluoromethyl)phenyl |
| 109 | CH₂Ph | O | CH | 2-(aminosulfonyl)phenyl |
| 110 | CH₂Ph | O | CH | 2-(methylsulfonyl)phenyl |
| 111 | CH₂Ph | O | CH | 2-(trifluoromethyl)phenyl |
| 112 | CH₂Ph | O | N | 2-(aminosulfonyl)phenyl |
| 113 | CH₂Ph | O | N | 2-(methylsulfonyl)phenyl |
| 114 | CH₂Ph | O | N | 2-(trifluoromethyl)phenyl |
| 115 | CH₂Ph | O | CF | 2-(aminosulfonyl)phenyl |
| 116 | CH₂Ph | O | CF | 2-(methylsulfonyl)phenyl |
| 117 | CH₂Ph | O | CF | 2-(trifluoromethyl)phenyl |
| 118 | CH₂Ph | O | CCl | 2-(aminosulfonyl)phenyl |
| 119 | CH₂Ph | O | CCl | 2-(methylsulfonyl)phenyl |
| 120 | CH₂Ph | O | CCl | 2-(trifluoromethyl)phenyl |
| 121 | H | CH₂ | CH | 2-(aminosulfonyl)phenyl |
| 122 | H | CH₂ | CH | 2-(methylsulfonyl)phenyl |
| 123 | H | CH₂ | CH | 2-(trifluoromethyl)phenyl |
| 124 | H | CH₂ | N | 2-(aminosulfonyl)phenyl |
| 125 | H | CH₂ | N | 2-(methylsulfonyl)phenyl |
| 126 | H | CH₂ | N | 2-(trifluoromethyl)phenyl |
| 127 | H | CH₂ | CF | 2-(aminosulfonyl)phenyl |
| 128 | H | CH₂ | CF | 2-(methylsulfonyl)phenyl |
| 129 | H | CH₂ | CF | 2-(trifluoromethyl)phenyl |
| 130 | H | CH₂ | CCl | 2-(aminosulfonyl)phenyl |
| 131 | H | CH₂ | CCl | 2-(methylsulfonyl)phenyl |
| 132 | H | CH₂ | CCl | 2-(trifluoromethyl)phenyl |
| 133 | H | O | CH | 2-(aminosulfonyl)phenyl |
| 134 | H | O | CH | 2-(methylsulfonyl)phenyl |
| 135 | H | O | CH | 2-(trifluoromethyl)phenyl |
| 136 | H | O | N | 2-(aminosulfonyl)phenyl |
| 137 | H | O | N | 2-(methylsulfonyl)phenyl |
| 138 | H | O | N | 2-(trifluoromethyl)phenyl |
| 139 | H | O | CF | 2-(aminosulfonyl)phenyl |
| 140 | H | O | CF | 2-(methylsulfonyl)phenyl |
| 141 | H | O | CF | 2-(trifluoromethyl)phenyl |
| 142 | H | O | CCl | 2-(aminosulfonyl)phenyl |
| 143 | H | O | CCl | 2-(methylsulfonyl)phenyl |
| 144 | H | O | CCl | 2-(trifluoromethyl)phenyl |

TABLE 11

[Structure: pyrrolidine with R-N, J linker, 3-aryl with para-amidine (H2N-C(=NH)-), and 4-carboxamide N-H to phenyl with Y and B substituents]

| Ex # | R | J | Y | B |
|---|---|---|---|---|
| 1 | SO₂Me | CH₂ | CH | 2-(aminosulfonyl)phenyl |
| 2 | SO₂Me | CH₂ | CH | 2-(methylsulfonyl)phenyl |
| 3 | SO₂Me | CH₂ | CH | 2-(trifluoromethyl)phenyl |
| 4 | SO₂Me | CH₂ | N | 2-(aminosulfonyl)phenyl |
| 5 | SO₂Me | CH₂ | N | 2-(methylsulfonyl)phenyl |
| 6 | SO₂Me | CH₂ | N | 2-(trifluoromethyl)phenyl |
| 7 | SO₂Me | CH₂ | CF | 2-(aminosulfonyl)phenyl |
| 8 | SO₂Me | CH₂ | CF | 2-(methylsulfonyl)phenyl |
| 9 | SO₂Me | CH₂ | CF | 2-(trifluoromethyl)phenyl |
| 10 | SO₂Me | CH₂ | CCl | 2-(aminosulfonyl)phenyl |
| 11 | SO₂Me | CH₂ | CCl | 2-(methylsulfonyl)phenyl |
| 12 | SO₂Me | CH₂ | CCl | 2-(trifluoromethyl)phenyl |
| 13 | SO₂Me | O | CH | 2-(aminosulfonyl)phenyl |
| 14 | SO₂Me | O | CH | 2-(methylsulfonyl)phenyl |
| 15 | SO₂Me | O | CH | 2-(trifluoromethyl)phenyl |
| 16 | SO₂Me | O | N | 2-(aminosulfonyl)phenyl |
| 17 | SO₂Me | O | N | 2-(methylsulfonyl)phenyl |
| 18 | SO₂Me | O | N | 2-(trifluoromethyl)phenyl |
| 19 | SO₂Me | O | CF | 2-(aminosulfonyl)phenyl |
| 20 | SO₂Me | O | CF | 2-(methylsulfonyl)phenyl |
| 21 | SO₂Me | O | CF | 2-(trifluoromethyl)phenyl |
| 22 | SO₂Me | O | CCl | 2-(aminosulfonyl)phenyl |
| 23 | SO₂Me | O | CCl | 2-(methylsulfonyl)phenyl |
| 24 | SO₂Me | O | CCl | 2-(trifluoromethyl)phenyl |
| 25 | CO₂Me | CH₂ | CH | 2-(aminosulfonyl)phenyl |
| 26 | CO₂Me | CH₂ | CH | 2-(methylsulfonyl)phenyl |
| 27 | CO₂Me | CH₂ | CH | 2-(trifluoromethyl)phenyl |
| 28 | CO₂Me | CH₂ | N | 2-(aminosulfonyl)phenyl |
| 29 | CO₂Me | CH₂ | N | 2-(methylsulfonyl)phenyl |
| 30 | CO₂Me | CH₂ | N | 2-(trifluoromethyl)phenyl |
| 31 | CO₂Me | CH₂ | CF | 2-(aminosulfonyl)phenyl |
| 32 | CO₂Me | CH₂ | CF | 2-(methylsulfonyl)phenyl |
| 33 | CO₂Me | CH₂ | CF | 2-(trifluoromethyl)phenyl |
| 34 | CO₂Me | CH₂ | CCl | 2-(aminosulfonyl)phenyl |
| 35 | CO₂Me | CH₂ | CCl | 2-(methylsulfonyl)phenyl |
| 36 | CO₂Me | CH₂ | CCl | 2-(trifluoromethyl)phenyl |
| 37 | CO₂Me | O | CH | 2-(aminosulfonyl)phenyl |
| 38 | CO₂Me | O | CH | 2-(methylsulfonyl)phenyl |
| 39 | CO₂Me | O | CH | 2-(trifluoromethyl)phenyl |
| 40 | CO₂Me | O | N | 2-(aminosulfonyl)phenyl |
| 41 | CO₂Me | O | N | 2-(methylsulfonyl)phenyl |
| 42 | CO₂Me | O | N | 2-(trifluoromethyl)phenyl |
| 43 | CO₂Me | O | CF | 2-(aminosulfonyl)phenyl |
| 44 | CO₂Me | O | CF | 2-(methylsulfonyl)phenyl |
| 45 | CO₂Me | O | CF | 2-(trifluoromethyl)phenyl |
| 46 | CO₂Me | O | CCl | 2-(aminosulfonyl)phenyl |
| 47 | CO₂Me | O | CCl | 2-(methylsulfonyl)phenyl |
| 48 | CO₂Me | O | CCl | 2-(trifluoromethyl)phenyl |
| 49 | COCH₃ | CH₂ | CH | 2-(aminosulfonyl)phenyl |
| 50 | COCH₃ | CH₂ | CH | 2-(methylsulfonyl)phenyl |
| 51 | COCH₃ | CH₂ | CH | 2-(trifluoromethyl)phenyl |
| 52 | COCH₃ | CH₂ | N | 2-(aminosulfonyl)phenyl |
| 53 | COCH₃ | CH₂ | N | 2-(methylsulfonyl)phenyl |
| 54 | COCH₃ | CH₂ | N | 2-(trifluoromethyl)phenyl |
| 55 | COCH₃ | CH₂ | CF | 2-(aminosulfonyl)phenyl |
| 56 | COCH₃ | CH₂ | CF | 2-(methylsulfonyl)phenyl |
| 57 | COCH₃ | CH₂ | CF | 2-(trifluoromethyl)phenyl |
| 58 | COCH₃ | CH₂ | CCl | 2-(aminosulfonyl)phenyl |
| 59 | COCH₃ | CH₂ | CCl | 2-(methylsulfonyl)phenyl |
| 60 | COCH₃ | CH₂ | CCl | 2-(trifluoromethyl)phenyl |
| 61 | COCH₃ | O | CH | 2-(aminosulfonyl)phenyl |
| 62 | COCH₃ | O | CH | 2-(methylsulfonyl)phenyl |
| 63 | COCH₃ | O | CH | 2-(trifluoromethyl)phenyl |

TABLE 11-continued

| Ex # | R | J | Y | B |
|---|---|---|---|---|
| 64 | COCH$_3$ | O | N | 2-(aminosulfonyl)phenyl |
| 65 | COCH$_3$ | O | N | 2-(methylsulfonyl)phenyl |
| 66 | COCH$_3$ | O | N | 2-(trifluoromethyl)phenyl |
| 67 | COCH$_3$ | O | CF | 2-(aminosulfonyl)phenyl |
| 68 | COCH$_3$ | O | CF | 2-(methylsulfonyl)phenyl |
| 69 | COCH$_3$ | O | CF | 2-(trifluoromethyl)phenyl |
| 70 | COCH$_3$ | O | CCl | 2-(aminosulfonyl)phenyl |
| 71 | COCH$_3$ | O | CCl | 2-(methylsulfonyl)phenyl |
| 72 | COCH$_3$ | O | CCl | 2-(trifluoromethyl)phenyl |
| 73 | CH$_3$ | CH$_2$ | CH | 2-(aminosulfonyl)phenyl |
| 74 | CH$_3$ | CH$_2$ | CH | 2-(methylsulfonyl)phenyl |
| 75 | CH$_3$ | CH$_2$ | CH | 2-(trifluoromethyl)phenyl |
| 76 | CH$_3$ | CH$_2$ | N | 2-(aminosulfonyl)phenyl |
| 77 | CH$_3$ | CH$_2$ | N | 2-(methylsulfonyl)phenyl |
| 78 | CH$_3$ | CH$_2$ | N | 2-(trifluoromethyl)phenyl |
| 79 | CH$_3$ | CH$_2$ | CF | 2-(aminosulfonyl)phenyl |
| 80 | CH$_3$ | CH$_2$ | CF | 2-(methylsulfonyl)phenyl |
| 81 | CH$_3$ | CH$_2$ | CF | 2-(trifluoromethyl)phenyl |
| 82 | CH$_3$ | CH$_2$ | CCl | 2-(aminosulfonyl)phenyl |
| 83 | CH$_3$ | CH$_2$ | CCl | 2-(methylsulfonyl)phenyl |
| 84 | CH$_3$ | CH$_2$ | CCl | 2-(trifluoromethyl)phenyl |
| 85 | CH$_3$ | O | CH | 2-(aminosulfonyl)phenyl |
| 86 | CH$_3$ | O | CH | 2-(methylsulfonyl)phenyl |
| 87 | CH$_3$ | O | CH | 2-(trifluoromethyl)phenyl |
| 88 | CH$_3$ | O | N | 2-(aminosulfonyl)phenyl |
| 89 | CH$_3$ | O | N | 2-(methylsulfonyl)phenyl |
| 90 | CH$_3$ | O | N | 2-(trifluoromethyl)phenyl |
| 91 | CH$_3$ | O | CF | 2-(aminosulfonyl)phenyl |
| 92 | CH$_3$ | O | CF | 2-(methylsulfonyl)phenyl |
| 93 | CH$_3$ | O | CF | 2-(trifluoromethyl)phenyl |
| 94 | CH$_3$ | O | CCl | 2-(aminosulfonyl)phenyl |
| 95 | CH$_3$ | O | CCl | 2-(methylsulfonyl)phenyl |
| 96 | CH$_3$ | O | CCl | 2-(trifluoromethyl)phenyl |
| 97 | CH$_2$Ph | CH$_2$ | CH | 2-(aminosulfonyl)phenyl |
| 98 | CH$_2$Ph | CH$_2$ | CH | 2-(methylsulfonyl)phenyl |
| 99 | CH$_2$Ph | CH$_2$ | CH | 2-(trifluoromethyl)phenyl |
| 100 | CH$_2$Ph | CH$_2$ | N | 2-(aminosulfonyl)phenyl |
| 101 | CH$_2$Ph | CH$_2$ | N | 2-(methylsulfonyl)phenyl |
| 102 | CH$_2$Ph | CH$_2$ | N | 2-(trifluoromethyl)phenyl |
| 103 | CH$_2$Ph | CH$_2$ | CF | 2-(aminosulfonyl)phenyl |
| 104 | CH$_2$Ph | CH$_2$ | CF | 2-(methylsulfonyl)phenyl |
| 105 | CH$_2$Ph | CH$_2$ | CF | 2-(trifluoromethyl)phenyl |
| 106 | CH$_2$Ph | CH$_2$ | CCl | 2-(aminosulfonyl)phenyl |
| 107 | CH$_2$Ph | CH$_2$ | CCl | 2-(methylsulfonyl)phenyl |
| 108 | CH$_2$Ph | CH$_2$ | CCl | 2-(trifluoromethyl)phenyl |
| 109 | CH$_2$Ph | O | CH | 2-(aminosulfonyl)phenyl |
| 110 | CH$_2$Ph | O | CH | 2-(methylsulfonyl)phenyl |
| 111 | CH$_2$Ph | O | CH | 2-(trifluoromethyl)phenyl |
| 112 | CH$_2$Ph | O | N | 2-(aminosulfonyl)phenyl |
| 113 | CH$_2$Ph | O | N | 2-(methylsulfonyl)phenyl |
| 114 | CH$_2$Ph | O | N | 2-(trifluoromethyl)phenyl |
| 115 | CH$_2$Ph | O | CF | 2-(aminosulfonyl)phenyl |
| 116 | CH$_2$Ph | O | CF | 2-(methylsulfonyl)phenyl |
| 117 | CH$_2$Ph | O | CF | 2-(trifluoromethyl)phenyl |
| 118 | CH$_2$Ph | O | CCl | 2-(aminosulfonyl)phenyl |
| 119 | CH$_2$Ph | O | CCl | 2-(methylsulfonyl)phenyl |
| 120 | CH$_2$Ph | O | CCl | 2-(trifluoromethyl)phenyl |
| 121 | H | CH$_2$ | CH | 2-(aminosulfonyl)phenyl |
| 122 | H | CH$_2$ | CH | 2-(methylsulfonyl)phenyl |
| 123 | H | CH$_2$ | CH | 2-(trifluoromethyl)phenyl |
| 124 | H | CH$_2$ | N | 2-(aminosulfonyl)phenyl |
| 125 | H | CH$_2$ | N | 2-(methylsulfonyl)phenyl |
| 126 | H | CH$_2$ | N | 2-(trifluoromethyl)phenyl |
| 127 | H | CH$_2$ | CF | 2-(aminosulfonyl)phenyl |
| 128 | H | CH$_2$ | CF | 2-(methylsulfonyl)phenyl |
| 129 | H | CH$_2$ | CF | 2-(trifluoromethyl)phenyl |
| 130 | H | CH$_2$ | CCl | 2-(aminosulfonyl)phenyl |
| 131 | H | CH$_2$ | CCl | 2-(methylsulfonyl)phenyl |
| 132 | H | CH$_2$ | CCl | 2-(trifluoromethyl)phenyl |
| 133 | H | O | CH | 2-(aminosulfonyl)phenyl |
| 134 | H | O | CH | 2-(methylsulfonyl)phenyl |
| 135 | H | O | CH | 2-(trifluoromethyl)phenyl |
| 136 | H | O | N | 2-(aminosulfonyl)phenyl |
| 137 | H | O | N | 2-(methylsulfonyl)phenyl |
| 138 | H | O | N | 2-(trifluoromethyl)phenyl |
| 139 | H | O | CF | 2-(aminosulfonyl)phenyl |
| 140 | H | O | CF | 2-(methylsulfonyl)phenyl |
| 141 | H | O | CF | 2-(trifluoromethyl)phenyl |
| 142 | H | O | CCl | 2-(aminosulfonyl)phenyl |
| 143 | H | O | CCl | 2-(methylsulfonyl)phenyl |
| 144 | H | O | CCl | 2-(trifluoromethyl)phenyl |

TABLE 12

| Ex # | R | J | Y | B |
|---|---|---|---|---|
| 1 | SO$_2$Me | CH$_2$ | CH | 2-(aminosulfonyl)phenyl |
| 2 | SO$_2$Me | CH$_2$ | CH | 2-(methylsulfonyl)phenyl |
| 3 | SO$_2$Me | CH$_2$ | CH | 2-(trifluoromethyl)phenyl |
| 4 | SO$_2$Me | CH$_2$ | N | 2-(aminosulfonyl)phenyl |
| 5 | SO$_2$Me | CH$_2$ | N | 2-(methylsulfonyl)phenyl |
| 6 | SO$_2$Me | CH$_2$ | N | 2-(trifluoromethyl)phenyl |
| 7 | SO$_2$Me | CH$_2$ | CF | 2-(aminosulfonyl)phenyl |
| 8 | SO$_2$Me | CH$_2$ | CF | 2-(methylsulfonyl)phenyl |
| 9 | SO$_2$Me | CH$_2$ | CF | 2-(trifluoromethyl)phenyl |
| 10 | SO$_2$Me | CH$_2$ | CCl | 2-(aminosulfonyl)phenyl |
| 11 | SO$_2$Me | CH$_2$ | CCl | 2-(methylsulfonyl)phenyl |
| 12 | SO$_2$Me | CH$_2$ | CCl | 2-(trifluoromethyl)phenyl |
| 13 | SO$_2$Me | O | CH | 2-(aminosulfonyl)phenyl |
| 14 | SO$_2$Me | O | CH | 2-(methylsulfonyl)phenyl |
| 15 | SO$_2$Me | O | CH | 2-(trifluoromethyl)phenyl |
| 16 | SO$_2$Me | O | N | 2-(aminosulfonyl)phenyl |
| 17 | SO$_2$Me | O | N | 2-(methylsulfonyl)phenyl |
| 18 | SO$_2$Me | O | N | 2-(trifluoromethyl)phenyl |
| 19 | SO$_2$Me | O | CF | 2-(aminosulfonyl)phenyl |
| 20 | SO$_2$Me | O | CF | 2-(methylsulfonyl)phenyl |
| 21 | SO$_2$Me | O | CF | 2-(trifluoromethyl)phenyl |
| 22 | SO$_2$Me | O | CCl | 2-(aminosulfonyl)phenyl |
| 23 | SO$_2$Me | O | CCl | 2-(methylsulfonyl)phenyl |

TABLE 12-continued

| Ex # | R | J | Y | B |
|---|---|---|---|---|
| 24 | SO₂Me | O | CCl | 2-(trifluoromethyl)phenyl |
| 25 | CO₂Me | CH₂ | CH | 2-(aminosulfonyl)phenyl |
| 26 | CO₂Me | CH₂ | CH | 2-(methylsulfonyl)phenyl |
| 27 | CO₂Me | CH₂ | CH | 2-(trifluoromethyl)phenyl |
| 28 | CO₂Me | CH₂ | N | 2-(aminosulfonyl)phenyl |
| 29 | CO₂Me | CH₂ | N | 2-(methylsulfonyl)phenyl |
| 30 | CO₂Me | CH₂ | N | 2-(trifluoromethyl)phenyl |
| 31 | CO₂Me | CH₂ | CF | 2-(aminosulfonyl)phenyl |
| 32 | CO₂Me | CH₂ | CF | 2-(methylsulfonyl)phenyl |
| 33 | CO₂Me | CH₂ | CF | 2-(trifluoromethyl)phenyl |
| 34 | CO₂Me | CH₂ | CCl | 2-(aminosulfonyl)phenyl |
| 35 | CO₂Me | CH₂ | CCl | 2-(methylsulfonyl)phenyl |
| 36 | CO₂Me | CH₂ | CCl | 2-(trifluoromethyl)phenyl |
| 37 | CO₂Me | O | CH | 2-(aminosulfonyl)phenyl |
| 38 | CO₂Me | O | CH | 2-(methylsulfonyl)phenyl |
| 39 | CO₂Me | O | CH | 2-(trifluoromethyl)phenyl |
| 40 | CO₂Me | O | N | 2-(aminosulfonyl)phenyl |
| 41 | CO₂Me | O | N | 2-(methylsulfonyl)phenyl |
| 42 | CO₂Me | O | N | 2-(trifluoromethyl)phenyl |
| 43 | CO₂Me | O | CF | 2-(aminosulfonyl)phenyl |
| 44 | CO₂Me | O | CF | 2-(methylsulfonyl)phenyl |
| 45 | CO₂Me | O | CF | 2-(trifluoromethyl)phenyl |
| 46 | CO₂Me | O | CCl | 2-(aminosulfonyl)phenyl |
| 47 | CO₂Me | O | CCl | 2-(methylsulfonyl)phenyl |
| 48 | CO₂Me | O | CCl | 2-(trifluoromethyl)phenyl |
| 49 | COCH₃ | CH₂ | CH | 2-(aminosulfonyl)phenyl |
| 50 | COCH₃ | CH₂ | CH | 2-(methylsulfonyl)phenyl |
| 51 | COCH₃ | CH₂ | CH | 2-(trifluoromethyl)phenyl |
| 52 | COCH₃ | CH₂ | N | 2-(aminosulfonyl)phenyl |
| 53 | COCH₃ | CH₂ | N | 2-(methylsulfonyl)phenyl |
| 54 | COCH₃ | CH₂ | N | 2-(trifluoromethyl)phenyl |
| 55 | COCH₃ | CH₂ | CF | 2-(aminosulfonyl)phenyl |
| 56 | COCH₃ | CH₂ | CF | 2-(methylsulfonyl)phenyl |
| 57 | COCH₃ | CH₂ | CF | 2-(trifluoromethyl)phenyl |
| 58 | COCH₃ | CH₂ | CCl | 2-(aminosulfonyl)phenyl |
| 59 | COCH₃ | CH₂ | CCl | 2-(methylsulfonyl)phenyl |
| 60 | COCH₃ | CH₂ | CCl | 2-(trifluoromethyl)phenyl |
| 61 | COCH₃ | O | CH | 2-(aminosulfonyl)phenyl |
| 62 | COCH₃ | O | CH | 2-(methylsulfonyl)phenyl |
| 63 | COCH₃ | O | CH | 2-(trifluoromethyl)phenyl |
| 64 | COCH₃ | O | N | 2-(aminosulfonyl)phenyl |
| 65 | COCH₃ | O | N | 2-(methylsulfonyl)phenyl |
| 66 | COCH₃ | O | N | 2-(trifluoromethyl)phenyl |
| 67 | COCH₃ | O | CF | 2-(aminosulfonyl)phenyl |
| 68 | COCH₃ | O | CF | 2-(methylsulfonyl)phenyl |
| 69 | COCH₃ | O | CF | 2-(trifluoromethyl)phenyl |
| 70 | COCH₃ | O | CCl | 2-(aminosulfonyl)phenyl |
| 71 | COCH₃ | O | CCl | 2-(methylsulfonyl)phenyl |
| 72 | COCH₃ | O | CCl | 2-(trifluoromethyl)phenyl |
| 73 | CH₃ | CH₂ | CH | 2-(aminosulfonyl)phenyl |
| 74 | CH₃ | CH₂ | CH | 2-(methylsulfonyl)phenyl |
| 75 | CH₃ | CH₂ | CH | 2-(trifluoromethyl)phenyl |
| 76 | CH₃ | CH₂ | N | 2-(aminosulfonyl)phenyl |
| 77 | CH₃ | CH₂ | N | 2-(methylsulfonyl)phenyl |
| 78 | CH₃ | CH₂ | N | 2-(trifluoromethyl)phenyl |
| 79 | CH₃ | CH₂ | CF | 2-(aminosulfonyl)phenyl |
| 80 | CH₃ | CH₂ | CF | 2-(methylsulfonyl)phenyl |
| 81 | CH₃ | CH₂ | CF | 2-(trifluoromethyl)phenyl |
| 82 | CH₃ | CH₂ | CCl | 2-(aminosulfonyl)phenyl |
| 83 | CH₃ | CH₂ | CCl | 2-(methylsulfonyl)phenyl |
| 84 | CH₃ | CH₂ | CCl | 2-(trifluoromethyl)phenyl |
| 85 | CH₃ | O | CH | 2-(aminosulfonyl)phenyl |
| 86 | CH₃ | O | CH | 2-(methylsulfonyl)phenyl |
| 87 | CH₃ | O | CH | 2-(trifluoromethyl)phenyl |
| 88 | CH₃ | O | N | 2-(aminosulfonyl)phenyl |
| 89 | CH₃ | O | N | 2-(methylsulfonyl)phenyl |
| 90 | CH₃ | O | N | 2-(trifluoromethyl)phenyl |
| 91 | CH₃ | O | CF | 2-(aminosulfonyl)phenyl |
| 92 | CH₃ | O | CF | 2-(methylsulfonyl)phenyl |
| 93 | CH₃ | O | CF | 2-(trifluoromethyl)phenyl |
| 94 | CH₃ | O | CCl | 2-(aminosulfonyl)phenyl |
| 95 | CH₃ | O | CCl | 2-(methylsulfonyl)phenyl |
| 96 | CH₃ | O | CCl | 2-(trifluoromethyl)phenyl |
| 97 | CH₂Ph | CH₂ | CH | 2-(aminosulfonyl)phenyl |
| 98 | CH₂Ph | CH₂ | CH | 2-(methylsulfonyl)phenyl |
| 99 | CH₂Ph | CH₂ | CH | 2-(trifluoromethyl)phenyl |
| 100 | CH₂Ph | CH₂ | N | 2-(aminosulfonyl)phenyl |
| 101 | CH₂Ph | CH₂ | N | 2-(methylsulfonyl)phenyl |
| 102 | CH₂Ph | CH₂ | N | 2-(trifluoromethyl)phenyl |
| 103 | CH₂Ph | CH₂ | CF | 2-(aminosulfonyl)phenyl |
| 104 | CH₂Ph | CH₂ | CF | 2-(methylsulfonyl)phenyl |
| 105 | CH₂Ph | CH₂ | CF | 2-(trifluoromethyl)phenyl |
| 106 | CH₂Ph | CH₂ | CCl | 2-(aminosulfonyl)phenyl |
| 107 | CH₂Ph | CH₂ | CCl | 2-(methylsulfonyl)phenyl |
| 108 | CH₂Ph | CH₂ | CCl | 2-(trifluoromethyl)phenyl |
| 109 | CH₂Ph | O | CH | 2-(aminosulfonyl)phenyl |
| 110 | CH₂Ph | O | CH | 2-(methylsulfonyl)phenyl |
| 111 | CH₂Ph | O | CH | 2-(trifluoromethyl)phenyl |
| 112 | CH₂Ph | O | N | 2-(aminosulfonyl)phenyl |
| 113 | CH₂Ph | O | N | 2-(methylsulfonyl)phenyl |
| 114 | CH₂Ph | O | N | 2-(trifluoromethyl)phenyl |
| 115 | CH₂Ph | O | CF | 2-(aminosulfonyl)phenyl |
| 116 | CH₂Ph | O | CF | 2-(methylsulfonyl)phenyl |
| 117 | CH₂Ph | O | CF | 2-(trifluoromethyl)phenyl |
| 118 | CH₂Ph | O | CCl | 2-(aminosulfonyl)phenyl |
| 119 | CH₂Ph | O | CCl | 2-(methylsulfonyl)phenyl |
| 120 | CH₂Ph | O | CCl | 2-(trifluoromethyl)phenyl |
| 121 | H | CH₂ | CH | 2-(aminosulfonyl)phenyl |
| 122 | H | CH₂ | CH | 2-(methylsulfonyl)phenyl |
| 123 | H | CH₂ | CH | 2-(trifluoromethyl)phenyl |
| 124 | H | CH₂ | N | 2-(aminosulfonyl)phenyl |
| 125 | H | CH₂ | N | 2-(methylsulfonyl)phenyl |
| 126 | H | CH₂ | N | 2-(trifluoromethyl)phenyl |
| 127 | H | CH₂ | CF | 2-(aminosulfonyl)phenyl |
| 128 | H | CH₂ | CF | 2-(methylsulfonyl)phenyl |
| 129 | H | CH₂ | CF | 2-(trifluoromethyl)phenyl |
| 130 | H | CH₂ | CCl | 2-(aminosulfonyl)phenyl |
| 131 | H | CH₂ | CCl | 2-(methylsulfonyl)phenyl |
| 132 | H | CH₂ | CCl | 2-(trifluoromethyl)phenyl |
| 133 | H | O | CH | 2-(aminosulfonyl)phenyl |
| 134 | H | O | CH | 2-(methylsulfonyl)phenyl |
| 135 | H | O | CH | 2-(trifluoromethyl)phenyl |
| 136 | H | O | N | 2-(aminosulfonyl)phenyl |
| 137 | H | O | N | 2-(methylsulfonyl)phenyl |
| 138 | H | O | N | 2-(trifluoromethyl)phenyl |
| 139 | H | O | CF | 2-(aminosulfonyl)phenyl |
| 140 | H | O | CF | 2-(methylsulfonyl)phenyl |
| 141 | H | O | CF | 2-(trifluoromethyl)phenyl |
| 142 | H | O | CCl | 2-(aminosulfonyl)phenyl |
| 143 | H | O | CCl | 2-(methylsulfonyl)phenyl |
| 144 | H | O | CCl | 2-(trifluoromethyl)phenyl |

TABLE 13

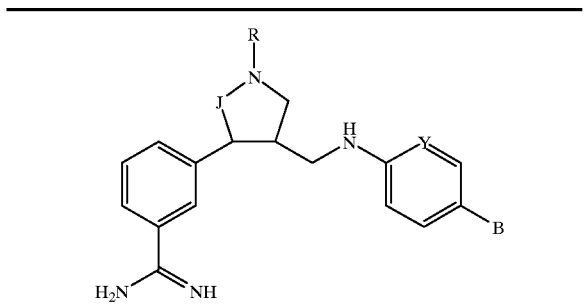

| Ex # | R | J | Y | B |
|---|---|---|---|---|
| 1 | SO₂Me | CH₂ | CH | 2-(aminosulfonyl)phenyl |
| 2 | SO₂Me | CH₂ | CH | 2-(methylsulfonyl)phenyl |
| 3 | SO₂Me | CH₂ | CH | 2-(trifluoromethyl)phenyl |
| 4 | SO₂Me | CH₂ | N | 2-(aminosulfonyl)phenyl |
| 5 | SO₂Me | CH₂ | N | 2-(methylsulfonyl)phenyl |
| 6 | SO₂Me | CH₂ | N | 2-(trifluoromethyl)phenyl |
| 7 | SO₂Me | CH₂ | CF | 2-(aminosulfonyl)phenyl |
| 8 | SO₂Me | CH₂ | CF | 2-(methylsulfonyl)phenyl |
| 9 | SO₂Me | CH₂ | CF | 2-(trifluoromethyl)phenyl |
| 10 | SO₂Me | CH₂ | CCl | 2-(aminosulfonyl)phenyl |
| 11 | SO₂Me | CH₂ | CCl | 2-(methylsulfonyl)phenyl |
| 12 | SO₂Me | CH₂ | CCl | 2-(trifluoromethyl)phenyl |
| 13 | SO₂Me | O | CH | 2-(aminosulfonyl)phenyl |
| 14 | SO₂Me | O | CH | 2-(methylsulfonyl)phenyl |
| 15 | SO₂Me | O | CH | 2-(trifluoromethyl)phenyl |
| 16 | SO₂Me | O | N | 2-(aminosulfonyl)phenyl |
| 17 | SO₂Me | O | N | 2-(methylsulfonyl)phenyl |
| 18 | SO₂Me | O | N | 2-(trifluoromethyl)phenyl |
| 19 | SO₂Me | O | CF | 2-(aminosulfonyl)phenyl |
| 20 | SO₂Me | O | CF | 2-(methylsulfonyl)phenyl |
| 21 | SO₂Me | O | CF | 2-(trifluoromethyl)phenyl |
| 22 | SO₂Me | O | CCl | 2-(aminosulfonyl)phenyl |
| 23 | SO₂Me | O | CCl | 2-(methylsulfonyl)phenyl |
| 24 | SO₂Me | O | CCl | 2-(trifluoromethyl)phenyl |
| 25 | CO₂Me | CH₂ | CH | 2-(aminosulfonyl)phenyl |
| 26 | CO₂Me | CH₂ | CH | 2-(methylsulfonyl)phenyl |
| 27 | CO₂Me | CH₂ | CH | 2-(trifluoromethyl)phenyl |
| 28 | CO₂Me | CH₂ | N | 2-(aminosulfonyl)phenyl |
| 29 | CO₂Me | CH₂ | N | 2-(methylsulfonyl)phenyl |
| 30 | CO₂Me | CH₂ | N | 2-(trifluoromethyl)phenyl |
| 31 | CO₂Me | CH₂ | CF | 2-(aminosulfonyl)phenyl |
| 32 | CO₂Me | CH₂ | CF | 2-(methylsulfonyl)phenyl |
| 33 | CO₂Me | CH₂ | CF | 2-(trifluoromethyl)phenyl |
| 34 | CO₂Me | CH₂ | CCl | 2-(aminosulfonyl)phenyl |
| 35 | CO₂Me | CH₂ | CCl | 2-(methylsulfonyl)phenyl |
| 36 | CO₂Me | CH₂ | CCl | 2-(trifluoromethyl)phenyl |
| 37 | CO₂Me | O | CH | 2-(aminosulfonyl)phenyl |
| 38 | CO₂Me | O | CH | 2-(methylsulfonyl)phenyl |
| 39 | CO₂Me | O | CH | 2-(trifluoromethyl)phenyl |
| 40 | CO₂Me | O | N | 2-(aminosulfonyl)phenyl |
| 41 | CO₂Me | O | N | 2-(methylsulfonyl)phenyl |
| 42 | CO₂Me | O | N | 2-(trifluoromethyl)phenyl |
| 43 | CO₂Me | O | CF | 2-(aminosulfonyl)phenyl |
| 44 | CO₂Me | O | CF | 2-(methylsulfonyl)phenyl |
| 45 | CO₂Me | O | CF | 2-(trifluoromethyl)phenyl |
| 46 | CO₂Me | O | CCl | 2-(aminosulfonyl)phenyl |
| 47 | CO₂Me | O | CCl | 2-(methylsulfonyl)phenyl |
| 48 | CO₂Me | O | CCl | 2-(trifluoromethyl)phenyl |
| 49 | COCH₃ | CH₂ | CH | 2-(aminosulfonyl)phenyl |
| 50 | COCH₃ | CH₂ | CH | 2-(methylsulfonyl)phenyl |
| 51 | COCH₃ | CH₂ | CH | 2-(trifluoromethyl)phenyl |
| 52 | COCH₃ | CH₂ | N | 2-(aminosulfonyl)phenyl |
| 53 | COCH₃ | CH₂ | N | 2-(methylsulfonyl)phenyl |
| 54 | COCH₃ | CH₂ | N | 2-(trifluoromethyl)phenyl |
| 55 | COCH₃ | CH₂ | CF | 2-(aminosulfonyl)phenyl |
| 56 | COCH₃ | CH₂ | CF | 2-(methylsulfonyl)phenyl |
| 57 | COCH₃ | CH₂ | CF | 2-(trifluoromethyl)phenyl |
| 58 | COCH₃ | CH₂ | CCl | 2-(aminosulfonyl)phenyl |
| 59 | COCH₃ | CH₂ | CCl | 2-(methylsulfonyl)phenyl |
| 60 | COCH₃ | CH₂ | CCl | 2-(trifluoromethyl)phenyl |
| 61 | COCH₃ | O | CH | 2-(aminosulfonyl)phenyl |
| 62 | COCH₃ | O | CH | 2-(methylsulfonyl)phenyl |
| 63 | COCH₃ | O | CH | 2-(trifluoromethyl)phenyl |
| 64 | COCH₃ | O | N | 2-(aminosulfonyl)phenyl |
| 65 | COCH₃ | O | N | 2-(methylsulfonyl)phenyl |
| 66 | COCH₃ | O | N | 2-(trifluoromethyl)phenyl |
| 67 | COCH₃ | O | CF | 2-(aminosulfonyl)phenyl |
| 68 | COCH₃ | O | CF | 2-(methylsulfonyl)phenyl |
| 69 | COCH₃ | O | CF | 2-(trifluoromethyl)phenyl |
| 70 | COCH₃ | O | CCl | 2-(aminosulfonyl)phenyl |
| 71 | COCH₃ | O | CCl | 2-(methylsulfonyl)phenyl |
| 72 | COCH₃ | O | CCl | 2-(trifluoromethyl)phenyl |
| 73 | CH₃ | CH₂ | CH | 2-(aminosulfonyl)phenyl |
| 74 | CH₃ | CH₂ | CH | 2-(methylsulfonyl)phenyl |
| 75 | CH₃ | CH₂ | CH | 2-(trifluoromethyl)phenyl |
| 76 | CH₃ | CH₂ | N | 2-(aminosulfonyl)phenyl |
| 77 | CH₃ | CH₂ | N | 2-(methylsulfonyl)phenyl |
| 78 | CH₃ | CH₂ | N | 2-(trifluoromethyl)phenyl |
| 79 | CH₃ | CH₂ | CF | 2-(aminosulfonyl)phenyl |
| 80 | CH₃ | CH₂ | CF | 2-(methylsulfonyl)phenyl |
| 81 | CH₃ | CH₂ | CF | 2-(trifluoromethyl)phenyl |
| 82 | CH₃ | CH₂ | CCl | 2-(aminosulfonyl)phenyl |
| 83 | CH₃ | CH₂ | CCl | 2-(methylsulfonyl)phenyl |
| 84 | CH₃ | CH₂ | CCl | 2-(trifluoromethyl)phenyl |
| 85 | CH₃ | O | CH | 2-(aminosulfonyl)phenyl |
| 86 | CH₃ | O | CH | 2-(methylsulfonyl)phenyl |
| 87 | CH₃ | O | CH | 2-(trifluoromethyl)phenyl |
| 88 | CH₃ | O | N | 2-(aminosulfonyl)phenyl |
| 89 | CH₃ | O | N | 2-(methylsulfonyl)phenyl |
| 90 | CH₃ | O | N | 2-(trifluoromethyl)phenyl |
| 91 | CH₃ | O | CF | 2-(aminosulfonyl)phenyl |
| 92 | CH₃ | O | CF | 2-(methylsulfonyl)phenyl |
| 93 | CH₃ | O | CF | 2-(trifluoromethyl)phenyl |
| 94 | CH₃ | O | CCl | 2-(aminosulfonyl)phenyl |
| 95 | CH₃ | O | CCl | 2-(methylsulfonyl)phenyl |
| 96 | CH₃ | O | CCl | 2-(trifluoromethyl)phenyl |
| 97 | CH₂Ph | CH₂ | CH | 2-(aminosulfonyl)phenyl |
| 98 | CH₂Ph | CH₂ | CH | 2-(methylsulfonyl)phenyl |
| 99 | CH₂Ph | CH₂ | CH | 2-(trifluoromethyl)phenyl |
| 100 | CH₂Ph | CH₂ | N | 2-(aminosulfonyl)phenyl |
| 101 | CH₂Ph | CH₂ | N | 2-(methylsulfonyl)phenyl |
| 102 | CH₂Ph | CH₂ | N | 2-(trifluoromethyl)phenyl |
| 103 | CH₂Ph | CH₂ | CF | 2-(aminosulfonyl)phenyl |
| 104 | CH₂Ph | CH₂ | CF | 2-(methylsulfonyl)phenyl |
| 105 | CH₂Ph | CH₂ | CF | 2-(trifluoromethyl)phenyl |
| 106 | CH₂Ph | CH₂ | CCl | 2-(aminosulfonyl)phenyl |
| 107 | CH₂Ph | CH₂ | CCl | 2-(methylsulfonyl)phenyl |
| 108 | CH₂Ph | CH₂ | CCl | 2-(trifluoromethyl)phenyl |
| 109 | CH₂Ph | O | CH | 2-(aminosulfonyl)phenyl |
| 110 | CH₂Ph | O | CH | 2-(methylsulfonyl)phenyl |
| 111 | CH₂Ph | O | CH | 2-(trifluoromethyl)phenyl |
| 112 | CH₂Ph | O | N | 2-(aminosulfonyl)phenyl |
| 113 | CH₂Ph | O | N | 2-(methylsulfonyl)phenyl |
| 114 | CH₂Ph | O | N | 2-(trifluoromethyl)phenyl |
| 115 | CH₂Ph | O | CF | 2-(aminosulfonyl)phenyl |
| 116 | CH₂Ph | O | CF | 2-(methylsulfonyl)phenyl |
| 117 | CH₂Ph | O | CF | 2-(trifluoromethyl)phenyl |
| 118 | CH₂Ph | O | CCl | 2-(aminosulfonyl)phenyl |
| 119 | CH₂Ph | O | CCl | 2-(methylsulfonyl)phenyl |
| 120 | CH₂Ph | O | CCl | 2-(trifluoromethyl)phenyl |
| 121 | H | CH₂ | CH | 2-(aminosulfonyl)phenyl |
| 122 | H | CH₂ | CH | 2-(methylsulfonyl)phenyl |
| 123 | H | CH₂ | CH | 2-(trifluoromethyl)phenyl |
| 124 | H | CH₂ | N | 2-(aminosulfonyl)phenyl |

TABLE 13-continued

[Structure: pyrrolidine with R on N, J in ring, connected to phenyl with amidine (H₂N-C(=NH)-) at meta, and CH₂-NH-pyridyl/phenyl with Y and B substituents]

| Ex # | R | J | Y | B |
|---|---|---|---|---|
| 125 | H | CH₂ | N | 2-(methylsulfonyl)phenyl |
| 126 | H | CH₂ | N | 2-(trifluoromethyl)phenyl |
| 127 | H | CH₂ | CF | 2-(aminosulfonyl)phenyl |
| 128 | H | CH₂ | CF | 2-(methylsulfonyl)phenyl |
| 129 | H | CH₂ | CF | 2-(trifluoromethyl)phenyl |
| 130 | H | CH₂ | CCl | 2-(aminosulfonyl)phenyl |
| 131 | H | CH₂ | CCl | 2-(methylsulfonyl)phenyl |
| 132 | H | CH₂ | CCl | 2-(trifluoromethyl)phenyl |
| 133 | H | O | CH | 2-(aminosulfonyl)phenyl |
| 134 | H | O | CH | 2-(methylsulfonyl)phenyl |
| 135 | H | O | CH | 2-(trifluoromethyl)phenyl |
| 136 | H | O | N | 2-(aminosulfonyl)phenyl |
| 137 | H | O | N | 2-(methylsulfonyl)phenyl |
| 138 | H | O | N | 2-(trifluoromethyl)phenyl |
| 139 | H | O | CF | 2-(aminosulfonyl)phenyl |
| 140 | H | O | CF | 2-(methylsulfonyl)phenyl |
| 141 | H | O | CF | 2-(trifluoromethyl)phenyl |
| 142 | H | O | CCl | 2-(aminosulfonyl)phenyl |
| 143 | H | O | CCl | 2-(methylsulfonyl)phenyl |
| 144 | H | O | CCl | 2-(trifluoromethyl)phenyl |

TABLE 14

[Structure: similar pyrrolidine with CH₂-O linker to aryl]

| Ex # | R | J | Y | B |
|---|---|---|---|---|
| 1 | SO₂Me | CH₂ | CH | 2-(aminosulfonyl)phenyl |
| 2 | SO₂Me | CH₂ | CH | 2-(methylsulfonyl)phenyl |
| 3 | SO₂Me | CH₂ | CH | 2-(trifluoromethyl)phenyl |
| 4 | SO₂Me | CH₂ | N | 2-(aminosulfonyl)phenyl |
| 5 | SO₂Me | CH₂ | N | 2-(methylsulfonyl)phenyl |
| 6 | SO₂Me | CH₂ | N | 2-(trifluoromethyl)phenyl |
| 7 | SO₂Me | CH₂ | CF | 2-(aminosulfonyl)phenyl |
| 8 | SO₂Me | CH₂ | CF | 2-(methylsulfonyl)phenyl |
| 9 | SO₂Me | CH₂ | CF | 2-(trifluoromethyl)phenyl |
| 10 | SO₂Me | CH₂ | CCl | 2-(aminosulfonyl)phenyl |
| 11 | SO₂Me | CH₂ | CCl | 2-(methylsulfonyl)phenyl |
| 12 | SO₂Me | CH₂ | CCl | 2-(trifluoromethyl)phenyl |
| 13 | SO₂Me | O | CH | 2-(aminosulfonyl)phenyl |
| 14 | SO₂Me | O | CH | 2-(methylsulfonyl)phenyl |
| 15 | SO₂Me | O | CH | 2-(trifluoromethyl)phenyl |
| 16 | SO₂Me | O | N | 2-(aminosulfonyl)phenyl |
| 17 | SO₂Me | O | N | 2-(methylsulfonyl)phenyl |
| 18 | SO₂Me | O | N | 2-(trifluoromethyl)phenyl |
| 19 | SO₂Me | O | CF | 2-(aminosulfonyl)phenyl |
| 20 | SO₂Me | O | CF | 2-(methylsulfonyl)phenyl |

TABLE 14-continued

| Ex # | R | J | Y | B |
|---|---|---|---|---|
| 21 | SO₂Me | O | CF | 2-(trifluoromethyl)phenyl |
| 22 | SO₂Me | O | CCl | 2-(aminosulfonyl)phenyl |
| 23 | SO₂Me | O | CCl | 2-(methylsulfonyl)phenyl |
| 24 | SO₂Me | O | CCl | 2-(trifluoromethyl)phenyl |
| 25 | CO₂Me | CH₂ | CH | 2-(aminosulfonyl)phenyl |
| 26 | CO₂Me | CH₂ | CH | 2-(methylsulfonyl)phenyl |
| 27 | CO₂Me | CH₂ | CH | 2-(trifluoromethyl)phenyl |
| 28 | CO₂Me | CH₂ | N | 2-(aminosulfonyl)phenyl |
| 29 | CO₂Me | CH₂ | N | 2-(methylsulfonyl)phenyl |
| 30 | CO₂Me | CH₂ | N | 2-(trifluoromethyl)phenyl |
| 31 | CO₂Me | CH₂ | CF | 2-(aminosulfonyl)phenyl |
| 32 | CO₂Me | CH₂ | CF | 2-(methylsulfonyl)phenyl |
| 33 | CO₂Me | CH₂ | CF | 2-(trifluoromethyl)phenyl |
| 34 | CO₂Me | CH₂ | CCl | 2-(aminosulfonyl)phenyl |
| 35 | CO₂Me | CH₂ | CCl | 2-(methylsulfonyl)phenyl |
| 36 | CO₂Me | CH₂ | CCl | 2-(trifluoromethyl)phenyl |
| 37 | CO₂Me | O | CH | 2-(aminosulfonyl)phenyl |
| 38 | CO₂Me | O | CH | 2-(methylsulfonyl)phenyl |
| 39 | CO₂Me | O | CH | 2-(trifluoromethyl)phenyl |
| 40 | CO₂Me | O | N | 2-(aminosulfonyl)phenyl |
| 41 | CO₂Me | O | N | 2-(methylsulfonyl)phenyl |
| 42 | CO₂Me | O | N | 2-(trifluoromethyl)phenyl |
| 43 | CO₂Me | O | CF | 2-(aminosulfonyl)phenyl |
| 44 | CO₂Me | O | CF | 2-(methylsulfonyl)phenyl |
| 45 | CO₂Me | O | CF | 2-(trifluoromethyl)phenyl |
| 46 | CO₂Me | O | CCl | 2-(aminosulfonyl)phenyl |
| 47 | CO₂Me | O | CCl | 2-(methylsulfonyl)phenyl |
| 48 | CO₂Me | O | CCl | 2-(trifluoromethyl)phenyl |
| 49 | COCH₃ | CH₂ | CH | 2-(aminosulfonyl)phenyl |
| 50 | COCH₃ | CH₂ | CH | 2-(methylsulfonyl)phenyl |
| 51 | COCH₃ | CH₂ | CH | 2-(trifluoromethyl)phenyl |
| 52 | COCH₃ | CH₂ | N | 2-(aminosulfonyl)phenyl |
| 53 | COCH₃ | CH₂ | N | 2-(methylsulfonyl)phenyl |
| 54 | COCH₃ | CH₂ | N | 2-(trifluoromethyl)phenyl |
| 55 | COCH₃ | CH₂ | CF | 2-(aminosulfonyl)phenyl |
| 56 | COCH₃ | CH₂ | CF | 2-(methylsulfonyl)phenyl |
| 57 | COCH₃ | CH₂ | CF | 2-(trifluoromethyl)phenyl |
| 58 | COCH₃ | CH₂ | CCl | 2-(aminosulfonyl)phenyl |
| 59 | COCH₃ | CH₂ | CCl | 2-(methylsulfonyl)phenyl |
| 60 | COCH₃ | CH₂ | CCl | 2-(trifluoromethyl)phenyl |
| 61 | COCH₃ | O | CH | 2-(aminosulfonyl)phenyl |
| 62 | COCH₃ | O | CH | 2-(methylsulfonyl)phenyl |
| 63 | COCH₃ | O | CH | 2-(trifluoromethyl)phenyl |
| 64 | COCH₃ | O | N | 2-(aminosulfonyl)phenyl |
| 65 | COCH₃ | O | N | 2-(methylsulfonyl)phenyl |
| 66 | COCH₃ | O | N | 2-(trifluoromethyl)phenyl |
| 67 | COCH₃ | O | CF | 2-(aminosulfonyl)phenyl |
| 68 | COCH₃ | O | CF | 2-(methylsulfonyl)phenyl |
| 69 | COCH₃ | O | CF | 2-(trifluoromethyl)phenyl |
| 70 | COCH₃ | O | CCl | 2-(aminosulfonyl)phenyl |
| 71 | COCH₃ | O | CCl | 2-(methylsulfonyl)phenyl |
| 72 | COCH₃ | O | CCl | 2-(trifluoromethyl)phenyl |
| 73 | CH₃ | CH₂ | CH | 2-(aminosulfonyl)phenyl |
| 74 | CH₃ | CH₂ | CH | 2-(methylsulfonyl)phenyl |
| 75 | CH₃ | CH₂ | CH | 2-(trifluoromethyl)phenyl |
| 76 | CH₃ | CH₂ | N | 2-(aminosulfonyl)phenyl |
| 77 | CH₃ | CH₂ | N | 2-(methylsulfonyl)phenyl |
| 78 | CH₃ | CH₂ | N | 2-(trifluoromethyl)phenyl |
| 79 | CH₃ | CH₂ | CF | 2-(aminosulfonyl)phenyl |
| 80 | CH₃ | CH₂ | CF | 2-(methylsulfonyl)phenyl |
| 81 | CH₃ | CH₂ | CF | 2-(trifluoromethyl)phenyl |
| 82 | CH₃ | CH₂ | CCl | 2-(aminosulfonyl)phenyl |

TABLE 14-continued

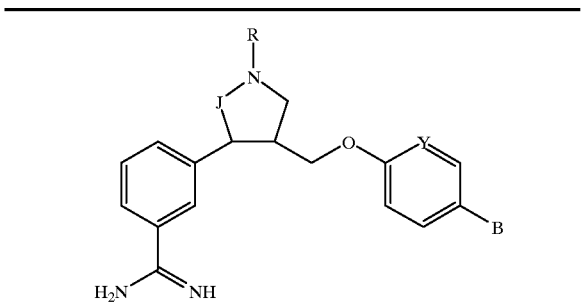

| Ex # | R | J | Y | B |
|---|---|---|---|---|
| 83 | CH$_3$ | CH$_2$ | CCl | 2-(methylsulfonyl)phenyl |
| 84 | CH$_3$ | CH$_2$ | CCl | 2-(trifluoromethyl)phenyl |
| 85 | CH$_3$ | O | CH | 2-(aminosulfonyl)phenyl |
| 86 | CH$_3$ | O | CH | 2-(methylsulfonyl)phenyl |
| 87 | CH$_3$ | O | CH | 2-(trifluoromethyl)phenyl |
| 88 | CH$_3$ | O | N | 2-(aminosulfonyl)phenyl |
| 89 | CH$_3$ | O | N | 2-(methylsulfonyl)phenyl |
| 90 | CH$_3$ | O | N | 2-(trifluoromethyl)phenyl |
| 91 | CH$_3$ | O | CF | 2-(aminosulfonyl)phenyl |
| 92 | CH$_3$ | O | CF | 2-(methylsulfonyl)phenyl |
| 93 | CH$_3$ | O | CF | 2-(trifluoromethyl)phenyl |
| 94 | CH$_3$ | O | CCl | 2-(aminosulfonyl)phenyl |
| 95 | CH$_3$ | O | CCl | 2-(methylsulfonyl)phenyl |
| 96 | CH$_3$ | O | CCl | 2-(trifluoromethyl)phenyl |
| 97 | CH$_2$Ph | CH$_2$ | CH | 2-(aminosulfonyl)phenyl |
| 98 | CH$_2$Ph | CH$_2$ | CH | 2-(methylsulfonyl)phenyl |
| 99 | CH$_2$Ph | CH$_2$ | CH | 2-(trifluoromethyl)phenyl |
| 100 | CH$_2$Ph | CH$_2$ | N | 2-(aminosulfonyl)phenyl |
| 101 | CH$_2$Ph | CH$_2$ | N | 2-(methylsulfonyl)phenyl |
| 102 | CH$_2$Ph | CH$_2$ | N | 2-(trifluoromethyl)phenyl |
| 103 | CH$_2$Ph | CH$_2$ | CF | 2-(aminosulfonyl)phenyl |
| 104 | CH$_2$Ph | CH$_2$ | CF | 2-(methylsulfonyl)phenyl |
| 105 | CH$_2$Ph | CH$_2$ | CF | 2-(trifluoromethyl)phenyl |
| 106 | CH$_2$Ph | CH$_2$ | CCl | 2-(aminosulfonyl)phenyl |
| 107 | CH$_2$Ph | CH$_2$ | CCl | 2-(methylsulfonyl)phenyl |
| 108 | CH$_2$Ph | CH$_2$ | CCl | 2-(trifluoromethyl)phenyl |
| 109 | CH$_2$Ph | O | CH | 2-(aminosulfonyl)phenyl |
| 110 | CH$_2$Ph | O | CH | 2-(methylsulfonyl)phenyl |
| 111 | CH$_2$Ph | O | CH | 2-(trifluoromethyl)phenyl |
| 112 | CH$_2$Ph | O | N | 2-(aminosulfonyl)phenyl |
| 113 | CH$_2$Ph | O | N | 2-(methylsulfonyl)phenyl |
| 114 | CH$_2$Ph | O | N | 2-(trifluoromethyl)phenyl |
| 115 | CH$_2$Ph | O | CF | 2-(aminosulfonyl)phenyl |
| 116 | CH$_2$Ph | O | CF | 2-(methylsulfonyl)phenyl |
| 117 | CH$_2$Ph | O | CF | 2-(trifluoromethyl)phenyl |
| 118 | CH$_2$Ph | O | CCl | 2-(aminosulfonyl)phenyl |
| 119 | CH$_2$Ph | O | CCl | 2-(methylsulfonyl)phenyl |
| 120 | CH$_2$Ph | O | CCl | 2-(trifluoromethyl)phenyl |
| 121 | H | CH$_2$ | CH | 2-(aminosulfonyl)phenyl |
| 122 | H | CH$_2$ | CH | 2-(methylsulfonyl)phenyl |
| 123 | H | CH$_2$ | CH | 2-(trifluoromethyl)phenyl |
| 124 | H | CH$_2$ | N | 2-(aminosulfonyl)phenyl |
| 125 | H | CH$_2$ | N | 2-(methylsulfonyl)phenyl |
| 126 | H | CH$_2$ | N | 2-(trifluoromethyl)phenyl |
| 127 | H | CH$_2$ | CF | 2-(aminosulfonyl)phenyl |
| 128 | H | CH$_2$ | CF | 2-(methylsulfonyl)phenyl |
| 129 | H | CH$_2$ | CF | 2-(trifluoromethyl)phenyl |
| 130 | H | CH$_2$ | CCl | 2-(aminosulfonyl)phenyl |
| 131 | H | CH$_2$ | CCl | 2-(methylsulfonyl)phenyl |
| 132 | H | CH$_2$ | CCl | 2-(trifluoromethyl)phenyl |
| 133 | H | O | CH | 2-(aminosulfonyl)phenyl |
| 134 | H | O | CH | 2-(methylsulfonyl)phenyl |
| 135 | H | O | CH | 2-(trifluoromethyl)phenyl |
| 136 | H | O | N | 2-(aminosulfonyl)phenyl |
| 137 | H | O | N | 2-(methylsulfonyl)phenyl |
| 138 | H | O | N | 2-(trifluoromethyl)phenyl |
| 139 | H | O | CF | 2-(aminosulfonyl)phenyl |
| 140 | H | O | CF | 2-(methylsulfonyl)phenyl |
| 141 | H | O | CF | 2-(trifluoromethyl)phenyl |
| 142 | H | O | CCl | 2-(aminosulfonyl)phenyl |

TABLE 14-continued

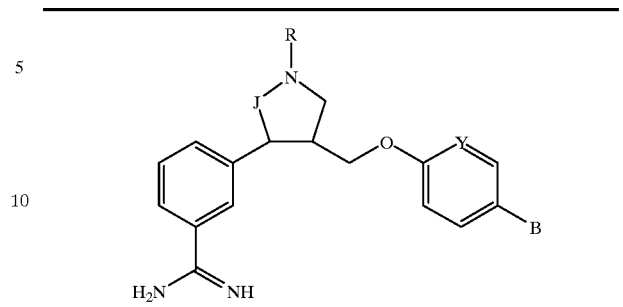

| Ex # | R | J | Y | B |
|---|---|---|---|---|
| 143 | H | O | CCl | 2-(methylsulfonyl)phenyl |
| 144 | H | O | CCl | 2-(trifluoromethyl)phenyl |

TABLE 15

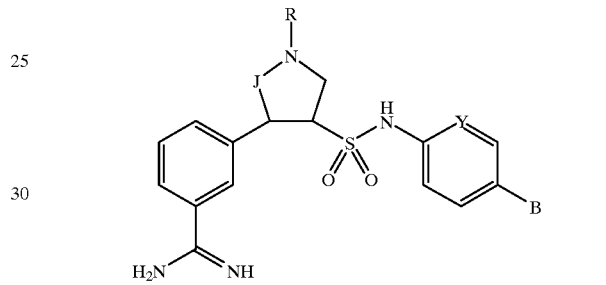

| Ex # | R | J | Y | B |
|---|---|---|---|---|
| 1 | SO$_2$Me | CH$_2$ | CH | 2-(aminosulfonyl)phenyl |
| 2 | SO$_2$Me | CH$_2$ | CH | 2-(methylsulfonyl)phenyl |
| 3 | SO$_2$Me | CH$_2$ | CH | 2-(trifluoromethyl)phenyl |
| 4 | SO$_2$Me | CH$_2$ | N | 2-(aminosulfonyl)phenyl |
| 5 | SO$_2$Me | CH$_2$ | N | 2-(methylsulfonyl)phenyl |
| 6 | SO$_2$Me | CH$_2$ | N | 2-(trifluoromethyl)phenyl |
| 7 | SO$_2$Me | CH$_2$ | CF | 2-(aminosulfonyl)phenyl |
| 8 | SO$_2$Me | CH$_2$ | CF | 2-(methylsulfonyl)phenyl |
| 9 | SO$_2$Me | CH$_2$ | CF | 2-(trifluoromethyl)phenyl |
| 10 | SO$_2$Me | CH$_2$ | CCl | 2-(aminosulfonyl)phenyl |
| 11 | SO$_2$Me | CH$_2$ | CCl | 2-(methylsulfonyl)phenyl |
| 12 | SO$_2$Me | CH$_2$ | CCl | 2-(trifluoromethyl)phenyl |
| 13 | SO$_2$Me | O | CH | 2-(aminosulfonyl)phenyl |
| 14 | SO$_2$Me | O | CH | 2-(methylsulfonyl)phenyl |
| 15 | SO$_2$Me | O | CH | 2-(trifluoromethyl)phenyl |
| 16 | SO$_2$Me | O | N | 2-(aminosulfonyl)phenyl |
| 17 | SO$_2$Me | O | N | 2-(methylsulfonyl)phenyl |
| 18 | SO$_2$Me | O | N | 2-(trifluoromethyl)phenyl |
| 19 | SO$_2$Me | O | CF | 2-(aminosulfonyl)phenyl |
| 20 | SO$_2$Me | O | CF | 2-(methylsulfonyl)phenyl |
| 21 | SO$_2$Me | O | CF | 2-(trifluoromethyl)phenyl |
| 22 | SO$_2$Me | O | CCl | 2-(aminosulfonyl)phenyl |
| 23 | SO$_2$Me | O | CCl | 2-(methylsulfonyl)phenyl |
| 24 | SO$_2$Me | O | CCl | 2-(trifluoromethyl)phenyl |
| 25 | CO$_2$Me | CH$_2$ | CH | 2-(aminosulfonyl)phenyl |
| 26 | CO$_2$Me | CH$_2$ | CH | 2-(methylsulfonyl)phenyl |
| 27 | CO$_2$Me | CH$_2$ | CH | 2-(trifluoromethyl)phenyl |
| 28 | CO$_2$Me | CH$_2$ | N | 2-(aminosulfonyl)phenyl |
| 29 | CO$_2$Me | CH$_2$ | N | 2-(methylsulfonyl)phenyl |
| 30 | CO$_2$Me | CH$_2$ | N | 2-(trifluoromethyl)phenyl |
| 31 | CO$_2$Me | CH$_2$ | CF | 2-(aminosulfonyl)phenyl |
| 32 | CO$_2$Me | CH$_2$ | CF | 2-(methylsulfonyl)phenyl |
| 33 | CO$_2$Me | CH$_2$ | CF | 2-(trifluoromethyl)phenyl |
| 34 | CO$_2$Me | CH$_2$ | CCl | 2-(aminosulfonyl)phenyl |
| 35 | CO$_2$Me | CH$_2$ | CCl | 2-(methylsulfonyl)phenyl |
| 36 | CO$_2$Me | CH$_2$ | CCl | 2-(trifluoromethyl)phenyl |
| 37 | CO$_2$Me | O | CH | 2-(aminosulfonyl)phenyl |
| 38 | CO$_2$Me | O | CH | 2-(methylsulfonyl)phenyl |

TABLE 15-continued

| Ex # | R | J | Y | B |
|---|---|---|---|---|
| 39 | CO₂Me | O | CH | 2-(trifluoromethyl)phenyl |
| 40 | CO₂Me | O | N | 2-(aminosulfonyl)phenyl |
| 41 | CO₂Me | O | N | 2-(methylsulfonyl)phenyl |
| 42 | CO₂Me | O | N | 2-(trifluoromethyl)phenyl |
| 43 | CO₂Me | O | CF | 2-(aminosulfonyl)phenyl |
| 44 | CO₂Me | O | CF | 2-(methylsulfonyl)phenyl |
| 45 | CO₂Me | O | CF | 2-(trifluoromethyl)phenyl |
| 46 | CO₂Me | O | CCl | 2-(aminosulfonyl)phenyl |
| 47 | CO₂Me | O | CCl | 2-(methylsulfonyl)phenyl |
| 48 | CO₂Me | O | CCl | 2-(trifluoromethyl)phenyl |
| 49 | COCH₃ | CH₂ | CH | 2-(aminosulfonyl)phenyl |
| 50 | COCH₃ | CH₂ | CH | 2-(methylsulfonyl)phenyl |
| 51 | COCH₃ | CH₂ | CH | 2-(trifluoromethyl)phenyl |
| 52 | COCH₃ | CH₂ | N | 2-(aminosulfonyl)phenyl |
| 53 | COCH₃ | CH₂ | N | 2-(methylsulfonyl)phenyl |
| 54 | COCH₃ | CH₂ | N | 2-(trifluoromethyl)phenyl |
| 55 | COCH₃ | CH₂ | CF | 2-(aminosulfonyl)phenyl |
| 56 | COCH₃ | CH₂ | CF | 2-(methylsulfonyl)phenyl |
| 57 | COCH₃ | CH₂ | CF | 2-(trifluoromethyl)phenyl |
| 58 | COCH₃ | CH₂ | CCl | 2-(aminosulfonyl)phenyl |
| 59 | COCH₃ | CH₂ | CCl | 2-(methylsulfonyl)phenyl |
| 60 | COCH₃ | CH₂ | CCl | 2-(trifluoromethyl)phenyl |
| 61 | COCH₃ | O | CH | 2-(aminosulfonyl)phenyl |
| 62 | COCH₃ | O | CH | 2-(methylsulfonyl)phenyl |
| 63 | COCH₃ | O | CH | 2-(trifluoromethyl)phenyl |
| 64 | COCH₃ | O | N | 2-(aminosulfonyl)phenyl |
| 65 | COCH₃ | O | N | 2-(methylsulfonyl)phenyl |
| 66 | COCH₃ | O | N | 2-(trifluoromethyl)phenyl |
| 67 | COCH₃ | O | CF | 2-(aminosulfonyl)phenyl |
| 68 | COCH₃ | O | CF | 2-(methylsulfonyl)phenyl |
| 69 | COCH₃ | O | CF | 2-(trifluoromethyl)phenyl |
| 70 | COCH₃ | O | CCl | 2-(aminosulfonyl)phenyl |
| 71 | COCH₃ | O | CCl | 2-(methylsulfonyl)phenyl |
| 72 | COCH₃ | O | CCl | 2-(trifluoromethyl)phenyl |
| 73 | CH₃ | CH₂ | CH | 2-(aminosulfonyl)phenyl |
| 74 | CH₃ | CH₂ | CH | 2-(methylsulfonyl)phenyl |
| 75 | CH₃ | CH₂ | CH | 2-(trifluoromethyl)phenyl |
| 76 | CH₃ | CH₂ | N | 2-(aminosulfonyl)phenyl |
| 77 | CH₃ | CH₂ | N | 2-(methylsulfonyl)phenyl |
| 78 | CH₃ | CH₂ | N | 2-(trifluoromethyl)phenyl |
| 79 | CH₃ | CH₂ | CF | 2-(aminosulfonyl)phenyl |
| 80 | CH₃ | CH₂ | CF | 2-(methylsulfonyl)phenyl |
| 81 | CH₃ | CH₂ | CF | 2-(trifluoromethyl)phenyl |
| 82 | CH₃ | CH₂ | CCl | 2-(aminosulfonyl)phenyl |
| 83 | CH₃ | CH₂ | CCl | 2-(methylsulfonyl)phenyl |
| 84 | CH₃ | CH₂ | CCl | 2-(trifluoromethyl)phenyl |
| 85 | CH₃ | O | CH | 2-(aminosulfonyl)phenyl |
| 86 | CH₃ | O | CH | 2-(methylsulfonyl)phenyl |
| 87 | CH₃ | O | CH | 2-(trifluoromethyl)phenyl |
| 88 | CH₃ | O | N | 2-(aminosulfonyl)phenyl |
| 89 | CH₃ | O | N | 2-(methylsulfonyl)phenyl |
| 90 | CH₃ | O | N | 2-(trifluoromethyl)phenyl |
| 91 | CH₃ | O | CF | 2-(aminosulfonyl)phenyl |
| 92 | CH₃ | O | CF | 2-(methylsulfonyl)phenyl |
| 93 | CH₃ | O | CF | 2-(trifluoromethyl)phenyl |
| 94 | CH₃ | O | CCl | 2-(aminosulfonyl)phenyl |
| 95 | CH₃ | O | CCl | 2-(methylsulfonyl)phenyl |
| 96 | CH₃ | O | CCl | 2-(trifluoromethyl)phenyl |
| 97 | CH₂Ph | CH₂ | CH | 2-(aminosulfonyl)phenyl |
| 98 | CH₂Ph | CH₂ | CH | 2-(methylsulfonyl)phenyl |
| 99 | CH₂Ph | CH₂ | CH | 2-(trifluoromethyl)phenyl |
| 100 | CH₂Ph | CH₂ | N | 2-(aminosulfonyl)phenyl |
| 101 | CH₂Ph | CH₂ | N | 2-(methylsulfonyl)phenyl |
| 102 | CH₂Ph | CH₂ | N | 2-(trifluoromethyl)phenyl |
| 103 | CH₂Ph | CH₂ | CF | 2-(aminosulfonyl)phenyl |
| 104 | CH₂Ph | CH₂ | CF | 2-(methylsulfonyl)phenyl |
| 105 | CH₂Ph | CH₂ | CF | 2-(trifluoromethyl)phenyl |
| 106 | CH₂Ph | CH₂ | CCl | 2-(aminosulfonyl)phenyl |
| 107 | CH₂Ph | CH₂ | CCl | 2-(methylsulfonyl)phenyl |
| 108 | CH₂Ph | CH₂ | CCl | 2-(trifluoromethyl)phenyl |
| 109 | CH₂Ph | O | CH | 2-(aminosulfonyl)phenyl |
| 110 | CH₂Ph | O | CH | 2-(methylsulfonyl)phenyl |
| 111 | CH₂Ph | O | CH | 2-(trifluoromethyl)phenyl |
| 112 | CH₂Ph | O | N | 2-(aminosulfonyl)phenyl |
| 113 | CH₂Ph | O | N | 2-(methylsulfonyl)phenyl |
| 114 | CH₂Ph | O | N | 2-(trifluoromethyl)phenyl |
| 115 | CH₂Ph | O | CF | 2-(aminosulfonyl)phenyl |
| 116 | CH₂Ph | O | CF | 2-(methylsulfonyl)phenyl |
| 117 | CH₂Ph | O | CF | 2-(trifluoromethyl)phenyl |
| 118 | CH₂Ph | O | CCl | 2-(aminosulfonyl)phenyl |
| 119 | CH₂Ph | O | CCl | 2-(methylsulfonyl)phenyl |
| 120 | CH₂Ph | O | CCl | 2-(trifluoromethyl)phenyl |
| 121 | H | CH₂ | CH | 2-(aminosulfonyl)phenyl |
| 122 | H | CH₂ | CH | 2-(methylsulfonyl)phenyl |
| 123 | H | CH₂ | CH | 2-(trifluoromethyl)phenyl |
| 124 | H | CH₂ | N | 2-(aminosulfonyl)phenyl |
| 125 | H | CH₂ | N | 2-(methylsulfonyl)phenyl |
| 126 | H | CH₂ | N | 2-(trifluoromethyl)phenyl |
| 127 | H | CH₂ | CF | 2-(aminosulfonyl)phenyl |
| 128 | H | CH₂ | CF | 2-(methylsulfonyl)phenyl |
| 129 | H | CH₂ | CF | 2-(trifluoromethyl)phenyl |
| 130 | H | CH₂ | CCl | 2-(aminosulfonyl)phenyl |
| 131 | H | CH₂ | CCl | 2-(methylsulfonyl)phenyl |
| 132 | H | CH₂ | CCl | 2-(trifluoromethyl)phenyl |
| 133 | H | O | CH | 2-(aminosulfonyl)phenyl |
| 134 | H | O | CH | 2-(methylsulfonyl)phenyl |
| 135 | H | O | CH | 2-(trifluoromethyl)phenyl |
| 136 | H | O | N | 2-(aminosulfonyl)phenyl |
| 137 | H | O | N | 2-(methylsulfonyl)phenyl |
| 138 | H | O | N | 2-(trifluoromethyl)phenyl |
| 139 | H | O | CF | 2-(aminosulfonyl)phenyl |
| 140 | H | O | CF | 2-(methylsulfonyl)phenyl |
| 141 | H | O | CF | 2-(trifluoromethyl)phenyl |
| 142 | H | O | CCl | 2-(aminosulfonyl)phenyl |
| 143 | H | O | CCl | 2-(methylsulfonyl)phenyl |
| 144 | H | O | CCl | 2-(trifluoromethyl)phenyl |

TABLE 16

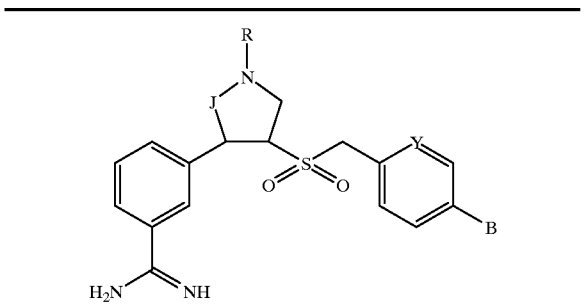

| Ex # | R | J | Y | B |
|---|---|---|---|---|
| 1 | SO₂Me | CH₂ | CH | 2-(aminosulfonyl)phenyl |
| 2 | SO₂Me | CH₂ | CH | 2-(methylsulfonyl)phenyl |
| 3 | SO₂Me | CH₂ | CH | 2-(trifluoromethyl)phenyl |
| 4 | SO₂Me | CH₂ | N | 2-(aminosulfonyl)phenyl |
| 5 | SO₂Me | CH₂ | N | 2-(methylsulfonyl)phenyl |
| 6 | SO₂Me | CH₂ | N | 2-(trifluoromethyl)phenyl |
| 7 | SO₂Me | CH₂ | CF | 2-(aminosulfonyl)phenyl |
| 8 | SO₂Me | CH₂ | CF | 2-(methylsulfonyl)phenyl |
| 9 | SO₂Me | CH₂ | CF | 2-(trifluoromethyl)phenyl |
| 10 | SO₂Me | CH₂ | CCl | 2-(aminosulfonyl)phenyl |
| 11 | SO₂Me | CH₂ | CCl | 2-(methylsulfonyl)phenyl |
| 12 | SO₂Me | CH₂ | CCl | 2-(trifluoromethyl)phenyl |
| 13 | SO₂Me | O | CH | 2-(aminosulfonyl)phenyl |
| 14 | SO₂Me | O | CH | 2-(methylsulfonyl)phenyl |
| 15 | SO₂Me | O | CH | 2-(trifluoromethyl)phenyl |
| 16 | SO₂Me | O | N | 2-(aminosulfonyl)phenyl |
| 17 | SO₂Me | O | N | 2-(methylsulfonyl)phenyl |
| 18 | SO₂Me | O | N | 2-(trifluoromethyl)phenyl |
| 19 | SO₂Me | O | CF | 2-(aminosulfonyl)phenyl |
| 20 | SO₂Me | O | CF | 2-(methylsulfonyl)phenyl |
| 21 | SO₂Me | O | CF | 2-(trifluoromethyl)phenyl |
| 22 | SO₂Me | O | CCl | 2-(aminosulfonyl)phenyl |
| 23 | SO₂Me | O | CCl | 2-(methylsulfonyl)phenyl |
| 24 | SO₂Me | O | CCl | 2-(trifluoromethyl)phenyl |
| 25 | CO₂Me | CH₂ | CH | 2-(aminosulfonyl)phenyl |
| 26 | CO₂Me | CH₂ | CH | 2-(methylsulfonyl)phenyl |
| 27 | CO₂Me | CH₂ | CH | 2-(trifluoromethyl)phenyl |
| 28 | CO₂Me | CH₂ | N | 2-(aminosulfonyl)phenyl |
| 29 | CO₂Me | CH₂ | N | 2-(methylsulfonyl)phenyl |
| 30 | CO₂Me | CH₂ | N | 2-(trifluoromethyl)phenyl |
| 31 | CO₂Me | CH₂ | CF | 2-(aminosulfonyl)phenyl |
| 32 | CO₂Me | CH₂ | CF | 2-(methylsulfonyl)phenyl |
| 33 | CO₂Me | CH₂ | CF | 2-(trifluoromethyl)phenyl |
| 34 | CO₂Me | CH₂ | CCl | 2-(aminosulfonyl)phenyl |
| 35 | CO₂Me | CH₂ | CCl | 2-(methylsulfonyl)phenyl |
| 36 | CO₂Me | CH₂ | CCl | 2-(trifluoromethyl)phenyl |
| 37 | CO₂Me | O | CH | 2-(aminosulfonyl)phenyl |
| 38 | CO₂Me | O | CH | 2-(methylsulfonyl)phenyl |
| 39 | CO₂Me | O | CH | 2-(trifluoromethyl)phenyl |
| 40 | CO₂Me | O | N | 2-(aminosulfonyl)phenyl |
| 41 | CO₂Me | O | N | 2-(methylsulfonyl)phenyl |
| 42 | CO₂Me | O | N | 2-(trifluoromethyl)phenyl |
| 43 | CO₂Me | O | CF | 2-(aminosulfonyl)phenyl |
| 44 | CO₂Me | O | CF | 2-(methylsulfonyl)phenyl |
| 45 | CO₂Me | O | CF | 2-(trifluoromethyl)phenyl |
| 46 | CO₂Me | O | CCl | 2-(aminosulfonyl)phenyl |
| 47 | CO₂Me | O | CCl | 2-(methylsulfonyl)phenyl |
| 48 | CO₂Me | O | CCl | 2-(trifluoromethyl)phenyl |
| 49 | COCH₃ | CH₂ | CH | 2-(aminosulfonyl)phenyl |
| 50 | COCH₃ | CH₂ | CH | 2-(methylsulfonyl)phenyl |
| 51 | COCH₃ | CH₂ | CH | 2-(trifluoromethyl)phenyl |
| 52 | COCH₃ | CH₂ | N | 2-(aminosulfonyl)phenyl |
| 53 | COCH₃ | CH₂ | N | 2-(methylsulfonyl)phenyl |
| 54 | COCH₃ | CH₂ | N | 2-(trifluoromethyl)phenyl |
| 55 | COCH₃ | CH₂ | CF | 2-(aminosulfonyl)phenyl |
| 56 | COCH₃ | CH₂ | CF | 2-(methylsulfonyl)phenyl |
| 57 | COCH₃ | CH₂ | CF | 2-(trifluoromethyl)phenyl |
| 58 | COCH₃ | CH₂ | CCl | 2-(aminosulfonyl)phenyl |
| 59 | COCH₃ | CH₂ | CCl | 2-(methylsulfonyl)phenyl |
| 60 | COCH₃ | CH₂ | CCl | 2-(trifluoromethyl)phenyl |
| 61 | COCH₃ | O | CH | 2-(aminosulfonyl)phenyl |
| 62 | COCH₃ | O | CH | 2-(methylsulfonyl)phenyl |
| 63 | COCH₃ | O | CH | 2-(trifluoromethyl)phenyl |
| 64 | COCH₃ | O | N | 2-(aminosulfonyl)phenyl |
| 65 | COCH₃ | O | N | 2-(methylsulfonyl)phenyl |
| 66 | COCH₃ | O | N | 2-(trifluoromethyl)phenyl |
| 67 | COCH₃ | O | CF | 2-(aminosulfonyl)phenyl |
| 68 | COCH₃ | O | CF | 2-(methylsulfonyl)phenyl |
| 69 | COCH₃ | O | CF | 2-(trifluoromethyl)phenyl |
| 70 | COCH₃ | O | CCl | 2-(aminosulfonyl)phenyl |
| 71 | COCH₃ | O | CCl | 2-(methylsulfonyl)phenyl |
| 72 | COCH₃ | O | CCl | 2-(trifluoromethyl)phenyl |
| 73 | CH₃ | CH₂ | CH | 2-(aminosulfonyl)phenyl |
| 74 | CH₃ | CH₂ | CH | 2-(methylsulfonyl)phenyl |
| 75 | CH₃ | CH₂ | CH | 2-(trifluoromethyl)phenyl |
| 76 | CH₃ | CH₂ | N | 2-(aminosulfonyl)phenyl |
| 77 | CH₃ | CH₂ | N | 2-(methylsulfonyl)phenyl |
| 78 | CH₃ | CH₂ | N | 2-(trifluoromethyl)phenyl |
| 79 | CH₃ | CH₂ | CF | 2-(aminosulfonyl)phenyl |
| 80 | CH₃ | CH₂ | CF | 2-(methylsulfonyl)phenyl |
| 81 | CH₃ | CH₂ | CF | 2-(trifluoromethyl)phenyl |
| 82 | CH₃ | CH₂ | CCl | 2-(aminosulfonyl)phenyl |
| 83 | CH₃ | CH₂ | CCl | 2-(methylsulfonyl)phenyl |
| 84 | CH₃ | CH₂ | CCl | 2-(trifluoromethyl)phenyl |
| 85 | CH₃ | O | CH | 2-(aminosulfonyl)phenyl |
| 86 | CH₃ | O | CH | 2-(methylsulfonyl)phenyl |
| 87 | CH₃ | O | CH | 2-(trifluoromethyl)phenyl |
| 88 | CH₃ | O | N | 2-(aminosulfonyl)phenyl |
| 89 | CH₃ | O | N | 2-(methylsulfonyl)phenyl |
| 90 | CH₃ | O | N | 2-(trifluoromethyl)phenyl |
| 91 | CH₃ | O | CF | 2-(aminosulfonyl)phenyl |
| 92 | CH₃ | O | CF | 2-(methylsulfonyl)phenyl |
| 93 | CH₃ | O | CF | 2-(trifluoromethyl)phenyl |
| 94 | CH₃ | O | CCl | 2-(aminosulfonyl)phenyl |
| 95 | CH₃ | O | CCl | 2-(methylsulfonyl)phenyl |
| 96 | CH₃ | O | CCl | 2-(trifluoromethyl)phenyl |
| 97 | CH₂Ph | CH₂ | CH | 2-(aminosulfonyl)phenyl |
| 98 | CH₂Ph | CH₂ | CH | 2-(methylsulfonyl)phenyl |
| 99 | CH₂Ph | CH₂ | CH | 2-(trifluoromethyl)phenyl |
| 100 | CH₂Ph | CH₂ | N | 2-(aminosulfonyl)phenyl |
| 101 | CH₂Ph | CH₂ | N | 2-(trimethylsulfonyl)phenyl |
| 102 | CH₂Ph | CH₂ | N | 2-(trifluoromethyl)phenyl |
| 103 | CH₂Ph | CH₂ | CF | 2-(aminosulfonyl)phenyl |
| 104 | CH₂Ph | CH₂ | CF | 2-(methylsulfonyl)phenyl |
| 105 | CH₂Ph | CH₂ | CF | 2-(trifluoromethyl)phenyl |
| 106 | CH₂Ph | CH₂ | CCl | 2-(aminosulfonyl)phenyl |
| 107 | CH₂Ph | CH₂ | CCl | 2-(methylsulfonyl)phenyl |
| 108 | CH₂Ph | CH₂ | CCl | 2-(trifluoromethyl)phenyl |
| 109 | CH₂Ph | O | CH | 2-(aminosulfonyl)phenyl |
| 110 | CH₂Ph | O | CH | 2-(methylsulfonyl)phenyl |
| 111 | CH₂Ph | O | CH | 2-(trifluoromethyl)phenyl |
| 112 | CH₂Ph | O | N | 2-(aminosulfonyl)phenyl |
| 113 | CH₂Ph | O | N | 2-(methylsulfonyl)phenyl |
| 114 | CH₂Ph | O | N | 2-(trifluoromethyl)phenyl |
| 115 | CH₂Ph | O | CF | 2-(aminosulfonyl)phenyl |
| 116 | CH₂Ph | O | CF | 2-(methylsulfonyl)phenyl |
| 117 | CH₂Ph | O | CF | 2-(trifluoromethyl)phenyl |
| 118 | CH₂Ph | O | CCl | 2-(aminosulfonyl)phenyl |
| 119 | CH₂Ph | O | CCl | 2-(methylsulfonyl)phenyl |
| 120 | CH₂Ph | O | CCl | 2-(trifluoromethyl)phenyl |
| 121 | H | CH₂ | CH | 2-(aminosulfonyl)phenyl |
| 122 | H | CH₂ | CH | 2-(methylsulfonyl)phenyl |
| 123 | H | CH₂ | CH | 2-(trifluoromethyl)phenyl |
| 124 | H | CH₂ | N | 2-(aminosulfonyl)phenyl |

TABLE 16-continued

| Ex # | R | J | Y | B |
|---|---|---|---|---|
| 125 | H | CH₂ | N | 2-(methylsulfonyl)phenyl |
| 126 | H | CH₂ | N | 2-(trifluoromethyl)phenyl |
| 127 | H | CH₂ | CF | 2-(aminosulfonyl)phenyl |
| 128 | H | CH₂ | CF | 2-(methylsulfonyl)phenyl |
| 129 | H | CH₂ | CF | 2-(trifluoromethyl)phenyl |
| 130 | H | CH₂ | CCl | 2-(aminosulfonyl)phenyl |
| 131 | H | CH₂ | CCl | 2-(methylsulfonyl)phenyl |
| 132 | H | CH₂ | CCl | 2-(trifluoromethyl)phenyl |
| 133 | H | O | CH | 2-(aminosulfonyl)phenyl |
| 134 | H | O | CH | 2-(methylsulfonyl)phenyl |
| 135 | H | O | CH | 2-(trifluoromethyl)phenyl |
| 136 | H | O | N | 2-(aminosulfonyl)phenyl |
| 137 | H | O | N | 2-(methylsulfonyl)phenyl |
| 138 | H | O | N | 2-(trifluoromethyl)phenyl |
| 139 | H | O | CF | 2-(aminosulfonyl)phenyl |
| 140 | H | O | CF | 2-(methylsulfonyl)phenyl |
| 141 | H | O | CF | 2-(trifluoromethyl)phenyl |
| 142 | H | O | CCl | 2-(aminosulfonyl)phenyl |
| 143 | H | O | CCl | 2-(methylsulfonyl)phenyl |
| 144 | H | O | CCl | 2-(trifluoromethyl)phenyl |

TABLE 17

| Ex # | R | Y | B |
|---|---|---|---|
| 1 | SO₂Me | CH | 2-(aminosulfonyl)phenyl |
| 2 | SO₂Me | CH | 2-(methylsulfonyl)phenyl |
| 3 | SO₂Me | CH | 2-(trifluoromethyl)phenyl |
| 4 | SO₂Me | N | 2-(aminosulfonyl)phenyl |
| 5 | SO₂Me | N | 2-(methylsulfonyl)phenyl |
| 6 | SO₂Me | N | 2-(trifluoromethyl)phenyl |
| 7 | SO₂Me | CF | 2-(aminosulfonyl)phenyl |
| 8 | SO₂Me | CF | 2-(methylsulfonyl)phenyl |
| 9 | SO₂Me | CF | 2-(trifluoromethyl)phenyl |
| 10 | SO₂Me | CCl | 2-(aminosulfonyl)phenyl |
| 11 | SO₂Me | CCl | 2-(methylsulfonyl)phenyl |
| 12 | SO₂Me | CCl | 2-(trifluoromethyl)phenyl |
| 13 | CO₂Me | CH | 2-(aminosulfonyl)phenyl |
| 14 | CO₂Me | CH | 2-(methylsulfonyl)phenyl |
| 15 | CO₂Me | CH | 2-(trifluoromethyl)phenyl |
| 16 | CO₂Me | N | 2-(aminosulfonyl)phenyl |
| 17 | CO₂Me | N | 2-(methylsulfonyl)phenyl |
| 18 | CO₂Me | N | 2-(trifluoromethyl)phenyl |
| 19 | CO₂Me | CF | 2-(aminosulfonyl)phenyl |
| 20 | CO₂Me | CF | 2-(methylsulfonyl)phenyl |

TABLE 17-continued

| Ex # | R | Y | B |
|---|---|---|---|
| 21 | CO₂Me | CF | 2-(trifluoromethyl)phenyl |
| 22 | CO₂Me | CCl | 2-(aminosulfonyl)phenyl |
| 23 | CO₂Me | CCl | 2-(methylsulfonyl)phenyl |
| 24 | CO₂Me | CCl | 2-(trifluoromethyl)phenyl |
| 25 | COCH₃ | CH | 2-(aminosulfonyl)phenyl |
| 26 | COCH₃ | CH | 2-(methylsulfonyl)phenyl |
| 27 | COCH₃ | CH | 2-(trifluoromethyl)phenyl |
| 28 | COCH₃ | N | 2-(aminosulfonyl)phenyl |
| 29 | COCH₃ | N | 2-(methylsulfonyl)phenyl |
| 30 | COCH₃ | N | 2-(trifluoromethyl)phenyl |
| 31 | COCH₃ | CF | 2-(aminosulfonyl)phenyl |
| 32 | COCH₃ | CF | 2-(methylsulfonyl)phenyl |
| 33 | COCH₃ | CF | 2-(trifluoromethyl)phenyl |
| 34 | COCH₃ | CCl | 2-(aminosulfonyl)phenyl |
| 35 | COCH₃ | CCl | 2-(methylsulfonyl)phenyl |
| 36 | COCH₃ | CCl | 2-(trifluoromethyl)phenyl |
| 37 | CH₃ | CH | 2-(aminosulfonyl)phenyl |
| 38 | CH₃ | CH | 2-(methylsulfonyl)phenyl |
| 39 | CH₃ | CH | 2-(trifluoromethyl)phenyl |
| 40 | CH₃ | N | 2-(aminosulfonyl)phenyl |
| 41 | CH₃ | N | 2-(methylsulfonyl)phenyl |
| 42 | CH₃ | N | 2-(trifluoromethyl)phenyl |
| 43 | CH₃ | CF | 2-(aminosulfonyl)phenyl |
| 44 | CH₃ | CF | 2-(methylsulfonyl)phenyl |
| 45 | CH₃ | CF | 2-(trifluoromethyl)phenyl |
| 46 | CH₃ | CCl | 2-(aminosulfonyl)phenyl |
| 47 | CH₃ | CCl | 2-(methylsulfonyl)phenyl |
| 48 | CH₃ | CCl | 2-(trifluoromethyl)phenyl |
| 49 | CH₂Ph | CH | 2-(aminosulfonyl)phenyl |
| 50 | CH₂Ph | CH | 2-(methylsulfonyl)phenyl |
| 51 | CH₂Ph | CH | 2-(trifluoromethyl)phenyl |
| 52 | CH₂Ph | N | 2-(aminosulfonyl)phenyl |
| 53 | CH₂Ph | N | 2-(methylsulfonyl)phenyl |
| 54 | CH₂Ph | N | 2-(trifluoromethyl)phenyl |
| 55 | CH₂Ph | CF | 2-(aminosulfonyl)phenyl |
| 56 | CH₂Ph | CF | 2-(methylsulfonyl)phenyl |
| 57 | CH₂Ph | CF | 2-(trifluoromethyl)phenyl |
| 58 | CH₂Ph | CCl | 2-(aminosulfonyl)phenyl |
| 59 | CH₂Ph | CCl | 2-(methylsulfonyl)phenyl |
| 60 | CH₂Ph | CCl | 2-(trifluoromethyl)phenyl |
| 61 | H | CH | 2-(aminosulfonyl)phenyl |
| 62 | H | CH | 2-(methylsulfonyl)phenyl |
| 63 | H | CH | 2-(trifluoromethyl)phenyl |
| 64 | H | N | 2-(aminosulfonyl)phenyl |
| 65 | H | N | 2-(methylsulfonyl)phenyl |
| 66 | H | N | 2-(trifluoromethyl)phenyl |
| 67 | H | CF | 2-(aminosulfonyl)phenyl |
| 68 | H | CF | 2-(methylsulfonyl)phenyl |
| 69 | H | CF | 2-(trifluoromethyl)phenyl |
| 70 | H | CCl | 2-(aminosulfonyl)phenyl |
| 71 | H | CCl | 2-(methylsulfonyl)phenyl |
| 72 | H | CCl | 2-(trifluoromethyl)phenyl |

TABLE 18

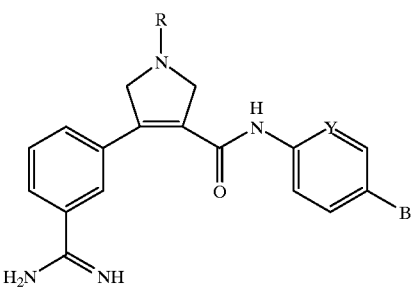

| Ex # | R | Y | B |
|---|---|---|---|
| 1 | SO₂Me | CH | 2-(aminosulfonyl)phenyl |
| 2 | SO₂Me | CH | 2-(methylsulfonyl)phenyl |
| 3 | SO₂Me | CH | 2-(trifluoromethyl)phenyl |
| 4 | SO₂Me | N | 2-(aminosulfonyl)phenyl |
| 5 | SO₂Me | N | 2-(methylsulfonyl)phenyl |
| 6 | SO₂Me | N | 2-(trifluoromethyl)phenyl |
| 7 | SO₂Me | CF | 2-(aminosulfonyl)phenyl |
| 8 | SO₂Me | CF | 2-(methylsulfonyl)phenyl |
| 9 | SO₂Me | CF | 2-(trifluoromethyl)phenyl |
| 10 | SO₂Me | CCl | 2-(aminosulfonyl)phenyl |
| 11 | SO₂Me | CCl | 2-(methylsulfonyl)phenyl |
| 12 | SO₂Me | CCl | 2-(trifluoromethyl)phenyl |
| 13 | CO₂Me | CH | 2-(aminosulfonyl)phenyl |
| 14 | CO₂Me | CH | 2-(methylsulfonyl)phenyl |
| 15 | CO₂Me | CH | 2-(trifluoromethyl)phenyl |
| 16 | CO₂Me | N | 2-(aminosulfonyl)phenyl |
| 17 | CO₂Me | N | 2-(methylsulfonyl)phenyl |
| 18 | CO₂Me | N | 2-(trifluoromethyl)phenyl |
| 19 | CO₂Me | CF | 2-(aminosulfonyl)phenyl |
| 20 | CO₂Me | CF | 2-(methylsulfonyl)phenyl |
| 21 | CO₂Me | CF | 2-(trifluoromethyl)phenyl |
| 22 | CO₂Me | CCl | 2-(aminosulfonyl)phenyl |
| 23 | CO₂Me | CCl | 2-(methylsulfonyl)phenyl |
| 24 | CO₂Me | CCl | 2-(trifluoromethyl)phenyl |
| 25 | COCH₃ | CH | 2-(aminosulfonyl)phenyl |
| 26 | COCH₃ | CH | 2-(methylsulfonyl)phenyl |
| 27 | COCH₃ | CH | 2-(trifluoromethyl)phenyl |
| 28 | COCH₃ | N | 2-(aminosulfonyl)phenyl |
| 29 | COCH₃ | N | 2-(methylsulfonyl)phenyl |
| 30 | COCH₃ | N | 2-(trifluoromethyl)phenyl |
| 31 | COCH₃ | CF | 2-(aminosulfonyl)phenyl |
| 32 | COCH₃ | CF | 2-(methylsulfonyl)phenyl |
| 33 | COCH₃ | CF | 2-(trifluoromethyl)phenyl |
| 34 | COCH₃ | CCl | 2-(aminosulfonyl)phenyl |
| 35 | COCH₃ | CCl | 2-(methylsulfonyl)phenyl |
| 36 | COCH₃ | CCl | 2-(trifluoromethyl)phenyl |
| 37 | CH₃ | CH | 2-(aminosulfonyl)phenyl |
| 38 | CH₃ | CH | 2-(methylsulfonyl)phenyl |
| 39 | CH₃ | CH | 2-(trifluoromethyl)phenyl |
| 40 | CH₃ | N | 2-(aminosulfonyl)phenyl |
| 41 | CH₃ | N | 2-(methylsulfonyl)phenyl |
| 42 | CH₃ | N | 2-(trifluoromethyl)phenyl |
| 43 | CH₃ | CF | 2-(aminosulfonyl)phenyl |
| 44 | CH₃ | CF | 2-(methylsulfonyl)phenyl |
| 45 | CH₃ | CF | 2-(trifluoromethyl)phenyl |
| 46 | CH₃ | CCl | 2-(aminosulfonyl)phenyl |
| 47 | CH₃ | CCl | 2-(methylsulfonyl)phenyl |
| 48 | CH₃ | CCl | 2-(trifluoromethyl)phenyl |
| 49 | CH₂Ph | CH | 2-(aminosulfonyl)phenyl |
| 50 | CH₂Ph | CH | 2-(methylsulfonyl)phenyl |
| 51 | CH₂Ph | CH | 2-(trifluoromethyl)phenyl |
| 52 | CH₂Ph | N | 2-(aminosulfonyl)phenyl |
| 53 | CH₂Ph | N | 2-(methylsulfonyl)phenyl |
| 54 | CH₂Ph | N | 2-(trifluoromethyl)phenyl |
| 55 | CH₂Ph | CF | 2-(aminosulfonyl)phenyl |
| 56 | CH₂Ph | CF | 2-(methylsulfonyl)phenyl |
| 57 | CH₂Ph | CF | 2-(trifluoromethyl)phenyl |
| 58 | CH₂Ph | CCl | 2-(aminosulfonyl)phenyl |
| 59 | CH₂Ph | CCl | 2-(methylsulfonyl)phenyl |
| 60 | CH₂Ph | CCl | 2-(trifluoromethyl)phenyl |
| 61 | H | CH | 2-(aminosulfonyl)phenyl |
| 62 | H | CH | 2-(methylsulfonyl)phenyl |

TABLE 18-continued

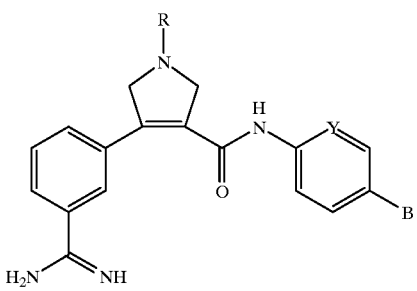

| Ex # | R | Y | B |
|---|---|---|---|
| 63 | H | CH | 2-(trifluoromethyl)phenyl |
| 64 | H | N | 2-(aminosulfonyl)phenyl |
| 65 | H | N | 2-(methylsulfonyl)phenyl |
| 66 | H | N | 2-(trifluoromethyl)phenyl |
| 67 | H | CF | 2-(aminosulfonyl)phenyl |
| 68 | H | CF | 2-(methylsulfonyl)phenyl |
| 69 | H | CF | 2-(trifluoromethyl)phenyl |
| 70 | H | CCl | 2-(aminosulfonyl)phenyl |
| 71 | H | CCl | 2-(methylsulfonyl)phenyl |
| 72 | H | CCl | 2-(trifluoromethyl)phenyl |

Utility

The compounds of this invention are useful as anticoagulants for the treatment or prevention of thromboembolic disorders in mammals. The term "thromboembolic disorders" as used herein includes arterial or venous cardiovascular or cerebrovascular thromboembolic disorders, including, for example, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, cerebral embolism, kidney embolisms, and pulmonary embolisms. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Kabi Pharmacia, Franklin, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10M sodium phosphate buffer, pH 7.5, containing 0.20M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o - v_s)/v_s = I/(K_i(1+S/K_m))$$

where:

$v_o$ is the velocity of the control in the absence of inhibitor;

$v_s$ is the velocity in the presence of inhibitor;

I is the concentration of inhibitor;

$K_i$ is the dissociation constant of the enzyme:inhibitor complex;

S is the concentration of substrate;

$K_m$ is the Michaelis constant.

Using the methodology described above, a number of compounds of the present invention were found to exhibit a $K_i$ of $\leq 1$ μM, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing which contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The ID50 values (dose which produces 50% inhibition of thrombus formation) are estimated by linear regression.

The compounds of formula (I) may also be useful as inhibitors of serine proteases, notably human thrombin, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm which arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 5 μm.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of Formula I that, when administered alone or in combination with an additional therapeutic agent to a mammal, is effective to prevent or ameliorate the thromboembolic disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin, as well as other factor Xa inhibitors such as those described in the publications identified above under Background of the Invention.

The term anti-platelet agents (or platelet inhibitory agents), as used herein, denotes agents that inhibit platelet function such as by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam are preferred. Other suitable anti-platelet agents include ticlopidine, including pharmaceutically acceptable salts or prodrugs thereof. Ticlopidine is also a preferred compound since it is known to be gentle on the gastrointestinal tract in use. Still other suitable platelet inhibitory agents include IIb/IIIa antagonists, thromboxane-A2-receptor antagonists and thromboxane-A2-synthetase inhibitors, as well as pharmaceutically acceptable salts or prodrugs thereof.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal a-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471,651 A2, the disclosures of which are hereby incorporated herein by reference.

The term thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but no compound of the present invention, then one would conclude factor Xa was present.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of Formula I are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are adminstered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Obviously, numerous modifications and variations of the present invention are possible in light of the above teachings. It is therefore to be understood that within the scope of the appended claims, the invention may be practiced otherwise that as specifically described herein.

What is claimed as new and desired to be secured by Letter Patent of United States is:

1. A compound of formula I:

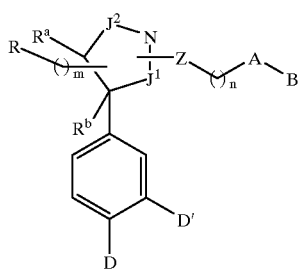

I or stereoisomers or pharmaceutically acceptable salts thereof, wherein;

one of D and D' is selected from CN, $C(=NR^7)NR^8R^9$, $NHC(=NR^7)NR^8R^9$, $NR^8CH(=NR^7)$, $C(O)NR^8R^9$, and $(CH_2)_rNR^8R^9$ and the other is H;

Z is selected from $CH_2$, $C=O$, $CH_2C(O)$, $C(O)O$, $CONH$, $CH_2NH_2$, $CH_2O$, $SO_2$, and $SO_2NH$;

$J^1$ and $J^2$ are independently selected from O and $CH_2$, provided that if $J^1$ is O, then $J^2$ is $CH_2$ and if $J^2$ is O, then $J^1$ is $CH_2$;

R is selected from $CO_2R^1$, $COR^1$, $OR^1$, $NR^2R^{2a}$, $CONR^2R^{2a}$, $S(O)_pR^{1a}$, and $S(O)_pNR^2R^{2a}$;

$R^a$ is selected from H and $C_{1-4}$ alkyl;

$R^b$ is H;

when $J^1$ and $J^2$ are $CH_2$, then $R^a$ and $R^b$ can combine to form a bond;

$R^1$ is selected from:
H,
$C_{1-4}$ alkyl substituted with 0–1 $R^3$,
$C_{3-6}$ carbocyclic group substituted with 0–2 $R^4$, and
furanyl, isoxazolidinyl, pyranyl, pyridyl, pyrrolidinyl, pyrrolinyl, pyrrolyl, tetrahydrofuranyl, and thienyl substituted with 0–2 $R^4$;

$R^{1a}$ is selected from:
$C_{1-4}$ alkyl substituted with 0–1 $R^3$,
$C_{3-6}$ carbocyclic group substituted with 0–2 $R^4$, and
furanyl, isoxazolidinyl, pyranyl, pyridyl, pyrrolidinyl, pyrrolinyl, pyrrolyl, tetrahydrofuranyl, and thienyl substituted with 0–2 $R^4$;

$R^2$ and $R^{2a}$ are independently selected from H, $C_{1-4}$ alkyl, and phenyl;

$R^{2a}$ may also be $C_{1-4}$ alkoxy;

$R^3$ is selected from:
phenyl substituted with 0–2 $R^4$, and
furanyl, isoxazolidinyl, pyranyl, pyridyl, pyrrolidinyl, pyrrolinyl, pyrrolyl, tetrahydrofuranyl, and thienyl substituted with 0–2 $R^4$;

A is selected from:
$C_{3-13}$ carbocyclic group substituted with 0–2 $R^4$, and
furanyl, isoxazolidinyl, pyranyl, pyridyl, pyrrolidinyl, pyrrolinyl, pyrrolyl, tetrahydrofuranyl, and thienyl substituted with 0–2 $R^4$;

B is selected from:
X-Y, $NR^2R^{2a}$, $C(=NR^2)NR^2R^{2a}$, $NR^2C(=NR^2)NR^2R^{2a}$,
benzyl substituted with 0–2 $R^{4a}$,
$C_{3-10}$ carbocyclic group substituted with 0–2 $R^{4a}$, and
furanyl, isoxazolidinyl, pyranyl, pyridyl, pyrrolidinyl, pyrrolinyl, pyrrolyl, tetrahydrofuranyl, and thienyl substituted with 0–2 $R^4$;

X is selected from $C_{1-4}$ alkylene, $—C(O)—$, $—C(O)CR^2R^{2a}—$, $—CR^2R^{2a}C(O)$, $—S(O)_p—$, $—S(O)_pCR^2R^{2a}—$, $—CR^2R^{2a}S(O)_p—$, $—S(O)_2NR^2—$, $—NR^2S(O)_2—$, $—NR^2S(O)_2CR^2R^{2a}—$, $—CR^2R^{2a}S(O)_2NR^2—$, $—NR^2S(O)_2NR^2—$, $—C(O)NR^2—$, $—NR^2C(O)—$, $—C(O)NR^2CR^2R^{2a}—$, $—NR^2C(O)CR^2R^{2a}—$, $CR^2R^{2a}C(O)NR^2—$, $—CR^2R^{2a}NR^2C(O)—$, $—NR^2C(O)O—$, $—OC(O)NR^2—$, $—NR^2C(O)NR^2—$, $—NR^2—$, $—NR^2CR^2R^{2a}—$, $—CR^2R^{2a}NR^2—$, O, $—CR^2R^{2a}O—$, $—OCR^2R^{2a}—$, and S;

Y is selected from:
$C_{3-10}$ carbocyclic group substituted with 0–2 $R^4$, and
furanyl, isoxazolidinyl, pyranyl, pyridyl, pyrrolidinyl, pyrrolinyl, pyrrolyl, tetrahydrofuranyl, and thienyl substituted with 0–2 $R^4$;

$R^4$ is selected from OH, $(CH_2)_rOR^2$, halo, $C_{1-4}$ alkyl, CN, $NO_2$, $(CH_2)_rNR^2R^{2a}$, $(CH_2)_rC(O)R^2$, $NR^2C(O)R^{2a}$, $NR^2C(O)NR^2R^{2a}$, $CH(=NH)NH_2$, $NHC(=NH)NH_2$, $SO_2NR^2R^{2a}$, $NR^2SO_2NR^2R^{2a}$, $NR^2SO_2—C_{1-4}$ alkyl, $NR^2SO_2R^5$, $S(O)_pR^{1a}$, and $CF_3$;

$R^{4a}$ is selected from OH, halo, $C_{1-4}$ alkyl, $NO_2$, $(CH_2)_r NR^2R^{2a}$, $(CH_2)_rC(O)R^2$, $NR^2C(O)R^{2a}$, $NR^2C(O)NR^2R^{2a}$, $CH(=NH)NH_2$, $NHC(=NH)NH_2$, $SO_2NR^2R^{2a}$, $NR^2SO_2NR^2R^{2a}$, $NR^2SO_2—C_{1-4}$ alkyl $NR^2SO_2R^5$, $S(O)_pR^{1a}$, and $CF_3$;

$R^5$ is selected from:
$C_{3-10}$ carbocyclic group substituted with 0–2 $R^6$, and
furanyl, isoxazolidinyl, pyranyl, pyridyl, pyrrolidinyl, pyrrolinyl, pyrrolyl, tetrahydrofuranyl, and thienyl substituted with 0–2 $R^6$;

$R^6$ is selected from H, OH, $(CH_2)_rOR^2$, halo, $C_{1-4}$ alkyl, CN, $NO_2$, $(CH_2)_rNR^2R^{2a}$, $(CH_2)_rC(O)R^2$, $NR^2C(O)R^{2a}$, $NR^2C(O)NR^2R^{2a}$, $CH(=NH)NH_2$, $NHC(=NH)NH_2$, $SO_2NR^2R^{2a}$, $NR^2SO_2NR^2R^{2a}$, and $NR^2SO_2—C_{1-4}$ alkyl;

$R^7$ is selected from H, OH, $C_{1-6}$ alkyl, $C_{1-6}$ alkylcarbonyl, $C_{1-6}$ alkoxy, $C_{1-4}$ alkoxycarbonyl, $C_{6-10}$ aryloxy, $C_{6-10}$ aryloxycarbonyl, $C_{6-10}$ arylmethylcarbonyl, $C_{1-4}$ alkylcarbonyloxy $C_{1-4}$ alkoxycarbonyl, $C_{6-10}$ arylcarbonyloxy $C_{1-4}$ alkoxycarbonyl, $C_{1-6}$ alkylaminocarbonyl, phenylaminocarbonyl, and phenyl $C_{1-4}$ alkoxycarbonyl;

$R^8$ is selected from H, $C_{1-6}$ alkyl and $(CH_2)_n$-phenyl;

$R^9$ is selected from H, $C_{1-6}$ alkyl and $(CH_2)_n$-phenyl;

n is selected from 0, 1, 2, and 3;

m is selected from 0, 1, and 2;

p is selected from 0, 1, and 2; and, r is selected from 0, 1, and 2.

2. A compound according to claim 1, wherein the compound is of formula Ia:

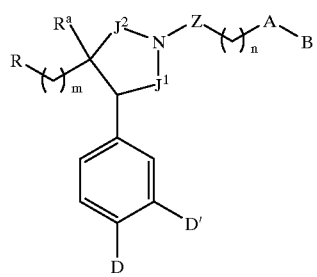

Ia or a stereoisomer or pharmaceutically acceptable salt form thereof, wherein;

Z is selected from $CH_2$, C=O, C(O)O, and $SO_2$.

3. A compound according to claim 2, wherein;

one of D and D' is $C(=NR^7)NH_2$ and the other is H;

B is selected from:
X-Y, $NR^2R^{2a}$,
benzyl substituted with 0–2 $R^{4a}$,
$C_{3-10}$ carbocyclic group substituted with 0–2 $R^{4a}$, and
furanyl, isoxazolidinyl, pyranyl, pyridyl, pyrrolidinyl, pyrrolinyl, pyrrolyl, tetrahydrofuranyl, and thienyl substituted with 0–2 $R^4$;

X is selected from $C_{1-4}$ alkylene, —C(O)—, —C(O)$CR^2R^{2a}$—, —$CR^2R^{2a}C(O)$, —$S(O)_p$—, —$S(O)_p CR^2R^{2a}$—, $CR^2R^{2a}S(O)_p$—, —$S(O)_2NR^2$—, —$NR^2S(O)_2$—, —C(O)$NR^2$—, —$NR^2C(O)$—, —$NR^2$—, —$NR^2CR^2R^{2a}$—, —$CR^2R^{2a}NR^2$—, O, —$CR^2R^{2a}O$—, and —$OCR^2R^{2a}$—;

$R^4$ is selected from OH, $(CH_2)_rOR^2$, halo, $C_{1-4}$ alkyl, CN, $NO_2$, $(CH_2)_rNR^2R^{2a}$, $(CH_2)_rC(O)R^2$, $NR^2C(O)R^{2a}$, $NR^2C(O)NR^2R^{2a}$, $CH(=NH)NH_2$, $NHC(=NH)NH_2$, $SO_2NR^2R^{2a}$, $NR^2SO_2NR^2R^{2a}$, $NR^2SO_2$—$C_{1-4}$ alkyl, $S(O)_pR^{1a}$, and $CF_3$;

$R^{4a}$ is selected from OH, halo, $C_{1-4}$ alkyl, $NO_2$, $(CH_2)_rNR^2R^{2a}$, $(CH_2)_rC(O)R^2$, $NR^2C(O)R^{2a}$, $NR^2C(O)NR^2R^{2a}$, $CH(=NH)NH_2$, $NHC(=NH)NH_2$, $SO_2NR^2R^{2a}$, $NR^2SO_2NR^2R^{2a}$, $NR^2SO_2$—$C_{1-4}$ alkyl, $S(O)_pR^{1a}$, and $CF_3$; and, n is selected from 0 and 1.

4. A compound according to claim 3, wherein the compound is of formula II:

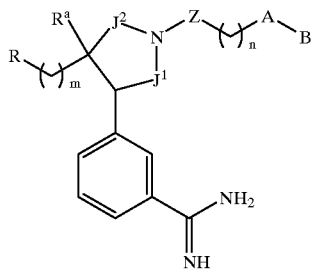

II or a stereoisomer or pharmaceutically acceptable salt form thereof, wherein;

R is selected from $CO_2R^1$, $COR^1$, $OR^1$, $CONR^2R^{2a}$, $S(O)_pR^{1a}$, and $S(O)_pNR^2R^{2a}$;

$R^1$ and $R^{1a}$ are independently selected from:
$C_{1-4}$ alkyl substituted with 0–1 $R^3$,
$C_{3-6}$ carbocyclic group substituted with 0–2 $R^4$, and
furanyl, isoxazolidinyl, pyranyl, pyridyl, pyrrolidinyl, pyrrolinyl, pyrrolyl, tetrahydrofuranyl, and thienyl substituted with 0–2 $R^4$;

X is selected from $C_{1-4}$ alkylene, —C(O)—, —$S(O)_p$—, —$NR^2$—, and O; and, m is selected from 0 and 1.

5. A compound according to claim 4, wherein;

R is selected from $CO_2R^1$, $COR^1$, $OR^1$, and $CONR^2R^{2a}$;

$R^1$ and $R^{1a}$ are independently selected from:
$C_{1-4}$ alkyl substituted with 0–1 $R^3$, and
$C_{3-6}$ carbocyclic residue substituted with 0–2 $R^4$; and, $R^2$ and $R^{2a}$ may be taken together to form a 5 or 6 membered ring substituted with 0–2 $R^4$.

6. A compound according to claim 5, wherein;

$R^a$ is selected from H and $C_{1-4}$ alkyl;

$R^1$ and $R^{1a}$ are independently selected from $C_{1-4}$ alkyl substituted with 0–1 $R^3$;

$R^3$ is phenyl substituted with 0–2 $R^4$; and,

Y is a $C_{3-10}$ carbocyclic residue substituted with 0–2 $R^4$.

7. A compound according to claim 1, wherein the compound or pharmaceutically acceptable salt form thereof is selected from the group consisting of:

trans-1-(4-amidinophenyl)methyl-3-carbomethoxy-4-(3-amidinophenyl)pyrrolidine;

trans-1-[(2'-aminosulfonyl-[1,1']-biphenyl-4-yl)methyl]-3-carbomethoxy-4-(3-amidinophenyl)pyrrolidine;

(3S,4R)-1-[(2'-aminosulfonyl-[1,1']-biphenyl-4-yl)methyl]-3-carbomethoxy-4-(3-amidinophenyl)pyrrolidine;

(3R,4S)-1-[(2'-aminosulfonyl-[1,1']-biphenyl-4-yl)methyl]-3-carbomethoxy-4-(3-amidinophenyl)pyrrolidine;

trans-1-[(2'-aminosulfonyl-[1,1']-biphenyl-4-yl)methyl]-4-(3-amidinophenyl)pyrrolidin-3-ylcarboxylic acid trans-1-[(2'-aminosulfonyl-[1,1']-biphenyl-4-yl)methyl]-4-(3-amidinophenyl)pyrrolidin-3-ylcarboxylic amide trans-1-[(2'-aminosulfonyl-[1,1']-biphenyl-4-yl)methyl]-4-(3-amidinophenyl)pyrrolidin-3-ylcarboxylic N,N-dimethylamide cis-1-[(2'-aminosulfonyl-[1,1']-biphenyl-4-yl)methyl]-3-carbomethoxy-4-(3-amidinophenyl)pyrrolidine;

cis-1-[(2'-aminosulfonyl-[1,1']-biphenyl-4-yl)methyl]-4-(3-amidinophenyl)pyrrolidin-3-ylcarboxylic acid trans-1-[(2'-aminosulfonyl-[1,1']-biphenyl-4-yl)methyl]-3-carboisopropoxy-4-(3-amidinophenyl)pyrrolidine;

trans-1-[(2'-aminosulfonyl-[1,1']-biphenyl-4-yl)methyl]-3-carbobutoxy-4-(3-amidinophenyl)pyrrolidine;

trans-1-[(2'-aminosulfonyl-[1,1']-biphenyl-4-yl)methyl]-3-acetyl-4-(3-amidinophenyl)pyrrolidine;

trans-1-[(2'-aminosulfonyl-[1,1']-biphenyl-4-yl)methyl]-3-carboethoxy-3-methyl-4-(3-amidinophenyl)pyrrolidine;

trans-1-[[2-(2-cyanophenylthio)phenyl]carbonyl]-3-carbomethoxy-4-(3-amidinophenyl)pyrrolidine;

trans-1-[[2-(2-cyanophenylthio)phenyl]methyl]-3-carbomethoxy-4-(3-amidinophenyl)pyrrolidine;

trans-1-[(2'-aminosulfonyl-[1,1']-biphenyl-4-yl)sulfonyl)-3-carbomethoxy-4-(3-amidinophenyl)pyrrolidine;

trans-1-[(2'-aminosulfonyl-[1,1']-biphenyl-4-yl)sulfonyl]-3-carboisopropoxy-4-(3-amidinophenyl)pyrrolidine;

trans-1-[9-fluorenylmethoxycarbonyl]-3-carbomethoxy-4-(3-amidinophenyl)pyrrolidine;

trans-2-benzyl-4-carbomethoxy-5-(3-amidinophenyl)isoxazolidine;

trans-2-[(2'-aminosulfonyl-[1,1']-biphenyl-4-yl)methyl]-4-carbomethoxy-5-(3-amidinophenyl)isoxazolidine;

trans-2-[(2'-aminosulfonyl-[1,1']-biphenyl-4-yl)methyl]-4-carboisopropoxy-5-(3-amidinophenyl)isoxazolidine; and, trans-2-[(2'-aminosulfonyl-[1,1']-biphenyl-4-yl)methyl]-4-methoxymethyl-5-(3-amidinophenyl)isoxazolidine.

8. A compound according to claim 1, wherein the compound is of formula Ib:

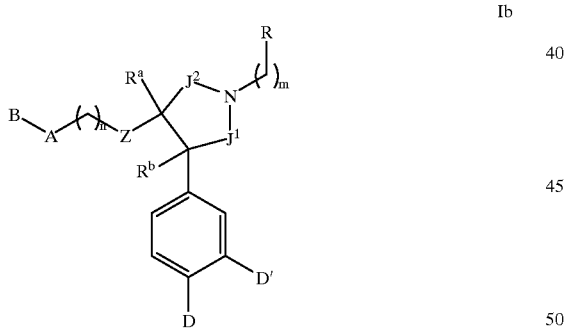

Ib or a stereoisomer or pharmaceutically acceptable salt form thereof.

9. A compound according to claim 8, wherein;

one of D and D' is $C(=NR^7)NH_2$ and the other is H;

B is selected from:
X-Y, $NR^2R^{2a}$,
benzyl substituted with 0–2 $R^{4a}$,
$C_{3-10}$ carbocyclic group substituted with 0–2 $R^{4a}$, and furanyl, isoxazolidinyl, pyranyl, pyridyl, pyrrolidinyl, pyrrolinyl, pyrrolyl, tetrahydrofuranyl, and thienyl substituted with 0–2 $R^4$;

X is selected from $C_{1-4}$ alkylene, —C(O)—, —C(O)$CR^2R^{2a}$—, —$CR^2R^{2a}$C(O)—, —C(O)O—, —OC(O)—, —S(O)$_p$—, —S(O)$_p CR^2R^{2a}$—, —$CR^2R^{2a}$S(O)$_p$—, —S(O)$_2 NR^2$—, —$NR^2$S(O)$_2$—, —C(O)$NR^2$—,
—$NR^2$C(O)—, —$NR^2$—, —$NR^2 CR^2 R^{2a}$—, —$CR^2R^{2a}NR^2$—, O, —$CR^2R^{2a}$O—, and —$OCR^2R^{2a}$—;

$R^4$ is selected from OH, $(CH_2)_r OR^2$, halo, $C_{1-4}$ alkyl, CN, $NO_2$, $(CH_2)_r NR^2R^{2a}$, $(CH_2)_r C(O)R^2$, $NR^2C(O)R^{2a}$, $NR^2C(O)NR^2R^{2a}$, $CH(=NH)NH_2$, $NHC(=NH)NH_2$, $SO_2NR^2R^{2a}$, $NR^2SO_2NR^2R^{2a}$, $NR^2SO_2$—$C_{1-4}$ alkyl, $S(O)_p R^{1a}$, and $CF_3$;

$R^{4a}$ is selected from OH, halo, $C_{1-4}$ alkyl, $NO_2$, $(CH_2)_r NR^2R^{2a}$, $(CH_2)_r C(O)R^2$, $NR^2C(O)R^{2a}$, $NR^2C(O)NR^2R^{2a}$, $CH(=NH)NH_2$, $NHC(=NH)NH_2$, $SO_2NR^2R^{2a}$, $NR^2SO_2NR^2R^{2a}$, $NR^2SO_2$—$C_{1-4}$ alkyl, $S(O)_p R^{1a}$, and $CF_3$; and, n is selected from 0 and 1.

10. A compound according to claim 9, wherein the compound is of formula IIa:

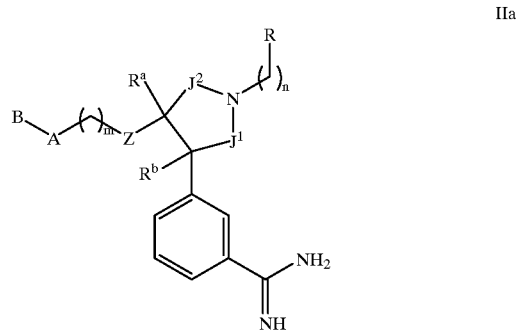

IIa or a stereoisomer or pharmaceutically acceptable salt form thereof, wherein;

R is selected from $CO_2R^1$, $COR^1$, $OR^1$, $CONR^2R^{2a}$, $S(O)_p R^{1a}$, and $S(O)_p NR^2R^{2a}$;

$R^1$ and $R^{1a}$ are independently selected from:
$C_{1-4}$ alkyl substituted with 0–1 $R^3$,
$C_{3-6}$ carbocyclic group substituted with 0–2 $R^4$, and furanyl, isoxazolidinyl, pyranyl, pyridyl, pyrrolidinyl, pyrrolinyl, pyrrolyl, tetrahydrofuranyl, and thienyl substituted with 0–2 $R^4$;

X is selected from $C_{1-4}$ alkylene, —C(O)—, —S(O)$_p$—, —$NR^2$—, and O; and, m is selected from 0 and 1.

11. A compound according to claim 10, wherein;

R is selected from $CO_2R^1$, $COR^1$, $OR^1$, and $CONR^2R^{2a}$;

$R^1$ and $R^{1a}$ are independently selected from:
$C_{1-4}$ alkyl substituted with 0–1 $R^3$, and
$C_{3-6}$ carbocyclic residue substituted with 0–2 $R^4$; and, $R^2$ and $R^{2a}$ may be taken together to form a 5 or 6 membered ring substituted with 0–2 $R^4$.

12. A compound according to claim 11, wherein;

$R^1$ and $R^{1a}$ are independently selected from $C_{1-4}$ alkyl substituted with 0–1 $R^3$;

$R^3$ is phenyl substituted with 0–2 $R^4$; and,

Y is a $C_{3-10}$ carbocyclic residue substituted with 0–2 $R^4$.

13. A compound according to claim 1, wherein the compound or pharmaceutically acceptable salt form thereof is selected from the group consisting of:

trans-1-(methylsulfonyl)-3-([2'-aminosulfonyl-[1,1']-biphenyl-4-yl)aminocarbonyl)-4-(3-amidinophenyl)pyrrolidine;

trans-1-(methylsulfonyl)-3-([2'-tert-butylaminosulfonyl-[1,1']-biphenyl-4-yl)aminocarbonyl)-4-(3-amidinophenyl)pyrrolidine;

cis-1-(methylsulfonyl)-3-([2'-aminosulfonyl-[1,1']-biphenyl-4-yl)aminocarbonyl)-4-(3-amidinophenyl) pyrrolidine;

trans-1-(methylsulfonyl)-3-[[5-(2'-aminosulfonylphenyl-1-yl)pyridin-2-yl]aminocarbonyl]-4-(3-amidinophenyl)pyrrolidine;

trans-1-(methylsulfonyl)-3-[[5-(2'-tert-butylaminosulfonylphenyl-1-yl)pyridin-2-yl]aminocarbonyl]-4-(3-amidinophenyl)pyrrolidine;

1-(methylsulfonyl)-3-([2'-aminosulfonyl-[1,1']-biphenyl-4-yl)aminocarbonyl)-4-(3-amidinophenyl)-$\Delta^3$-pyrroline;

1-(benzyl)-3-([2'-aminosulfonyl-[1,1']-biphenyl-4-yl) aminocarbonyl)-4-(3-amidinophenyl)-$\Delta^3$-pyrroline; and trans-1-(methylsulfonyl)-3-([2'-aminosulfonyl-[1,1']-biphenyl-4-yl)methylcarbonyl)-4-(3-amidinophenyl) pyrrolidine.

14. A pharmaceutical composition, comprising: a pharmaceutically acceptable carrier and a therapeutically effective amount of a compound according to claim 1 or a pharmaceutically acceptable salt thereof.

15. A pharmaceutical composition, comprising: a pharmaceutically acceptable carrier and a therapeutically effective amount of a compound according to claim 2 or a pharmaceutically acceptable salt thereof.

16. A pharmaceutical composition, comprising: a pharmaceutically acceptable carrier and a therapeutically effective amount of a compound according to claim 8 or a pharmaceutically acceptable salt thereof.

17. A method for treating or preventing a thromboembolic disorder, comprising administering to a patient in need thereof a therapeutically effective amount of a compound according to claim 1 or a pharmaceutically acceptable salt thereof.

18. A method for treating or preventing a thromboembolic disorder, comprising administering to a patient in need thereof a therapeutically effective amount of a compound according to claim 2 or a pharmaceutically acceptable salt thereof.

19. A method for treating or preventing a thromboembolic disorder, comprising administering to a patient in need thereof a therapeutically effective amount of a compound according to claim 8 or a pharmaceutically acceptable salt thereof.

* * * * *